(12) United States Patent
Coleman et al.

(10) Patent No.: US 6,800,651 B2
(45) Date of Patent: Oct. 5, 2004

(54) POTENTIATORS OF GLUTAMATE RECEPTORS

(75) Inventors: Darrell Stephen Coleman, Cary, NC (US); Gunnar Erik Jagdmann, Apex, NC (US); Kirk Willis Johnson, Carmel, IN (US); Michael Parvin Johnson, Carmel, IN (US); Thomas Hallett Large, Zionsville, IN (US); James Allen Monn, Indianapolis, IN (US); Darryle Darwin Schoepp, Indianapolis, IN (US); Thomas Charles Britton, Carmel, IN (US); Steven Scott Henry, New Palestine, IN (US); Joseph Patrick Tizzano, Holmdel, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 2 days.

(21) Appl. No.: 10/182,961

(22) PCT Filed: Jan. 22, 2001

(86) PCT No.: PCT/US01/00643

§ 371 (c)(1),
(2), (4) Date: Nov. 20, 2002

(87) PCT Pub. No.: WO01/56990

PCT Pub. Date: Aug. 9, 2001

(65) Prior Publication Data

US 2004/0006114 A1 Jan. 8, 2004

Related U.S. Application Data

(60) Provisional application No. 60/180,047, filed on Feb. 3, 2000, and provisional application No. 60/180,089, filed on Feb. 3, 2000.

(51) Int. Cl.[7] .................. A01K 31/44; C07D 213/02
(52) U.S. Cl. ........................ 514/357; 546/338
(58) Field of Search ..................... 546/338; 514/357

(56) References Cited

U.S. PATENT DOCUMENTS

| | | |
|---|---|---|
| 3,923,992 A | 12/1975 | Riley et al. |
| 4,083,980 A | 4/1978 | Schromm et al. |
| 4,855,308 A | 8/1989 | Kester et al. |
| 4,874,775 A | 10/1989 | Krumkalns et al. |

FOREIGN PATENT DOCUMENTS

| | | | |
|---|---|---|---|
| EP | 0 124 154 A2 | 11/1984 | |
| EP | 0 174 272 B1 | 3/1986 | |
| EP | 206581 * | 12/1986 | ......... C07D/213/43 |
| EP | 0 434 357 A2 | 6/1991 | |
| EP | 0 617 891 B1 | 10/1994 | |
| EP | 0 937 708 B1 | 8/1999 | |
| EP | 0 970 954 A1 | 1/2000 | |
| EP | 1 004 573 A1 | 5/2000 | |
| GB | 2 056 974 A | 3/1981 | |
| JP | 2000 001476 A | 1/2000 | |
| WO | WO 96/05818 A1 | 2/1996 | |
| WO | WO 99 06353 A1 | 2/1999 | |
| WO | 0 860 428 A2 | 5/2000 | |

OTHER PUBLICATIONS

Nakasato, Atsuo et al: "Aryloxy–substituted nitrogen–heteroarylamines, their use, and MDR ligands containing them" retrieved from STN Database accession No. 132–59185.

Chemical Abstracts Service; retrieved from STN Database accession No. 132:59185, XP002181343.

V. Carelli, et al., "Synthesis of N1–(pyridylmethyl)–N'–(diethylaminoethyl)–sulfonamides and their penicillin salts" Chemical Abstracts Service; retrieved from STN Database accession No. CA55:2110812009705–31.

Chemical Abstracts Service; retrieved from STN Database accession No. CA55:2110812009705–31 XP002181344 CAS RN: 110491–53–7.

Shigenobu Okuda, et al: "Synthesis of 5–azaindole" Chemical Abstracts Service; retrieved from STN Database accession No. CA54:22631B20P90–05–31.

Chemical Abstracts Service; retrieved from STN Database accession No. CA54:22631B20P90–05–31 XPO02181345 CAS RN: 108955–05–1.

Parker, Julie A. et al: "Diastereoselective Methylations of Enolates Derived from Pyridyl Amides" J. Chem. Research (S), (1998), 362–363, 1453–1460.

Chemical Abstracts Service; retrieved from STN Database accession No. 129:148890 XP002181346 (1998), (7), 362–363, 1453–1460.

Mehta, Lina K. et al: "The elimination of an alkoxy group in the photo–Graebe–Ullmann conversion of 1–(2,5–dialkoxypenyl)triazolopyridines into carbolines, and the preparation of α–,γ–and δ–carboline quinones" J. Chem.. Soc. Perkin Trans (1993) 1261–1267; STN Database accession No. 120:30745 XP002181347.

Greiner, Alfred: "An improvement of the N–arylation of amides; application to the synthesis of substituted 3–(N–acetyl–N–phenylamino)pyridines" retrieved from STN Database accession No. 111:232522 XP002181348.

Tilley, Jefferson W. et al: "Palladium–catalyzed carbonyl insertion route to pyrido'2–1– b!quinazoline derivatives" J. Org. Chem. (1987) 2469–2474; STN Database accession No. 107:39747 XP002181349.

(List continued on next page.)

Primary Examiner—Zinna Northington Davis
(74) Attorney, Agent, or Firm—Arvie J. Anderson; Mark A. Winter

(57) ABSTRACT

The present invention relates to potentiators of metabotropic glutamate receptor function and specifically provides compounds of formula I, compositions thereof and methods of using the same.

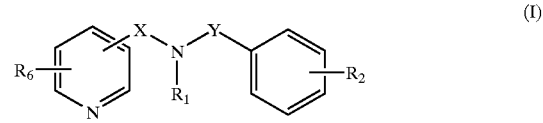

(I)

30 Claims, No Drawings

OTHER PUBLICATIONS

Moerkved, Eva H. et al: "Synthesis of some derivatives of 4–(dialkylamino)–2–aminopyridine" Journal f. prakt. Chemie, Band, 322, Heft 2, (1980), S. 343–347, STN Database accession No. 93:186108 XP002181350.

Abramovitch, R. A. et al: "Direct acylamination of pyridine 1–oxides" Journal of Organic Chemistry, vol. 39, No. 13, Jun. 28, 1974 1975–1802; STN Database accession No. 81:91312 XP002181351.

* cited by examiner

POTENTIATORS OF GLUTAMATE RECEPTORS

This application is a U.S. national phase entry, prudent to 35 USC 371, of PCT/US01/00643, filed Jan. 22, 2001 and published on Aug. 9, 2001, International Publication No. WO 01/56990 A2, which claims the benefit of U.S. Provisional Application Nos. 60/180,047 and 60/180,089 both filed Feb. 3, 2000.

The present invention provides potentiators of glutamate receptors (compounds of formula I), pharmaceutical compositions thereof, and methods of using the same, processes for preparing the same, and intermediates thereof.

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGlu) receptor. Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The present invention relates to potentiators of mGlu receptors. The mGlu receptors belong to the Type III G-protein coupled receptor (GPCR) superfamily. This superfamily of GPCR's, including the calcium-sensing receptors, $GABA_B$ receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, *Prog. Neurobio.*, 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, *Prog. Neurobio.*, 54, 581 (1998). For instance, the Group I mGlu receptors, which include the $mGlu_1$ and $mGlu_5$, are known to activate phospholipase C (PLC) via $G\alpha q$-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, *J. Neurochem.*, 63, 769 (1994); Ito, et al., *Neurorep.*, 3, 1013 (1992). The Group II mGlu receptors consist of the two distinct receptors, $mGlu_2$ and $mGlu_3$ receptors. Both have been found to be negatively coupled to adenylate cyclase via activation of $G\alpha i$-protein. These receptors can be activated by a group-selective compound such as 1S,2S,5R,6S-2-aminobicyclo[3.1.0]hexane-2,6-dicarboxylate. Monn, et al., *J. Med. Chem.*, 40, 528 (1997); Schoepp, et al., *Neuropharmacol.*, 36, 1 (1997). Similarly, the Group III mGlu receptors, including $mGlu_4$, $mGlu_6$, $mGlu_7$ and $mGlu_8$, are negatively coupled to adenylate cyclase via $G\alpha i$ and are potently activated by $L$-$AP_4$ (L-(+)-2-amino-4-phosphonobutyric acid). Schoepp, *Neurochem. Int.*, 24, 439 (1994).

It should be noted that many of the available pharmacological tools are not ideal in that they cross react not only on the receptors within a Group of mGlu receptors but also often have some activity between Groups of mGlu receptors. For instance, compounds such as 1S,3R-ACPD, (1S,3R)-1-aminocyclopentane-trans-1,3-dicarboxylic acid, are believed to activate all of the Group I, II and III mGlu receptors depending upon the dose utilized while others, such as 1S,3S-ACPD, (1S, 3S)-1-aminocyclopentane-trans-1,3-dicarboxylic acid, are more selective for the Group II receptors ($mGlu_{2/3}$) than the Group I ($mGlu_{1/5}$) or Group III ($mGlu_{4/6/7/8}$). Schoepp, *Neurochem. Int.*, 24, 439 (1994). To date, there are very few examples of selective agents for the mGlu receptors. Schoepp, Jane, and Monn, *Neuropharmacol.*, 38, 1431 (1999).

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, *Ann. Rev. Pharmacol. Toxicol.*, 29, 365–402 (1989); Schoepp and Sacann, *Neurobio. Aging*, 15, 261–263 (1994); Meldrum and Garthwaite, *Tr. Pharmacol. Sci.*, 11, 379–387 (1990). The medical consequences of such glutamate dysfunction makes the abatement of these neurological processes an important therapeutic goal.

SUMMARY OF THE INVENTION

This invention provides compounds of formula I:

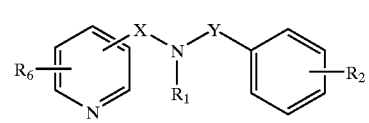

formula I wherein
$R_1$ is selected from the group consisting of —$C(O)R_3$, —$C(O)OR_4$, and —$SO_2R_5$
   wherein $R_3$ is selected from the group consisting of alkyl and cycloalkyl, $R_4$ is selected from the group consisting of alkyl and cycloalkyl, $R_5$ is selected from the group consisting of alkyl, cycloalkyl, and fluorinated alkyl;
$R_2$ is from 1 to 3 substituents independently selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

or two $R_2$ substituents are taken together, on adjacent positions, to form a fused cycloalkyl or a methylenedioxy ring, and one $R_2$ substituent is selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

$R_6$ is from 1 to 2 substituents independently selected from the group consisting of hydrogen, alkyl, alkoxy, trifluoromethyl, halogen, phenoxy, and substituted phenoxy;

X is selected from the group consisting of a bond, —$CH_2$—, —$CHR_7$—, and —$CH_2CH_2$— wherein $R_7$ is lower alkyl;

Y is selected from the group consisting of a bond, —$CH_2$—, —$CHR_8$—, —$CH_2CH_2$—, —$CHR_9CH_2$—, and —$CH_2CHR_9$— wherein $R_8$ is lower alkyl and $R_9$ is lower alkyl;

and the pharmaceutically acceptable salts thereof and the pyridyl N-oxide thereof.

The present invention also provides for novel pharmaceutical compositions, comprising: a compound of the formula I and a pharmaceutically acceptable diluent.

Because the compounds of formula I enhance the normal physiological function of the mGlu receptors, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders-(including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

In another embodiment the present invention provides methods of treating neurological and psychiatric disorders associated with glutamate dysfunction, comprising: administering to a patient in need thereof an effective amount of a compound of formula I. That is, the present invention provides for the use of a compound of formula I or pharmaceutical composition thereof for the treatment neurological and psychiatric disorders associated with glutamate dysfunction.

Of the disorders above, the treatment of migraine, anxiety, schizophrenia, and epilepsy are of particular importance.

In a preferred embodiment the present invention provides a method for treating migraine, comprising: administering to a patient in need thereof an effective amount of a compound of formula I.

In another preferred embodiment the present invention provides a method for treating anxiety, comprising: administering to a patient in need thereof an effective amount of a compound of formula I. Particularly preferred anxiety disorders are generalized anxiety disorder, panic disorder, and obsessive compulsive disorder.

In another preferred embodiment the present invention provides a method for treating schizophrenia, comprising: administering to a patient in need thereof an effective amount of a compound of formula I.

In yet another preferred embodiment the present invention provides a method for treating epilepsy, comprising: administering to a patient in need thereof an effective amount of a compound of formula I.

In another embodiment of the present invention provides methods of treating neurological and psychiatric disorders associated with glutamate dysfunction, comprising: administering to a patient in need thereof an effective amount of a potentiator of metabotropic glutamate receptors.

Specifically, the present invention provides a method of treating neurological and psychiatric disorders associated with glutamate dysfunction, comprising: administering to a patient in need thereof an effective amount of a potentiator of $mGlu_2$ and/or $mGlu_3$ receptors.

In a preferred embodiment the present invention provides a method for treating migraine, comprising: administering to a patient in need thereof an effective amount of a metabotropic glutamate potentiator, in particular a potentiator of $mGlu_2$ and/or $mGlu_3$ receptors.

In another preferred embodiment the present invention provides a method for treating anxiety, comprising: administering to a patient in need thereof an effective amount of a metabotropic glutamate potentiator, in particular a potentiator of $mGlu_2$ and/or $mGlu_3$ receptors.

Particularly preferred anxiety disorders are generalized anxiety disorder, panic disorder, and obsessive compulsive disorder.

In another preferred embodiment the present invention provides a method for treating schizophrenia, comprising: administering to a patient in need thereof an effective amount of a metabotropic glutamate potentiator, in particular a potentiator of $mGlu_2$ and/or $mGlu_3$ receptors.

In yet another preferred embodiment the present invention provides a method for treating epilepsy, comprising: administering to a patient in need thereof an effective amount of a metabotropic glutamate potentiator, in particular a potentiator of $mGlu_2$ and/or $mGlu_3$ receptors.

Because such potentiators, including the compounds of formula I, positively modulate metabotropic glutamate receptor response to glutamate, it is an advantage that the present methods utilize endogenous glutamate.

Because such potentiators positively modulate metabotropic glutamate receptor response to glutamate agonists it is understood that the present invention extends to the treatment of neurological and psychiatric disorders associated with glutamate dysfunction by administering an effective amount of a metabotropic glutamate potentiator, including the compounds of formula I, in combination with a potentiated amount of a metabotropic glutamate receptor agonist. Such a combination may be advantageous in that it may augment the activity and selectivity of an agonist of metabotropic glutamate receptors, in particular a potentiator of $mGlu_2$ and/or $mGlu_3$ receptors.

DETAILED DESCRIPTION OF THE INVENTION

This invention provides methods of potentiating metabotropic glutamate receptors, in particular a $mGlu_2$ and/or $mGlu_3$ receptors. In the present methods an effective amount of a potentiator of metabotropic glutamate receptors, including a compound of formula I, is administered which positively modulates the effect of glutamate or glutamate agonists on the subject receptors.

Before describing the present invention in greater detail, it is understood that the invention in its broadest sense is not limited to particular embodiments described herein, as variations of the particular embodiments described herein are within the scope of the claimed invention.

Thus, compounds useful in the present invention are those which are potentiators of metabotropic glutamate receptors, particularly, those that potentiate the effects of glutamate and glutamate agonists at Group II metabotropic glutamate receptors, and even more particularly, those that potentiate the effects of glutamate and glutamate agonists at $mGlu_2$ receptors and/or $mGlu_3$ receptors. Useful compounds are varied in structure, and so long as they embrace the above properties, they are suitable for use in the present invention. Preferred compounds include, but are not limited to, those described herein.

The compounds of formula I potentiate the function of glutamate receptors. Specifically, the compounds of formula I are potentiators of the Group II metabotropic glutamate receptors, and in particular, the compounds of formula I are potentiators of the $mGlu_2$ receptor and/or the $mGlu_3$ receptor.

As used herein, the following terms have the meanings indicated:

The term "alkyl" refers to a straight or branched alkyl chain having from one to ten carbon atoms, and includes methyl, ethyl, propyl, iso-propyl, butyl, iso-butyl, sec-butyl, t-butyl, pentyl, hexyl, heptyl, octyl, nonyl, decyl, and the like.

The term "substituted alkyl" refers to a straight or branched alkyl chain having from one to ten carbon atoms, and includes methyl, ethyl, propyl, iso-propyl, butyl, iso-butyl, sec-butyl, t-butyl, pentyl, hexyl, heptyl, octyl, nonyl, decyl, and the like having from 1 to 3 substituents selected from the group consisting of hydroxy, halogen, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, substituted benzyloxy, pyridyl, substituted pyridyl, thienyl, and substituted thienyl.

The term "lower alkyl" refers to a straight or branched alkyl chain having from one to four carbon atoms, and includes methyl, ethyl, propyl, iso-propyl, butyl, iso-butyl, sec-butyl, and t-butyl.

The term "alkenyl" refers to a straight or branched alkyl chain having from one to ten carbon atoms and one or more carbon-carbon double bonds, and includes ethylene, propylene, iso-propylene, butylene, iso-butylene, sec-butylene, pentylene, hexylene, heptylene, octylene, nonylene, decylene, and the like.

The term "substituted alkenyl" refers to a straight or branched alkyl chain having from one to ten carbon atoms and one or more carbon-carbon double bonds, and includes ethylene, propylene, iso-propylene, butylene, iso-butylene, sec-butylene, pentylene, hexylene, heptylene, octylene, nonylene, decylene, and the like having from 1 to 3 substituents selected from the group consisting of carboxy, alkoxycarbonyl, amido, substituted amido, phenyl, and substituted phenyl.

The term "cycloalkyl" refers to saturated cyclic alkyl group having from three to seven carbon atoms and includes, cyclopropyl, cyclobutyl, cyclopentyl, cyclohexyl, and cycloheptyl.

The term "substituted cycloalkyl" refers to saturated cyclic alkyl group having from three to seven carbon atoms and includes, cyclopropyl, cyclobutyl, cyclopentyl, cyclohexyl, and cycloheptyl having from 1 to 3 substituents selected from the group consisting of hydroxy, halogen, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, and substituted benzyloxy.

The terms "benzyloxy and substituted benzyloxy" refer to a radical of the formula

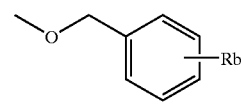

wherein $R_b$ is from 1 to 3 groups independently selected from the group consisting of hydrogen, alkyl, alkoxy, cyano, nitro, trifluoromethyl, halogen, phenyl, and substituted phenyl. The substituent is benzyloxy where each $R_b$ is hydrogen and is a substituted benzyloxy where at least one $R_b$ is not hydrogen.

The term "halogen" refers to a chloro, fluoro, bromo or iodo atom.

The term "fluorinated alkyl" refers to a straight or branched alkyl chain having from one to ten carbon atoms substituted with one or more fluorine atoms, and includes fluoromethyl, difluoromethyl, trifluoromethyl, 2,2,2-trifluoroethyl, 1,1,2,2,2-pentafluoroethyl 3,3,3-trifluoropropyl, 4,4,4-trifluorobutyl, and the like.

The term "alkoxy" refers to straight or branched alkyl chain having from one to ten carbon atoms attached to an oxygen atom, and includes methoxy, ethoxy, propoxy, iso-propoxy, butoxy, iso-butoxy, sec-butoxy, t-butoxy, pentoxy, hexoxy, heptoxy, octoxy, nonoxy, decoxy, and the like.

The term "substituted alkoxy" refers to a straight or branched alkyl chain having from one to ten carbon atoms attached to an oxygen atom, and includes methoxy, ethoxy, propoxy, iso-propoxy, butoxy, iso-butoxy, sec-butoxy, t-butoxy, pentoxy, hexoxy, heptoxy, octoxy, nonoxy, decoxy, and the like having from 1 to 3 substituents selected from the group consisting of hydroxy, halogen, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, and substituted benzyloxy; and when one or more of the substituents is hydroxy, halogen, alkoxy, acyloxy, amino, acylamino, sulfonamide, phenoxy, substituted phenoxy, benzyloxy, or substituted benzyloxy then those substituents are not attached to the same carbon as the alkoxy oxygen atom.

The term "cycloalkoxy" refers to saturated cyclic alkyl group having from three to seven carbon atoms attached to an oxygen atom, and includes, cyclopropyloxy, cyclobutyloxy, cyclopentyloxy, cyclohexyloxy, and cycloheptyloxy.

The term "substituted cycloalkoxy" refers to saturated cyclic alkyl group having from three to seven carbon atoms attached to an oxygen atom, and includes, cyclopropyloxy, cyclobutyloxy, cyclopentyloxy, cyclohexyloxy, and cycloheptyloxy having from 1 to 3 substituents selected from the group consisting of hydroxy, halogen, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, and substituted benzyloxy; and when one or more of the substituents is hydroxy, halogen, alkoxy, acyloxy, amino, acylamino, sulfonamide, phenoxy, substituted phenoxy, benzyloxy, or substituted benzyloxy then those substituents are not attached to the same carbon as the cycloalkoxy oxygen atom.

The term "pyridyloxy" refers to a radical of the formula

wherein G is selected from the group consisting of pyrid-2-yl, pyrid-3-yl, and pyrid-4-yl.

The terms "phenoxy and substituted phenoxy" refer to a radical of the formula

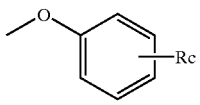

wherein $R_c$ is from 1 to 3 groups independently selected from the group consisting of hydrogen, hydroxy, alkyl, substituted alkyl, cycloalkyl, substituted cylcoalkyl, alkoxy, substituted alkoxy, halogen, acyloxy, carboxy, alkoxycarbonyl, amido, substituted amido, amino, acylamino, sulfonylamido, sulfonamide, cyano, nitro, phenyl, substituted phenyl, and —S(O)$_p$alkyl (wherein p is 0, 1, or 2). The substituent is phenoxy where each $R_c$ is hydrogen and is a substituted phenoxy where at least one $R_c$ is not hydrogen.

The terms "thiophenoxy and substituted thiophenoxy" refer to a radical of the formula

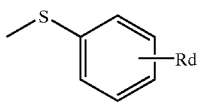

wherein $R_d$ is from 1 to 3 groups independently selected from the group consisting of hydrogen, hydroxy, alkyl, substituted alkyl, cycloalkyl, substituted cylcoalkyl, alkoxy, substituted alkoxy, halogen, acyloxy, carboxy, alkoxycarbonyl, amido, substituted amido, amino, acylamino, sulfonylamido, sulfonamide, cyano, nitro, phenyl, substituted phenyl, and —S(O)$_p$alkyl (wherein p is 0, 1, or 2). The substituent is thiophenoxy where each $R_d$ is hydrogen and is a substituted thiophenoxy where at least one $R_d$ is not hydrogen.

The term "trisubstituted silyloxy" refer to a radical of the formula

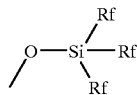

wherein $R_f$ is independently selected from the group consisting of alkyl, phenyl, and benzyl.

The terms "phenylsulfinyl and substituted phenylsulfinyl" refer to a radical of the formula

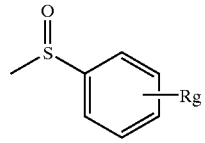

wherein $R_g$ is from 1 to 3 groups independently selected from the group consisting of hydrogen, hydroxy, alkyl, substituted alkyl, cycloalkyl, substituted cylcoalkyl, alkoxy, substituted alkoxy, halogen, acyloxy, carboxy, alkoxycarbonyl, amido, substituted amido, amino, acylamino, sulfonylamido, sulfonamide, cyano, nitro, phenyl, substituted phenyl, and —S(O)$_p$alkyl (wherein p is 0, 1, or 2). The substituent is phenylsulfinyl where each $R_g$ is hydrogen and is a substituted phenylsulfinyl where at least one $R_g$ is not hydrogen.

The term "phenylsulfonyl and substituted phenylsulfonyl, refer to a radical of the formula

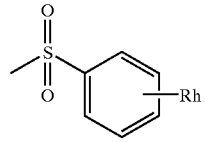

wherein $R_h$ is from 1 to 3 groups independently selected from the group consisting of hydrogen, hydroxy, alkyl, substituted alkyl, cycloalkyl, substituted cylcoalkyl, alkoxy, substituted alkoxy, halogen, acyloxy, carboxy, alkoxycarbonyl, amido, substituted amido, amino, acylamino, sulfonylamido, sulfonamide, cyano, nitro, phenyl, substituted phenyl, and —S(O)$_p$alkyl (wherein p is 0, 1, or 2). The substituent is phenylsulfonyl is where each $R_h$ is hydrogen and is a substituted phenylsulfonyl where at least one $R_h$ is not hydrogen.

The term "benzoyl and substituted benzoyl refer to a radical of the formula

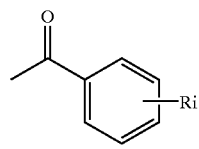

wherein $R_i$ is from 1 to 3 groups independently selected from the group consisting of hydrogen, hydroxy, alkyl, substituted alkyl, cycloalkyl, substituted cylcoalkyl, alkoxy, substituted alkoxy, halogen, acyloxy, carboxy, alkoxycarbonyl, amido, substituted amido, amino, acylamino, sulfonylamido, sulfonamide, cyano, nitro, phenyl, substituted phenyl, and —S(O)$_p$alkyl (wherein p is 0, 1, or 2). The substituent is benzoyl where each $R_i$ is hydrogen and is a substituted benzoyl where at least one $R_i$ is not hydrogen.

The term "acyloxy" refers to a radical of the formula

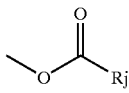

wherein $R_j$ is selected from the group consisting of alkyl, phenyl, and benzyl.

The term "carboxy" refers to a radical of the formula

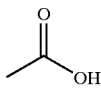

The term "alkoxycarbonyl" refers to a radical of the formula

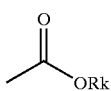

wherein $R_k$ is selected from the group consisting of alkyl, benzyl, and substituted benzyl.

The term "amido" refers to a radical of the formula

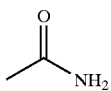

The term "substituted amido" refers to a radical of the formula

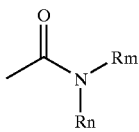

wherein $R_m$ is selected from the group consisting of alkyl and benzyl and $R_n$ is selected from the group consisting of hydrogen, alkyl, benzyl, substituted benzyl, phenyl and substituted phenyl.

The term "acylamino" refers to a radical of the formula

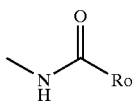

wherein $R_o$ is selected from the group consisting of alkyl, phenyl, substituted phenyl, benzyl, and substituted benzyl.

The term "sulfonylamido" refers to a radical of the formula

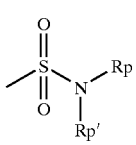

wherein $R_p$ is selected from the group consisting of alkyl, phenyl, and substituted phenyl; and $R_{p'}$ is selected from the group consisting of hydrogen and alkyl.

The term "sulfonamide" refers to a radical of the formula

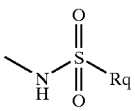

wherein $R_q$ is selected from the group consisting of alkyl, phenyl, and substituted phenyl.

The terms "phenyl and substituted phenyl" refer to a radical of the formula

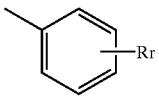

wherein $R_r$ is from 1 to 3 groups independently selected from the group consisting of hydrogen, hydroxy, alkyl, substituted alkyl, cycloalkyl, substituted cylcoalkyl, alkoxy, substituted alkoxy, halogen, acyloxy, carboxy, alkoxycarbonyl, amido, substituted amido, amino, acylamino, sulfonylamido, sulfonamide, cyano, nitro, phenyl, substituted phenyl, and —S(O)$_p$alkyl (wherein p is 0, 1, or 2). The substituent is phenyl where each $R_r$ is hydrogen and is a substituted phenyl where at least one $R_r$ is not hydrogen.

The terms "pyridyl and substituted pyridyl" refer to a radical of the formula

wherein $R_s$ is from 1 to 2 groups independently selected from the group consisting of hydrogen, alkyl, halogen, and trifluoromethyl. The substituent is pyridyl where each $R_s$ is hydrogen and is a substituted pyridyl where at least one $R_s$ is not hydrogen. It is understood that the radical may be attached by the 2-, 3-, or 4-positions.

The terms "thienyl and substituted thienyl" refer to a radical of the formula

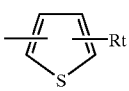

wherein $R_t$ is from 1 to 2 groups independently selected from the group consisting of hydrogen and alkyl. The substituent is thienyl where each $R_t$ is hydrogen and is a substituted thienyl where at least one $R_t$ is not hydrogen. It is understood that the radical may be attached by the 2- or 3-positions.

The terms "benzyl or substituted benzyl" refer to a radical of the formula

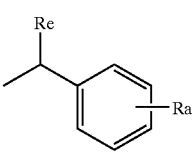

wherein $R_e$ is from selected from the group consisting of hydrogen, hydroxy, lower alkyl, and fluoro; and wherein $R_a$ is from 1 to 3 groups independently selected from the group consisting of hydrogen, alkyl, alkoxy, cyano, nitro, trifluoromethyl, and halogen. The substituent is benzyl where each $R_a$ is hydrogen (which term includes compounds having all the allowed values of $R_e$) and is a substituted benzyl where at least one $R_a$ is not hydrogen, including those compounds having all the allowed values of $R_e$.

Two $R_2$ substituents taken together, on adjacent positions, to form a "fused cycloalkyl" having from 5 to 7 carbon atoms refers to compounds in which a cycloalkyl ring having a total of 5 to 7 ring atoms is formed on adjacent positions of the phenyl to which they are attached. For example, the compound of formula I in which two $R_2$ substituents are taken together to form a fused cycloalkyl having 5 carbon atoms at the adjacent 3- and 4-positions and having hydrogen as the other $R_2$ is depicted by the formula below:

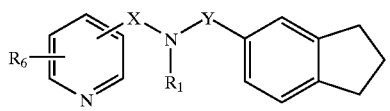

It is understood that formula I encompasses the compounds in which the X is attached to the pyridyl moiety in the 2-position, the 3-position, and the 4-position. For example, the compound of formula I in which X is attached to the pyridyl moiety in the 3-position is depicted by the formula below:

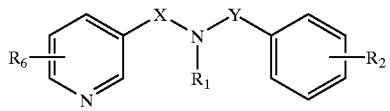

The term "pyridyl N-oxide" refers to the compounds of the formula

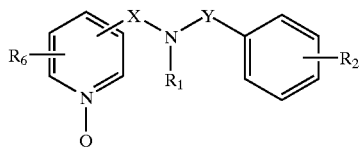

The term "pharmaceutically-acceptable addition salt" refers to an acid addition salt.

The compound of formula I and the intermediates described herein form pharmaceutically acceptable acid addition salts with a wide variety of organic and inorganic acids and include the physiologically acceptable salts which are often used in pharmaceutical chemistry. Such salts are also part of this invention. A pharmaceutically-acceptable addition salt is formed from a pharmaceutically-acceptable acid as is well known in the art. Such salts include the pharmaceutically acceptable salts listed in *Journal of Pharmaceutical Science*, 66, 2–19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, nahthalene-1,5-sulfonate, p-toluenesulfonate, xylenesulfonate, tartarate, and the like.

As with any group of pharmaceutically active compounds, some groups are preferred in their end use application. Preferred embodiments of the present invention are given below:

Compounds in which $R_1$ is selected from the group consisting of —C(O)OR$_4$, and —SO$_2$R$_5$ are preferred.

When $R_1$ is —SO$_2$R$_5$, compounds in which $R_5$ is selected from the group consisting of alkyl and fluorinated alkyl are preferred.

When $R_1$ is —C(O)OR$_4$, compounds in which $R_4$ is alkyl are preferred.

As potentiators of mGluR$_2$, the compounds in which the pyridyl moiety is attached to X at the 3-position and $R_1$ is —SO$_2$R$_5$ are preferred.

As potentiators of mGluR$_3$, compounds in which the pyridyl moiety is attached to X at the 4-position and $R_1$ is —C(O)OR$_4$ are preferred.

Compounds in which $R_2$ is from 1 to 3 substituents independently selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy are preferred, with compound in which one $R_2$ is selected from the group consisting of substituted alkyl, phenyl, substituted phenyl, thiophenoxy, substituted thiophenoxy, phenoxy, and substituted phenoxy being more preferred, and with benzyl, substituted benzyl, phenyl, substituted phenyl, phenoxy and substituted phenoxy being more preferred, and with benzyl, substituted benzyl, phenyl, substituted phenyl, phenoxy and substituted phenoxy being even more preferred.

When one $R_2$ is substituted alkyl preferred substituents are halogen, alkoxy, phenyl, substituted phenyl having from 1 to 3 substituents selected from the group consisting of hydroxy, halogen, alkoxy, carboxy, alkoxycarbonyl, amido, amino, and pyridyl, thienyl, and phenoxy.

Particularly preferred substituted alkyls are those depicted as the radical of the formula

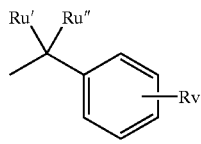

wherein $R_{u'}$ is from selected from the group consisting of hydrogen, hydroxy, lower alkyl, and fluoro; $R_{u''}$ is from selected from the group consisting of hydrogen, lower alkyl, alkoxy, and fluoro; provided that when $R_{u'}$ is hydroxy then $R_{u''}$ is not alkoxy or fluoro, and when $R_{u'}$ is fluoro then $R_{u''}$ is not alkoxy; and $R_v$ is from 1 to 3 groups independently selected from the group consisting of hydrogen, alkyl, alkoxy, cyano, nitro, trifluoromethyl, and halogen.

When one of $R_2$ is substituted phenyl preferred substituents are from 1 to 3 groups independently selected from the group consisting of hydrogen, trifluoromethyl, trifluoromethoxy, hydroxy, alkyl, alkoxy, halogen, amido, substituted amido, sulfonylamido, cyano, and nitro.

When one of $R_2$ is substituted thiophenoxy preferred substituents are from 1 to 3 groups independently selected from the group consisting of hydrogen, trifluoromethyl, trifluoromethoxy, alkyl, alkoxy, halogen, amido, cyano, and nitro.

When one of $R_2$ is substituted phenoxy preferred substituents are from 1 to 3 groups independently selected from the group consisting of hydrogen, hydroxy, alkyl, substituted alkyl having from 1 to 3 groups independently selected from the group consisting of hydroxy, alkyl, cycloalkyl, alkoxy, halogen, amido, substituted amido, sulfonylamido, cyano, nitro, phenyl, and —S(O)$_p$alkyl (wherein p is 0, 1, or 2), cycloalkyl, alkoxy, trifluoromethoxy, halogen, acyloxy, carboxy, amido, substituted amido, amino, acylamino, sulfonylamido, sulfonamide, cyano, nitro, phenyl, substituted phenyl having from 1 to 3 groups independently selected from the group consisting of trifluoromethyl, hydroxy, alkyl, alkoxy, halogen, amido, cyano, and nitro.

Compounds in which one $R_2$ is sulfonylamido wherein $R_p$ is selected from the group consisting of alkyl, phenyl, and substituted phenyl having from 1 to 3 groups independently selected from the group consisting of hydrogen, alkyl, alkoxy, halogen, cyano, nitro, and trifluoromethoxy, and $R_{p'}$ is selected from the group consisting of hydrogen and alkyl are preferred.

Compounds in which at least one of the $R_2$ substituents is attached in the 3-position are preferred.

Compounds in which at least one of the $R_2$ substituents is attached in the 4-position are preferred.

Compounds in which $R_6$ is from 1 to 2 substituents independently selected from the group consisting of hydrogen, alkyl, alkoxy, trifluoromethyl, and halogen are preferred.

Compounds in which X is selected from the group consisting of a —CH$_2$—, —CHR$_7$—, and —CH$_2$CH$_2$— are preferred, with compounds in which X is —CH$_2$— being more preferred.

Compounds in which Y is selected from the group consisting of a bond, —CH$_2$—, —CHR$_8$—, —CH$_2$CH$_2$— are preferred, with compounds in which is Y is a bond being more preferred.

Compounds in which X is a —CH$_2$— and Y is bond are even most preferred.

The compounds of formula I are prepared as described in Reaction Scheme A. In Reaction Schemes below all substituents, unless otherwise indicated, are as previously defined, and all reagents are well known and appreciated in the art.

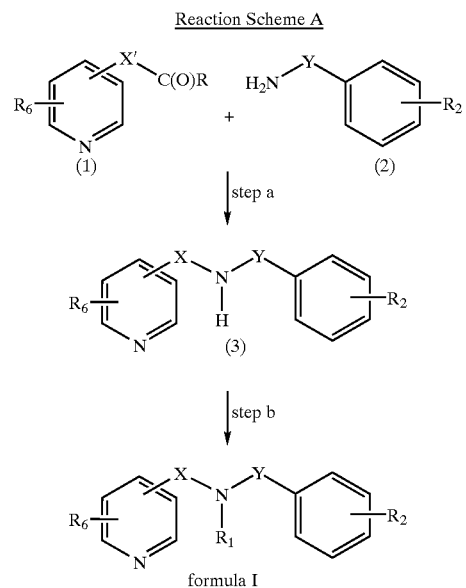

Reaction Scheme A formula I

Reaction Scheme A, step a, depicts the reductive amination of an appropriate compound of formula (1) and an appropriate amine of formula (2) to give a compound of formula (3). An appropriate compound of formula (1) is one in which $R_6$ is as desired in the final compound of formula I, X' is a bond or —CH$_2$— and R is hydrogen, giving X to be —CH$_2$— or —CH$_2$CH$_2$—, respectively, as desired for the compound of formula I, or X' is a bond and R is $R_7$ as desired in the final compound of formula I, and the point of attachment of X' is the point of attachment of X as desired in the final compound of formula I. Compounds of formula (1) are well known in the art. An appropriate compound of formula (2) is one in which $R_2$ is as desired in the final product of formula I or gives rise after modification or deprotection to $R_2$ as desired in the final compound of formula I and Y is as desired in the final product of formula I. Compounds of formula (2) are known in the art and can be obtained by procedures well known in the art and those described herein. As described herein, compounds of formula (2) in which Y is a bond can be obtained by reduction of nitro groups. Compounds of formula (2) in which Y is —CH$_2$—, —CH$_2$CH$_2$—, —CHR$_8$— —CHR$_9$CH$_2$—, or —CH$_2$CHR$_9$— can be obtained by reduction of a nitrile, transforming a carboxylic acid to an amine as is well known in the art, for example such transformations can be carried out by reduction of an amide, transformation to the aldehyde followed by reductive amination, or reduction to the alcohol followed by elaboration to the amine (such as by Mitzunobu reaction using phthalimide followed by deprotection). All of these transformations may involve the introduction and removal of appropriate protecting groups as is well known and appreciated in the art.

The reductive amination depicted in Reaction Scheme A, step a, can be carried out under a variety of conditions, such as by hydrogenation using a suitable catalyst or using a suitable reducing agent. For example, an appropriate aldehyde of formula (1) is contacted with an appropriate amine of formula (2) and a suitable reducing agent to give a compound of formula (3). The reaction is carried out in a suitable solvent, such as methanol, ethanol, tetrahydrofuran, or mixtures of methanol or ethanol and tetrahydrofuran. The reaction may be carried out in the presence of a drying agent, such as sodium sulfate, cupric sulfate, or molecular sieves.

The reaction is carried out in the presence of from 1.0 to 6.0 molar equivalents of a suitable reducing agent, such as, sodium borohydride or sodium cyanoborohydride. It may be advantageous to allow Schiff base formation to proceed before addition of the suitable reducing agent. When sodium cyanoborohydride is used it may be advantageous to monitor and adjust the pH during the course of the reaction as is known in the art. The reaction is generally carried out at temperatures of from 0° C. to the refluxing temperature of the solvent. Generally, the reactions require 1 to 72 hours. The product can be isolated and purified by techniques well known in the art, such as filtration, extraction, evaporation, trituration, chromatography, and recrystallization.

Reaction Scheme A, step b, depicts the acylation or sulfonation, using appropriate reagents, of a compound of formula (3) to give a compound or formula (I) or a protected compound of formula I. An appropriate reagent is one that transfers a —C(O)R$_3$, —C(O)OR$_4$, or —SO$_2$R$_5$ group as required to give the desired R$_1$ group. In the case of —C(O)R$_3$ such reagents include acids, acid halides, anhydrides (including mixed anhydrides), activated amides (such as imidazoylides), and activated esters. In the case of —C(O)OR$_4$ such reagents include esters of chloroformate and pyrocarbonates (such as BOC anhydride). In the case of —SO$_2$R$_5$ such reagents includes halosulfonates and sulfonate anhydrides with the use of sulfonyl chlorides are preferred. Acylation and sulfonation reactions using such reagents are well known an appreciated in the art.

For example, acylation reactions to transfer —C(O)R$_3$ involve an amide formation reaction similar to those which are conventionally conducted for peptide synthesis and synthetic methods used therein can also be employed. For example, well known coupling reagents such as carbodiimides with or without the use of well known additives such as N-hydroxysuccinimide, 1-hydroxybenzotriazole, etc. can be used to facilitate amide formation. The reaction is conventionally conducted in an inert aprotic solvent such as pyridine, dimethylformamide, dichloromethane, chloroform, 1,2-dichloroethane, acetonitrile, tetrahydrofuran and the like.

Alternatively, for example an acid halide can be employed in the reaction. It may be advantageous to use a suitable base to scavenge the acid generated during the reaction. Suitable bases include, by way of example, triethylamine, N,N-diisopropylethylamine, N-methylmorpholine, pyridine, sodium carbonate, potassium carbonate, sodium bicarbonate, and the like. The reaction is preferably conducted at from about 0° C. to about 60° C. until reaction completion which typically occurs within 1 to about 24 hours. Upon reaction completion, the product of formula I or protected compound of formula I can be isolated and purified by techniques well known in the art, such as filtration, extraction, evaporation, trituration, chromatography, and recrystallization.

For example, acylation reactions to transfer —C(O)OR$_4$ involve a reaction of a chloroformate ester with a compound of formula (3). For example, the reaction is conventionally conducted in an inert aprotic polar diluent such as dimethylformamide, dichloromethane, chloroform, acetonitrile, 1,2-dichloroethane, pyridine, tetrahydrofuran and the like. The reaction may be carried out in the presence of a suitable base to scavenge the acid generated during the reaction. Suitable bases include, by way of example, pyridine, triethylamine, N,N-diisopropylethylamine, N-methylmorpholine, and the like. The reaction is prefer ably conducted at from about 0° C. to about 80° C. until reaction completion which typically occurs within 1 to about 24 hours. Upon reaction completion, the product of formula I or protected product of formula I can be isolated and purified by techniques well known in the art, such as filtration, extraction, evaporation, trituration, chromatography, and recrystallization.

For example, sulfonation reactions to transfer —SO$_2$R$_5$ involve the reaction of halosulfonates or sulfonate anhydrides with compounds of formula (3). Such reactions are carried out in a suitable solvent, such as pyridine, tetrahydrofuran, dioxane, diethyl ether or dimethylformamide, dichloromethane, chloroform, acetonitrile, 1,2-dichloroethane, tetrahydrofuran, and the like, at a temperature from about 0° C. to about ambient temperature, and are carried out in the presence of a suitable base such as pyridine, triethylamine, N,N-diisopropylethylamine, sodium carbonate, potassium carbonate, sodium bicarbonate, potassium bicarbonate, and the like. The resultant sulfonamide is isolated by methods well known in the art, such as filtration, extraction, evaporation, trituration, chromatography, and recrystallization.

Reaction Scheme A, optional step c, not shown, a protected compound of formula I is deprotected to give a compound of formula I. Such deprotection reactions are well known and appreciated in the art. *Protecting Groups in Organic Synthesis,* Theodora Greene (Wiley-Interscience).

Reaction Scheme A, optional step d, not shown, an acid addition salt is formed using a pharmaceutically acceptable acid. The formation of acid addition salts is well known and appreciated in the art.

A variety of compounds of formula I and related compounds (such as compounds of formula (3) above) can be used as starting materials which upon further elaboration give rise to compounds of formula I. Some of these transformations are trivial, such as hydrolysis of a nitrile to an amide or acid, hydrolysis of an ester to an acid, formation of an amide from an acid or an ester, alkylation and acylation of hydroxy groups, oxidation, reduction, deprotection, displacements, and the like. A number other transformations, while readily apparent to the skilled artisan, are described in detail in the Reaction Schemes below.

Reaction Scheme B

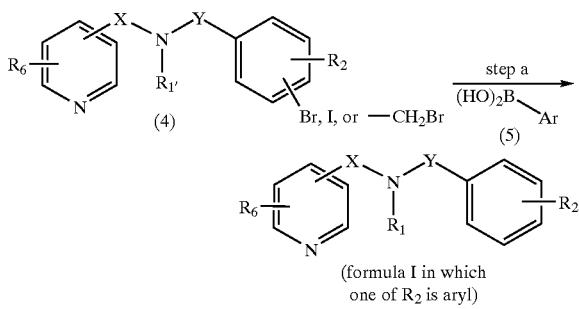

(formula I in which one of R$_2$ is aryl)

Reaction Scheme B, step a, depicts a coupling reaction of an appropriate compound of formula (4) and an appropriate aryl compound of formula (5). An appropriate compound of formula (4) is one in which X, Y, R$_6$, R$_2$ is as defined for the compound of formula I, except one of R$_2$ is a bromo or iodo or triflate or —CH$_2$Br, and R$_1$ is a hydrogen or R$_1$ as desired in the final compound of formula I. Compounds of formula (4) are readily prepared as described in Reaction Scheme A. An appropriate aryl compound of formula (5) is one in which Ar is one of the $R_2$ groups as desired in the final product of formula I, such as phenyl, substituted phenyl, pyridyl, substituted pyridyl, thienyl, or substituted thienyl. It is appreciated in the art that boronic esters are also suitable for use in such coupling reactions. The preparation and use of such arylboronic acids (and boronic esters) is well known and appreciated in the art. W. J. Thompson and J Gaudino, J. Org. Chem., 49, 5237–5243 (1984). Arylboronic acids are frequently contaminated with their corresponding anhydrides which do not perform well in the Suzuki coupling. Material contaminated by detrimental amounts of anhydride can be converted to the corresponding acid by hydrolysis. The hydrolysis is performed, if required, by briefly boiling in water.

As will be appreciated by the skilled person, Reaction Scheme B, step a, depicts a Suzuki coupling. See for example, A. Suzuki, Pure Appl. Chem., 66, 213–222 (1994); A. Suzuki, Pure Appl. Chem., 63, 419–422 (1991), N. Miyaura et al., J. Org. Chem., 51, 5467–5471 (1986); Y. Hoshino et al., Bull. Chem. Soc. Japan, 61, 3008–3010 (1988); N. Miyaura et al., J. Am. Chem. Soc., 111, 314–321 (1989); W. J. Thompson et al., J. Org. Chem., 53, 2052–2055 (1988); and T. I. Wallow and B. M. Novak, J. Org. Chem., 59, 5034–5037 (1994). Other coupling reactions, such as the Stille reaction, can be used.

It is appreciated that the coupling gives a compound of formula I when, the compound of formula (4), $R_{1'}$ is $R_1$ as desired in the final product and when $R_{1'}$ is hydrogen the product will required acylation or sulfonation, as depicted in Reaction Scheme A, step b, to give a compound of formula I.

For example, an appropriate compound of formula (4) and an appropriate aryl compound of formula (5) can be coupled under Suzuki conditions to give a compound of formula I or a compound that gives rise to a compound of formula I. The Suzuki coupling reaction is performed in a suitable solvent, such as toluene, dichloromethane, or tetrahydrofuran. The reaction is performed using from about 1.1 to about 3 molar equivalents of an appropriate arylboronic acid or ester. The reaction is carried out in the presence of from about 1 to about 3 molar equivalents of a suitable base, such as potassium carbonate or sodium carbonate. The coupling is performed using a suitable palladium catalyst, such as tetrakis(triphenylphosphine) palladium (0), bis(acetonitrile) palladium (II) chloride, palladium (II) chloride, palladium (II) acetoacetate, and tris(dibenzylidneacetone)dipalladium (0). The suitable palladium catalyst chosen may be modified by the use of ligands, such as tri(fur-2-yl)phosphine and tri(o-tolyl)phosphine: V. Farina and B. Krishnan, J. Am. Chem. Soc., 113, 9586–9595 (1991). The coupling is performed at a temperature ranging from 0° C. to the refluxing temperature of the solvent. The Suzuki coupling reactions depicted in Reaction Scheme B generally require from 6 hours to 14 days. The product of the coupling reaction can be isolated and purified using techniques well known in the art. These techniques include extraction, evaporation, chromatography and recrystallization.

Reaction Scheme C.1

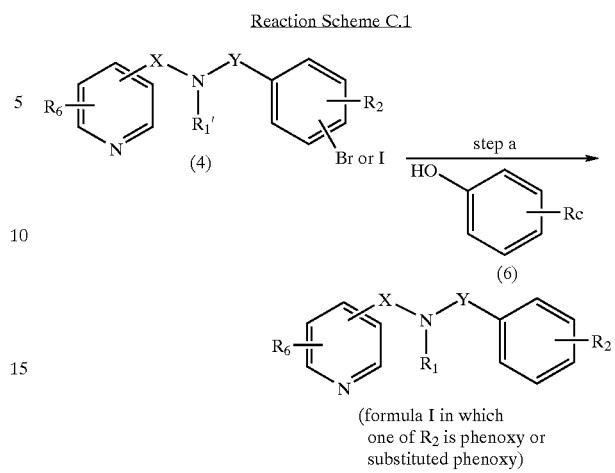

(formula I in which one of $R_2$ is phenoxy or substituted phenoxy)

Reaction Scheme C.1, step a, depicts a coupling reaction of an appropriate compound of formula (4) and an appropriate phenol compound of formula (6). An appropriate compound of formula (4) is as described above in Reaction Scheme B, except that $R_2$ is not —$CH_2Br$. An appropriate phenol compound of formula (6) is one in which $R_c$ is as desired in the final product of formula I or gives rise upon modification to the desired final product of formula I.

As will be appreciated by the skilled person, Reaction Scheme C, step a, depicts an Ullmann coupling. See for example, F. D. Rychnozsky and K. Hwang, J. Org. Chem., 59, 5414 (1994). It is appreciated that the coupling gives a compound of formula I when $R_{1'}$ is $R_1$ as desired in the final product and when $R_{1'}$ is hydrogen the product will required acylation or sulfonation, as depicted in Reaction Scheme A, step b, to give a compound of formula I.

For example, an appropriate compound of formula (4) and an appropriate phenol compound of formula (6) are coupled give a compound of formula I or a compound that gives rise to a compound of formula I. The Ullmann coupling reaction is performed in a suitable solvent, such as pyridine. The reaction is performed using from about 1.1 to about 3 molar equivalents of an appropriate phenol. The reaction is carried out in the presence of from about 1 to about 3 molar equivalents of a suitable base, such as potassium carbonate or sodium carbonate. The coupling is performed using a suitable catalyst, such as copper salts. These Ullmann coupling reactions depicted in Reaction Scheme C generally require from 6 hours to 24 hours. The product of the coupling reaction can be isolated and purified using techniques well known in the art. These techniques include extraction, evaporation, chromatography and recrystallization.

Reaction Scheme C.2

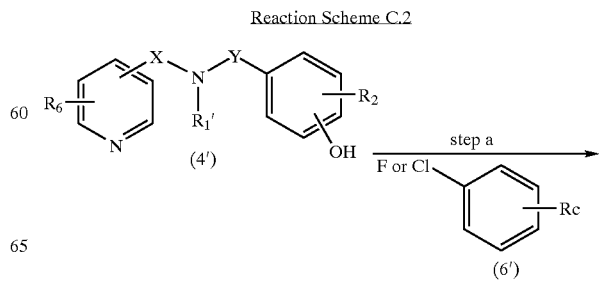

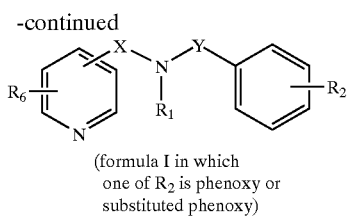

(formula I in which
one of R₂ is phenoxy or
substituted phenoxy)

Reaction Scheme C.2, step a, depicts a coupling reaction of an appropriate compound of formula (4') and an appropriate compound of formula (6'). An appropriate compound of formula (4') is one in which X, Y, R₆, R₂ is as defined for the compound of formula I, except one of R₂ is a hydroxy, and R₁' is a hydrogen or R₁ as desired in the final compound of formula I. An appropriate compound of formula (6') is one in which R_c is one or more electron withdrawing group as desired in the final product of formula I or gives rise upon modification to the desired final product of formula I.

It is appreciated that the coupling gives a compound of formula I when R₁' is R₁ as desired in the final product and when R₁' is hydrogen the product will required acylation or sulfonation, as depicted in Reaction Scheme A, step b, to give a compound of formula I. For the reaction depicted in Scheme C.2 it is preferred that the compound of formula (4') is one in which R₁' is hydrogen.

For example, an appropriate compound of formula (4') and an appropriate compound of formula (6') are coupled give a compound of formula I or a compound that gives rise to a compound of formula I. The reaction is performed in a suitable solvent, such as dimethylformamide, dimethylacetamide, and dimethyl sulfoxide. The reaction is performed using from about 1.1 to about 3 molar equivalents of an appropriate phenol. The reaction is carried out in the presence of from about 1 to about 3 molar equivalents of a suitable base, such as potassium hydride, sodium hydroxide, or sodium hydride. The coupling is performed using a suitable catalyst, such as copper salts. The reaction generally require from 6 hours to 48 hours. The product of the coupling reaction can be isolated and purified using techniques well known in the art. These techniques include extraction, evaporation, chromatography and recrystallization.

Reaction Scheme D

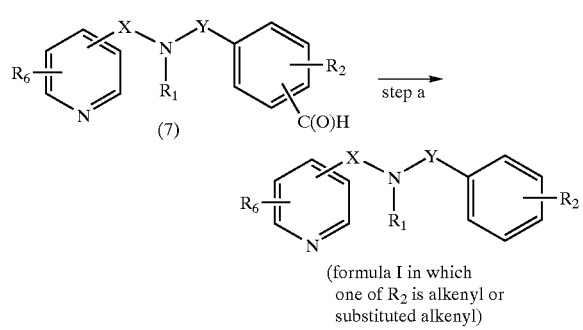

(formula I in which
one of R₂ is alkenyl or
substituted alkenyl)

Reaction Scheme D, step a, depicts a reaction of an appropriate compound of formula (7) with appropriate organophosphorous ylid in a Wittig-type reaction to give a compound of formula I. An appropriate compound of formula (7) is one in which X, Y, R₁, R₂, and R₆, are as definded for the compound of formula I. As will be appreciated by the skilled person, in addition to the aldehyde depicted in Scheme D, a variety of carbonyl compounds can be used in the reaction of Reaction Scheme D, step a, depending of the substitution desired in the final compound of formula I. An appropriate organophosphorous ylid is one which converts the carbonyl of a compound of formula (7) to an alkenyl or substituted alkenyl as desired in the final product of formula I. Appropriate organophosphorous reagents, such as Wittig, Wittig-Horner, Horner-Emmons-Wadswoth reagents, and the use of appropriate organophosphorous reagents is well known and appreciated in the art.

For example, an appropriate compound of formula (7) is reacted with appropriate organophosphorous ylid to give a compound of formula I. An appropriate organophosphorous ylid is formed by contacting an appropriate organophosphorous reagent with a suitable base, such as lithium diisopropylamide, sodium hydride, lithium bis (trimethylsilyl)amide or potassium t-butoxide. The ylid formation is carried out in a suitable solvent, such as tetrahydrofuran, benzene, or diethyl ether. The ylid formation is generally carried out at a temperature of from −78° C. to ambient temperature. An appropriate organophosphorous ylid is contacted with an appropriate compound of formula (7). The reaction is carried out in a suitable solvent, such as tetrahydrofuran, benzene, or diethyl ether. Generally, the reaction is carried out in the same solvent and temperatures used to form the appropriate organophosphorous ylid. The reaction generally requires from 1 hour to 48 hours. The product can be isolated by techniques well known in the art, such as extraction and evaporation. The product can then be purified by techniques well known in the art, such as distillation, chromatography, or recrystallization.

Reaction Scheme E

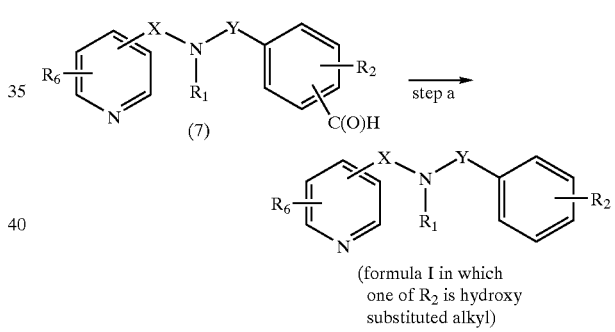

(formula I in which
one of R₂ is hydroxy
substituted alkyl)

Reaction Scheme E, step a, depicts a reaction of an appropriate compound of formula (7) with appropriate organometallic reagent, such as a Grignard reagent to give a compound of formula I. An appropriate compound of formula (7) is as defined in Reaction Scheme D. An appropriate organometallic reagent is one which converts the carbonyl of a compound of formula (7) to a hydroxy substituted group as desired in the final product of formula I. Appropriate organometallic reagents and their use is well known and appreciated in the art.

For example, an appropriate compound of formula (7) is reacted with appropriate Grignard reagent to give a compound of formula I. Generally, 1 to 2 equivalents of Grignard reagent are used. The reaction is carried out in a suitable solvent, such as tetrahydrofuran, diethyl ether. The reaction is generally carried out at temperatures of from −40° C. to ambient temperature. The reaction generally requires from 1 hour to 48 hours. The product can be isolated by techniques well known in the art, such as extraction and evaporation. The product can then be purified by techniques well known in the art, such as distillation, chromatography, or recrystallization.

As will be appreciated by the skilled person, the hydroxy compound thus obtained can undergo a variety of further reactions, such as halogenation, acylation, alkylation, reduction, oxidation, elimination, and the like to give further compounds of formula I.

In addition, the compounds of formula I in which $R_1$ is —$S(O)_2R_5$, X is —$CH_2$—, and Y is a bond can be prepared as described in Reaction Scheme F.

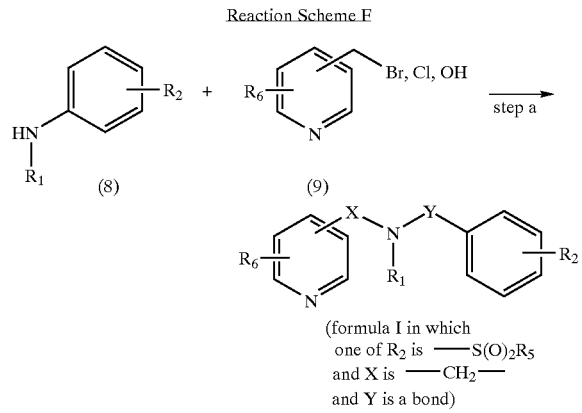

Reaction Scheme F, step a, depicts coupling of an appropriate compound of formula (8) with an appropriate compound of formula (9) to give a compound of formula I. An appropriate compound of formula (8) is one in which $R_2$ is as defined for the compound of formula I and $R_1$ is —$S(O)_2R_5$. An appropriate compound of formula (9) is one in which $R_6$ is as defined for the compound of formula I. Compounds of formula (8) and (9) are readily prepared by methods known in the art and as described herein.

For example, where the appropriate compound of formula (9) is one substituted with —$CH_2Br$ or, preferably —$CH_2Cl$, a compound of formula (8) is treated with a suitable base, such as sodium hydride, potassium hydride, potassium t-butoxide, potassium carbonate, and cesium carbonate. Generally, from 2 to about 5 molar equivalents of base are used and additional base may be added if the compound of formula (9) is used in the form of a salt. Generally, the reaction is carried out in a suitable solvent, such as tetrahydrofuran, diethyl ether, and dimethylformamide. The reaction is generally carried out at temperatures of from –10° C. to 80° C. The reaction generally requires from 1 hour to 48 hours. The product can be isolated by techniques well known in the art, such as extraction and evaporation. The product can then be purified by techniques well known in the art, such as distillation, chromatography, or recrystallization.

For example, where the appropriate compound of formula (9) is on substituted with —$CH_2OH$ the coupling is carried out under Mitsunobu conditions which are well known in the art. The reaction is carried out in a suitable solvent, such as tetrahydrofuran and diethyl ether using a phosphine, such as triphenylphosphine or a resin bound phosphine and a dialkyl azodicarboxylate, such as diethyl azodicarboxylate, di-iso-propyl azodicarboxylate or di-t-butyl azodicarboxylate. The reaction is generally carried out at temperatures of from ambient temperatures to 60° C. The reaction generally requires from 1 hour to 12 hours. The product can be isolated by techniques well known in the art, such as extraction and evaporation. The product can then be purified by techniques well known in the art, such as distillation, chromatography, or recrystallization.

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "N" refers to normal or normality; "M" refers to molar or molarity; "mol" refers to mole or moles; "mmol" refers to millimole or millimoles; "μmol" refers to micromole or micromoles; "kg" refers to kilogram or kilograms; "g" refers to gram or grams; "μg" refers to microgram or micrograms; "mg" refers to milligram or milligrams; "μL" refers to microliter or microliters; "mL" refers milliliter or milliliters; "L" refers to liter or liters; "bp" refers to boiling point; mp" refers to melting point; "brine" refers to a saturated aqueous sodium chloride solution; "h" refers to hour or hours; "min" refers to minute or minutes; "MS" refers to mass spectrometry; "NMR" refers to nuclear magnetic resonance spectroscopy; "TFA" refers to trifluoroacetic acid; "$CH_2Cl_2$" or "DCM" refers to dichloromethane; "DCE" refers to dichloroethane; "MeOH" refers to methanol; "$NH_4OH$" refers to a concentrated aqueous ammonia solution; "KOH" refers to potassium hydroxide; "$H_2O$" refers to water; "HCl" refers to hydrogen chloride; etc. Chemical shifts are give in δ and NMR spectra were obtained in $CDCL_3$, unless otherwise indicated.

Preparation 1

3-(2-Methoxyphenoxy)aniline

A solution of 3-fluoronitrobenzene (3.53 g, 25 mmol) and 2-methoxyphenol (3.72 g, 30 mmol) in anhydrous N,N-dimethylformamide (25 mL) under nitrogen was treated with anhydrous potassium carbonate (7.6 g, 55 mmol) and heated to 110° C. for 65 h, then cooled to room temperature. The solution was diluted with dichloromethane (50 ml) and treated with DOWEX® 550A OH anion exchange resin (log) which had been washed dry with methanol. Stirring was continued for one hour, the mixture was filtered, and the filtrate concentrated in vacuo (exhaustively at end to remove DMF) to give 3-(2-methoxyphenoxy)nitrobenzene as a residue.

The residue was dissolved in 2:1 hexane/dichloromethane and passed through a short column of silica gel (eluted with 1:1 hexane/dichloromethane). The concentrated product was recrystallized from ethyl acetate/hexane (two crops) then placed in a Parr® bottle under nitrogen with methanol (50 mL), carefully treated with Raney® nickel (one tsp.), placed on a Parr® apparatus, and hydrogenated at 40–50 psi pressure for 18 h. The mixture was carefully filtered through celite® under nitrogen without allowing the filter cake to dry, and the filtrate was concentrated in vacuo to afford the title compound (2.79 g, 52%) as a colorless viscous oil. $^1H$ NMR: 7.05–7.15 (m,1H), 7.00–7.05 (m,1H), 6.95–7.00 (m,2H), 6.85–6.95 (m,1H), 6.30–6.35 (m,2H), 6.25 (m,1H), 3.81 (s,3H), 3.60 (br s,2H).

Preparation 2

4-(2-Benzyloxyphenoxy)aniline

A solution of 2-benzyloxyphenol (6.01 g, 30 mmol) in anhydrous N,N-dimethylformamide (25 mL) was treated with anhydrous potassium carbonate (7.6 g, 55 mmol), then with 4-fluoronitrobenzene (3.53 g, 25 mmol), and heated to 90° C. for 5 h under nitrogen. The solution was cooled to room temperature, diluted with dichloromethane (50 mL), and treated with DOWEX® 550A OH anion exchange resin (10 g) which had been washed dry with methanol. The mixture was stirred for 3 h, filtered, and the filtrate concentrated in vacuo (exhaustively at end to remove DMF). The residue was chromatographed on silica gel (eluted with 2:1 hexane/ethyl acetate) to afford 4-(2-benzyloxyphenoxy) nitrobenzene (6.40 g, 66%) as a white solid.

4-(2-Benzyloxyphenoxy)nitrobenzene (2.57 g, 8 mmol) was dissolved in reagent grade ethanol (20 mL) and treated with concentrated aqueous hydrochloric acid (2.5 mL). The solution was heated to 55° C. under nitrogen, then cautiously treated with iron powder (3.1 g, 55 mmol) in portions with cooling needed after initial exotherm to 75° C. After addition was complete, stirring was continued at 50–60° C. for 45 minutes, then the mixture was cooled to room temperature and filtered through celite® (rinse filter cake with dichloromethane). The filtrate was concentrated in vacuo, the residue dissolved in dichloromethane and the solution washed with saturated aqueous sodium carbonate. The organic layer was separated and the aqueous layer extracted with dichloromethane. The combined organic solution was dried (sodium sulfate), concentrated in vacuo, and chromatographed on silica gel (eluted with dichloromethane, then 10% ethyl acetate/dichloromethane, then 20% ethyl acetate/dichloromethane) to afford the title compound (2.22 g, 95%) as a tan solid; mp 111–112.5° C. $^1$H NMR: 7.30 (m,4H), 7.20–7.30 (m,1H), 6.97 (m,2H), 6.80–6.90 (m,4H), 6.60–6.65 (m,2H), 5.12 (s,2H), 3.50 (br s, 2H).

EXAMPLE 1

N-(3-(2-Methoxyphenoxy)phenyl)-N-(2,2,2-trifluoroethylsulfonyl)pyrid-3-ylmethylamine

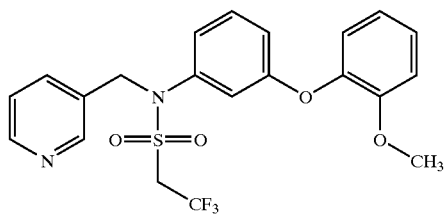

A solution of 3-(2-methoxyphenoxy)aniline (269 mg, 1.25 mmol) and pyridine-3-carboxaldehyde (107 mg, 1.00 mmol) was refluxed in methanol (2.5 mL) for 2 h, then cooled on an ice bath to 5° C. Sodium borohydride (95 mg, 2.5 mmol) was added and the mixture was warmed to room temperature, stirred for 2 h, concentrated in vacuo, and taken up in dichloromethane. The resultant suspension was filtered, the filtrate concentrated in vacuo, and the residue chromatographed on silica gel (eluted with 2% methanol/dichloromethane) to give N-(3-(2-methoxyphenoxy)phenyl) pyrid-3-ylmethylamine.

The resultant N-(3-(2-methoxyphenoxy)phenyl)pyrid-3-ylmethylamine was dissolved in 2:1 1,2-dichloroethane/pyridine (6 mL) under nitrogen, cooled (5° C.), and treated with 2,2,2-trifluoroethylsulfonyl chloride (300 mg, 1.64 mmol). After one hour at 5° C., the mixture was allowed to warm to room temperature and stirred for 18 h. The product mixture was treated with anhydrous potassium carbonate (500 mg), stirred 30 min, filtered, and the filtrate concentrated in vacuo. The residue was chromatographed on silica gel (eluted with 2:1 dichloromethane/ethyl acetate) to afford the title compound (226 mg, 50%) as a viscous pale amber oil. The hydrochloride salt was obtained by treatment of this material in methanol with ethereal HCl. $^1$H NMR: 8.49 (d,1H,J=4 Hz), 8.29 (s,1H), 7.60–7.65 (m,1H), 7.20–7.25 (m,2H), 7.10–7.20 (m,1H), 6.97 (d,1H,J=8 Hz), 6.90 (m,2H), 6.80–6.85 (m,2H), 6.76 (m,1H), 4.82 (s,2H), 3.70–3.85 (m,2H), 3.75 (s,3H). MS calcd. 452.4; MS (M+1) 453.3

EXAMPLE 2

N-(3-(2-Benzyloxyphenoxy)phenyl)-N-(2,2,2-trifluoroethylsulfonyl)pyrid-3-ylmethylamine

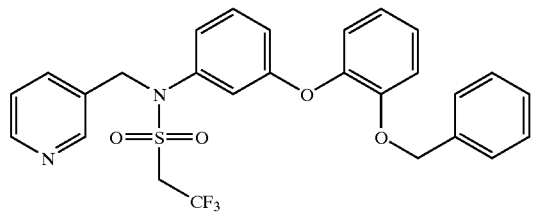

The title compound was prepared using a method similar to the method of Example 1 using 3-(2-benzyloxyphenoxy) aniline. $^1$H NMR: 8.45 (m,1H), 8.28 (s,1H), 7.77 (d,1H,J=8 Hz), 7.20–7.25 (m,5H),7.10–7.15 (m,2H), 7.00–7.10 (m,3H), 6.97 (t,1H,J=8 Hz), 6.85–6.90 (m,2H), 6.77 (m,1H), 4.99 (s,2H), 4.79 (s,2H), 3.55–3.65 (m,2H). MS calcd. 528.6; MS (M+1) 529.4

EXAMPLE 3

N-(4-Phenoxy)phenyl)-N-(ethylsulfonyl)-2-(pyrid-3-yl) ethylamine

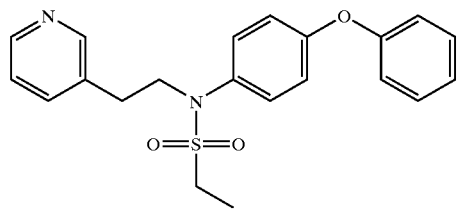

The title compound was prepared using a method similar to the method of Example 1 using (4-phenoxy)aniline, 2-(pyrid-3-yl)acetaldehyde, and ethylsulfonyl chloride. $^1$H NMR: 8.45 (m,1H), 8.36 (s,1H), 7.50 (m,1H), 7.35–7.40 (m,2H), 7.15–7.25 (m,3H), 7.10–7.15 (m,1H), 7.03 (d,2H, J=8 Hz), 6.97 (d,2H,J=8 Hz), 3.91 (t,2H,J=7 Hz), 2.95 (q,2H,J=7 Hz), 2.83 (t,2H,J=7 Hz), 1.31 (t,3H,J=7 Hz). MS calcd. 382.5; MS (M+1) 383.4

EXAMPLE 4

N-(4-Phenoxy)phenylethyl)-N-(ethylsulfonyl)pyrid-3-ylmethylamine

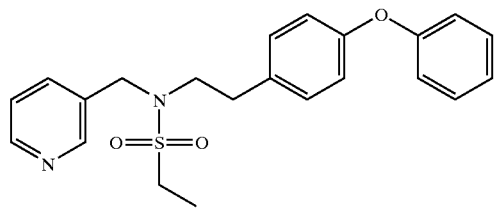

A solution of pyridine-3-carboxaldehyde (322 mg, 3.0 mmol) and 4-phenoxyphenethylamine (747 mg, 3.5 mmol)

in reagent grade methanol (5 mL) under nitrogen was refluxed for 2 h, then cooled to 5° C. (ice bath), and diluted with more methanol (5 mL). Sodium borohydride (0.23 g, 6 mmol) was added, and the mixture was slowly allowed to reach room temperature and stirred at room temperature overnight (18 h). The mixture was concentrated in vacuo, taken up in dichloromethane, and filtered. The filtrate was concentrated in vacuo and chromatographed on silica gel (eluted with 7% methanol/dichloromethane) to afford N-((4-phenoxy)phenylethyl)pyridine-3-methylamine (863 mg, 94%).

A cooled (5° C.) solution of N-((4-phenoxy)phenylethyl) pyridine-3-methylamine (304 mg, 1.0 mmol) in anhydrous 1,2-dichloroethane (4 mL) with anhydrous potassium carbonate (0.50 g, 3.6 mmol) under nitrogen was treated dropwise with ethylsulfonyl chloride (257 mg, 2.0 mmol), then slowly warmed to room temperature and stirred at room temperature for 44 h. The mixture was treated with tris(2-aminoethyl)amine resin (4 meq/g, 1.0 g), stirred 1 h, treated with DOWEX® 550A OH anion exchange resin (1.5 g), stirred 30 min, then filtered and the filter cake was rinsed with dichloromethane. The filtrate was concentrated in vacuo and the residue chromatographed on silica gel (eluted with 4:1 ethyl acetate/dichloromethane) to afford the title compound (100 mg, 25%) as a pale yellow oil. The title compound was converted to the hydrochloride salt by treatment of this material in methanol with ethereal HCl. $^1$H NMR: 8.55 (m,2H), 7.78 (m,1H), 7.25–7.35 (m,3H), 7.00–7.10 (m,3H), 6.94 (d,2H,J=8 Hz), 6.89 (d,2H,J=9 Hz), 4.43 (s,2H), 3.38 (t,2H,J=8 Hz), 2.88 (q,2H,J=7 Hz), 2.74 (t,2H,J=8 Hz), 1.31 (t,3H,J=7 Hz). MS calcd. 396.5; MS(M+1) 397.5

EXAMPLE 5

N-(4-Phenoxy)phenylmethyl)-N-(ethylsulfonyl) pyrid-3-ylmethylamine

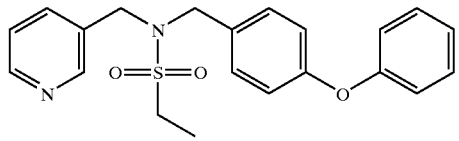

The title compound was prepared using a method similar to the method of Example 4 using 4-phenoxyphenylmethylamine. $^1$H NMR: 8.50 (m,1H), 8.40 (s,1H), 7.66 (d,1H,J=8 Hz), 7.30–7.35 (m,2H), 7.20–7.25 (m,1H), 7.17 (d,2H,J=8 Hz), 7.10 (m,1H), 6.95 (d,2H,J=8 Hz), 6.90 (d,2H,J=8 Hz), 4.36 (s,2H), 4.30 (s,2H), 2.99 (q,2H,J=7 Hz), 1.35 (t,3H,J=7 Hz). MS calcd. 382.5; MS (M+1) 383.4

EXAMPLE 6

N-(4-(Phenoxy)phenyl)-N-(iso-propylsulfonyl)pyrid-3-ylmethylamine

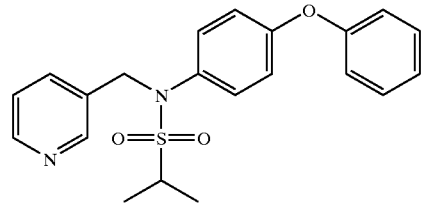

The title compound was prepared using a method similar to the method of Example 1 using (4-phenoxy)aniline and iso-propylsulfonyl chloride. $^1$H NMR: 8.47 (m,1H), 8.32 (m,1H), 7.70 (m.1H), 7.30–7.35 (m,2H), 7.20–7.25(m,$_1$H), 7.10–7.15 (m,3H), 6.97 (d,2H,J=8 Hz), 6.85 (d,2H,J=8 Hz), 4.84 (s,2H), 3.20–3.30 (m,1H), 1.42 (d,6H,J=7 Hz). MS calcd. 382.5; MS (M+1) 383.4.

EXAMPLE 7

N-(2-(Phenoxy)phenyl)-N-(2,2,2-trifluoroethylsulfonyl)pyrid-3-ylmethylamine

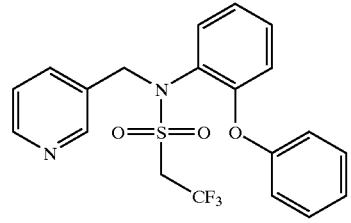

The title compound was prepared using a method similar to the method of Example 1 using (2-phenoxy)aniline. $^1$H NMR: 8.50 (m,1H), 8.31 (m,1H), 7.75 (m,1H), 7.40 (t, 2H, J=8 Hz), 7.15–7.25(m,3H), 6.95–7.05 (m,3H), 6.95 (t,1H, J=8 Hz), 6.83 (d,2H,J=8 Hz), 4.84 (s,2H), 3.90–4.00 (m,2H). MS calcd. 422.4; MS (M+1) 423.4.

EXAMPLE 8

N-(4-(Phenoxy)phenyl)-N-(ethylsulfonyl)pyrid-3-ylmethylamine

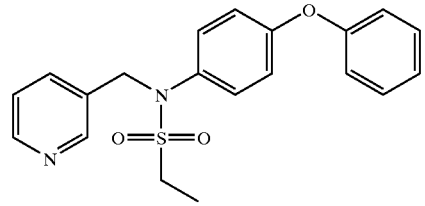

The title compound was prepared using a method similar to the method of Example 1 using (4-phenoxy)aniline and ethylsulfonyl chloride. $^1$H NMR: 8.50 (m,1H), 8.37 (s,1H), 7.70 (d,1H,J=8 Hz), 7.30–7.35 (m,2H), 7.20–7.25 (m,1H), 7.10–7.15 (m,3H), 6.98 (d,2H,J=8 Hz),6.87 (d,2H,J=9 Hz), 4.83 (s,2H), 3.09 (q,2H,J=7 Hz), 1.42 (t,3H,J=7 Hz). MS calcd. 368.5; MS (M+1) 369.3

EXAMPLE 9

N-(4-(2-Methoxyphenoxy)-3-chlorophenyl)-N-(2,2,2-trifluoroethylsulfonyl)pyrid-3-ylmethylamine

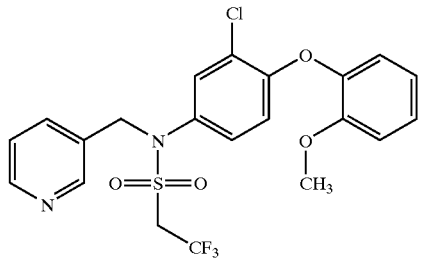

The title compound was prepared using a method similar to the method of Example 1 using 4-(2-methoxyphenoxy)-3-chloroaniline. The hydrochloride salt was obtained by treatment of this material in methanol with ethereal HCl. $^1$H NMR: 8.51 (m,1H), 8.32 (s,1H), 7.66 (m,1H), 7.25–7.30 (m,2H), 7.15–7.20 (m,1H), 6.85–7.00 (m,4H), 6.55 (d,1H, J=8.5 Hz), 4.82 (s,2H), 3.75–3.85 (m,2H), 3.76 (s,3H). MS calcd. 486.9; MS (M+1) 487.6

EXAMPLE 10

N-(4-(2,6-Dimethoxyphenoxy)-3-chlorophenyl)-N-(2,2,2-trifluoroethylsulfonyl)pyrid-3-ylmethylamine

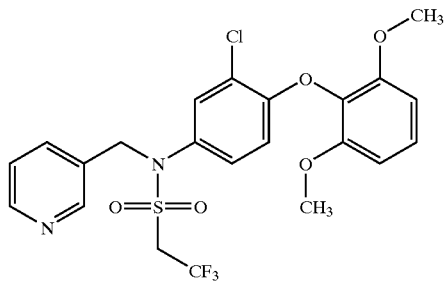

The title compound was prepared using a method similar to the method of Example 1 using 4-(2,6-dimethoxyphenoxy)-3-chloroaniline. $^1$H NMR: 8.51 (m,1H), 8.32 (s,1H), 7.66 (m,1H), 7.25–7.30 (m,2H), 7.15–7.20 (m,1H), 6.85–7.00 (m,4H), 6.55 (d,1H,J=8.5 Hz), 4.82 (s,2H), 3.75–3.85 (m,2H), 3.76 (s,3H). MS calcd. 486.9; MS (M+1) 487.6

EXAMPLE 11

N-(4-(2-Benzyloxyphenoxy)phenyl)-N-(2,2,2-trifluoroethylsulfonyl)pyrid-3-ylmethylamine

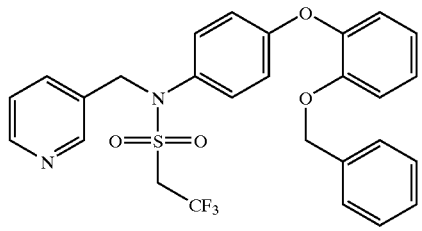

The title compound was prepared using a method similar to the method of Example 1 using 4-(2-benzyloxyphenoxy) aniline. $^1$H NMR: 8.48 (m,1H), 8.33 (s,1H), 7.60–7.65 (m,1H), 7.15–7.25 (m,5H), 7.05–7.15 (m,5H), 7.03 (t,1H, J=8 Hz), 6.94 (t,1H,J=8 Hz), 6.84 (d,2H,J=9 Hz), 5.02 (s,2H), 4.82 (s,2H), 3.70–3.80 (m,2H). MS calcd. 528.6; MS (M+1) 529.4

EXAMPLE 12

N-(4-(2-Methoxyphenoxy)phenyl)-N-(ethylsulfonyl)pyrid-3-ylmethylamine

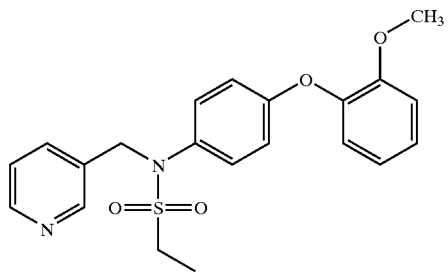

The title compound was prepared using a method similar to the method of Example 1 using 4-(2-methoxyphenoxy) aniline and ethylsulfonyl chloride. $^1$H NMR: δ 8.46 (d,1H, J=4.8 Hz), 8.33 (s,1H), 7.67–7.69 (d,1H, J=7.7 Hz), 7.19–7.24 (m,1H), 7.10–7.16 (m,1H), 7.06–7.10 (d,2H, J=7.0), 6.94–6.99 (d,2H, J=8.1 Hz), 6.89–6.92 (d,1H, J=7.7 Hz), 6.78–6.82 (d,2H, J=8.8 Hz), 4.81 (s,2H), 3.76 (s,3H), 3.02–3.10 (dd, 2H, J=14.7, 7.3 Hz), 1.4 (t, 3H, J=7.7 Hz). MS calcd. 398.5; MS (M+1) 399.2.

EXAMPLE 13

N-(4-(2-Methopxyphenoxy)phenyl)-N-(cyclopropylsulfonyl)pyrid-3-ylmethylamine

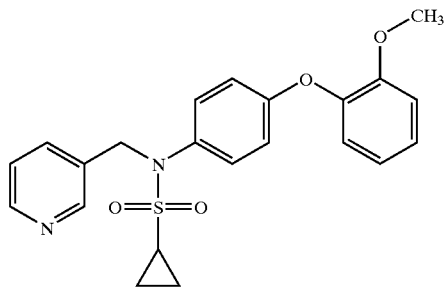

The title compound was prepared using a method similar to the method of Example 1 using 4-(2-methoxyphenoxy) aniline and cyclopropylsulfonyl chloride. $^1$H NMR: 8.49 (d,1H), 8.34 (s,1H), 7.62–7.68 (m,1H), 7.17–7.23 (m,2H), 7.10–7.18 (m,3H), 6.85–6.96 (m,3H), 6.78 (m,2H), 4.81(s, 2H), 3.76 (s,3H), 2.42 (m, 1H), 1.10 (m 2H), 0.96 (m, 2H). MS calcd. 410.5; MS (M+1) 411.4.

EXAMPLE 14

N-(4-(2-Methoxyphenoxy)-3-chlorophenyl)-N-ethylsulfonyl)pyrid-3-ylmethylamine

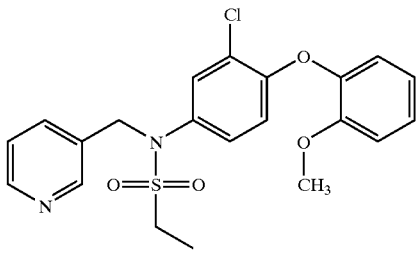

The title compound was prepared using a method similar to the method of Example 1 using 4-(2-methoxyphenoxy)-3-chloroaniline and ethylsulfonyl chloride. $^1$H NMR: 8.48 (d,1H, J=4.8 Hz), 8.35 (s,1H), 7.64–7.73 (d,1H, J=8.0 Hz), 7.28–7.33 (d,1H, J=2.5 Hz), 7.21–7.27 (m,2H), 7.10–7.20 (m,1H), 6.87–7.00 (m,3H), 6.51–6.62 (d,1H, J=8.8 Hz), 4.81 (s,2H), 3.76 (s,3H), 3.01–3.15 (dd, 2H, J=14.7, 7.3 Hz), 1.41 (t, 3H, J=7.3 Hz). MS calcd. 432.9; MS (M+1) 433.6

EXAMPLE 15

N-(4-(2-Methoxyphenoxy)-3-chlorophenyl)-N-cyclopropylsulfonyl)pyrid-3-ylmethylamine

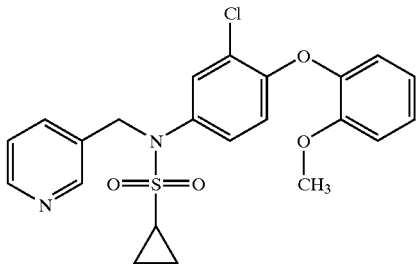

The title compound was prepared using a method similar to the method of Example 1 using 4-(2-methoxyphenoxy)-3-chloroaniline and cyclopropylsulfonyl chloride. $^1$H NMR: 8.55 (d,1H, J=8.1 Hz), 8.35 (s,1H), 8.03 (s,1H), 7.88 (s, 1H), 7.65 (s, 1H), 7.12–7.29 (m,3H), 6.89–7.02 (m,2H), 6.49–6.58 (d,1H, J=19.4 Hz), 5.06 (s, 2H), 3.67 (s,3H), 2.87 (m,1H), 1.01 (d, 2H, J=5.5 Hz), 0.84 (m, 2H). MS calcd. 444.9; MS (M+1) 445.5

EXAMPLE 16

N-(4-(2-Methoxyphenoxy)phenyl)-N-(2,2,2-trifluoroethylsulfonyl)pyrid-3-ylmethylamine

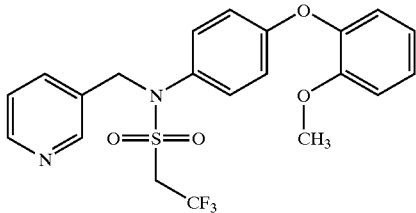

The title compound was prepared using a method similar to the method of Example 1 using 4-(2-methoxyphenoxy) aniline. The hydrochloride salt was obtained by treatment of this material in methanol with ethereal HCl. $^1$H NMR: 8.49. (d,1H), 8.29 (s,1H), 7.62–7.68 (m,1H), 7.20–7.28 (m,2H), 7.10–7.20 (m,1H), 7.03 (d,1H,), 6.96 (m,2H), 6.85–6.90 (m,1H), 6.80 (m,2H), 4.82 (s,2H), 3.75 (s,3H), 1.6 (s,2H). MS calcd. 452.5; MS (M+1) 453.3

EXAMPLE 17

N-(4-(2-Ethoxyphenoxy)phenyl)-N-(2,2,2-trifluoroethylsulfonyl)pyrid-3-ylmethylamine

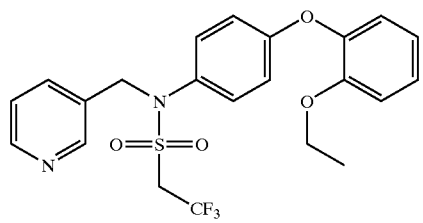

The title compound was prepared using a method similar to the method of Example 1 using 4-(2-ethoxyphenoxy) aniline. $^1$H NMR: 8.54 (d,2H, J=22 Hz), 8.03 (d,1H, J=7.7 Hz), 7.63 (m,1H), 7.20–7.25 (d,2H, J=6.8 Hz), 7.10–7.20 (m,2H), 7.00 (d,1H, J=6.6 Hz), 6.92 (t,1H, J=7.7 Hz), 6.70–6.80 (d,2H, J=8.8 Hz), 4.94 (s,2H), 4.64–4.81 (dd,2H, J=20.2, 9.9 Hz), 3.84–3.97 (dd,2H, J=13.9, 7.0 Hz), 0.99 (t,3H, J=7.0 Hz). MS calcd. 466.5; MS (M+1) 467.8

EXAMPLE 18

N-(4-(2-Ethoxyphenoxy)phenyl)-N-(ethylsulfonyl)pyrid-3-ylmethylamine

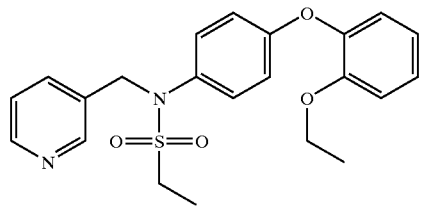

The title compound was prepared using a method similar to the method of Example 1 using 4-(2-ethoxyphenoxy) aniline and ethylsulfonyl chloride. $^1$H NMR: 8.61 (d,2H, J=13.2 Hz), 8.13 (d,1H, J=8.1 Hz), 7.70–7.75 (m,1H), 7.27 (d,2H, J=8.8 Hz), 7.08–7.20 (m,2H), 7.00 (d,1H, J=6.2 Hz), 6.92 (t,1H, J=7.7 Hz), 6.72–6.76 (d,2H, J=8.8 Hz), 4.97 (s,2H), 3.85–3.95 (dd,2H, J=13.9,6.7), 3.16–3.30 (dd,2H, J=14.7,7.3 Hz), 1.25 (t,3H, J=7.3 Hz), 0.98 (t,3H, J=7.0 Hz). MS calcd. 412.4; MS (M+1) 413.6

EXAMPLE 19

N-(4-(2-Ethoxyphenoxy)phenyl)-N-(cyclopropylsulfonyl)pyrid-3-ylmethylamine

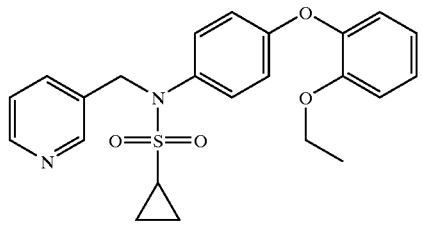

The title compound was prepared using a method similar to the method of Example 1 using 4-(2-ethoxyphenoxy) aniline and cyclopropylsulfonyl chloride. $^1$H NMR: 7.88 (d,1H, J=7.7 Hz), 7.26 (d,2H, J=8.8 Hz), 7.5–7.18 (m,2H), 6.97–7.05 (d,1H, J=7.7 Hz), 6.87–6.96 (m,1H), 6.67–6.77 (d,2H, J=8.8 Hz), 4.92 (s,2H), 3.84–3.94 (dd,2H, J=7.0 Hz), 2.71–2.83(m,1H), 0.98 (m,5H), 0.84 (m,2H). MS calcd. 424.4; MS (M+1) 425.2

EXAMPLE 20

N-(3-(2-Methoxyphenoxy)phenyl)-N-(cyclopropylsulfonyl)pyrid-3-ylmethylamine

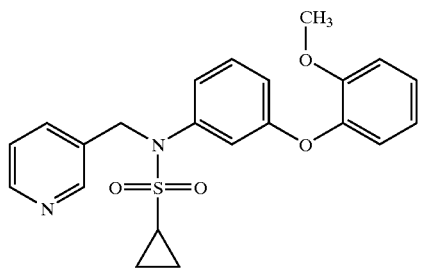

The title compound was prepared using a method similar to the method of Example 1 using 3-(2-methoxyphenoxy) aniline and cyclopropylsulfonyl chloride. $^1$H NMR: 8.49 (d,2H), 7.60 (d,1H), 7.10–7.35 (m,4H), 7.03–7.10 (d,2H), 6.85–6.99 (m,2H), 6.89 (s,1H), 6.76 (m,1H), 4.86 (s,2H), 3.65 (s,3H), 2.77 (m,1H), 0.93 (m, 2H), 0.84 (m, 2H). MS calcd. 410.4; MS (M+1) 411.5

EXAMPLE 21

N-(3-(2-Methoxyphenoxy)phenyl)-N-(ethylsulfonyl)pyrid-3-ylmethylamine

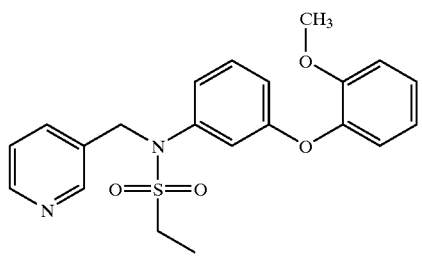

The title compound was prepared using a method similar to the method of Example 1 using 3-(2-methoxyphenoxy) aniline and ethylsulfonyl chloride. $^1$H NMR: 8.64 (d,2H, J=4.3 Hz), 8.00 (t,2H, J=6.6 Hz), 7.72–7.76 (t,1H, J=5.5 Hz), 7.07–7.27 (m,4H), 6.84–6.93 (m,3H), 6.66 (d,1H, J=8.1 Hz), 5.00 (s,2H), 3.64 (s,3H), 3.25 (dd,2H, J=15.0, 7.3 Hz), 1.23 (t,3H, J=7.7 Hz). MS calcd. 398.3; MS (M+1) 399.2.

EXAMPLE 22

N-(4-(Phenoxy)phenyl)-N-(2,2,2-trifluoroethylsulfonyl)pyrid-3-ylmethylamine

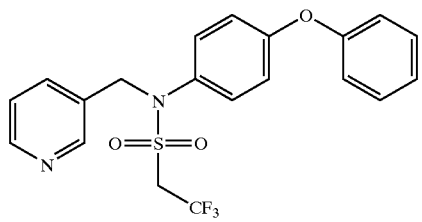

The title compound was prepared using a method similar to the method of Example 1 using (4-phenoxy)aniline. The hydrochloride salt was obtained by treatment of this material in methanol with ethereal HCl. $^1$H NMR: 8.50 (m,1H), 8.30 (s,1H), 7.67 (m,1H), 7.30–7.35 (m,2H), 7.20–7.25 (m,1H), 7.10–7.15 (m,1H), 7.11 (d,2H,J=9 Hz), 6.99 (d,2H,J=8 Hz), 6.89 (d,2H,J=9 Hz), 4.83 (s,2H), 3.80 (q,2H,J=9 Hz). MS calcd. 422.4; MS (M+1) 423.4.

EXAMPLE 23

N-(3-(2-Hydroxyphenoxy)phenyl)-N-(2,2,2-trifluoroethylsulfonyl)pyrid-3-ylmethylamine

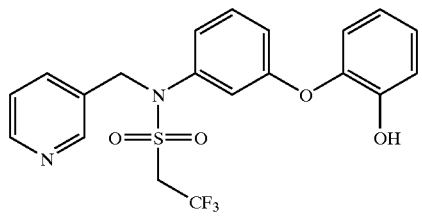

A solution of N-(3-(2-benzyloxyphenoxy)phenyl)-N-(2,2,2-trifluoroethylsulfonyl)pyrid-3-ylmethylamine (529 mg, 1.00 mmol) in methanol (50 mL) was carefully treated with Raney® nickel (one tsp.), placed on a Parr® apparatus, and hydrogenated at 45–50 psi pressure for 3 h. The mixture was carefully filtered through celite® under nitrogen without allowing the filter cake to dry, and the filtrate was concentrated in vacuo. The residual solid was triturated from petroleum ethers (30°–60°) to afford the title compound (394 mg, 90%) as a white solid; mp 57.5–60.0° C. The title compound was converted to the hydrochloride salt by treatment in methanol with ethereal HCl. $^1$H NMR: 8.50 (br s,1H), 8.25 (br s,1H), 7.68 (d,1H, J=8 Hz), 7.25–7.30 (m,2H); 6.95–7.10 (m,2H), 6.90–6.95 (m,2H), 6.70–6.85 (m,3H), 6.05 (br s,1H), 4.82 (s,2H), 3.75–3.85 (m,2H).MS calcd. 438.4; MS(M+1) 439.3

EXAMPLE 24

N-(4-(2-Hydroxyphenoxy)phenyl)-N-(2,2,2-trifluoroethylsulfonyl)pyrid-3-ylmethylamine

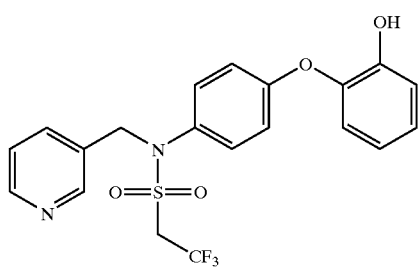

The title compound was prepared using a method similar to the method of Example 23 using N-(4-(2-benzyloxyphenoxy)phenyl)-N-(2,2,2-trifluoroethylsulfonyl) pyrid-3-ylmethylamine $^1$H NMR: 8.48 (m,1H), 8.28 (s,1H), 7.70 (d,1H,J=8 Hz), 7.20–7.25 (m,2H), 7.11 (d,2H,J=9 Hz), 7.00–7.10 (m,2H), 6.90 (d,2H,J=9 Hz), 6.80–6.85 (m,1H), 6.00 (br s,1H), 4.83 (s,2H), 3.75–3.85 (m,2H). MS calcd. 438.4; MS (M+1) 439.4

GENERAL EXAMPLE A

General Synthesis of Compound of Formula I

Compounds in the table below were prepared using substantially the procedure described as follows, using the corresponding reagents to provide the desired compound of formula I: Each well of a multi-well, 1.2 mL, glass, reaction plate was charged with an appropriate aryl aldehyde solution in methanol (1.0N, 100 µL, 100 µmol) followed by an appropriate aniline solution in methanol (0.65N, 200 µL, 130 µmol), and an additional 100 µL of methanol was added to each well. The plate was capped and heated with shaking to 60° C. for 18 h, then cooled and uncapped. Sodium borohydride on alumina (10%, 60 mg) was added via solid addition plate, and the reaction plate was shaken for 2 h without caps and for 4 h with caps. Plate contents were filtered through a filter plate into another multi-well, 1.2 mL, glass, reaction plate, and the empty plate was rinsed twice with 9:1 dichloromethane/methanol (200 µL each) into the filter plate. The receiving plate was concentrated to dryness. A slurry made from polystyrene carboxaldehyde resin (1.8 meq/g) and 4:1 1,2-dichloroethane/methanol (1 g resin for each 10 mL solvents) was added to each well (600 µL/well), followed by 15% acetic acid/1,2-dichloroethane (100 µL/well), and the plate was capped and shaken for 18 h. The plate was uncapped, and DOWEX® 550A OH anion exchange resin (which had been washed dry with methanol) was added by solid addition plate (100 mg per well). The plate was recapped and shaken for 2 h, then uncapped and plate contents were filtered through a filter plate into a multi-well, 2 mL square well, plastic plate. The empty plate was rinsed twice with 9:1 dichloromethane/methanol (200 µL each) into the filter plate, and the receiving plate was concentrated to dryness. The plate contents were dissolved in 9:1 dichloromethane/methanol (400 µL/well), and the solutions were passed through a filter plate containing a half volume of silica gel into a 96-well 1.2 mL vial glass plate. The empty plate was rinsed twice with 9:1 dichloromethane/methanol (200 µL each) into the filter plate, and the receiving plate was concentrated to dryness. In the case of sulfonation, each well is dissolved with 1:1 anhydrous 1,2-dichloroethane/pyridine (400 µL), then treated with the appropriate sulfonyl chloride in anhydrous 1,2-dichloroethane (1.0N, 200 µL, 200 µM). In the case of acylation, each well is dissolved with anhydrous 1,2-dichloroethane (400 µL), then treated with the appropriate acid chloride or chloroformate ester in anhydrous 1,2-dichloroethane (1.0N, 200 µL, 200 µM). In either case, the plate was capped and shaken for 48 h, then uncapped, and each well was treated with tris(2-aminoethyl)amine resin (4 meq/g, 70 mg/well) by solid addition plate. Shaking with caps was continued for 3–4 h, then the plate was opened, treated with dry DOWEX® 550A OH anion exchange resin (120 mg/well) by solid addition plate, and shaken with caps for 2–3 h more. The plate contents were filtered through a filter plate into a 96-well receiving plate, the empty plate was rinsed twice with 9:1 dichloromethane/methanol (200 µL each) into the filter plate, and the receiving plate was concentrated to dryness to give a compound of formula I. The product plate was analyzed by whole plate mass spec and HPLC to give the compounds described in the table below. The HPLC conditions were as follows: a 4.6×50 mm C18 ODS$_{am}$ column (YMC, Inc. CombiScreen™) having a 3 micron particle size and 120 angstrom pore size was eluted at ambient temperature at a flow rate of 3 mL/min. The fluent was a gradient from 5–100% acetonitrile/water (containing 0.1% trifluoroacetic acid) over 4 min. The methods of detection employed included a Gilson 170 diode array detector monitoring 254 nm and a SEDEX Model 75 evaporative light scattering detector held at a 40° C. Injection volumes were held between 5–10 µL per injection. The product can optionally be obtained as the hydrochloride salt by dissolving the free base in minimum methanol and adding 1.3 eq of 2.0N HCl in ether, concentrating in vacuo to obtain a residue, and the residue triturated from ether. In the table below the point of attachment of the pyridyl moiety is designated with the substituent X. In the table below "M+1" refers to the mass ion, where observed, from mass spectral analysis using P.E. Sciex API 100 using was Positive APCI (Atmospheric Pressure Chemical Ionization) and heated nebulizer technique by (flow injection analysis) with a run time of 30 sec per sample. All results yielded M+1 from positive APCI. The mobile phase used was 100% MeOH with 10 mM ammonium acetate using a Gilson 215 liquid handler injector and 1 µL injections.

formula I

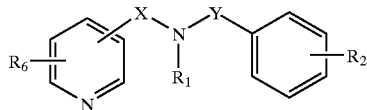

| No. | X | Y | $R_1$ | $R_2$ | $R_6$ | M + 1 |
|---|---|---|---|---|---|---|
| 25 | 2-$CH_2$ | bond | $SO_2CH_3$ | 4-phenoxy | H | 355.28 |
| 26 | 2-$CH_2$ | bond | $SO_2CH_2CH_3$ | 4-phenoxy | H | 369.34 |
| 27 | 2-$CH_2$ | bond | $SO_2(CH_2)_3CH_3$ | 4-phenoxy | H | 383.39 |
| 28 | 2-$CH_2$ | bond | $SO_2CH_2CF_3$ | 4-phenoxy | H | 423.39 |
| 29 | 2-$CH_2$ | bond | $C(O)OCH_3$ | 4-phenoxy | H | 335.83 |
| 30 | 3-$CH_2$ | bond | $SO_2CH_3$ | 4-phenoxy | H | 355.43 |
| 31 | 3-$CH_2$ | bond | $SO_2(CH_2)_3CH_3$ | 4-phenoxy | H | 369.35 |
| 32 | 3-$CH_2$ | bond | $SO_2CH_2CF_3$ | 4-phenoxy | H | 423.39 |
| 33 | 3-$CH_2$ | bond | $C(O)OCH_3$ | 4-phenoxy | H | 335.85 |
| 34 | 4-$CH_2$ | bond | $SO_2CH_3$ | 4-phenoxy | H | 355.23 |
| 35 | 4-$CH_2$ | bond | $SO_2CH_2CH_3$ | 4-phenoxy | H | 369.34 |
| 36 | 4-$CH_2$ | bond | $SO_2(CH_2)_3CH_3$ | 4-phenoxy | H | 397.51 |
| 37 | 4-$CH_2$ | bond | $SO_2CH_2CF_3$ | 4-phenoxy | H | 423.41 |
| 38 | 4-$CH_2$ | bond | $C(O)OCH_3$ | 4-phenoxy | H | 335.84 |
| 39 | 2-$CH_2$ | bond | $C(O)CH_2CH_3$ | 4-phenoxy | H | 333.57 |
| 40 | 2-$CH_2$ | bond | C(O)-cyclopentyl | 4-phenoxy | H | 373.32 |
| 41 | 3-$CH_2$ | bond | $C(O)CH_2CH_3$ | 4-phenoxy | H | 333.58 |
| 42 | 3-$CH_2$ | bond | C(O)-cyclopentyl | 4-phenoxy | H | 373.53 |
| 43 | 4-$CH_2$ | bond | $C(O)CH_2CH_3$ | 4-phenoxy | H | 333.59 |
| 44 | 4-$CH_2$ | bond | C(O)-cyclopentyl | 4-phenoxy | H | 373.32 |
| 45 | 2-$CH_2$ | bond | $SO_2CF_3$ | 4-phenoxy | H | 423.34 |
| 46 | 3-$CH_2$ | bond | $SO_2CF_3$ | 4-phenoxy | H | 423.4 |
| 47 | 4-$CH_2$ | bond | $SO_2CF_3$ | 4-phenoxy | H | 423.4 |
| 48 | 2-$CH_2$ | bond | $SO_2(CH_2)_2CH_3$ | 4-phenoxy | H | 383.38 |
| 49 | 3-$CH_2$ | bond | $SO_2(CH_2)_2CH_3$ | 4-phenoxy | H | 383.4 |
| 50 | 4-$CH_2$ | bond | $SO_2(CH_2)_2CH_3$ | 4-phenoxy | H | 383.4 |
| 51 | 2-$CH_2$ | bond | $C(O)CH_2CH(CH_3)_2$ | 4-phenoxy | H | 361.93 |
| 52 | 3-$CH_2$ | bond | $C(O)CH_2CH(CH_3)_2$ | 4-phenoxy | H | 361.93 |
| 53 | 4-$CH_2$ | bond | $C(O)CH_2CH(CH_3)_2$ | 4-phenoxy | H | 361.9 |
| 54 | 2-$CH_2$ | bond | $C(O)CH_3$ | 4-phenoxy | H | 319.18 |
| 55 | 3-$CH_2$ | bond | $C(O)CH_3$ | 4-phenoxy | H | 319.23 |
| 56 | 4-$CH_2$ | bond | $C(O)CH_3$ | 4-phenoxy | H | 319.17 |
| 57 | 2-$CH_2$ | bond | C(O)-cyclopropyl | 4-phenoxy | H | 345.16 |
| 58 | 3-$CH_2$ | bond | C(O)-cyclopropyl | 4-phenoxy | H | 345.15 |
| 59 | 4-$CH_2$ | bond | C(O)-cyclopropyl | 4-phenoxy | H | 345.12 |
| 60 | 3-$CH_2$ | bond | C(O)-cyclopropyl | 4-(4-benzyloxy-phenoxy) | H | 359.57 |
| 61 | 3-$CH_2$ | bond | C(O)-cyclopropyl | 4-(4-cyclohexyl-phenoxy) | H | 335.93 |
| 62 | 3-$CH_2$ | bond | C(O)-cyclopropyl | 4-(4-benzyl-phenoxy) | H | 343.41 |
| 63 | 3-$CH_2$ | bond | C(O)-cyclopropyl | 4-(4-thiophenoxy-phenoxy) | H | 361.88 |
| 64 | 3-$CH_2$ | bond | $SO_2CH_3$ | 4-(4-benzyloxy-phenoxy) | H | 369.32 |
| 65 | 3-$CH_2$ | bond | $SO_2CH_3$ | 4-(4-cyclohexyl-phenoxy) | H | 345.18 |
| 66 | 3-$CH_2$ | bond | $SO_2CH_3$ | 4-(4-benzyl-phenoxy) | H | 353.62 |
| 67 | 3-$CH_2$ | bond | $SO_2CH_3$ | 4-(4-thiophenoxy-phenoxy) | H | 371.08 |
| 68 | 3-$CH_2$ | bond | $SO_2CH_2CH_3$ | 4-(4-benzyloxy-phenoxy) | H | 383.42 |
| 69 | 3-$CH_2$ | bond | $SO_2CH_2CH_3$ | 4-(4-cyclohexyl-phenoxy) | H | 359.5 |
| 70 | 3-$CH_2$ | bond | $SO_2CH_2CH_3$ | 4-(4-benzyl-phenoxy) | H | 367.55 |
| 71 | 3-$CH_2$ | bond | $SO_2CH_2CH_3$ | 4-(4-thiophenoxy-phenoxy) | H | 385.5 |
| 72 | 3-$CH_2$ | bond | $SO_2CH_2CF_3$ | 4-(4-benzyloxy-phenoxy) | H | 437.78 |
| 73 | 3-$CH_2$ | bond | $SO_2CH_2CF_3$ | 4-(4-cyclohexyl-phenoxy) | H | 413.65 |
| 74 | 3-$CH_2$ | bond | $SO_2CH_2CF_3$ | 4-(4-benzyl-phenoxy) | H | 421.19 |
| 75 | 3-$CH_2$ | bond | $SO_2CH_2CF_3$ | 4-(4-thiophenoxy-phenoxy) | H | 439.52 |
| 76 | 3-$CH_2$ | bond | $SO_2CF_3$ | 4-(4-benzyloxy-phenoxy) | H | 423.4 |

-continued

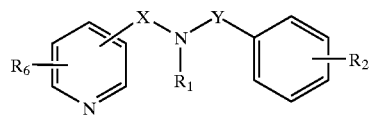

formula I

| No. | X | Y | R₁ | R₂ | R₆ | M + 1 |
|---|---|---|---|---|---|---|
| 77 | 3-CH₂ | bond | SO₂CF₃ | 4-(4-cyclohexyl-phenoxy) | H | 399.4 |
| 78 | 3-CH₂ | bond | SO₂CF₃ | 4-(4-benzyl-phenoxy) | H | 407.4 |
| 79 | 3-CH₂ | bond | SO₂CF₃ | 4-(4-thiophenoxy-phenoxy) | H | 425.5 |
| 80 | 3-CH₂ | bond | SO₂(CH₂)₂CH₃ | 4-(4-benzyloxy-phenoxy) | H | 397.5 |
| 81 | 3-CH₂ | bond | SO₂(CH₂)₂CH₃ | 4-(4-cyclohexyl-phenoxy) | H | 373.5 |
| 82 | 3-CH₂ | bond | SO₂(CH₂)₂CH₃ | 4-(4-benzyl-phenoxy) | H | 381.63 |
| 83 | 3-CH₂ | bond | SO₂(CH₂)₂CH₃ | 4-(4-thiophenoxy-phenoxy) | H | 399.5 |
| 84 | 2-CH₂ | bond | SO₂CH₂CH₃ | 4-(4-benzyloxy-phenoxy) | H | 383.57 |
| 85 | 2-CH₂ | bond | SO₂CH₂CH₃ | 4-(4-cyclohexyl-phenoxy) | H | 359.55 |
| 86 | 2-CH₂ | bond | SO₂CH₂CH₃ | 4-(4-benzyl-phenoxy) | H | 367.5 |
| 87 | 2-CH₂ | bond | SO₂CH₂CH₃ | 4-(4-thiophenoxy-phenoxy) | H | 385.5 |
| 88 | 2-CH₂ | bond | SO₂CH₂CF₃ | 4-(4-benzyloxy-phenoxy) | H | 437.78 |
| 89 | 2-CH₂ | bond | SO₂CH₂CF₃ | 4-(4-cyclohexyl-phenoxy) | H | 413.65 |
| 90 | 2-CH₂ | bond | SO₂CH₂CF₃ | 4-(4-benzyl-phenoxy) | H | 421.16 |
| 91 | 2-CH₂ | bond | SO₂CH₂CF₃ | 4-(4-thiophenoxy-phenoxy) | H | 439.49 |
| 92 | 3-CH₂ | bond | C(O)-cyclopropyl | 4-pentoxy | H | 339.31 |
| 93 | 3-CH₂ | bond | C(O)-cyclopropyl | 4-[benzodioxole-O-] | H | 297.63 |
| 94 | 3-CH₂ | bond | C(O)-cyclopropyl | 4-methoxy | H | 283.69 |
| 95 | 3-CH₂ | bond | C(O)-cyclopropyl | 4-[tetrahydronaphthyl-O-] | H | 399.33 |
| 96 | 3-CH₂ | bond | C(O)-cyclopropyl | 4-(4-cyclohexoxy-phenoxy) | H | 351.86 |
| 97 | 3-CH₂ | bond | C(O)-cyclopropyl | 4-(-pyrid-2-yloxy-phenoxy) | H | 346.31 |
| 98 | 3-CH₂ | bond | SO₂CH₃ | 4-pentoxy | H | 349.82 |
| 99 | 3-CH₂ | bond | SO₂CH₃ | 4-[benzodioxole-O-] | H | 307.71 |
| 100 | 3-CH₂ | bond | SO₂CH₃ | 4-methoxy | H | 293.21 |
| 101 | 3-CH₂ | bond | SO₂CH₃ | 4-[tetrahydronaphthyl-O-] | H | 409.41 |
| 102 | 3-CH₂ | bond | SO₂CH₃ | 4-(4-cyclohexoxy-phenoxy) | H | 361.9 |
| 103 | 3-CH₂ | bond | SO₂CH₃ | 4-(4-pyrid-2-yloxy-phenoxy) | H | 356.37 |
| 104 | 3-CH₂ | bond | SO₂CH₂CH₃ | 4-pentoxy | H | 363.83 |

-continued

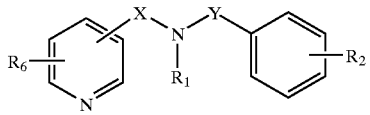

formula I

| No. | X | Y | R₁ | R₂ | R₆ | M + 1 |
|---|---|---|---|---|---|---|
| 105 | 3-CH$_2$ | bond | SO$_2$CH$_2$CH$_3$ | 4-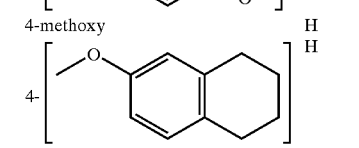 | H | 321.41 |
| 106 | 3-CH$_2$ | bond | SO$_2$CH$_2$CH$_3$ | 4-methoxy | H | 307.71 |
| 107 | 3-CH$_2$ | bond | SO$_2$CH$_2$CH$_3$ | 4-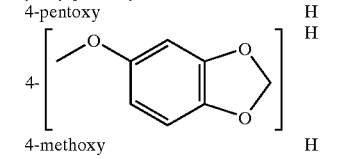 | H | 423.49 |
| 108 | 3-CH$_2$ | bond | SO$_2$CH$_2$CH$_3$ | 4-(4-cyclohexoxy-phenoxy) | H | 375.65 |
| 109 | 3-CH$_2$ | bond | SO$_2$CH$_2$CH$_3$ | 4-(4-pyrid-2-yloxy-phenoxy | H | 370.05 |
| 110 | 3-CH$_2$ | bond | SO$_2$CH$_2$CF$_3$ | 4-pentoxy | H | 417.65 |
| 111 | 3-CH$_2$ | bond | SO$_2$CH$_2$CF$_3$ | 4-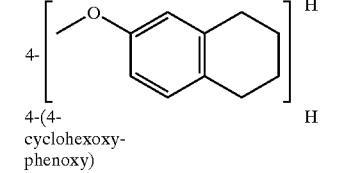 | H | 375.53 |
| 112 | 3-CH$_2$ | bond | SO$_2$CH$_2$CF$_3$ | 4-methoxy | H | 361.81 |
| 113 | 3-CH$_2$ | bond | SO$_2$CH$_2$CF$_3$ | 4-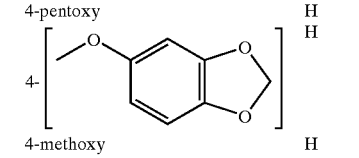 | H | 477.29 |
| 114 | 3-CH$_2$ | bond | SO$_2$CH$_2$CF$_3$ | 4-(4-cyclohexoxy-phenoxy) | H | 429.83 |
| 115 | 3-CH$_2$ | bond | SO$_2$CH$_2$CF$_3$ | 4-(4-pyrid-2-yloxy-phenoxy | H | 424.41 |
| 116 | 3-CH$_2$ | bond | SO$_2$CF$_3$ | 4-pentoxy | H | 403.4 |
| 117 | 3-CH$_2$ | bond | SO$_2$CF$_3$ | 4-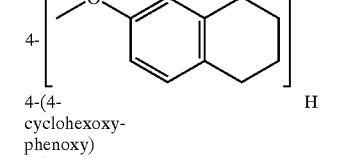 | H | 361.3 |
| 118 | 3-CH$_2$ | bond | SO$_2$CF$_3$ | 4-methoxy | H | 347.3 |
| 119 | 3-CH$_2$ | bond | SO$_2$CF$_3$ | 4-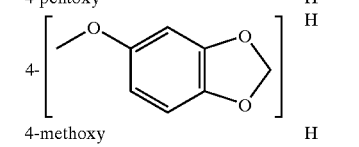 | H | 463.5 |
| 120 | 3-CH$_2$ | bond | SO$_2$CF$_3$ | 4-(4-cyclohexoxy-phenoxy) | H | 415.4 |
| 121 | 3-CH$_2$ | bond | SO$_2$CF$_3$ | 4-(4-pyrid-2-yloxy-phenoxy) | H | 401.4 |
| 122 | 3-CH$_2$ | bond | SO$_2$(CH$_2$)$_2$CH$_3$ | 4-pentoxy | H | 377.76 |
| 123 | 3-CH$_2$ | bond | SO$_2$(CH$_2$)$_2$CH$_3$ | 4-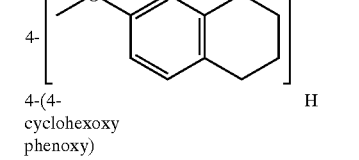 | H | 335.85 |
| 124 | 3-CH$_2$ | bond | SO$_2$(CH$_2$)$_2$CH$_3$ | 4-methoxy | H | 321.41 |
| 125 | 3-CH$_2$ | bond | SO$_2$(CH$_2$)$_2$CH$_3$ | 4- | H | 437.87 |
| 126 | 3-CH$_2$ | bond | SO$_2$(CH$_2$)$_2$CH$_3$ | 4-(4-cyclohexoxy phenoxy) | H | 389.88 |
| 127 | 3-CH$_2$ | bond | SO$_2$(CH$_2$)$_2$CH$_3$ | 4-(4-pyrid-2-yloxy-phenoxy) | H | 384.61 |

-continued

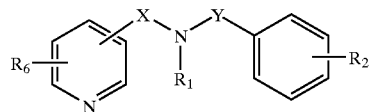

formula I

| No. | X | Y | R₁ | R₂ | R₆ | M + 1 |
|---|---|---|---|---|---|---|
| 128 | 2-CH₂ | bond | SO₂CH₂CH₃ | 4-pentoxy | H | 363.81 |
| 129 | 2-CH₂ | bond | SO₂CH₂CH₃ | 4-[benzo[1,3]dioxol-5-yloxy] | H | 321.4 |
| 130 | 2-CH₂ | bond | SO₂CH₂CH₃ | 4-methoxy | H | 307.71 |
| 131 | 2-CH₂ | bond | SO₂CH₂CH₃ | 4-[5,6,7,8-tetrahydronaphthalen-2-yloxy] | H | 423.47 |
| 132 | 2-CH₂ | bond | SO₂CH₂CH₃ | 4-(4-cyclohexoxy phenoxy) | H | 375.67 |
| 133 | 2-CH₂ | bond | SO₂CH₂CH₃ | 4-(4-pyrid-2-yloxy-phenoxy | H | 361.5 |
| 134 | 2-CH₂ | bond | SO₂CH₂CF₃ | 4-pentoxy | H | 417.66 |
| 135 | 2-CH₂ | bond | SO₂CH₂CF₃ | 4-[benzo[1,3]dioxol-5-yloxy] | H | 375.52 |
| 136 | 2-CH₂ | bond | SO₂CH₂CF₃ | 4-methoxy | H | 361.79 |
| 137 | 2-CH₂ | bond | SO₂CH₂CF₃ | 4-[5,6,7,8-tetrahydronaphthalen-2-yloxy] | H | 477.5 |
| 138 | 2-CH₂ | bond | SO₂CH₂CF₃ | 4-(4-cyclohexoxy phenoxy) | H | 429.62 |
| 139 | 2-CH₂ | bond | SO₂CH₂CF₃ | 4-(4-pyrid-2-yloxy-phenoxy) | H | 424.36 |
| 140 | 3-CH₂ | bond | C(O)-cyclopropyl | 3-phenoxy | H | 345.16 |
| 141 | 3-CH₂ | bond | C(O)-cyclopropyl | 2-phenoxy | H | 345.18 |
| 142 | 3-CH₂ | bond | C(O)-cyclopropyl | 4-(4-chloro-phenoxy) | H | 379.4 |
| 143 | 3-CH₂ | bond | C(O)-cyclopropyl | 4-(3-trifluoromethyl-phenoxy) | H | 413.68 |
| 144 | 3-CH₂ | bond | C(O)-cyclopropyl | 4-(2-methoxy-phenoxy) | H | 375.65 |
| 145 | 3-CH₂ | bond | C(O)-cyclopropyl | 4-(4-cyano-phenoxy) | H | 370.14 |
| 146 | 3-CH₂ | bond | C(O)-cyclopropyl | 4-(2,4-difluoro-phenoxy) | H | 381.62 |
| 147 | 3-CH₂ | bond | SO₂CH₃ | 3-phenoxy | H | 355.28 |
| 148 | 3-CH₂ | bond | SO₂CH₃ | 2-phenoxy | H | 355.4 |
| 149 | 3-CH₂ | bond | SO₂CH₃ | 4-(4-chloro-phenoxy) | H | 389.78 |
| 150 | 3-CH₂ | bond | SO₂CH₃ | 4-(3-trifluoromethyl-phenoxy) | H | 423.4 |
| 151 | 3-CH₂ | bond | SO₂CH₃ | 4-(2-methoxy-phenoxy) | H | 385.44 |
| 152 | 3-CH₂ | bond | SO₂CH₃ | 4-(4-cyano-phenoxy) | H | 380.52 |
| 153 | 3-CH₂ | bond | SO₂CH₃ | 4-(2,4-difluoro-phenoxy) | H | 391.63 |
| 154 | 2-CH₂ | bond | SO₂CH₂CH₃ | 3-phenoxy | H | 369.3 |
| 155 | 2-CH₂ | bond | SO₂CH₂CH₃ | 2-phenoxy | H | 369.3 |
| 156 | 2-CH₂ | bond | SO₂CH₂CH₃ | 4-(4-chloro-phenoxy) | H | 403.9 |
| 157 | 2-CH₂ | bond | SO₂CH₂CH₃ | 4-(3-trifluoromethyl-phenoxy) | H | 437.5 |

-continued formula I

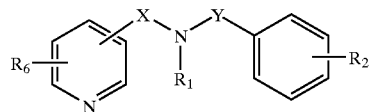

| No. | X | Y | $R_1$ | $R_2$ | $R_6$ | M + 1 |
|---|---|---|---|---|---|---|
| 158 | 2-$CH_2$ | bond | $SO_2CH_2CH_3$ | 4-(2-methoxy-phenoxy) | H | 399.26 |
| 159 | 2-$CH_2$ | bond | $SO_2CH_2CH_3$ | 4-(4-cyano-phenoxy) | H | 448.44 |
| 160 | 2-$CH_2$ | bond | $SO_2CH_2CH_3$ | 4-(2,4-difluro-phenoxy) | H | 459.37 |
| 161 | 2-$CH_2$ | bond | $SO_2CH_2CF_3$ | 3-phenoxy | H | 423.43 |
| 162 | 2-$CH_2$ | bond | $SO_2CH_2CF_3$ | 2-phenoxy | H | 423.39 |
| 163 | 2-$CH_2$ | bond | $SO_2CH_2CF_3$ | 4-(4-chloro-phenoxy) | H | 457.68 |
| 164 | 2-$CH_2$ | bond | $SO_2CH_2CF_3$ | 4-(3-trifluoromethyl-phenoxy) | H | 491.56 |
| 165 | 2-$CH_2$ | bond | $SO_2CH_2CF_3$ | 4-(2-methoxy-phenoxy) | H | 453.36 |
| 166 | 2-$CH_2$ | bond | $SO_2CH_2CF_3$ | 4-(4-cyano-phenoxy) | H | 448.44 |
| 167 | 2-$CH_2$ | bond | $SO_2CH_2CF_3$ | 4-(2,4-difluoro-phenoxy) | H | 459.37 |
| 168 | 3-$CH_2$ | bond | $SO_2CH_2CH_3$ | 3-phenoxy | H | 369.5 |
| 169 | 3-$CH_2$ | bond | $SO_2CH_2CH_3$ | 2-phenoxy | H | 369.5 |
| 170 | 3-$CH_2$ | bond | $SO_2CH_2CH_3$ | 4-(4-chloro-phenoxy) | H | 403.75 |
| 171 | 3-$CH_2$ | bond | $SO_2CH_2CH_3$ | 4-(3-trifluoromethyl-phenoxy) | H | 437.78 |
| 172 | 3-$CH_2$ | bond | $SO_2CH_2CH_3$ | 4-(2-methoxy-phenoxy) | H | 399.28 |
| 173 | 3-$CH_2$ | bond | $SO_2CH_2CH_3$ | 4-(4-cyano-phenoxy) | H | 394.5 |
| 174 | 3-$CH_2$ | bond | $SO_2CH_2CH_3$ | 4-(2,4-difluoro-phenoxy) | H | 405.5 |
| 175 | 3-$CH_2$ | bond | $SO_2CH_2CF_3$ | 3-phenoxy | H | 423.41 |
| 176 | 3-$CH_2$ | bond | $SO_2CH_2CF_3$ | 3-phenoxy | H | 423.4 |
| 177 | 3-$CH_2$ | bond | $SO_2CH_2CF_3$ | 4-(4-chloro-phenoxy) | H | 457.7 |
| 178 | 3-$CH_2$ | bond | $SO_2CH_2CF_3$ | 4-(3-trifluoromethyl-phenoxy) | H | 491.57 |
| 179 | 3-$CH_2$ | bond | $SO_2CH_2CF_3$ | 4-(2-methoxy-phenoxy) | H | 453.63 |
| 180 | 3-$CH_2$ | bond | $SO_2CH_2CF_3$ | 4-(4-cyano-phenoxy) | H | 448.45 |
| 181 | 3-$CH_2$ | bond | $SO_2CH_2CF_3$ | 4-(2,4-difluoro-phenoxy) | H | 459.37 |
| 182 | 3-$CH_2$ | bond | $SO_2CF_3$ | 3-phenoxy | H | 409.4 |
| 183 | 3-$CH_2$ | bond | $SO_2CF_3$ | 2-phenoxy | H | 409.4 |
| 184 | 3-$CH_2$ | bond | $SO_2CF_3$ | 4-(4-chloro-phenoxy) | H | 443.8 |
| 185 | 3-$CH_2$ | bond | $SO_2CF_3$ | 4-(3-trifluoromethyl-phenoxy) | H | 477.4 |
| 186 | 3-$CH_2$ | bond | $SO_2CF_3$ | 4-(2-methoxy-phenoxy) | H | 439.4 |
| 187 | 3-$CH_2$ | bond | $SO_2CF_3$ | 4-(4-cyano-phenoxy) | H | 434.4 |
| 188 | 3-$CH_2$ | bond | $SO_2CF_3$ | 4-(2,4-difluoro-phenoxy) | H | 445.4 |
| 189 | 3-$CH_2$ | bond | $SO_2(CH_2)_2CH_3$ | 3-phenoxy | H | 383.5 |
| 190 | 3-$CH_2$ | bond | $SO_2(CH_2)_2CH_3$ | 2-phenoxy | H | 383.5 |
| 191 | 3-$CH_2$ | bond | $SO_2(CH_2)_2CH_3$ | 4-(4-chloro-phenoxy) | H | 417.9 |
| 192 | 3-$CH_2$ | bond | $SO_2(CH_2)_2CH_3$ | 4-(3-trifluoromethyl-phenoxy) | H | 451.5 |
| 193 | 3-$CH_2$ | bond | $SO_2(CH_2)_2CH_3$ | 4-(2-methoxy-phenoxy) | H | 413.5 |
| 194 | 3-$CH_2$ | bond | $SO_2(CH_2)_2CH_3$ | 4-(4-cyano-phenoxy) | H | 408.5 |

-continued

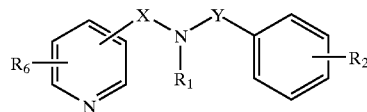

formula I

| No. | X | Y | R$_1$ | R$_2$ | R$_6$ | M + 1 |
|---|---|---|---|---|---|---|
| 195 | 3-CH$_2$ | bond | SO$_2$(CH$_2$)$_2$CH$_3$ | 4-(2,4-difluoro-phenoxy) | H | 419.35 |
| 196 | 3-CH$_2$ | bond | C(O)-cyclopropyl | 2-chloro-5-methyl-4-phenoxy | H | 393.9 |
| 197 | 3-CH$_2$ | bond | C(O)-cyclopropyl | 3-chloro-4-phenoxy | H | 379.33 |
| 198 | 3-CH$_2$ | bond | C(O)-cyclopropyl | 2-methyl-4-phenoxy | H | 359.55 |
| 199 | 3-CH$_2$ | bond | C(O)-cyclopropyl | 3-trifluoromethyl-4-phenoxy | H | 413.63 |
| 200 | 3-CH$_2$ | bond | C(O)-cyclopropyl | 4-(4-nitro-phenoxy) | H | 390.75 |
| 201 | 3-CH$_2$ | bond | SO$_2$CH$_3$ | 2-chloro-5-methyl-4-phenoxy | H | 403.9 |
| 202 | 3-CH$_2$ | bond | SO$_2$CH$_3$ | 3-chloro-4-phenoxy | H | 389.71 |
| 203 | 3-CH$_2$ | bond | SO$_2$CH$_3$ | 2-methyl-4-phenoxy | H | 369.3 |
| 204 | 3-CH$_2$ | bond | SO$_2$CH$_3$ | 3-trifluoromethyl-4-phenoxy | H | 423.4 |
| 205 | 3-CH$_2$ | bond | SO$_2$CH$_3$ | 4-(4-nitro-phenoxy) | H | 400.4 |
| 206 | 3-CH$_2$ | bond | SO$_2$CH$_2$CH$_3$ | 2-chloro-5-methyl-4-phenoxy | H | 417.9 |
| 207 | 3-CH$_2$ | bond | SO$_2$CH$_2$CH$_3$ | 3-chloro-4-phenoxy | H | 403.9 |
| 208 | 3-CH$_2$ | bond | SO$_2$CH$_2$CH$_3$ | 2-methyl-4-phenoxy | H | 383.5 |
| 209 | 3-CH$_2$ | bond | SO$_2$CH$_2$CH$_3$ | 3-trifluoromethyl-4-phenoxy | H | 437.5 |
| 210 | 3-CH$_2$ | bond | SO$_2$CH$_2$CH$_3$ | 4-(4-nitro-phenoxy | H | 414.5 |
| 211 | 3-CH$_2$ | bond | SO$_2$CH$_2$CF$_3$ | 2-chloro-5-methyl-4-phenoxy | H | 417.9 |
| 212 | 3-CH$_2$ | bond | SO$_2$CH$_2$CF$_3$ | 3-chloro-4-phenoxy | H | 457.9 |
| 213 | 3-CH$_2$ | bond | SO$_2$CH$_2$CF$_3$ | 2-methyl-4-phenoxy | H | 437.72 |
| 214 | 3-CH$_2$ | bond | SO$_2$CH$_2$CF$_3$ | 3-trifluoromethyl-4-phenoxy | H | 491.51 |
| 215 | 3-CH$_2$ | bond | SO$_2$CH$_2$CF$_3$ | 4-(4-nitro-phenoxy) | H | 468.89 |
| 216 | 3-CH$_2$ | bond | SO$_2$CF$_3$ | 2-chloro-5-methyl-4-phenoxy | H | 457.9 |
| 217 | 3-CH$_2$ | bond | SO$_2$CF$_3$ | 3-chloro-4-phenoxy | H | 443.8 |
| 218 | 3-CH$_2$ | bond | SO$_2$CF$_3$ | 2-methyl-4-phenoxy | H | 423.4 |
| 219 | 3-CH$_2$ | bond | SO$_2$CF$_3$ | 3-trifluoromethyl-4-phenoxy | H | 477.4 |
| 220 | 3-CH$_2$ | bond | SO$_2$CF$_3$ | 4-(4-nitro-phenoxy) | H | 454.4 |
| 221 | 3-CH$_2$ | bond | SO$_2$(CH$_2$)$_2$CH$_3$ | 2-chloro-5-methyl-4-phenoxy | H | 432.0 |
| 222 | 3-CH$_2$ | bond | SO$_2$(CH$_2$)$_2$CH$_3$ | 3-chloro-4-phenoxy | H | 417.9 |
| 223 | 3-CH$_2$ | bond | SO$_2$(CH$_2$)$_2$CH$_3$ | 2-methyl-4-phenoxy | H | 397.5 |
| 224 | 3-CH$_2$ | bond | SO$_2$(CH$_2$)$_2$CH$_3$ | 3-trifluromethyl-4-phenoxy | H | 451.5 |
| 225 | 3-CH$_2$ | bond | SO$_2$(CH$_2$)$_2$CH$_3$ | 4-(4-nitro-phenoxy) | H | 428.5 |
| 226 | 2-CH$_2$ | bond | SO$_2$CH$_2$CH$_3$ | 2-chloro-5-methyl-4-phenoxy | H | 417.9 |
| 227 | 2-CH$_2$ | bond | SO$_2$CH$_2$CH$_3$ | 3-chloro-4-phenoxy | H | 403.9 |
| 228 | 2-CH$_2$ | bond | SO$_2$CH$_2$CH$_3$ | 2-methyl-4-phenoxy | H | 383.5 |

-continued

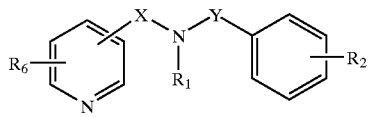

formula I

| No. | X | Y | R₁ | R₂ | R₆ | M + 1 |
|---|---|---|---|---|---|---|
| 229 | 2-CH₂ | bond | SO₂CH₂CH₃ | 3-trifluoromethyl-4-phenoxy | H | 437.5 |
| 230 | 2-CH₂ | bond | SO₂CH₂CH₃ | 4-(4-nitro-phenoxy) | H | 414.5 |
| 231 | 2-CH₂ | bond | SO₂CH₂CF₃ | 2-chloro-5-methyl-4-phenoxy | H | 471.6 |
| 232 | 2-CH₂ | bond | SO₂CH₂CF₃ | 3-chloro-4-phenoxy | H | 457.66 |
| 233 | 2-CH₂ | bond | SO₂CH₂CF₃ | 2-methyl-4-phenoxy | H | 437.73 |
| 234 | 2-CH₂ | bond | SO₂CH₂CF₃ | 3-trifluoromethyl-4-phenoxy | H | 491.52 |
| 235 | 2-CH₂ | bond | SO₂CH₂CF₃ | 4-(4-nitro-phenoxy) | H | 466.87 |
| 236 | 3-CH₂ | bond | SO₂CH₂CF₃ | 4-phenoxy | 6-methoxy | 453 |
| 237 | 3-CH₂ | bond | SO₂CH₂CF₃ | 3-phenoxy | 6-methoxy | 453 |
| 238 | 3-CH₂ | bond | SO₂CH₂CF₃ | 4-(2-methoxy-phenoxy) | 6-methoxy | 484 |
| 239 | 3-CH₂ | bond | SO₂CH₂CH₃ | 4-phenoxy | 6-methoxy | 399 |
| 240 | 3-CH₂ | bond | SO₂CH₂CH₃ | 3-phenoxy | 6-methoxy | 400 |
| 241 | 3-CH₂ | bond | SO₂CH₂CH₃ | 4-(2-methoxy-phenoxy) | 6-methoxy | 430 |
| 242 | 3-CH₂ | bond | SO₂CH₂CF₃ | 4-phenoxy | 6-methyl | 438 |
| 243 | 3-CH₂ | bond | SO₂CH₂CF₃ | 3-phenoxy | 6-methyl | 438 |
| 244 | 3-CH₂ | bond | SO₂CH₂CF₃ | 4-(2-methoxy-phenoxy) | 6-methyl | 468 |
| 245 | 3-CH₂ | bond | SO₂CH₂CH₃ | 4-phenoxy | 6-methyl | 384 |
| 246 | 3-CH₂ | bond | SO₂CH₂CH₃ | 3-phenoxy | 6-methyl | 384 |
| 247 | 3-CH₂ | bond | SO₂CH₂CH₃ | 4-(2-methoxy-phenoxy) | 6-methyl | 414 |
| 248 | 3-CH₂ | bond | SO₂CH₂CF₃ | 4-phenoxy | 6-(4-chloro-phenoxy) | 550 |
| 249 | 3-CH₂ | bond | SO₂CH₂CF₃ | 3-phenoxy | 6-(4-chloro-phenoxy) | 550 |
| 250 | 3-CH₂ | bond | SO₂CH₂CF₃ | 4-(2-methoxy-phenoxy) | 6-(4-chloro-phenoxy) | 580 |
| 251 | 3-CH₂ | bond | SO₂CH₂CH₃ | 4-phenoxy | 6-(4-chloro-phenoxy) | 496 |
| 252 | 3-CH₂ | bond | SO₂CH₂CH₃ | 3-phenoxy | 6-(4-chloro-phenoxy) | 496 |
| 253 | 3-CH₂ | bond | SO₂CH₂CH₃ | 4-(2-methoxy-phenoxy) | 6-(4-chloro-phenoxy) | 526 |
| 254 | 3-CH₂ | bond | SO₂CH₂CF₃ | 4-phenoxy | 2-chloro | 458 |
| 255 | 3-CH₂ | bond | SO₂CH₂CF₃ | 3-phenoxy | 2-chloro | 458 |
| 256 | 3-CH₂ | bond | SO₂CH₂CF₃ | 4-(2-methoxy-phenoxy) | 2-chloro | 488 |
| 257 | 3-CH₂ | bond | SO₂CH₂CH₃ | 4-phenoxy | 2-chloro | 404 |
| 258 | 3-CH₂ | bond | SO₂CH₂CH₃ | 3-phenoxy | 2-chloro | 404 |
| 259 | 3-CH₂ | bond | SO₂CH₂CH₃ | 4-(2-methoxy-phenoxy) | 2-chloro | 434 |
| 260 | 3-CH₂ | bond | SO₂CH₂CF₃ | 4-phenoxy | 2-phenoxy | 516 |
| 261 | 3-CH₂ | bond | SO₂CH₂CF₃ | 3-phenoxy | 2-phenoxy | 516 |
| 262 | 3-CH₂ | bond | SO₂CH₂CF₃ | 4-(2-methoxy-phenoxy) | 2-phenoxy | 546 |
| 263 | 3-CH₂ | bond | SO₂CH₂CH₃ | 4-phenoxy | 2-phenoxy | 462 |
| 264 | 3-CH₂ | bond | SO₂CH₂CH₃ | 3-phenoxy | 2-phenoxy | 462 |
| 265 | 3-CH₂ | bond | SO₂CH₂CH₃ | 4-(2-methoxy-phenoxy) | 2-phenoxy | 492 |
| 266 | 3-CH₂ | bond | SO₂CH₂CF₃ | 4-phenoxy | 6-chloro | 458 |
| 267 | 3-CH₂ | bond | SO₂CH₂CF₃ | 3-phenoxy | 6-chloro | 458 |
| 268 | 3-CH₂ | bond | SO₂CH₂CF₃ | 4-(2-methoxy-phenoxy) | 6-chloro | 488 |
| 269 | 3-CH₂ | bond | SO₂CH₂CH₃ | 4-phenoxy | 6-chloro | 404 |

-continued

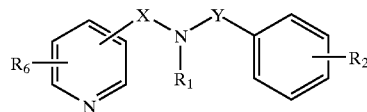

formula I

| No. | X | Y | R₁ | R₂ | R₆ | M + 1 |
|---|---|---|---|---|---|---|
| 270 | 3-CH₂ | bond | SO₂CH₂CH₃ | 3-phenoxy | 6-chloro | 404 |
| 271 | 3-CH₂ | bond | SO₂CH₂CH₃ | 4-(2-methoxy-phenoxy) | 6-chloro | 434 |
| 272 | 3-CH₂ | bond | SO₂CH₂CF₃ | 4-phenoxy | 2-chloro 6-methyl | 472 |
| 273 | 3-CH₂ | bond | SO₂CH₂CF₃ | 3-phenoxy | 2-chloro 6-methyl | 471 |
| 274 | 3-CH₂ | bond | SO₂CH₂CF₃ | 4-(2-methoxy-phenoxy) | 2-chloro 6-methyl | 501 |
| 275 | 3-CH₂ | bond | SO₂CH₂CH₃ | 4-phenoxy | 2-chloro 6-methyl | 418 |
| 276 | 3-CH₂ | bond | SO₂CH₂CH₃ | 3-phenoxy | 2-chloro 6-methyl | 418 |
| 277 | 3-CH₂ | bond | SO₂CH₂CH₃ | 4-(2-methoxy-phenoxy) | 2-chloro 6-methyl | 448 |
| 278 | 3-CH₂ | bond | SO₂-cyclopropyl | 4-phenoxy | H | 382 |
| 279 | | | | | | |
| 280 | 4-CH₂ | bond | SO₂CH₂CF₃ | 4-(2-methoxy-phenoxy) | H | 453 |
| 281 | 4-CH₂ | bond | SO₂CH₂CH₃ | 4-(2-methoxy-phenoxy) | H | 399 |
| 282 | 3-CH₂ | bond | SO₂-cyclopropyl | 4-(2,6-dimethoxy-phenoxy) | H | 442 |
| 283 | 3-CH₂ | bond | SO₂CH₂CH₃ | 4-(2,6-dimethoxy-phenoxy) | H | 484 |
| 284 | 3-CH₂ | bond | SO₂CH₂CF₃ | 4-(2,6-dimethoxy-phenoxy) | H | 430 |
| 285 | 2-CH₂ | bond | SO₂CH₂CH₃ | 4-(2,6-dimethoxy-phenoxy) | H | 399 |
| 286 | 2-CH₂ | bond | SO₂CH₂CF₃ | 4-(2,6-dimethoxy-phenoxy) | H | 453 |
| 287 | 4-CH₂ | bond | SO₂CH₂CH₃ | 4-(2,6-dimethoxy-phenoxy) | H | 399 |
| 288 | 4-CH₂ | bond | SO₂CH₂CF₃ | 4-(2,6-dimethoxy-phenoxy) | H | 453 |
| 289 | 3-CH₂ | CH₂ | SO₂-cyclopropyl | 2-phenoxy-6-chloro | H | 430 |
| 290 | 3-CH₂ | CH₂ | SO₂CH₂CH₃ | 2-phenoxy-6-chloro | H | 418 |
| 291 | 3-CH₂ | CH₂ | SO₂CH₂CF₃ | 2-phenoxy-6-chloro | H | 472 |
| 292 | 2-CH₂ | CH₂ | SO₂CH₂CH₃ | 2-phenoxy-6-chloro | H | 418 |
| 293 | 2-CH₂ | CH₂ | SO₂CH₂CF₃ | 2-phenoxy-6-chloro | H | 472 |
| 294 | 4-CH₂ | CH₂ | SO₂CH₂CH₃ | 2-phenoxy-6-chloro | H | 418 |
| 295 | 4-CH₂ | CH₂ | SO₂CH₂CF₃ | 2-phenoxy-6-chloro | H | 472 |
| 296 | 3-CH₂ | bond | SO₂-cyclopropyl | 4-(2,6-dichloro-phenoxy) | H | 449 |
| 297 | 3-CH₂ | bond | SO₂CH₂CH₃ | 4-(2,6-dichloro-phenoxy) | H | 493 |
| 298 | 3-CH₂ | bond | SO₂CH₂CF₃ | 4-(2,6-dichloro-phenoxy) | H | 439 |
| 299 | 2-CH₂ | bond | SO₂CH₂CH₃ | 4-(2,6-dichloro-phenoxy) | H | 439 |
| 300 | 2-CH₂ | bond | SO₂CH₂CF₃ | 4-(2,6-dichloro-phenoxy) | H | 494 |
| 301 | 4-CH₂ | bond | SO₂CH₂CH₃ | 4-(2,6-dichloro-phenoxy) | H | 439 |
| 302 | 4-CH₂ | bond | SO₂CH₂CF₃ | 4-(2,6-dichloro-phenoxy) | H | 493 |
| 303 | 3-CH₂ | bond | SO₂-cyclopropyl | 4-(2-isopropoxy-phenoxy) | H | 440 |
| 304 | 3-CH₂ | bond | SO₂CH₂CH₃ | 4-(2-isopropoxy-phenoxy) | H | 482 |
| 305 | 3-CH₂ | bond | SO₂CH₂CF₃ | 4-(2-isopropoxy-phenoxy) | H | 427 |

-continued

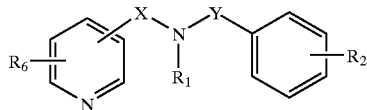

formula I

| No. | X | Y | R₁ | R₂ | R₆ | M + 1 |
|---|---|---|---|---|---|---|
| 306 | 2-CH₂ | bond | SO₂CH₂CH₃ | 4-(2-isopropoxy-phenoxy) | H | 427 |
| 307 | 2-CH₂ | bond | SO₂CH₂CF₃ | 4-(2-isopropoxy-phenoxy) | H | 481 |
| 308 | 4-CH₂ | bond | SO₂CH₂CH₃ | 4-(2-isopropoxy-phenoxy) | H | 427 |
| 309 | 4-CH₂ | bond | SO₂CH₂CF₃ | 4-(2-isopropoxy-phenoxy) | H | 481 |
| 310 | 3-CH₂ | bond | SO₂-cyclopropyl | 4-(2-fluoro-6-methoxy phenoxy) | H | 430 |
| 311 | 3-CH₂ | bond | SO₂CH₂CF₃ | 4-(2-fluoro-6-methoxy phenoxy) | H | 472 |
| 312 | 3-CH₂ | bond | SO₂CH₂CH₃ | 4-(2-fluoro-6-methoxy-phenoxy) | H | 418 |
| 313 | 2-CH₂ | bond | SO₂CH₂CH₃ | 4-(2-fluoro-6-methoxy-phenoxy) | H | 418 |
| 314 | 2-CH₂ | bond | SO₂CH₂CF₃ | 4-(2-fluoro-6-methoxy-phenoxy) | H | 472 |
| 315 | 4-CH₂ | bond | SO₂CH₂CH₃ | 4-(2-fluoro-6-methoxy-phenoxy) | H | 418 |
| 316 | 4-CH₂ | bond | SO₂CH₂CF₃ | 4-(2-fluoro-6-methoxy-phenoxy) | H | 471 |
| 317 | 3-CH₂ | bond | SO₂-cyclopropyl | 4-(2-trifluoromethyl-phenoxy) | H | 449 |
| 318 | 3-CH₂ | bond | SO₂CH₂CF₃ | 4-(2-trifluoromethyl-phenoxy) | H | 492 |
| 319 | 3-CH₂ | bond | SO₂CH₂CH₃ | 4-(2-trifluoromethyl-phenoxy) | H | 438 |
| 320 | 2-CH₂ | bond | SO₂CH₂CH₃ | 4-(2-trifluoromethyl-phenoxy) | H | 437 |
| 321 | 2-CH₂ | bond | SO₂CH₂CF₃ | 4-(2-trifluoromethyl-phenoxy) | H | 492 |
| 322 | 4-CH₂ | bond | SO₂CH₂CH₃ | 4-(2-trifluoromethyl-phenoxy) | H | 437 |
| 323 | 4-CH₂ | bond | SO₂CH₂CF₃ | 4-(2-trifluoromethyl-phenoxy) | H | 492 |
| 324 | 3-CH₂ | bond | SO₂-cyclopropyl | 4-(2-isopropyl-5-methyl-phenoxy) | H | 438 |
| 325 | 3-CH₂ | bond | SO₂CH₂CF₃ | 4-(2-isopropyl-5-methyl-phenoxy) | H | 479 |
| 326 | 3-CH₂ | bond | SO₂CH₂CH₃ | 4-(2-isopropyl-5-methyl-phenoxy) | H | 425 |
| 327 | 2-CH₂ | bond | SO₂CH₂CH₃ | 4-(2-isopropyl-5-methyl-phenoxy) | H | 426 |
| 328 | 2-CH₂ | bond | SO₂CH₂CF₃ | 4-(2-isopropyl-5-methyl-phenoxy) | H | 479 |
| 329 | 4-CH₂ | bond | SO₂CH₂CH₃ | 4-(2-isopropyl-5-methyl-phenoxy) | H | 425 |
| 330 | 4-CH₂ | bond | SO₂CH₂CF₃ | 4-(2-isopropyl-5-methyl-phenoxy) | H | 479 |
| 331 | 3-CH₂ | bond | SO₂-cyclopropyl | 4-(2-cyclopentyl-phenoxy) | H | 450 |
| 332 | 3-CH₂ | bond | SO₂CH₂CF₃ | 4-(2-cyclopentyl-phenoxy) | H | 492 |

-continued formula I

| No. | X | Y | R₁ | R₂ | R₆ | M + 1 |
|---|---|---|---|---|---|---|
| 333 | 3-CH₂ | bond | SO₂CH₂CH₃ | 4-(2-cyclopentyl-phenoxy) | H | 438 |
| 334 | 2-CH₂ | bond | SO₂CH₂CH₃ | 4-(2-cyclopentyl-phenoxy) | H | 438 |
| 335 | 2-CH₂ | bond | SO₂CH₂CF₃ | 4-(2-cyclopentyl-phenoxy) | H | 492 |
| 336 | 4-CH₂ | bond | SO₂CH₂CH₃ | 4-(2-cyclopentyl-phenoxy) | H | 438 |
| 337 | 4-CH₂ | bond | SO₂CH₂CF₃ | 4-(2-cyclopentyl-phenoxy) | H | 492 |

Preparation 3

4-(4-Benzyloxyphenoxy)aniline

A solution of 4-benzyloxyphenol (6.01 g, 30 mmol) in anhydrous dimethylformamide (50 ml) under a nitrogen cover was treated with sodium hydride (1.2 g of 60% oil dispersion, 30 mmol) in one portion at room temperature. A moderate gas evolution ensued, and the reaction temperature rose to 41° C. After stirring an additional 35 minutes, 4-Fluoronitrobenzene was added rapidly dropwise, neat via syringe. A mild exotherm brought the reaction temperature to 32° C., after which the reaction was stirred for 18 hours at room temperature. The reaction mixture was poured over ice/water (250 ml), stirred for thirty minutes and the yellow solid collected by suction filtration. Silica gel chromatography (Waters® LC2000; two Pre-Pak® columns, P eluting with 3/1 hexanes/methylene chloride) afforded 4-(4-benzyloxyphenoxy)-1-nitrobenzene (5.9 g, 73%) as a white solid. ¹H NMR(400 MHZ): 5.08(2H,s), 6.94–6.99(2H,m), 7.02(4H,s), 7.32–7.47(5H,m), 8.15–8.20(2H,m); MS(ESI) m/z 320.2([M⁻H]−,100).

A mechanically-stirred solution of 4-(4-benzyloxyphenoxy)-1-nitrobenzene (5.6 g, 17 mmol) in absolute ethanol (50 ml) was treated with concentrated hydrochloric acid (6 ml). The solution was warmed to 55–60° C. under a nitrogen cover. Iron powder (6.5 g, 115 mmol) was added in several portions. A mild exotherm (while still being heated) brought the reaction temperature to 68° C. After completing the iron addition the reaction temperature was brought to 70° C. and maintained at that temperature for 1.5 hours. The mixture was then cooled to room temperature and filtered through a pad of Celite®. The filter cake was washed with ethanol (100 ml) and methylene chloride (50 ml), and the filtrate partitioned between methylene chloride and 1M potassium carbonate. The green aqueous layer was extracted a second time with methylene chloride and then dried over anhydrous magnesium sulfate. Filtration and concentration in vacuo afforded crude product (5.4 g), contaminated with unreacted starting material. Silica gel chromatography (Waters® LC2000 with 2 PrePak® columns, eluting with methylene chloride) provided the title compound (3.75 g, 76%), as well as unreacted starting material (1.2 g). ¹H NMR(400 MHz): 3.53(2H,br s), 5.02 (2H,s), 6.62–6.67(2H,m), 6.79–6.84(2H,m), 6.86–6.93(4H,m), 7.29–7.44(5H,m); MS(ESI)m/z 291.9([M+H]+,100).

EXAMPLE 338

N-(4-(4-Benzyloxyphenoxy)phenyl)-N-(2,2,2-trifluoroethanesulfonyl)pyrid-3-ylmethylamine

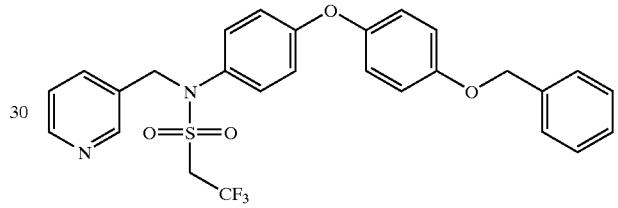

4-(4-Benzyloxyphenoxy)aniline (3.4 g, 11.67 mmol) was suspended in methanol (100 ml) and treated with pyridine-3-carboxaldehyde (1.25 g, 11.67 mmol) in one portion via syringe. This solution was heated to reflux for two hours, and then cooled to −5° C. Solid sodium borohydride (0.88 g, 23 mmol) was added in one portion. A mild gas evolution ensued, and the reaction temperature rose to −2° C. The mixture was then stirred at room temperature for two hours, after which TLC analysis of an aliquot showed incomplete reduction. An additional quantity of sodium borohydride was added (0.45 g, 12 mmol) was added and the mixture stirred another two hours. The solvent was removed in vacuo and the residue slurried in methlyene chloride. After filtration to remove insolubles and concentration in vacuo, the crude oil thereby obtained was purified via silica gel chromatography (Waters® LC2000 using two PrePak® columns, eluting with 99/1 methylene chloride/methanol). N-4-(4-Benzyloxyphenoxy)phenylpyrid-3-ylmethylamine was obtained as a white solid (3.6 g, 81%). ¹H NMR(400 MHz): 4.33(2H,s), 5.02(2H,s), 6.56–6.62(2H,m), 6.83–6.92(6H,m), 7.24–7.44(6H,m), 7.70(1H,ddd,J=7.8, ~2.0, ~2.0), 8.53(1H, dd, J=4.9,1.5), 8.63(1H,d,J=1.5); MS(ESI)m/z 382.9([M+H]+,100).

N-4-(4-Benzyloxyphenoxy)phenylpyrid-3-ylmethylamine (3.55 g, 9.3 mmol) was dissolved in 1,2-dichloroethane (46 ml) in a flame-dried, serum-capped round bottom flask under a nitrogen cover. Anhydrous pyridine (24 ml) was added via syringe, the solution cooled to −5° C., and trifluoroethanesulfonyl chloride was added neat, dropwise via syringe. After stirring thirty minutes at 0° C. the solution was stirred at room temperature for 18 hours. Potassium carbonate (6.0 g) was added to the mixture and it was stirred another hour. The mixture was then filtered and the filtrate concentrated in vacuo to a dark oil. Silica gel chromatography (Waters® LC2000 using two PrePak® columns, eluting with 99/1 methylene chloride/methanol). Product-containing fractions were combined and concentrated, and the resulting mixture chromatographed a second time using a 90/10 to 84/16 methylene chloride/ethyl acetate gradient. The title compound was obtained (4.36 g, 89%) as an off-white solid. $^1$H NMR(400 MHz): 3.81(2H, q,J=9.3), 4.84(2H,s), 5.05(2H,s), 6.83–6.88(2H,m), 6.96 (4H,s), 7.07–7.12(2H,m), 7.26(1H,dd,J=4.9, 3.9), 7.30–7.46 (4H,m), 7.71(1H,ddd,J=7.8, 2.0, 2.0), 8.32(1H,d,J=1.9), 8.52(1H,dd, J=4.9, 1.4); MS(ESI)m/z 529.0([M+H]+,100); Anal. Calcd. for $C_{27}H_{23}F_3N_2O_4S$ C,61.36; H,4.39; N,5.30. Found: C,61.32; H,4.44; N,5.31.

EXAMPLE 339

N-(4-(4-Hydroxyphenoxy)phenyl)-N-(2,2,2-trifluoroethanesulfonyl)pyrid-3-ylmethylamine

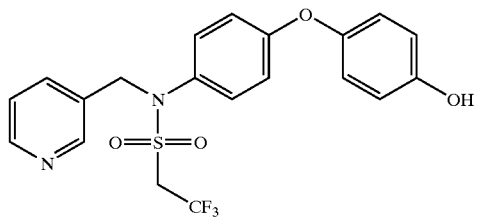

N-4-(4-Benzyloxyphenoxy)phenyl-N-(2,2,2-trifluoroethanesulfonyl)pyrid-3-ylmethylamine (3.0 g, 5.68 mmol) was dissolved in absolute ethanol/ethyl acetate (100 ml, 1/1) in a Parr® bottle. Raney nickel (approximately 1–1.5 tsp.) was added and the mixture hydrogenated at 40 psi on a shaker for twenty-two hours. After filtering to remove the catalyst, the filtrate was concentrated in vacuo to provide crude product as a white solid. Recrystallization from hot ethyl acetate/methanol (6/1) provided the title compound (1.9 g, 76%). $^1$H NMR(400 MHz, DMSO-d$_6$): 4.73(2H,q,J=10.3), 4.88(2H,s), 6.75–6.84(4H,m), 6.85–6.91 (2H,m), 7.23–7.29(2H,m), 7.34(1H,dd,J=7.8, 4.9), 7.67(1H, m), 8.38(1H,d,J=2.0), 8.45(1H,dd,J=4.9, 1.5), 9.4(1H,s); MS(ESI)m/z 439.1([M+H]+,100); Anal. Calcd. for $C_{20}H_{17}F_3N_2O_4{}_s$ C,54.79; H,3.91; N,6.39. Found: C,54.72; H,3.85; N,6.32.

Preparation 4

3-(2-Methoxyphenylsulfinyl)aniline

A solution of 3-fluoronitrobenzene (9.50 g, 67.3 mmol) and 2-methoxythiophenol (7.50 g, 53.5 mmol) in anhydrous DMF (40 mL) under nitrogen was treated with anhydrous potassium carbonate (14 g, 110 mmol), and heated to 115° C. for 18 h. The solution was cooled, filtered (solid rinsed with methylene chloride), and the filtrate concentrated exhaustively in vacuo under high vacuum to remove all DMF. The residue was taken up in water and extracted with ether (2×75 mL). The combined ether solution was dried (MgSO$_4$), filtered, the filtrate concentrated in vacuo and the residue chromatographed on silica gel (eluted with 2:1 hexane/methylene chloride) to afford 4.01 g (29%) of 2-methoxy-3'-nitrodiphenylsulfide as a viscous orange oil. $^1$H NMR: 3.82(3H,s), 6.95–7.00(2H,m), 7.35–7.45(4H,m), 7.95–8.00(2H,m).

2-Methoxy-3'-nitrodiphenylsulfide (332 mg, 1.27 mmol) was taken up in chloroform (1.5 ml) and treated with trichloroacetone (250 µl, 2.8 mmol), followed immediately by the addition of aqueous hydrogen peroxide (250 µl of 30%, 2.4 mmol). The reaction was stirred at room temperature for twenty-four hours and then partitioned between methylene chloride and aqueous sodium bisulfite. The organic layer was washed once with brine, dried over magnesium sulfate, filtered and concentrated to an oil. Purification by radial silica gel chromatography (4 mm Chromatotron® plate, eluting with 2/1 hexanes/ethyl acetate) afforded 1-methoxy-2-(3-nitrophenylsulfinyl) benzene (272 mg, 77%) as an oil which crystallized on standing. $^1$H NMR(400 MHz): 3.89(3H,s), 6.90(1H,d,J= 7.3), 7.18(1H,dt,J=7.8, 1.0), 7.41–7.47(1H,m), 7.63(1H,t, J=7.8), 7.89(1H,dd,J=7.8, 1.4), 8.07–8.12(1H,m), 8.22–8.28 (1H,m), 8.61(1H,m,); MS(ESI)m/z 276.8([M–H]–,70); Anal. Calcd. for $C_{13}H_{11}NO_4S$ C,56.31; H,4.00; N,5.05. Found: C,56.34; H,4.01; N,5.05.

1-Methoxy-2-(3-nitrophenylsulfinyl)benzene (217 mg, 0.78 mmol) was dissolved in ethyl alcohol (5.0 ml) and water (1.75 ml), to which was added iron powder (488 mg, 8.7 mmol) and ammonium chloride (77 mg, 1.4 mmol). This mixture was heated to reflux for four hours, cooled to room temperature and the supernatant decanted. The insoluble material was rinsed with methylene chloride, followed by aqueous 1M potassium carbonate. All decanted solutions were combined and the organic layer separated. The aqueous layer was extracted again with methylene chloride, and the combined organics washed once with brine. After drying over magnesium sulfate and concentration in vacuo, the title compound was obtained as a white solid (145 mg, 75%). $^1$H NMR(400 MHz): 3.89(3H,s), 6.69–6.74(1H,m), 6.86(1H,d, J=8.4), 7.03–7.09(2H,m), 7.10–7.20(2H,m), 7.38(1H,dt,J= 8.3, 1.5), 7.86(1H,dd,J=7.8, 1.5).

EXAMPLE 340

N-(3-(2-Methoxyphenylsulfinyl)phenyl)-N-(ethanesulfonyl)pyrid-3-ylmethylamine

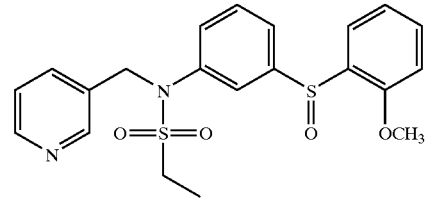

3-(1-Methoxyphenylsulfinyl)aniline (145 mg, 0.59 mmol) and pyridine-3-carboxaldehyde (63 mg, 0.59 mmol) were reacted in anhydrous methanol (3.0 ml), followed by treatment with sodium borohydride (44 mg, 1.17 mmol) as previously described (Intermediate 3). Silica gel chromatography (2 mm Chromatotron® plate, eluting with 20/1 ethyl acetate/hexanes) afforded N-(3-(2-methoxyphenylsulfinyl) phenyl)pyrid-3-ylmethylamine (162 mg, 82%) as an oil. $^1$H NMR(400 MHz): 3.77(3H,s), 4.35(2H,br s), 6.61(1H,m), 6.83(1H,d,J=8.0), 6.96(1H,br t), 7.01–7.04(1H,m), 7.11(1H, dt,J=7.8, 1.0), 7.18(1H,t,J=7.8), 7.21–7.28(1H,br s), 7.35–7.41(1H,m), 7.63(1H,br d), 7.82(2H,dd,J=7.8, 1.5), 8.40–8.80(2H,br s); MS(ESI)m/z 339.1([M+H]+,100)

N-(3-(2-Methoxyphenylsulfinyl)phenyl)pyrid-3-ylmethylamine (159 mg, 0.44 mmol) was taken up in 1,2-dichloroethane (2.0 ml) and anhydrous pyridine (1.0 ml) and cooled under nitrogen to 0° C. Ethanesulfonyl chloride (103 mg, 0.80 mmol) is added dropwise via syringe and the reaction allowed to stir at 0° C. for thirty minutes. The ice bath is removed and the mixture stirred 88 hours at room temperature, as a matter of convenience. Solid potassium carbonate was added, the reaction stirred an additional hour, and then filtered and concentrated to a dark oil. Radial silica gel chromatography (2 mm Chromatotron® plate, eluting with 20/1 methylene chloride/methanol) afforded the title compound (16 mg, 8%). $^1$H NMR(400 MHz): 1.39(3H,t,J=7.3), 3.04(2H,q,J=7.3), 3.78(3H,s), 4.88(2H,s), 6.86(1H,d,J=7.8), 7.11–7.21(2H,m), 7.25–7.30(1H,m), 7.35(1H,t,J=7.8), 7.42(1H,dt,J=7.3, 2.0), 7.56–7.62(2H,m), 7.68(1H,m), 7.81(1H,dd,J=7.3, 1.5), 8.31(1H,br s), 8.46(1H,br s); MS(HRMS)m/z 431.1116([M+H]+calcd for $C_{21}H_{23}N_2O_4S$ 431.1099).

Preparation 5

4-(2,4-Difluorophenoxy)aniline 1-(2,4-Difluorophenoxy)-4-nitrobenzene A biphasic mixture of potassium carbonate (304 g, 2.20 mol), 1-fluoro-4-nitrobenzene (148 mL, 1.40 mol) and 2,4-difluorophenol (200 g, 1.54 mol) in N,N-dimethylformamide (1.0 L) was heated at 90° C. under nitrogen for 22 h, after which the mixture was cooled to room temperature. The mixture was poured into water (1.0 L) and was extracted with ethyl acetate (2×1.5 L). The combined organic extracts were washed with water (1×1.0 L), dried over MgSO$_4$, filtered and the solvent was removed under reduced pressure to afford the crude product as a yellow semi-solid. This residue was triturated with hexanes (500 mL) and gravity filtered, washing with hexanes (2×100 mL) to provide 1-(2,4-difluorophenoxy)-4-nitrobenzene as off-white crystals (209 g, 60%), mp 58–62° C. $^1$H NMR(300 MHz, DMSO-d$_6$): 7.15(2H,d,J=9.4), 7.27–7.20(1H,m), 7.62–7.48(2H,m), 8.25 (2H,d,J=9.4).

A suspension of 1-(2,4-difluorophenoxy)-4-nitrobenzene (209 g, 1.17 mol) and 10% palladium-on-carbon (20 g, 50% wet) in methanol (1.0 L) was shaken under an atmosphere of hydrogen (60 psi) at room temperature for 5 h. The mixture was filtered through a plug of Celite® (150 g), washing with methanol (2×300 mL) and the solvent was removed under reduced pressure to afford the crude product as a dark red oil. This residue was triturated with hexanes (500 mL) and filtered to provide the title compound as a gray solid (175 g, 95%).$^1$H NMR(300 MHz, DMSO-d$_6$): 6.55(2H,d,J=8.8), 6.73(2H,d,J=8.8), 7.02–6.95(2H,m), 7.40(1H,t,J=11.4).

EXAMPLE 341

N-(4-(2,4-Difluorophenoxy)phenyl)-N-(2,2,2-trifluoroethanesulfonyl)pyrid-3-ylmethylamine

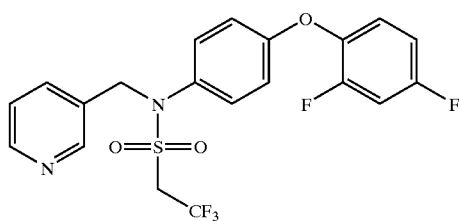

4-(2,4-Difluorophenoxy)aniline (2.21 g, 10.0 mmol) and pyridine-3-carboxaldehyde (1.12 g, 10.5 mmol) were dissolved in anhydrous methanol (35 ml) and the solution was heated at 55° C. for three hours. The solution was cooled and concentrated in vacuo to a residual oil, which was maintained under a 90 µm Hg vacuum for twenty-four hours. N-(4-(2,4-Difluorophenoxy)phenyl)pyrid-3-ylmethyleneamine was obtained in quantitative yield. $^1$H NMR(400 MHz): 6.83–6.90(1H,m), 6.93–7.00(3H,m), 7.05–7.13(1H,m), 7.21–7.27(2H,m), 7.40(1H,dd, J=8.1, 4.9), 8.27(1H,dd,J=8.1, 1.7), 8.50(1H,s), 8.69(1H,dd,J=4.9, 1.7), 9.00(1H,d,J=1.7); MS(ESI)m/z 311.1([M+H]+,100); Anal. Calcd. for $C_{18}H_{12}F_2N_2O$ C,69.67; H,3.90; N,9.03. Found: C,69.28; H,3.99; N,8.91.

N-(4-(2,4-Difluorophenoxy)phenyl)pyrid-3-ylmethyleneamine (205 mg, 0.66 mmol) was taken up in anhydrous methanol (3.0 ml) and was treated, at room temperature, with solid sodium borohydride (50 mg, 1.32 mmol) in one portion. There was an initial foaming and mild exotherm to 29 C, after which the mixture was stirred under ambient conditions for four hours. Aqueous 1N sodium hydroxide was added and the mixture extracted four times with methylene chloride. The combined organics were washed once with brine, dried over magnesium sulfate and the solvent removed in vacuo to provide N-4-(2,4-difluorophenoxy)phenylpyrid-3-ylmethylamine (200 mg, 97%) as a colorless oil which crystallized on standing. $^1$H NMR(400 MHZ): 4.34(2H,s), 6.56–6.62(2H,m), 6.73–6.80 (1H,m), 6.82–6.87(2H,m), 6.87–6.94(2H,m), 7.28(1H,dd,J=7.8, 2.9), 7.70(1H,ddd,J=7.8, 1.5, 1.5).

N-4-(2,4-Difluorophenoxy)phenylpyrid-3-ylmethylamine (184 mg, 0.59 mmol) was stirred in anhydrous acetonitrile (2.0 ml) under a nitrogen cover. The solution was treated, via syringe, with anhydrous triethylamine (99 µl, 0.71 mmol) and then cooled to −8° C. Trifluoroethanesulfonyl chloride (87 µl, 0.71 mmol) was added neat, dropwise via syringe, at such a rate that the reaction temperature did not exceed −3° C. The mixture was stirred for two hours at −8–(−2)° C. and then quenched with 1M potassium carbonate (3.0 ml). The upper layer was separated and the aqueous portion extracted three times with ethyl acetate. The combined organics were washed once with saturated sodium chloride, dried over magnesium sulfate and concentrated in vacuo to provide the crude product as a yellow solid. Radial silica gel chromatography (2 mm Chromatotron® plate, eluting with 1/1 hexanes/ethyl acetate) provided the title compound (193 mg, 71%) as an off-white solid. $^1$H NMR(400 MHz): 3.81(2H, q,J=9.0), 4.85(2H,s), 6.83–6.92(3H,m), 6.92–6.99(1H,m), 7.06–7.16(3H,m), 7.24–7.31(1H,m), 7.70(1H,ddd,J=9.5, 1.7, 1.7), 8.33(1H,br s), 8.53(1H,br s); MS(ESI)m/z 4549.1 ([M+H]+,100); Anal. Calcd. for $C_{20}H_{15}F_5N_2O_3S$ C,52.40; H,3.30; N,6.11. Found: C,52.13; H,3.28; N,5.99.

Preparation 6

(4-Bromophenyl)pyridin-3-ylmethylamine

A solution of 4-bromoaniline (Aldrich; 1.3 equiv.) in methanol (0.4 M) was treated with 3-pyridinecarboxaldehyde (Aldrich; 1.0 equiv.). The solution was heated to reflux for 2 hours. The reaction was cooled to 0° C. and treated slowly with sodium borohydride (3.4 equiv.). After 1 hour the cooling bath was removed and stirring continued overnight. The reaction was concentrated in vacuo. The residue was partitioned between DCM and water. The aqueous phase was back-extracted once with DCM. The combined organics were washed with water and brine. The organic layer was concentrated to a white solid, which was purified via recrystallization from 1.2:4 ethyl acetate/hexanes to give the title compound. Anal Calcd for $C_{12}H_{11}BrN_2.0.1H_2O$: C, 54.40; H, 4.26; N, 10.57. Found: C, 54.30; H, 4.12; N, 10.44. MS found 262.84, 264.83 [M+H]+.

EXAMPLE 342

N-(4-(2-Methoxyphenoxy)phenyl)-N-(2,2,2-trifluoroethanesulfonyl)pyrid-3-ylmethylamine

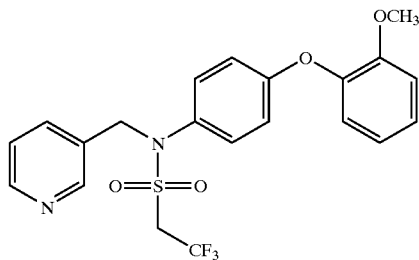

A solution of N—N-(4-bromophenyl)pyridin-3-ylmethylamine the (1.0 equiv.) in pyridine (0.9 M) was treated with the guaiacol (Aldrich) (3.0 equiv.) and anhydrous potassium carbonate (1.5 equiv.). The reaction was warmed to 90° C. then treated with cupric oxide. The mixture was heated to reflux for 48 hours. The reaction was cooled and diluted with ethyl acetate. The mixture was extracted with 10% aqueous ethylenediamine (3–6 times), 0.1 M potassium carbonate, and brine. The organic layer was dried over sodium sulfate, filtered, and concentrated. The reaction mixture was purified via preparative HPLC eluting with 70:30 to 60:40 DCM/ethyl acetate to give N-(4-(2-methoxyphenoxy)phenyl)pyridin-3-ylmethylamine. $^1$H NMR (400 MHz) 3.88 (3H, s), 4.33 (2H, s), 6.60 (2H, m), 6.79–6.89 (4H, m), 6.95–7.04 (2H, m), 7.23–7.29 (1H, m), 7.70 (1H, m), 8.53 (1H, m), 8.64 (1H, bs). MS found 307.0 [M+H]+

A solution of N-(4-(2-methoxyphenoxy)phenyl)pyridin-3-ylmethylamine (1.0 equiv.) in 2:1 DCE/Pyridine (0.15 M) was cooled to 0° C. and treated with 2,2,2-trifluoroethanesulfonyl chloride (1.8 equiv.). The mixture was allowed to warm to ambient temperature and stir overnight. The reaction was treated with anhydrous potassium carbonate, stirred for 40 min, and filtered. The filtrate was purified via preparative HPLC eluting with 98:2 to 96:4 DCM/MeOH to give the title compound. Anal Calcd for $C_{21}H_{19}F_3N_2O_4S$: C, 55.75; H, 4.23; N, 6.19. Found: C, 55.65; H, 4.27; N, 6.19. MS found 4.53.0 [M+H]+

EXAMPLE 343

N-(4-(3-Benzyloxyphenyl)-N-(2,2,2-trifluoroethanesulfonyl)pyrid-3-ylmethylamine

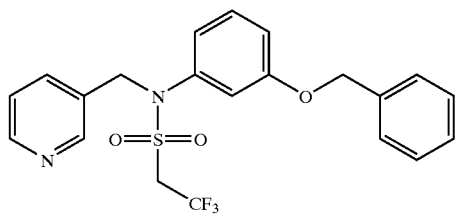

A solution of an 3-benzyloxyaniline (1.2 equiv.) in methanol (0.4 M) was treated with 3-pyridinecarboxaldehyde (1.0 equiv.). The solution was heated to reflux for 2.5 hours. The reaction was cooled to 0° C. and treated with sodium borohydride (2.5 equiv.) in 3 portions. The cooling bath was removed and stirring continued for 2 hours. The reaction was concentrated in vacuo. The residue was taken up in DCM and filtered through celite. The filtrate was concentrated in vacuo and purified via preparative HPLC eluting with 85:15 to 70:30 DCM/ethyl acetate to give N-(4-(3-benzyloxyphenyl)pyridin-3-ylmethylamine. Anal Calcd for $C_{19}H_{18}N_2O \cdot 0.1H_2O$: C, 78.11; H, 6.28; N, 9.59. Found: C, 77.86; H, 6.21; N, 9.56. MS found 291.1 (M+H)+

A solution of N-(4-(3-benzyloxyphenyl)pyridin-3-ylmethylamine (1.0 equiv.) in 2:1 DCE/Pyridine (0.15 M) was cooled to 0° C. and treated with 2,2,2-trifluoroethanesulfonyl chloride (1.8 equiv.). The mixture was allowed to warm to ambient temperature and stir overnight. The reaction was treated with anhydrous potassium carbonate, stirred for 40 min, and filtered. The filtrate was purified via preparative HPLC eluting with 70:30 to 60:40 DCM/ethyl acetate, evaporated, and then triturated with diethyl ether to give the title compound. Anal Calcd for $C_{21}H_{19}F_3N_2O_3S$: C, 57.79; H, 4.39; N, 6.42. Found: C, 57.60; H, 4.47; N, 6.41. $^1$H NMR (400 MHz) 3.77 (2H, q, J=9.0 Hz), 4.86 (2H, d), 4.99 (2H, d), 6.82 (2H, m), 6.95 (1H, m), 7.25 (2H, m), 7.34–7.40 (5H, m), 7.67 (1H, td, J=2.0, 8.0 Hz), 8.32 (1H, bs), 8.50 (1H, d, J=4.0 Hz). MS found 437.1 [M+H]+

Example 344

N-(4-(3-Hydroxyphenoxy)phenyl)-N-(2,2,2-trifluoroethanesulfonyl)pyrid-3-ylmethylamine

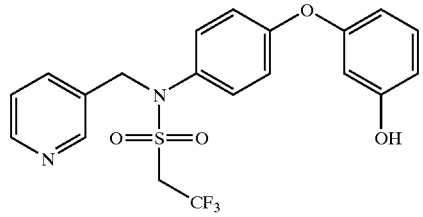

To a mixture of 2 N-4-(3-benzyloxyphenoxy)phenyl-N-(2,2,2-trifluoroethanesulfonyl)pyrid-3-ylmethylamine in ethanol (0.1 M) in a well-purged par bottle was added Raney® Nickel. The catalyst was rinsed into the mixture with ethyl acetate. The reaction was placed under 37 psi of hydrogen gas for 5 hours. The contents were filtered through celite and concentrated in vacuo to give the title compound. Anal Calcd for $C_{14}H_{13}F_3N_2O_3S \cdot 0.3H_2O$: C, 47.81; H, 3.90; N, 7.96. Found: C, 47.81; H, 3.80; N, 7.86. $^1$H NMR (400 MHz) 3.84 (2H, q, J=9.1 Hz), 4.88 (2H, s), 6.68 (1H, m), 6.72–6.78 (2H, m), 7.19 (1H, t, J=8.2 Hz), 7.34 (1H, dd, J=5.1, 7.9 Hz), 7.75 (1H, d, J=7.6 Hz), 8.30 (1H, s), 8.46 (1H, d, J=3.9 Hz). MS found 347 [M+]+

EXAMPLE 345

N-(4-t-Butyldimethylsilyloxy)phenyl)-N-(ethanesulfonyl)pyrid-3-ylmethylamine

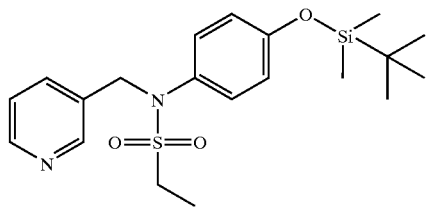

To a mixture of 4-aminophenol (Aldrich; 1.0 equiv.) in benzene (1 M) was added 3-pyridenecarboxaldehyde (Aldrich; 1.0 equiv.). The flask was fitted with a Dean-Stark trap and heated to reflux overnight. (A solid mass formed on the bottom of the flask, which was difficult to break up). The reaction was cooled to ambient and concentrated in vacuo. The solid was taken up in methanol (0.2 M), cooled to 0° C., and treated with sodium borohydride (1.5 equiv.) in 4 portions. The cooling bath was removed and stirring continued for 2 hours. A small amount of was added to quench unreacted hydride. The reaction was concentrated in vacuo. The residue was partitioned between ethyl acetate and water. The aqueous layer was back-extracted with ethyl acetate. The combined organics were washed with brine, dried over sodium sulfate, filtered, and concentrated. The crude solid was recrystallized from hexanes/ethyl acetate to give N-(4-hydroxyphenyl)pyridin-3-ylmethylamine. $^1$H NMR (400 MHz, DMSO d$_6$) 4.16 (2H, s), 6.41 (2H, m), 6.48 (2H, m), 7.28 (1H, ddd, J=0.73, 4.8, 7.7 Hz), 7.7 (1H, td, J=2.2, 7.3 Hz), 8.38 (1H, m), 8.39 (1H, s), 8.52 (1H, d, J=1.5 Hz).

Alternately, a solution of 4-aminophenol (1.0 equiv.) (Aldrich) in 2:1 methanol/ethanol was treated with 3-pyridinecarboxaldehyde (1.05 equiv.). The solution was allowed to stir for 1 hour. The reaction was cooled to 0° C. and treated with sodium borohydride (4.2 equiv.) in 5 portions. The cooling bath was removed and stirring continued for 20 hours. The reaction mixture was concentrated in vacuo. The residue was mixed with 1M HCl, warmed, and partitioned between ethyl acetate and 0.1M K$_2$CO$_3$. The pH of the aqueous phase was adjusted to pH=7 (using 1M HCl and 1M K$_2$CO$_3$) and the product extracted 4–6 times with ethyl acetate. The organic phases were combined, washed with brine, dried over anhydrous MgSO$_4$, and concentrated to afford N-(4-hydroxyphenyl)pyridin-3-ylmethylamine. $^1$H NMR(400 MHz, DMSO-d$_6$): d 4.18(2H, s), 5.65(1H, s), 6.41–6.53(4H, m), 7.29–7.32(1H, m), 7.70–7.72(1H, m), 8.39–8.40(2H, m), 8.53–8.54(1H, m). MS Found 201.2 [M+H]$^+$.

A solution of N-(4-hydroxyphenyl)pyridin-3-ylmethylamine (1.0 equiv.) in THF (0.1 M) was cooled to 0° C. and treated with imidazole (1.0 equiv.) and t-butyldimethylsilyl chloride (1.1 equiv.). The reaction was warmed to ambient temperature and stirred overnight. The THF was removed in vacuo. The residue was dissolved in ethyl acetate and washed with 0.1 N HCl, saturated aqueous NaHCO$_3$, water, and brine. The residue was purified via preparative HPLC eluting with 80:20 to 68:32 DCM/ethyl acetate to give N-(4-(t-butyldimethylsilyloxy)phenyl) pyridin-3-ylmethylamine. Anal Calcd for C$_{18}$H$_{26}$N$_2$OSi: C, 68.74; H, 8.33; N, 8.91. Found: C, 68.62; H, 8.28; N, 8.74. $^1$H NMR (400 MHz) 0.15 (6H, s), 0.96 (9H, s), 3.77 (1H, bs), 4.30 (2H, s), 6.53 (2H, m), 6.70 (2H, m), 7.26 (1H, m), 7.70 (1H, td, J=1.9, 7.7 Hz), 8.53(1H, dd, J=1.4, 4.6 Hz), 8.62 (1H, d, J=1.6 Hz). MS found 315.2 [M+H]+

Following the procedure of Example 342 using N-(4-(t-butyldimethylsilyloxy)phenyl)pyridin-3-ylmethylamine and ethanesulfonyl chloride (Aldrich) and purifying via preparative HPLC eluting with 90:10 to 82:18 DCM/ethyl acetate gave the title compound. Anal Calcd for C$_{20}$H$_3$0N$_2$O$_3$SSi: C, 59.08; H, 7.43; N, 6.89. Found: C, 58.87; H, 7.11; N, 6.85. MS found 407.2 [M+H]+

Example 346

N-(4-Hydroxyphenyl)-N-(ethanesulfonyl)pyrid-3-ylmethylamine

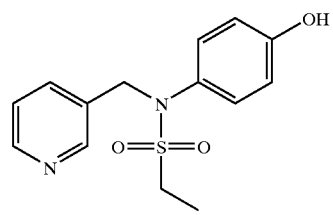

A mixture of N-((4-t-butyldimethylsilyloxy)phenyl)-N-(ethanesulfonyl)pyrid-3-ylmethylamine 4-aminophenol was added THF (0.5 M), water (0.5 M), and acetic acid (0.16 M) was heated to reflux for 3 days. The reaction was cooled to ambient temperature and concentrated in vacuo. The resultant solid was recrystallized from ethyl acetate to give the title compound. Anal Calcd for C$_{14}$H$_{16}$N$_2$O$_3$S: C, 57.52; H, 5.52; N, 9.58. Found: C, 57.25; H, 5.50; N, 9.48. MS found 293.1 [M+H]+

EXAMPLE 347

N-(4-t-Butyldimethylsilyloxy)phenyl)-N-(2,2,2-trifluoro ethanesulfonyl)pyrid-3-ylmethylamine

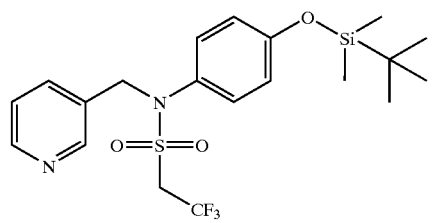

Following the procedure of Example 342 using N-(4-(t-butyldimethylsilyloxy)phenyl)pyridin-3-ylmethylamine and 2,2,2-trifluoroethanesulfonyl chloride (Aldrich) and purifying via preparative HPLC eluting with 92:8 to 86:14 DCM/ethyl acetate gave the title compound. Anal Calcd for C$_{20}$H$_{27}$F$_3$N$_2$O$_3$SSi: C, 52.15; H, 5.91; N, 6.08. Found: C, 52.10; H, 5.80; N, 6.01. $^1$H NMR (400 MHz) 0.18 (6H, s), 0.96 (9H, s), 3.80 (2H, q, J=9.2 Hz), 4.83, (2H, s), 6.77 (2H, m), 7.04 (2H, m), 7.24 (1H, dd, J=4.5, 7.4 Hz), 7.66 (1H, td, J=1.8, 8.0 Hz), 8.33 (1H, d, J=1.8 Hz), 8.51 (1H, dd, J=1.5, 4.8 Hz). MS found 461.1 [M+H]+

EXAMPLE 348

N-(4-Hydroxyphenyl)-N-(2,2,2-trifluoroethanesulfonyl)pyrid-3-ylmethylamine

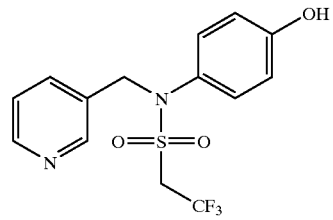

To N-(4-t-butyldimethylsilyloxy)phenyl-N-(2,2,2-trifluoro ethanesulfonyl)pyrid-3-ylmethylamine was added THF (0.5 M), water (0.5 M), and acetic acid (0.16 M). The solution was heated to reflux for 3 days. The reaction was cooled to ambient temperature and concentrated in vacuo. The resultant solid was recrystallized from ethyl acetate to give the title compound. $^1$H NMR (400 MHz) 3.82 (2H, q, J=8.8 Hz), 4.84 (2H, s), 6.73 (2H, m), 6.99 (2H, m), 7.43 (1H, dd, J=5.4, 7.3 Hz), 7.91 (1H, m), 8.22 (1H, bs), 8.52 (1H, m).

EXAMPLE 349

N-(4-(Phenoxy)phenyl)-N-(2,2,2-trifluoroethanesulfonyl)pyrid-3-ylmethylamine

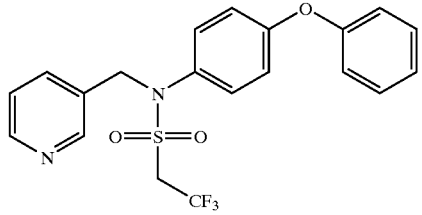

Using the method of Example 343 using 4-phenoxyaniline (Aldrich) and 3-pyridinecarboxaldehyde (Aldrich) and purifying via preparative HPLC eluting with 95:5 to 60:40 DCM/ethyl acetate gave N-(4-phenoxypheny)pyridin-3-ylmethylamine. Anal Calcd for $C_{18}H_{16}N_2O$: C, 78.24; H, 5.84; N, 10.14. Found: C, 78.19; H, 5.67; N, 10.03. $^1$H NMR (400 MHz, DMSO) 4.00 (1H, bt), 4.35 (2H, d, J=5.1 Hz), 6.62 (2H, m), 6.89–6.93 (4H, m), 6.99–7.03 (1H, m), 7.25–7.30 (3H, m), 7.71 (1H, m), 8.54 (1H, dd, J=1.8, 4.8 Hz), 8.64 (1H, d, J=1.8 Hz) MS found 277.0 [M+H]+

Using the method of Example 343 using N-(4-phenoxypheny)pyridin-3-ylmethylamine and 2,2,2-trifluoroethanesulfonyl chloride (Aldrich) and purifying via preparative HPLC eluting with 90:10 to 70:30 DCM/ethyl acetate gave the title compound. Anal Calcd for $C_{20}H_{17}F_3N_2O_3S$: C, 56.87; H, 4.06; N, 6.63. Found: C, 56.76; H, 4.09; N, 6.69. MS found 423.1 [M+H]+

EXAMPLE 350

N-(4-(Phenoxy)phenyl)-N-(2,2,2-trifluoroethanesulfonyl)-1-oxypyrid-3-ylmethylamine

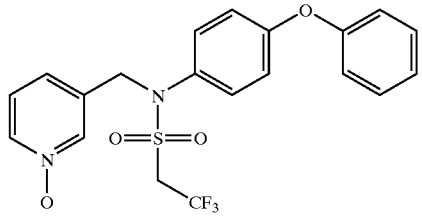

A solution of N-(4-(phenoxy)phenyl)-N-(2,2,2-trifluoroethanesulfonyl)-1-oxypyrid-3-ylmethylamine (1.0 equiv.) in DCM (0.1 M) was treated with mCPBA (55%; 1.1 equiv.; Lancaster). The resulting mixture was stirred at ambient temperature for 3 hours. The reaction was diluted with DCM, washed with saturated aqueous NaHCO3, and brine. The organic layer was dried over sodium sulfate, filtered, and concentrated. The residue was purified via preparative HPLC eluting with 96:4 DCM/MeOH to give the title compound. Anal Calcd for $C_{20}H_{17}F_3N_2O_4S$: C, 54.79; H, 3.91; N, 6.39. Found: C, 54.68; H, 3.78; N, 6.30. MS found 439.0 [M+H]+

EXAMPLE 351

N-(4-(2-Cyanophenoxy)phenyl)-N-(2,2,2-trifluoroethanesulfonyl)pyrid-3-ylmethylamine

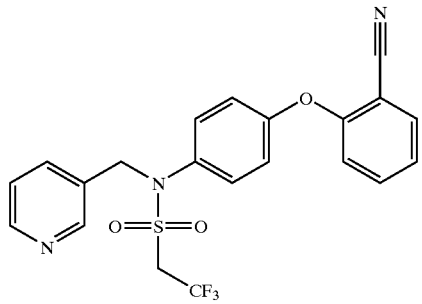

A solution of N-(4-hydroxyphenoxyphenyl)pyridin-3-ylmethylamine (1.0 equiv.) in DMF (0.15 M) was treated with sodium hydride (1.2 equiv.; as a 60% dispersion in oil). After stirring for 40 min., 2-fluorobenzonitrile (Aldrich; 1.7 equiv.) was added. After 2 hours the reddish reaction was diluted with ethyl acetate and washed with 0.25 M phosphate buffer, water, and brine. The organic phase was dried over $Na_2SO_4$, filtered, and concentrated. The oil was purified via radial chromatography eluting with 70:30 to 50:50 DCM/ethyl acetate to give N-(4-(2-cyanophenoxy)phenyl) pyridin-3-ylmethylamine. Anal Calcd for $C_{19}H_{15}N_3O\cdot0.2H_2O$: C, 74.83; H, 5.09; N, 13.78. Found: C, 74.86; H, 4.99; N, 13.97. $^1$H NMR (400 MHz) 4.10 (1H, bs), 4.38 (2H, s), 6.64 (2H, m), 6.77 (1H, d, J=8.3 Hz), 6.94 (2H, m), 7.04 (1H, t, J=7.3 Hz), 7.30 (1H, dd, J=4.9, 7.8 Hz), 7.41 (1H, m), 7.61 (1H, dd, J=1.5, 7.3 Hz), 7.72 (1H, d, J=7.8 Hz), 8.55 (1H, d, J=3.4 Hz), 8.65 (1H, d, J=1.5 Hz). MS found 302.1 [M+H]+

Using the method of Example 342 using N-(4-(2-cyanophenoxy)phenyl)pyridin-3-ylmethylamine and 2,2,2-trifluoroethanesulfonyl chloride (Aldrich) and purifying via preparative HPLC eluting with 90:10 to 78:22 DCM/ethyl acetate gave the title compound. Anal Calcd for $C_{21}H_{16}F_3N_3O_3S\cdot0.2H_2O$: C, 55.92; H, 3.67; N, 9.32. Found: C, 55.77; H, 3.51; N, 9.18. MS found 447.8 [M+H]+

EXAMPLE 352

N-(4-(2-Cyanophenoxy)phenyl)-N-(ethanesulfonyl)pyrid-3-ylmethylamine

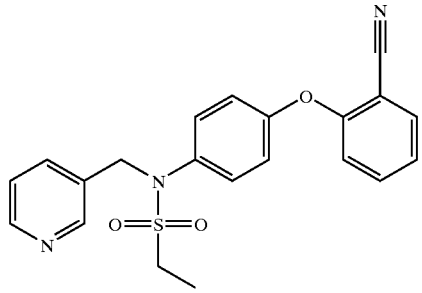

Using the method of Example 342 using N-(4-(2-cyanophenoxy)phenyl)pyridin-3-ylmethylamine and

Example 353

N-(3-(2-Methoxyphenoxy)phenyl)-N-(ethylsulfonyl) pyrid-3-ylmethylamine

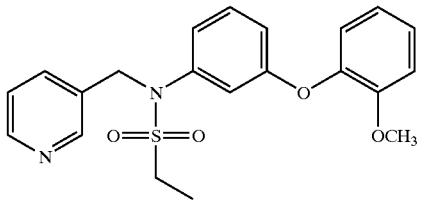

A solution of 3-bromoaniline (Aldrich; 1.3 equiv.) in methanol (0.4 M) was treated with 3-pyridinecarboxaldehyde (Aldrich; 1.0 equiv.). The solution was heated to reflux for 2 hours. The reaction was cooled to 0° C. and treated slowly with sodium borohydride (3.4 equiv.). After 1 hour the cooling bath was removed and stirring continued overnight. The reaction was concentrated in vacuo. The residue was partitioned between DCM and water. The aqueous phase was back-extracted once with DCM. The combined organics were washed with water and brine. The organic layer was concentrated to a white solid, which was purified via column chromatography eluting with 90:10 DCM/ethyl acetate to give N-(3-bromophenyl) pyridin-3-ylmethylamine. Anal Calcd for $C_{12}H_{11}BrN_2$: C, 54.77; H, 4.21; N, 10.64. Found: C, 54.67; H, 4.19; N, 10.57. MS found 262.99, 264.99 [M+H]+

Using the method of Example 342 using N-(3-bromophenyl)pyridin-3-ylmethylamine and guaiacol (Aldrich) and purifying via preparative HPLC eluting with 1:1 DCM/ethyl acetate gave N-(3-(2-Methoxyphenoxy)phenyl) pyrid-3-ylmethylamine. Anal Calcd for $C_{19}H_{18}N_2O_2 \cdot 0.5H_2O$: C, 72.36; H, 6.07; N, 8.88. Found: C, 72.43; H, 5.80; N, 8.96. MS found 307.2 [M+H]+

Using the method of Example 342 using N-(3-(2-methoxyphenoxy)phenyl)pyridin-3-ylmethylamine and ethanesulfonyl chloride (Aldrich) and purifying via preparative HPLC eluting with 98:2 to 96:4 DCM/MeOH gave the title compound. Anal Calcd for $C_{21}H_{22}N_2O_4S$: C, 63.30; H, 5.56; N, 7.03. Found: C, 63.16; H, 5.51; N, 6.64. MS found 398.9 [M+H]+

EXAMPLE 354

N-(3-(2-phenylphenoxy)phenyl)-N-(ethylsulfonyl) pyrid-3-ylmethylamine

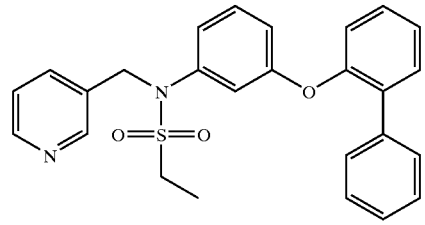

Using the procedure of Example 342 using N-(3-bromophenyl)pyridin-3-ylmethylamine and 2-phenylphenol (Aldrich) and purifying via preparative HPLC eluting with 90:10 to 80:20 DCM/ethyl acetate gave N-(3-(2-phenylphenoxy)phenyl)pyrid-3-ylmethylamine. Anal Calcd for $C_{24}H_{20}N_2O \cdot 0.2H_2O$: C, 80.96; H, 5.78; N, 7.87. Found: C, 81.07; H, 5.73; N, 7.63. MS found 353.1 [M+H]+

Using the procedure of Example 342 using N-(3-(2-phenylphenoxy)phenyl)pyrid-3-ylmethylamine and ethanesulfonyl chloride (Aldrich) and purifying via preparative HPLC eluting with 99:1 to 97:3 DCM/MeOH gave the title compound. Anal Calcd for $C_{26}H_{24}N_2O_3S$: C, 70.25; H, 5.44; N, 6.30. Found: C, 70.13; H, 5.39; N, 6.26. MS found 445.1 [M+H]+

EXAMPLE 355

N-(4-Bromophenyl)-N-(ethanesulfonyl)pyrid-3-ylmethylamine

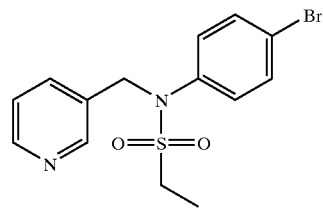

Using the procedure of Example 343 using N-(4-bromophenyl)pyridin-3-ylmethylamine and ethanesulfonyl chloride (Aldrich) and purifying via preparative HPLC eluting with 90:10 to 70:30 DCM/ethyl acetate gave the title compound. Anal Calcd for $C_{14}H_{15}BrN_2O_2S$: C, 47.33; H, 4.26; N, 7.88. Found: C, 47.24; H, 4.23; N, 7.79. MS found 354.0, 355.9 FD.

--- ethanesulfonyl chloride (Aldrich) and purifying via preparative HPLC eluting with 98:2 to 96:4 DCM/MeOH. Anal Calcd for $C_{21}H_{19}N_3O_3S \cdot 0.2H_2O$: C, 63.52; H, 4.92; N, 10.58. Found: C, 63.51; H, 4.79; N, 10.55. MS found 394.0 [M+H]+

EXAMPLE 356

N-(4-(2-Fluorophenoxy)phenyl)-N-(ethanesulfonyl)pyrid-3-ylmethylamine

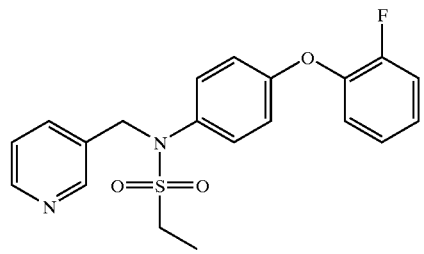

Using the method of Example 342 using N-(4-bromophenyl)pyridin-3-ylmethylamine and 2-fluorophenol (Aldrich) and purifying via preparative HPLC eluting with 90:10 to 80:20 DCM/ethyl acetate gave N-(4-(2-fluorophenoxy)phenyl)pyrid-3-ylmethylamine. Anal Calcd for $C_{18}H_{15}FN_2O$: C, 73.45; H, 5.14; N, 9.52. Found: C, 73.36; H, 5.22; N, 9.35. MS found 295.1 [M+H]+

Using the method of Example 342 using N-(4-(2-fluorophenoxy)phenyl)pyrid-3-ylmethylamine and ethanesulfonyl chloride (Aldrich) and purifying via preparative HPLC eluting with 99:1 to 97:3 DCM/MeOH gave the title compound. Anal Calcd for $C_{20}H_{19}FN_2O_3S \cdot 0.2H_2O$: C, 61.59; H, 5.01; N, 7.18. Found: C, 61.65; H, 4.85; N, 7.14. MS found 387.1 [M+H]+

By the method of Example 356 the following compounds were prepared and purified by preparative HPLC:

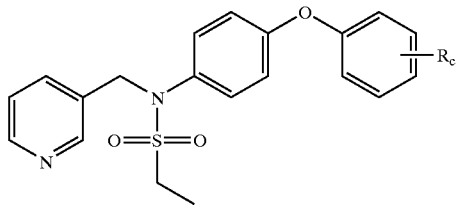

| No. | $R_1$' | $R_c$ | Data |
|---|---|---|---|
| 357 | H | 3-fluoro | Anal Calcd for $C_{18}H_{15}FN_2O \cdot 0.4H_2O$: C, 71.70; H, 5.28; N, 9.29. Found: C, 71.87; H, 5.04; N, 9.47. MS found 295.1 [M + H]+ |
| 358 | $SO_2CH_2CH_3$ | 3-fluoro | Anal Calcd for $C_{20}H_{19}FN_2O_3S$: C, 62.16; H, 4.96; N, 7.25. Found: C, 61.91; H, 4.95; N, 7.24. MS found 387.1 [M + H]+ |
| 359 | H | 4-fluoro | Anal Calcd for $C_{18}H_{15}FN_2O$: C, 73.45; H, 5.14; N, 9.52. Found: C, 73.23; H, 5.10; N, 9.32. MS found 295.1 [M + H]+ |
| 360 | $SO_2CH_2CH_3$ | 4-fluoro | Anal Calcd for $C_{20}H_{19}FN_2O_3S$: C, 62.16; H, 4.96; N, 7.25. Found: C, 62.18; H, 4.98; N, 7.15. MS found 387.2 [M + H]+ |

EXAMPLE 361

N-(4-(2,4-Difluorophenoxy)phenyl)-N-(ethanesulfonyl)pyrid-3-ylmethylamine

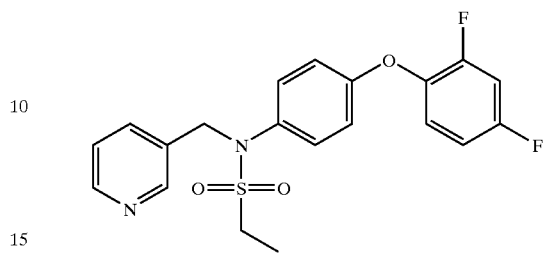

Using the method of Example 342 using N-(4-Bromophenyl)-N-(ethanesulfonyl)pyrid-3-ylmethylamine and 2,4-difluorophenol and purifying via reverse phase chromatography affording the HCl salt. Anal Calcd for $C_{20}H_{18}F_2N_2O_3S \cdot 1.2HCl$: C, 53.60; H, 4.32; N, 6.25. Found: C, 53.55; H, 4.18; N, 6.23. MS found 405.1 [M+H]+

By the method of Example 342 the following compounds were prepared and purified via reverse phase chromatography affording the HCl salt, except where noted:

| No. | Rc | Data |
|---|---|---|
| 362 | 2-trifluoromethoxy | Anal Calcd for $C_{21}H_{19}F_3N_2O_4S \cdot 1.2HCl$: C, 50.83; H, 4.10; N, 5.65. Found: C, 50.66; H, 3.79; N, 5.62. MS found 453.0 [M + H]+ |
| 363 | 4-trifluoromethoxy | Anal Calcd for $C_{21}H_{19}F_3N_2O_4S$: C, 55.75; H, 4.23; N, 6.19. Found: C, 55.60; H, 4.26; N, 6.16. MS found 453.1 [M + H]+ (analysis on free-base) |
| 364 | 4-fluoro-2-methyl | Anal Calcd for $C_{21}H_{21}FN_2O_3S$: C, 62.98; H, 5.28; N, 7.00. Found: C, 62.76; H, 5.28; N, 6.95. MS found 401.1 [M + H]+ (analysis on free-base) |
| 365 | 2,4-dimethyl | Anal Calcd for $C_{22}H_{24}N_2O_3S \cdot H_2O \cdot HCl$: C, 58.59; H, 6.03; N, 6.21. Found: C, 58.34; H, 5.67; N, 6.23. MS found 397.0 [M + H]+ |
| 366 | 4-methyl | Anal Calcd for $C_{21}H_{22}N_2O_3S \cdot 0.5H_2O$: C, 64.43; H, 5.92; N, 7.16. Found: C, 64.19; H, 5.52; N, 7.03. HRMS calculated 383.1429 [M + H]+ Found 383.1428 (analysis on free-base) |
| 367 | 4-isopropyl | Anal Calcd for $C_{23}H_{26}N_2O_3S \cdot 0.1H_2O$: C, 67.00; H, 6.40; N, 6.79. Found: C, 66.87; H, 6.27; N, 6.78. MS found 411.1 [M + H]+ (analysis on free-base) |
| 368 | 4-t-butyl | Anal Calcd for $C_{24}H_{28}N_2O_3S$: C, 67.90; H, 6.65; N, 6.60. Found: C, 68.02; H, 6.63; N, 6.57. MS found 425.1 [M + H]+ (analysis on free-base) |
| 369 | 2-methyl | Anal Calcd for $C_{21}H_{22}N_2O_3S \cdot 0.3H_2O$: C, 65.03; H, 5.87; N, 7.22. Found: C, 64.94; H, 5.73; N, 7.14. MS found 383.1 [M + H]+ (analysis on free-base) |

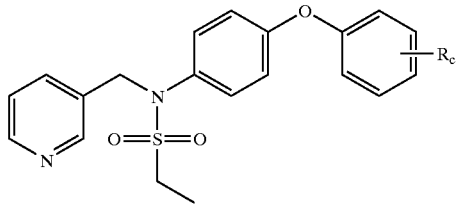

| No. | Rc | Data |
|---|---|---|
| 370 | 2-C(O)NH$_2$ | Anal Calcd for C$_{21}$H$_{21}$N$_3$O$_4$S: C, 61.30; H, 5.14; N, 10.21. Found: C, 61.16; H, 4.89; N, 9.95. MS found 412.1 [M + H]+ (analysis on free-base) |
| 372 | 2-S(O)CH$_3$ | Anal Calcd for C$_{21}$H$_{22}$N$_2$O$_4$S$_2$•0.5H$_2$O: C, 57.38; H, 5.27; N, 6.37. Found: C, 57.31; H, 5.32; N, 5.98. MS found 431.1 [M + H]+ (purified by radial chromatography eluting with 60:40 to 90:10 THF/hexanes) |
| 373 | 4-t-butyl-2-fluoro | Anal Calcd for C$_{24}$H$_{27}$FN$_2$O$_3$S•0.2H$_2$O: C, 64.61; H, 6.19; N, 6.28. Found: C, 64.28; H, 5.83; N, 6.19. MS found 443.3 [M + H]+ (purified via radial chromatography eluting with 50:50 to 70:30 THF/hexanes) |
| 374 | 4-fluoro-2-n-propyl | $^1$H NMR (400MHz) 0.89(3H, t, J=7.3Hz), 1.44(3H, t, J=7.3Hz), 1.56(2H, sextet, J=7.8Hz), 2.48(2H, t, J=7.8Hz), 3.10(2H, q, J=7.3Hz), 4.85(2H, s), 6.78(2H, m), 6.85(2H, m), 6.94(1H, m), 7.13(2H, m), 7.32(1H, bs), 7.79(1H, d, J=7.8Hz), 8.4(1H, bs), 8.55(1H, bs). HRMS calculated 429.1648 [M + H]+ Found 429.1656 (analysis of free-base) |
| 375 | 4-C(O)OCH$_3$ | $^1$H NMR (400MHz, DMSO-d$_6$) 1.28(3H, t, J=7.3Hz), 3.26(2H, q, J=7.3Hz), 3.80(3H, s), 4.96(2H, s), 7.00–7.05(4H, m), 7.40(2H, m), 7.56(1H, bs), 7.86(1H, d, J=7.8Hz), 7.93(2H, m), 2 protons alpha to the pyridyl N broadened into the baseline. HRMS calculated 427.1328 [M + H]+ Found 427.1338 |
| 376 | 4-CH$_2$C(O)NH$_2$ | Anal Calcd for C$_{22}$H$_{23}$N$_3$O$_4$S: C, 53.40; H, 5.07; N, 8.49. Found: C, 53.50; H, 4.90; N, 8.46. MS found 426.0 [M + H]+ (analysis on free-base) |
| 377 | 3-t-butyl | Anal Calcd for C$_{24}$H$_{28}$N$_2$O$_3$S: C, 67.90; H, 6.65; N, 6.60. Found: C, 68.02; H, 6.34; N, 6.49. MS found 425.1 [M + H]+ purified by radial chromatography eluting with 50:50 hexanes/THF |
| 378 | 2-methoxy | Anal Calcd for C$_{21}$H$_{22}$N$_2$O$_4$S: C, 63.30; H, 5.56; N, 7.03. Found: C, 63.25; 11, 5.59; N, 7.02. MS found 399.1 [M + H]+ (purified via radial chromatography eluting with 50:50 hexanes/THF) |
| 379 | 3-methyl | Anal Calcd for C$_{21}$H$_{22}$N$_2$O$_3$S: C, 65.95; H, 5.80; N, 7.32. Found: C, 65.55; H, 5.64; N, 7.21. MS found 383.1 [M + H]+ (analysis on free-base) |
| 380 | 2-chloro | Anal Calcd for C$_{20}$H$_{19}$ClN$_2$O$_3$S: C, 59.62; H, 4.75; N, 6.95. Found: C, 59.63; H, 4.61; N, 6.88. MS found 403.1 [M + H]+ (purified via radial chromatography eluting with 60:40 to 50:50 hexanes/THF) |
| 381 | 4-C(O)HN$_2$ | Anal Calcd for C$_{21}$H$_{21}$N$_3$O$_4$S•1.1HCl•1H$_2$O: C, 53.71; H, 5.17; N, 8.95. Found: C, 53.65; H, 4.79; N, 8.39. MS found 412.1 [M + H]+ |
| 382 | 2-methyl | Anal Calcd for C$_{21}$H$_{22}$N$_2$O$_3$S•0.3H$_2$O: C, 65.03; H, 5.87; N, 7.22. Found: C, 64.94; H, 5.73; N, 7.14. MS found 383.1 [M + H]+. (isolated as the free-base) |
| 383 | 4-S(O)$_2$CH$_3$ | Anal Calcd for C$_{21}$H$_{22}$N$_2$O$_5$S$_2$: C, 56.48; H, 4.96; N, 6.27. Found: C, 56.33; H, 5.03; N, 6.20. MS found 447.1 [M + H]+ (purified via radial chromatography eluting with 50:50 to 70:30 THF/hexanes) |

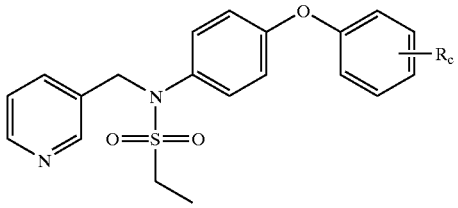

| No. | Rc | Data |
|---|---|---|
| 384 | 2-(prop-2-yl) | Anal Calcd for C$_{23}$H$_{26}$N$_2$O$_3$S: C, 67.29; H, 6.38; N, 6.82. Found: C, 66.91; H, 6.30; N, 6.68. MS found 411.2 [M + H]+ (purified via normal phase radial chromatography eluting with 1:1 THF/hexanes) |
| 385 | 2-ethyl | Anal Calcd for C$_{22}$H$_{24}$N$_2$O$_3$S: C, 66.64; H, 6.10; N, 7.07. Found: C, 66.49; H, 6.02; N, 6.87. MS found 397.2 [M + H]+ (purified via flash chromatography eluting with 1:1 ethyl acetate/hexanes to 100% ethyl acetate) |
| 386 | 4-S(O)$_2$NH$_2$ | Anal Calcd for C$_{20}$H$_{21}$N$_3$O$_5$S$_2$: C, 53.68; H, 4.73; N, 9.39. Found: C, 53.29; H, 4.70; N, 9.29. MS found 448.1 [M + H]+ (purified via normal phase radial chromatography eluting with 5% (methanol/7M ammonia)/dichloromethane) |

EXAMPLE 387

N-(4-(2,4-Difluorophenoxy)phenyl)-N-(ethanesulfonyl)-1-pyrid-3-ylethylamine

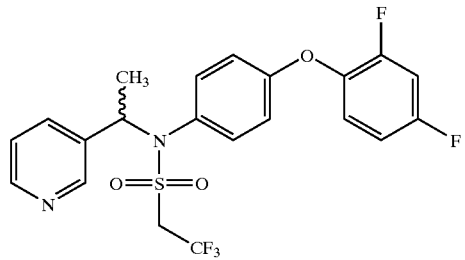

A solution of N-(4-(2,4-difluorophenoxy)phenyl)amine (1.0 equiv.) in dichloromethane (0.2 M) was cooled to 0° C. and treated with 3-acetylpyridine (Aldrich; 1.4 equiv.), acetic acid (5.0 equiv.), and sodium triacetoxyborohydride (2.5 equiv.). The reaction was allowed to warm to ambient temperature and stirred an additional 22 hours. The reaction was cautiously quenched with saturated aqueous NaHCO$_3$ then adjusted to pH=10 with 1 N NaOH. The mixture was stirred for 4 hours then the layers were separated. The aqueous layer was extracted twice with DCM. The combined organics were washed with brine, dried over sodium sulfate, filtered, and concentrated. The crude material was purified via radial chromatography eluting with 50:50 to 60:40 ethyl acetate/hexanes to give N-(4-(2,4-difluorophenoxy)phenyl)-1-pyrid-3-ylethylamine. $^1$H NMR (400 MHz) 1.54 (3H, d, J=6.7 Hz), 3.96 (1H, bs), 4.48 (1H, q, J=6.7 Hz), 6.44 (2H, m), 6.76 (2H, m), 6.83–6.93 (2H, m), 7.24 (1H, m), 7.44 (1H, m), 7.68 (1H, td, J=1.8, 7.9 Hz), 8.50 (1H, d, J=3.8 Hz), 8.64 (1H, bs). HRMS calcd 327.1309. Found 327.1308.

Using the method of Example 342 using N-(4-(2,4-difluorophenoxy)phenyl)-1-pyrid-3-ylethylamine and 2,2,2- trifluoroethanesulfonyl chloride and purifying via radial chromatography eluting with 95:5 to 85:15 CHCl$_3$/ethyl acetate gave the title compound. Anal Calcd for C$_{21}$H$_{17}$F$_5$N$_2$O$_3$S.0.2H$_2$O: C, 52.98; H, 3.68; N, 5.89. Found: C, 52.88; H, 3.73; N, 5.67. MS found 473.1 [M+H]+

EXAMPLE 388

N-((3-Benzyloxyphenoxy)phenyl)-N-(ethanesulfonyl)pyrid-3-ylmethylamine

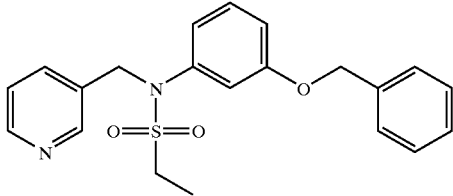

Using the method of Example 342 using (3-benzyloxyphenyl)pyridin-3-ylmethylamine and ethanesulfonyl chloride and purifying via preparative HPLC eluting with 90:10 to 75:25 DCM/ethyl acetate gave, after trituration with diethyl ether, the title compound. Anal Calcd for C$_{21}$H$_{22}$N$_2$O$_3$S: C, 65.95; H, 5.80; N, 7.32. Found: C, 65.85; H, 5.75; N, 7.38. MS found 383.1 [M+H]+

Preparation 7

2-(3-Hydroxy-3-methyl)butyl-4-fluorophenol

A solution of 6-fluoro-2,2-dimethyl-chroman-4-one (EP 193493; 1 equiv.) in ethanol (0.24 M) was treated with copper chromite (0.6 equiv.). The reaction was heated to 200° C. for 6 hours at 3000 psi of hydrogen gas. The reaction was filtered and concentrated to a solid. The crude material was recrystallized form hot hexanes to give the title compound. MS found 198 [M+H]+

EXAMPLE 389

N-(3-(Bromophenyl)-N-(ethylsulfonyl)pyrid-3-ylmethylamine

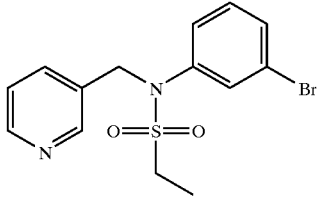

Using the method of Example 342 using (3-bromophenyl)pyridin-3-ylmethylamine and ethanesulfonyl chloride and purifying via preparative HPLC eluting with 90:10 to 70:30 DCM/ethyl acetate gave the title compound. Anal Calcd for C$_{14}$H$_{15}$BrN$_2$O$_2$S: C, 47.33; H, 4.26; N, 7.88. Found: C, 47.07; H, 4.05; N, 7.67. MS found 354.9, 356.9 [M+H]+.

By the method of Example 342 using N-(3-(bromophenyl)-N-(ethylsulfonyl)pyrid-3-ylmethylamine the following compounds were prepared and purified via reverse phase chromatography and isolated as the free-base, except where noted:

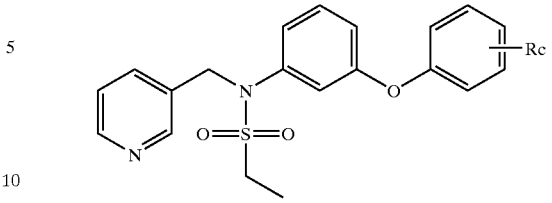

| No. | Rc | Data |
|---|---|---|
| 390 | 2-fluoro | Anal Calcd for C$_{20}$H$_{19}$FN$_2$O$_3$S: C, 62.16; H, 4.96; N, 7.25. Found: C, 61.85; H, 4.92; N, 7.02. MS found 387.1 [M + H]+ |
| 391 | 3-fluoro | Anal Calcd for C$_{20}$H$_{19}$FN$_2$O$_3$S: C, 62.16; H, 4.96; N, 7.25. Found: C, 61.84; H, 5.00; N, 7.13. MS found 387.1 [M + H]+ |
| 392 | 4-fluoro | Anal Calcd for C$_{20}$H$_{19}$FN$_2$O$_3$S: C, 62.16; H, 4.96; N, 7.25. Found: C, 62.02; H, 4.70; N, 7.23. MS found 387.1 [M + H]+ |
| 393 | 2,4-difluoro | Anal Calcd for C$_{20}$H$_{17}$F$_3$N$_2$O$_3$S: C, 56.87; H, 4.06; N, 6.63. Found: C, 56.93; H, 4.00; N, 6.43. MS found 423.0 [M + H]+ |
| 394 | 2-ethoxy | Anal Calcd for C$_{22}$H$_{24}$N$_2$O$_4$S: C, 64.06; H, 5.86; N, 6.79. Found: C, 64.10; H, 5.61; N, 6.75. MS found 413.0 [M + H]+ |
| 395 | 2-phenyl | Anal Calcd for C$_{26}$H$_{24}$N$_2$O$_3$S: C, 70.25; H, 5.44; N, 6.30. Found: C, 70.43; H, 5.35; N, 6.18. MS found 445.1 [M + H]+ |
| 396 | 4-trifluoromethoxy | Anal Calcd for C$_{21}$H$_{19}$F$_3$N$_2$O$_4$S: C, 55.75; H, 4.23; N, 6.19. Found: C, 55.46; H, 4.20; N, 6.10. MS found 453.0 [M + H]+ |
| 397 | 4-methyl | $^1$H NMR (400MHz) 1.42(3H, t, J=7.3Hz), 2.34(3H, s), 3.10(2H, q, J=7.3Hz), 4.85(2H, s), 6.83(4H, m), 6.95(1H, m), 7.13(2H, m), 7.23(2H, m), 7.70(1H, d, J=7.8Hz), 8.37(1H, bs), 8.51(1H, bs). HRMS calculated 383.1429 [M + H]+ Found 383.1426. |
| 398 | 2-methyl-4-fluoro | $^1$H NMR (400MHz) 1.42(3H, t, J=7.3Hz), 2.09(3H, s), 3.11(2H, q, J=7.3Hz), 4.84(2H, s), 6.68–6.95(6H, m), 7.22(2H, m), 7.69(1H, d, J=7.8Hz), 8.33(1H, bs), 8.51(1H, bs). HRMS calculated 401.1335 [M + H]+Found 401.1327. |
| 399 | 2-trifluoromethoxy | Anal Calcd for C$_{21}$H$_{19}$F$_3$N$_2$O$_4$S: C, 55.75; H, 4.23; N, 6.19. Found: C, 55.60; H, 4.12; N, 6.05. MS found 453.1 [M + H]+ |
| 400 | 4-CH$_2$C(O)NH$_2$ | Anal Calcd for C$_{22}$H$_{23}$N$_3$O$_4$S•0.5H$_2$O: C, 60.81; H, 5.27; N, 9.67. Found: C, 60.69; H, 5.27; N, 9.48. MS found 426.1 [M + H]+ |
| 401 | 4-C(O)NH$_2$ | Anal Calcd for C$_{21}$H$_{21}$N$_3$O$_4$S•2.1HCl•1.1H$_2$O: C, 49.66; H, 5.02; N, 8.27. Found: C, 49.67; H, 4.92; N, 8.11. MS found 412.1 [M + H]+ (isolated as the HCl salt) |
| 402 | 4-S(O)$_2$CH$_3$ | Anal Calcd for C$_{21}$H$_{22}$N$_2$O$_5$S$_2$•0.2H$_2$O: C, 56.03; H, 5.02; N, 6.22. Found: C, 56.02; H, 4.78; N, 6.12. MS found 447.1 [M + H]+ (purified via radial chromatography eluting with 50:50 to 70:30 THF/hexanes) |
| 403 | 2-S(O)CH$_3$ | Anal Calcd for C$_{21}$H$_{22}$N$_2$O$_4$S$_2$•0.4H$_2$O: C, 57.62; H, 5.25; N, 6.40. Found: C, 57.62; H, 5.25; N, 6.24. HRMS calculated 431.1099 [M + H]+ Found 431.1114 (purified via radial chromatography eluting with 50:50 to 70:30 THF/hexanes) |
| 404 | 4-t-butyl | $^1$H NMR (400MHz) 1.33(9H, s), 1.42(3H, t, J=7.8Hz), 3.11(2H, q, J=7.8Hz), 4.87(2H, s), 6.83–6.97(5H, m), 7.22–7.36(4H, m), 7.76(1H, d, J=7.8Hz), 8.38(1H, bs), 8.53(1H, bs). HRMS calculated 425.1899 [M + H]+ Found 425.1906 (purified via radial chromatography eluting with 50:50 hexanes/THF) |
| 405 | 3-methyl | Anal Calcd for C$_{21}$H$_{22}$N$_2$O$_3$S: C, 65.95; 11, 5.80; N, 7.32. Found: C, 66.09; H, 5.86; N, 7.29. MS found 383.1 [M + H]+ |

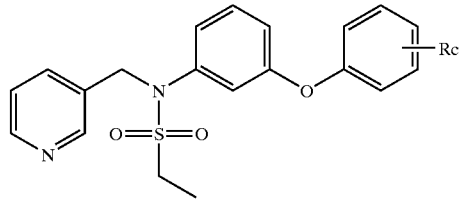

| No. | Rc | Data |
|---|---|---|
| 406 | 2-n-propyl-4-fluoro | Anal Calcd for $C_{23}H_{25}FN_2O_3S$: C, 64.47; H, 5.88; N, 6.54. fluoro Found: C, 64.31; H, 5.79; N, 6.45. MS found 429.1 [M + H]+ |
| 407 | 2-chloro | $^1$H NMR (400MHz) 1.42(3H, t, J=7.3Hz), 3.11(2H, q, J=7.3Hz), 4.86(2H, s), 6.8–6.92(3H, m), 7.00(1H, dd, J=2.0, 7.8Hz), 7.12(1H, dt, J=2.0, 7.8Hz), 7.21–7.28(3H, m), 7.45(1H, dd, J=2.0, 8.3Hz), 7.68(1H, d, J=7.8Hz), 8.36(1H, bs), 8.50(1H, bs). HRMS calculated 403.0883 [M + H]+ Found 403.0896 (purified via radial chromatography eluting with 60:40 to 50:50 hexanes/THF) |
| 408 | 2-methyl | $^1$H NMR (400MHz) 1.42(3H, t, J=7.3Hz), 2.13(3H, s), 3.11(2H, q, J=7.3Hz), 4.84(2H, s), 6.74–6.80(3H, m), 6.93–6.95 (1H, m), 7.07–7.24(5H, m), 7.68(1H, td, J=2.0, 7.8Hz), 8.34(1H, bs), 8.50(1H, d, J=3.4Hz). HRMS calculated 383.1429 [M + H]+ Found 383.1429 (purified via radial chromatography eluting with 60:40 to 50:50 hexanes/THE) |
| 409 | H | Anal Calcd for $C_{20}H_{20}N_2O_3S$: C, 65.20; H, 5.47; N, 7.60. Found: C, 64.86; H, 5.25; N, 7.26. MS found 369.1 [M + H]+ (purified via radial chromatography eluting with 60:40 to 50:50 hexanes/THF) |
| 410 | 4-C(O)OCH$_3$ | Anal Calcd for $C_{22}H_{22}N_2O_5S \cdot 1HCl$: C, 57.07; H, 5.01; N, 6.05. Found: C, 56.73; H, 5.01; N, 6.01. MS found 427.1 [M + H]+ (isolated as the HCl salt) |
| 411 | 3-t-butyl | Anal Calcd for $C_{24}H_{28}N_2O_3S$: C, 67.90; H, 6.65; N, 6.60. Found: C, 68.17; H, 6.45; N, 6.51. MS found 425.2 [M + H]+ (purified via radial chromatography eluting with 60:40 to 50:50 hexanes/THF) |
| 412 | 4-fluoro-2-(3-hydroxy-3-methylbutyl) | Anal Calcd for $C_{25}H_{29}FN_2O_4S$: C, 63.54; H, 6.18; N, 5.93. Found: C, 63.16; H, 6.05; N, 5.84. MS found 473.2 [M + H]+ |
| 413 | 2-fluoro-4-t-butyl | Anal Calcd for $C_{24}H_{27}FN_2O_3S$: C, 65.14; H, 6.15; N, 6.33. Found: C, 65.28; H, 6.24; N, 6.30. MS found 442.1 (FD). (purified via radial chromatography eluting with 50:50 to 70:30 THF/hexanes) |
| 414 | 4-CH$_2$CO$_2$CH$_3$ | Anal Calcd for $C_{23}H_{24}N_2O_5S \cdot 0.5H_2O$: C, 61.45; H, 5.61; N, 6.23. Found: C, 61.43; H, 5.43; N, 6.45. MS found 441.1 [M + H]+ (purified via radial chromatography eluting with 50:50 to 75:25 THF/hexanes) |
| 415 | 3-C(O)NH$_2$ | $^1$H NMR (400MHz) 1.44(3H, t, J=7.3Hz), 3.13(2H, q, J=7.8Hz), 4.87(2H, s), 5.7(1H, bs), 6.74(1H, bs), 6.86(1H, t, J=2.0Hz), 6.96(1H, m), 7.06(1H, m), 7.12(1H, ddd, J=0.98, 2.4, 8.3Hz), 7.28(2H, m), 7.33(1H, t, J=7.8Hz), 7.43(1H, t, J=7.8Hz), 7.60(1H, m), 7.72(1H, d, J=7.8Hz), 8.32(1H, bs), 8.48(1H, bs). HRMS calculated 412.1331 [M + H]+ Found 412.1329 (purified via radial chromatography eluting with 60:40 to 70:30 THF/hexanes) |
| 416 | 2,4-difluro | Anal Calcd for $C_{20}H_{18}F_2N_2O_3S \cdot 0.1DCM$: C, 58.46; H, 4.44; N, 6.78. Found: C, 58.65; H, 4.19; N, 6.59. HRMS calcd 405.1084. Found 405.1083 [M + H]+ |

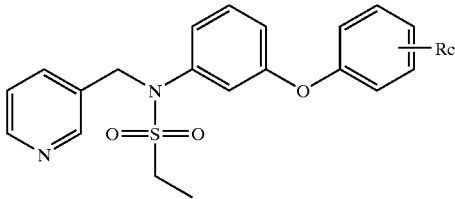

| No. | Rc | Data |
|---|---|---|
| 417 | 4-CH$_2$CO$_2$CH$_3$ | Anal Calcd for $C_{23}H_{24}N_2O_5S \cdot 0.5H_2O$: C, 61.45; H, 5.61; N, 6.23. Found: C, 61.43; H, 5.43; N, 6.45. MS found 441.1 [M + H]+ (purified via radial chromatography eluting with 50:50 to 75:25 THF/hexanes) |
| 418 | 2,4,6-trifluro | Anal Calcd for $C_{20}H_{17}F_3N_2O_3S$: C, 56.87; H, 4.06; N, 6.63. Found: C, 56.93; H, 4.00; N, 6.43. MS found 423.0 [M + H]+ |
| 419 | 2-(prop-2-yl) | Anal Calcd for $C_{23}H_{26}N_2O_3S$: C, 67.29; H, 6.38; N, 6.82. Found: C, 67.37; H, 6.25; N, 6.66. MS found 411.2 [M + H]+ (purified via normal phase radial chromatography eluting with 1:1 THF/hexanes) |
| 420 | 2-ethyl | Anal Calcd for $C_{22}H_{24}N_2O_3S$: C, 66.64; H, 6.10; N, 7.07. Found: C, 66.72; H, 6.09; N, 6.88. MS found 397.2 [M + H]+ (purified via flash chromatography eluting with 1:1 ethyl acetate/hexanes to 100% ethyl acetate) |
| 421 | 4-S(O)$_2$NH$_2$ | Anal Calcd for $C_{20}H_{21}N_3O_5S_2 \cdot HCl$: C, 49.63; H, 4.58; N, 8.68. Found: C, 49.58; H, 4.42; N, 8.43. MS found 448.1 [M + H]+ (isolate as the HCl salt from reverse phase chromatography) |

EXAMPLE 422

N-(4-(3-Methoxybenzyloxy)phenyl)-N-(ethanesulfonyl)pyrid-3-ylmethylamine

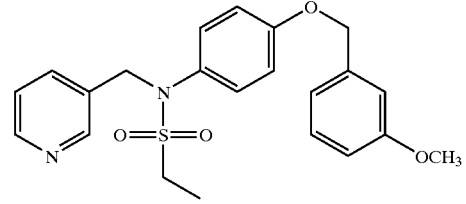

A solution of N-(4-(4-hydroxyphenyl)-N-(ethanesulfonyl) pyrid-3-ylmethylamine (1.0 equiv.) in DMSO (0.15 M) was cooled to 0° C. Sodium hydride (1.1 equiv.; 60% dispersion in oil) was added; after 20 minutes at 0° C. 3-methoxybenzyl bromide (Aldrich; 1.3 equiv.) was added and the reaction warmed to ambient temperature. After stirring overnight the reaction was diluted with ethyl acetate and washed with 0.1 M potassium carbonate, and brine. The organic layer was dried over sodium sulfate, filtered, and concentrated in vacuo. The residue was purified via preparative HPLC eluting with 90:10 to 70:30 DCM/ethyl acetate to give the title compound. Anal Calcd for $C_{22}H_{24}N_2O_4S \cdot 0.1H_2O$: C, 64.06; H, 5.86; N, 6.79. Found: C, 63.78; H, 5.89; N, 6.76. MS found 413.0 [M+H]+.

EXAMPLE 443

N-(3-(2-Fluorophenoxy)phenyl)-N-(2,2,2-trifluorethanesulfonyl)pyrid-3-ylmethylamine

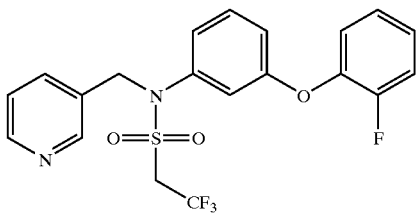

Using the method of Example 342 using N-(3-(2-fluorophenoxy)phenyl)pyridin-3-ylmethylamine and 2,2,2-trifluoroethanesulfonyl chloride and purifying via radial chromatography eluting with 40:60 to 50:50 THF/hexanes gave the title compound. Anal Calcd for $C_{20}H_{16}F_4N_2O_3S$: C, 54.54; H, 3.66; N, 6.36. Found: C, 54.23; H, 3.40; N, 6.31. MS found 441.2 [M+H]+

EXAMPLE 444

N-(3-(2-Methylphenoxy)phenyl)-N-(2,2,2-trifluorethanesulfonyl)pyrid-3-ylmethylamine

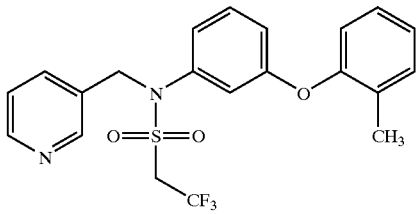

Using the method of Example 342 using N-(3-(2-methylphenoxy)phenyl)pyridin-3-ylmethylamine and 2,2,2-trifluoroethanesulfonyl chloride and purifying via radial chromatography eluting with 40:60 to 50:50 THF/hexanes gave the title compound. Anal Calcd for $C_{21}H_{19}F_3N_2O_3S.0.1H_2O$: C, 57.55; H, 4.42; N, 6.39. Found: C, 57.28; H, 4.15; N, 6.33. MS found 437.2 [M+H]+

EXAMPLE 445

N-(3-(4-Carboxymethylphenoxy)phenyl)-N-(ethanesulfonyl)pyrid-3-ylmethylamine

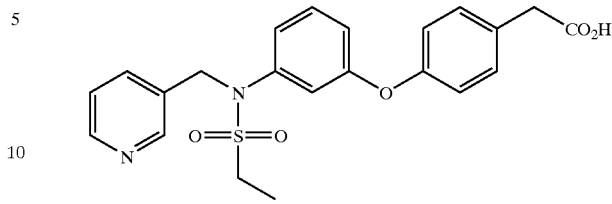

N-(3-(4-Carbomethoxymethylphenoxy)phenyl)-N-(ethanesulfonyl)pyrid-3-ylmethylamine (1.0 equiv.) was dissolved in THF (3.3 M) and treated with 1N NaOH (3 equiv.). The reaction was stirred overnight then concentrated in vacuo to remove THF. The pH was adjusted to 4 with HCl, which caused the title compound to precipitate. The solid was collected via filtration washing with pH=4 water to give the title compound. Anal Calcd for $C_{22}H_{22}N_2O_5S.0.2H_2O$: C, 61.44; H, 5.25; N, 6.51. Found: C, 61.39; H, 5.12; N, 6.59. MS found 427.0 [M+H]+

EXAMPLE 446

N-(4-(2-Fluoro-4-methylphenoxy)phenyl)-N-(ethanesulfonyl)pyrid-3-ylmethylamine

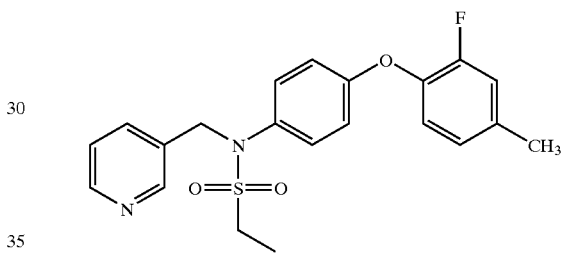

Using the method of Example 342 using N-(4-hydroxyphenyl)-N-(ethanesulfonyl)pyridin-3-ylmethylamine and 4-bromo-2-fluorotoluene (Strem) and purifying via preparative HPLC eluting with 90:10 to 70:30 DCM/ethyl acetate) gave the title compound. Anal Calcd for $C_{21}H_{21}FN_2O_3S.0.2H_2O$: C, 62.42; H, 5.34; N, 6.93. Found: C, 62.48; H, 5.33; N, 6.72. $^1$H NMR (400 MHz) 1.42 (3H, t, J=7.3 Hz), 2.35 (3H, s), 3.10 (2H, q, J=7.3 Hz), 4.82 (2H, s), 6.82–7.00 (5H, m), 7.12 (2H, m), 7.30 (1H, bs), 7.78 (1H, d, J=7.8 Hz), 8.40 (1H, bs), 8.55 (1H, bs).

By a method similar to the method of Example 1 the following compounds were prepared:

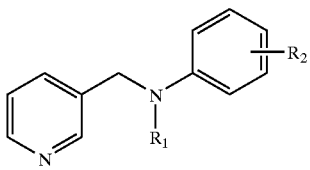

| No. | R1 | R2 | Data |
|---|---|---|---|
| 447 | $SO_2CH_2CH_3$ | 3-(2-methoxy-phenylsulfanyl) | $^1$H NMR: 8.30(d, 1H, J=3Hz), 7.62(s, 1H), 7.30(d, 1H, J=7Hz), 7.20(m, 1H), 7.05–7.18 (m, 6H), 4.79(s, 2H), 3.79(s, 3H), 3.00–3.05 (m, 2H), 1.35(t, 3H, J=7Hz). MS calcd. 414.5; MS (M+1) 416.1. |

-continued

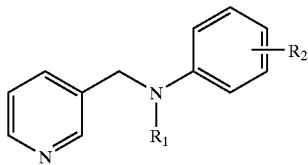

| No. | R1 | R2 | Data |
|---|---|---|---|
| 448 | SO$_2$CH$_2$CF$_3$ | 3-(2-methoxy-phenylsulfanyl) | $^1$H NMR: 8.48(d, 1H, J=4Hz), 8.26(s, 1H), 7.60(m, 1H), 7.32–7.36(m, 1H), 7.15–7.22 (m, 6H), 6.90–7.00(m, 2H), 4.78(s, 2H), 3.69–3.79(m, 5H). MS calcd. 468.5; MS (M+1) 469.9. |
| 449 | SO$_2$CH$_2$CF$_3$ | 3-(2-methoxy-phenoxy)- | $^1$H NMR: 8.50(d, 1H, J=4Hz), 8.30(s, 1H), 7.64(d, 1H, J=8Hz), 7.14–7.24(m, 4H), 6.99(d, 1H, J=8Hz), 6.93(s, 1H), 6.84–6.86(m, 2H), 6.76(s, 1H), 4.82(s, 2H), 3.75–3.82(m, 5H). MS calcd. 452.5; MS (M+1) 453.3. |
| 450 | SO$_2$CH$_2$CF$_3$ | 4-(2-benzyloxy-phenoxy) | $^1$H NMR: 8.5(s, 1H), 8.28(s, 1H), 7.69 (d, 1H, J=8Hz), 7.26(m, 2H), 7.02–7.12 (m, 4H), 6.84–6.91(m, 4H), 4.83(s, 2H), 3.76–3.83(dd, 2H). MS calcd. 438.4; MS (M+1) 439.4. |
| 451 | SO$_2$CH$_2$CH$_3$ | 3-(4-fluoro-2-methoxy-phenoxy) | $^1$H NMR: 8.5(dd, 1H), 8.32(d, 1H, J=1Hz), 7.67(d, 1H, J=8Hz), 7.16–7.22(m, 3H), 6.87 (m, 2H), 6.75(m, 2H), 6.62(m, 1H), 4.83 (s, 2H), 3.73(s, 3H), 3.08(dd, 2H), 1.37–1.41 (t, 3H). MS calcd. 416.5; MS (M+1) 417.6 |
| 452 | SO$_2$CH$_2$CF$_3$ | 3-(4-fluoro-2-methoxy-phenoxy) | $^1$H NMR: 8.49(d, 1H, J=4Hz), 8.28(s, 1H), 7.65(d, 1H, J=8Hz), 7.20–7.22(m, 3H), 6.80–6.90(m, 2H), 6.70(m, 1H), 6.60(m, 1H), 4.82 (s, 2h), 3.72–3.82(m, 4H). MS calcd. 470.5; MS (M+1) 471.6 |
| 453 | SO$_2$CH$_2$CH$_3$ | 3-(2-bromo-phenoxy) | $^1$H NMR: 8.47(dd, 1H), 8.33(d, 1H, J=2Hz), 7.65(m, 1H), 7.61(m, 1H), 7.19–7.27(m, 4H), 6.96–7.05(m, 3H), 6.78–6.86(m, 3H), 4.84 (s, 2H), 3.06–3.10(m, 2H), 1.37–1.41(t, 3H). MS calcd. 447.4, MS (M+1) 449.0 |
| 454 | SO$_2$CH$_2$CH$_3$ | 3-(2,3-dimethoxy-phenoxy) | $^1$H NMR: 8.47(dd, 1H), 8.35(d, 1H, J=1Hz), 7.65(dd, 1H), 7.17–7.22(m, 3H), 6.81–7.00 (m, 3H), 6.84(m, 2H), 6.72(dd, 1H), 6.47 (dd, 1H), 4.83(s, 2H), 3.87(s, 3H), 3.71(s, 3H), 3.05–3.11(dd, 2H), 1.38(t, 3H). MS calcd. 428.5; MS (M+1) 429.6 |
| 455 | SO$_2$CH$_2$CH$_3$ | 3-(2-chloro-phenoxy) | $^1$H NMR: 8.47(dd, 1H), 8.33(d, 1H, J=2Hz), 7.65(d, 1H, J=8Hz), 7.42(dd, 1H), 7.19–7.25 (m, 4H), 7.11(dd, 1H), 6.97(dd, 1H), 6.86–6.89 (m, 1H), 6.82(d, 2H, J=2Hz), 6.78–6.80 (m, 2H), 4.84(s, 3H), 3.11(dd, 3H), 1.39 (t, 2H). MS calcd. 402.9; MS (M+1) 403.8. |
| 456 | SO$_2$CH$_2$CH$_3$ | 3-(2-chloro-6-methyl-phenoxy) | $^1$H NMR: 8.45(m, 1H), 8.31(d, 1H, J=1Hz), 7.61(d, 1H, J=8Hz), 7.06–7.26(m, 5H), 6.90 (dd, 1H), 6.69(dd, 1H), 6.58(t, 1H), 4.81 (s, 2H), 3.05–3.10(dd, 2H), 2.07(s, 3H), 1.37 (t, 3H). MS calcd. 416.9; MS (M+1) 417.7 |
| 457 | SO$_2$CH$_2$CH$_3$ | 3-(2-isopropoxy-phenoxy) | $^1$H NMR: 8.47(dd, 1H), 8.35(d, 1H, J=2Hz), 7.68(d, 1H, J=8Hz), 7.21(dd, 1H), 7.09–7.22 (m, 3H), 6.84–6.98(m, 4H), 6.82(s, 1H), 6.74 (dd, 1H), 4.84(s, 2H), 4.39(m, 1H), 3.08 (dd, 2H), 1.38(t, 3H), 1.12(d, 6H, J=7Hz). MS calcd. 426.5; MS (M+1) 427.6 |
| 458 | SO$_2$CH$_2$CF$_3$ | 3-fluoro-5-(2-methoxy-phenoxy) | $^1$H NMR (CD3OD): 8.79(m, 2H), 8.56 (d, 1H, J=8Hz), 8.05(dd, 1H), 7.22(t, 1H), 7.11 (d, J=7Hz), 6.90–7.03(m, 3H), 6.68(s, 1H), 6.49–6.53(m, 1H), 5.14(s, 2H), 4.41(dd, 2H), 3.70(s, 3H). MS calcd. 470.45; MS (M+1) 471.6 |
| 459 | SO$_2$CH$_2$CH$_3$ | 3-fluoro-5-(2-methoxy-phenoxy) | $^1$H NMR (CD$_3$OD): 8.77(s, 2H), 8.57(s, 1H), 8.04(s, 1H), 7.21(s, 1H), 7.09(s, 1H), 6.95 (m, 3H), 6.71(s, 1H), 6.42(d, 1H, J=9Hz), 5.15 (s, 2H), 3.69(s, 3H), 3.27(m, 2H), 1.34 (m, 3H). MS calcd. 416.48; MS (M+1) 417.7 |
| 460 | SO$_2$CH$_2$CH$_2$CF$_3$ | 3-(2-methoxy-phenoxy) | $^1$H NMR (CD$_3$OD): 8.53–8.83(m, 3H), 7.90–8.08(m, 1H), 6.74–7.26(m, 8H), 5.13(s, 2H), 3.66(s, 3H), 3.25(m, 2H), 2.65(m, 2H). MS calcd. 466.38; MS (M+1) 467.6 |

-continued

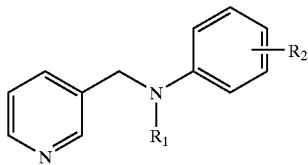

| No. | R1 | R2 | Data |
|---|---|---|---|
| 461 | $SO_2CH_2CF_3$ | 3-(2-bromo-phenoxy) | $^1$H NMR: 7.63(m, 2H), 7.37(m, 3H), 7.04–7.19(m, 4H), 6.91(s, 2H), 6.77(br, 1H), 4.10 (dd, 1H), 3.85(s, NH), 2.02(s, 1H), 1.24 (t, 2H). MS calcd. 501.1; MS (M+1) 501.4 (502.4, due to Br). |
| 462 | $SO_2CH_2CF_3$ | 3-(2,3-dimethoxy-phenoxy) | $^1$H NMR ($CD_3OD$): 8.69–8.77(m, 2H), 8.51 (s, 1H), 8.00(s, 1H), 7.33(s, 1H), 7.03–7.11 (m, 2H), 6.89(m, 2H), 6.69(s, 1H), 6.56 (m, 1H), 5.10(s, 2H), 4.35(m, 2H), 3.85 (s, 3H), 3.58(s, 3H). MS calcd. 482.18; MS (M+1) 483.8 |
| 463 | $SO_2CH_2CH_3$ | 3-(2-chloro-phenoxy) | $^1$H NMR: 8.47(dd, 1H), 8.33(d, 1H, J=2Hz), 7.65(d, 1H, J=8Hz), 7.42(dd, 1H), 7.19–7.25 (m, 4H), 7.11(dd, 1H), 6.97(dd, 1H), 6.86–6.89 (m, 1H), 6.82(d, 2H, J=2Hz), 6.78–6.80 (m, 2H), 4.84(s, 3H), 3.11(dd, 3H), 1.39 (t, 2H). MS calcd. 402.9; MS (M+1) 403.8. |
| 464 | $SO_2CH_2CF_3$ | 3-(2-chloro-phenoxy) | $^1$H NMR: 7.34–7.50(m, 5H), 7.19(m, 3H), 6.91(m, 4H), 4.10(dd, 1H), 3.85(br, NH), 2.02(s, 1H), 1.24(t, 1H). MS calcd. 456.87; MS (M+1) 457. |
| 465 | $SO_2CH_2CF_3$ | 3-(2-chloro-6-methyl-phenoxy) | $^1$H NMR: 6.65–7.90(m, 11H), 3.70(br, NH), 3.43(m, 1H), 2.13(s, 3H), 1.95(m, 2H), 1.20 (m, 1H). MS calcd. 470.9; MS (M+1) 471.6 |
| 466 | $SO_2CH_2CF_3$ | 3-(2-isopropoxy-phenoxy) | $^1$H NMR: 8.73(m, 2H), 8.50(s, 1H), 7.98 (s, 1H), 7.27(s, 1H), 6.94–7.12(m, 6H), 6.77 (s, 2H), 5.10(br, NH), 4.29–4.36(m, 4H), 1.02 (s, 3H). MS calcd. 480.51; MS (M+1) 481.4 |

Preparation 8

N-(4-Methoxycarbonylphenyl)pyrid-3-ylmethylamine

A mixture of 3-pyridinecarboxaldehyde (4.72 mL, 50 mmol) and methyl 4-aminobenzoate (9.83 g, 65 mmol) in 140 mL of methanol was heated to reflux for 2.5 h then cooled to 0° C. Solid $NaBH_4$ was added slowly and the reaction mixture was warmed to ambient temperature and stirred for 14 h. The mixture was concentrated and partitioned between DCM and $H_2O$. The aqueous layer was extracted with DCM and the combined organic layers were washed with $H_2O$ and brine and concentrated. The residue was chromatographed on silica gel with DCM to 2% MeOH in DCM to give 8.08 g of a white solid (67% yield). $^1$H NMR ($DMSO_{d6}$): 8.57 (d,J=1.8 Hz, 1H), 8.46 (dd,J=4.7, 1.8 Hz, 1H), 7.73 (dt,J=8.4, 2.2 Hz, 1H), 7.68 (d,J=8.8 Hz, 2H), 7.35 (ddd,J=8.1, 4.8, 0.7 Hz, 1H), 7.13 (br t,J=5.9 Hz, 1H), 6.64 (d,J=8.8 Hz, 2H), 4.38 (d,J=6.2 Hz, 2H), 2.75 (s,3H). MS calcd. 242.1; MS (M+1) 243.2.

Alternately, 3-pyridinecarboxaldehyde ((61.6 g, 0.575 moles, 1 eq) and methyl 4-aminobenzoate (1–03.87 g, 0.687 moles, 1.2 eq) with p-toluenesulfonic acid (2.19 g, 0.012 moles, 0.02 eq) were refluxed in methanol (25 volumes) for 2 hours. The reaction mixture was cooled to 0° C. and sodium borohydride (67.6 g, 1.787 moles, 3.5 eq) added slowly then it was allowed to warm to ambient overnight. The reaction was concentrated, dissolved with dichloromethane and washed with water then brine, and evaporated to give the title compound.

Preparation 9

N-(3-Methoxycarbonylphenyl)pyrid-3-ylmethylamine

The title compound was prepared using a method similar to Preparation 8 using 3-aminobenzoate. $^1$H NMR: 8.64 (d,J=2.4 Hz, 1H), 8.54 (dd,J=4.9, 1.5 Hz, 1H), 7.69 (dt,J=7.8, 2.0 Hz, 1H), 7.41 (dt,J=7.8, 1.3 Hz, 2H), 7.32 (dd,J=2.5, 1.5,Hz,1H), 7.27 (dd,J=7.8, 3.9 Hz, 1H), 7.23 (t,J=8.3 Hz, 1H), 6.79 (ddd,J=7.8, 2.5, 1.0 Hz, 1H), 4.40 (d,J=5.9 Hz, 2H), 4.19 (br t,J=5.9 Hz, 1H) 3.88 (s,3H).

Preparation 10

N-(4-Benzylphenyl)pyrid-3-ylmethylamine

The title compound was prepared using a method similar to Preparation 8 using 4-aminodiphenylmethane (purchased from TCI). $^1$H NMR: 8.63 (br s,1H), 8.53 (br d,J=4.4 Hz, 1H) 7.50 (br d,J=7.8 Hz, 1H), 7.26 (m,3H), 7.18 (m,3H), 7.00 (m,2H), 6.57 (m,2H), 4.34 (s,2H), 3.99 (br s,1H), 3.88 (s,2H).

EXAMPLE 467

N-(4-(Benzyl)phenyl)-N-(2,2,2-trifluoroethanesulfonyl)pyrid-3-ylmethylamine

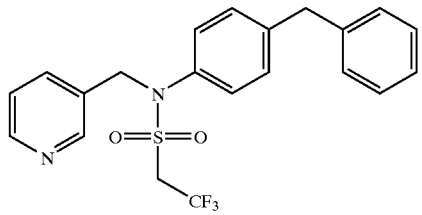

To a solution of N-(4-benzylphenyl)pyrid-3-ylmethylamine (0.517 g, 1.88 mmol) dissolved in 8 mL dichloroethane and 4 mL pyridine at 0° C. was added 2,2,2-trifluoroethylsulfonyl chloride (0.313 mL, 2.83 mmol). The reaction was stirred at ambient temperature overnight. The mixture was treated with 1.5 g anhydrous $K_2CO_3$ and stirred for 2 h. Then the mixture was filtered and concentrated. The residue was chromatographed on silica gel with 3:1 to 2:1 DCM/EtOAc to give an amorphous white solid. $^1$H NMR: 8.52 (br d,J=3.3 Hz, 1H), 8.32 (br s,1H), 7.71 (dt,J=6.8, 1.4 Hz, 1H), 7.33–7.20 (m,4H), 7.18–7.10 (m,6H), 4.88 (s,2H), 3.95 (s,2H), 3.79 (q,J=9.3 Hz, 2H).

EXAMPLE 468

N-(4-(Benzyl)phenyl)-N-(ethanesulfonyl)pyrid-3-ylmethylamine

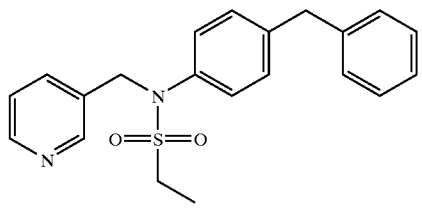

The title compound was prepared using a method similar to the method of Example 467 using ethanesulfonyl chloride. $^1$H NMR: 8.50 (br d,J=3.4 Hz, 1H), 8.36 (br s,1H), 7.77 (dd,J=7.8, 1.5 Hz, 1H), 7.31–7.19 (m,4H), 7.17–7.09 (m,6H), 4.87 (s,2H), 3.92 (s,2H), 3.08 (q,J=7.3 Hz, 2H), 1.42 (t,J=7.3 Hz, 3H). MS calcd. 366.1; MS (M+1) 367.1.

EXAMPLE 469

N-(4-Methoxycarbonylphenyl)-N-(2,2,2-trifluoroethanesulfonyl)pyrid-3-ylmethylamine

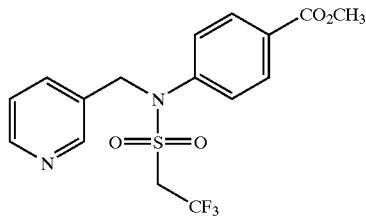

The title compound was prepared using a method similar to the method of Example 467 using N-(4-methoxycarbonylphenyl)pyrid-3-ylmethylamine. $^1$H NMR: 8.52 (br s,1H), 8.37 (br s,1H), 8.02 (m,2H), 7.68 (d,J=7.8 Hz, 1H), 7.33 (m,2H), 7.27 (m,1H), 4.95 (s,2H), 3.90 (s,3H), 3.82 (q,J=9.3 Hz, 2H).

EXAMPLE 470

N-(3-Methoxycarbonylphenyl)-N-(2,2,2-trifluoroethanesulfonyl)pyrid-3-ylmethylamine

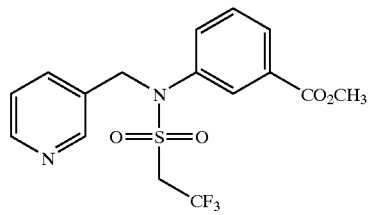

The title compound was prepared using a method similar to the method of Example 467 using N-(3-methoxycarbonylphenyl)pyrid-3-ylmethylamine. $^1$H NMR: 88.51 (dd,J=4.8, 1.8 Hz, 1H), 8.33 (d,J=1.8 Hz, 1H), 8.00 (dt,J=7.3, 1.5 Hz, 1H), 7.93 (t,J=1.5 Hz, 1H), 7.68 (dt,J=7.7, 2,2 Hz, 1H), 7.43 (t,J=7.7 Hz, 1H), 7.39 (dt,J=7.7, 1.5 Hz, 1H), 7.25 (ddd,J=7.3, 4.8, 1.5 Hz, 1H), 4.93 (s,2H), 3.92 (s,2H),3.82 (q,J=9.3 Hz, 2H).

EXAMPLE 471

N-(4-(Hydoxymethyl)phenyl)-N-(2,2,2-trifluoroethanesulfonyl)pyrid-3-ylmethylamine

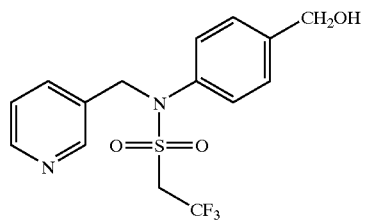

To a solution of N-(4-hydroxymethyl-phenyl)pyrid-3-ylmethylamine (0.472 g, 1.22 mmol) dissolved in 15 mL THF at, −78° C. was DIBAL (1.0 M in toluene, 3.04 mL, 3.04 mmol). The reaction was stirred for 1 h and then warmed to 0° C. for 1 h. It was quenched with 0.5 mL methanol and stirred overnight with 60 mL ether and 30 mL saturated Rochelle's salt. The mixture was extracted with ether, dried over $MgSO_4$, filtered and concentrated. The residue was chromatographed on silica gel with 1:1 DCM/EtOAc to give the title compound as an amorphous white solid. $^1$H NMR: 8.43 (d,J=3.8 Hz, 1H), 8.27 (s,1H), 7.68 (d,J=7.8 Hz, 1H), 7.32 (m,2H), 7.23 (m,1H), 7.19 (m,2H), 4.88 (s,2H), 4.63 (s,2H), 3.80 (q,J=9.3 Hz, 2H), 3.10 (br s,1H).

EXAMPLE 472

N-(3-(Hydroxymethyl)phenyl)-N-(2,2,2-trifluoroethanesulfonyl)pyrid-3-ylmethylamine

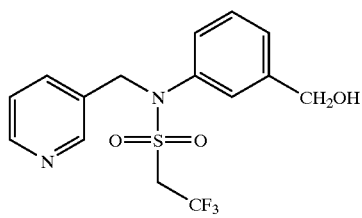

The title compound was prepared using a method similar to the method of Example 471 using N-(3-methoxycarbonylphenyl)-N-(2,2,2-trifluoroethylsulfonyl)pyrid-3-ylmethylamine. $^1$H NMR: 8.50 (dd,J=4.9, 1.5 Hz, 1H), 8.31 (J=2.0 Hz, 1H), 7.70 (dt,J=7.8, 2.0 Hz, 1H), 7.34 (m,2H), 7.25 (m,2H), 7.14 (dt,J=7.3, 2.5 Hz, 1H), 4.90 (s,2H), 4.67 (d,J=5.4 Hz, 2H), 3.81 (q,J=9.3 Hz, 1H), 1.92 (br t,J=5.4 Hz, 1H).

EXAMPLE 473

N-(4-Formylphenyl)-N-(2,2,2-trifluoroethanesulfonyl)pyrid-3-ylmethylamine

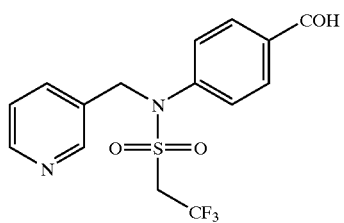

To a solution of DMSO (0.190 mL, 2.68 mmol) in 4 mL DCM at −78° C. was added oxalyl chloride (0.146 mL, 1.67 mmol) dropwise. After 15 min a solution of N-(4-(hydroxymethyl)phenyl)-N-(2,2,2-trifuoroethylsulfonyl)pyrid-3-ylmethylamine (0.241 g, 0.669 mmol) was added via cannula. The reaction was stirred for 30 min and triethylamine (0.932 mL, 6.69 mmol) was added and warmed to 0° C. over 1 h. The mixture was poured into saturated NaHCO$_3$ solution and diluted with ether. The organic layer was washed with H$_2$O and brine, dried over MgSO$_4$, filtered, and concentrated. The residue was chromatographed on silica gel with 5:1 DCM/EtOAc to give 173 mg of a clear oil (72%). $^1$H NMR: 9.97 (s,1H), 8.50 (dd,J=4.9, 1.5 Hz, 1H), 8.35 (d,J=2.0 Hz, 1H), 7.87 (m,2H), 7.66 (dt,J=7.8, 2.0 Hz, 1H), 7.44 (m,2H), 7.24 (ddd,J=7.8, 4.9, 1.0 Hz, 1H), 4.97 (s,2H), 3.84 (q,J=9.3 Hz, 2H).

EXAMPLE 474

N-(3-Formylphenyl)-N-(2,2,2-trifluoroethanesulfonyl)pyrid-3-ylmethylamine

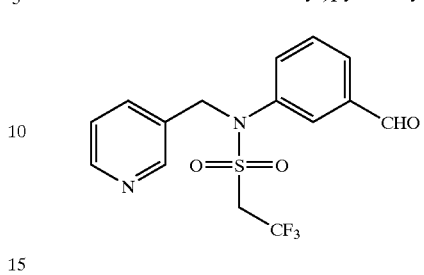

The title compound was prepared using a method similar to the method of Example 473 using N-(3-hydroxymethylphenyl)-N-(2,2,2-trifluoroethylsulfonyl)pyrid-3-ylmethylamine. $^1$H NMR: 9.97 (s,1H), 8.51 (dd,J=4.9, 1.5 Hz, 1H), 8.33 (d,J=2.0 Hz, 1H), 7.85 (dt,J=7.8, 2.0 Hz, 1H), 7.77 (t,J=2.0 Hz, 1H), 7.69 (dt,J=7.8, 2.0 Hz, 1H), 7.54 (t,J=7.8 Hz, 1H), 7.48 (dt,J=7.8, 2.0 Hz, 1H), 7.26 (dd,J=7.8, 4.9 Hz, 1H), 4.95 (s,2H), 3.83 (q,J=9.3 Hz, 2H).

EXAMPLE 475

N-(3-(α-Hydroxybenzyl)phenyl)-N-(2,2,2-trifluoroethanesulfonyl)pyrid-3-ylmethylamine

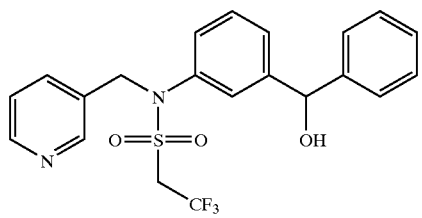

To a solution of N-(3-formylphenyl)-N-(2,2,2-trifuoroethylsulfonyl)pyrid-3-ylmethylamine (0.174 g, 0.486 mmol) in 4 mL THF at 0° C. was added phenyl magnesium chloride (2.0 M in THF, 0.364 mL, 0.728 mmol). After 1 h at ambient temperature, the reaction was poured in to saturated NaHCO$_3$ solution and extracted with DCM. The extracts were dried over MgSO$_4$, filtered and concentrated. The residue was chromatographed on silica gel with 1:1 DCM/EtOAc to give a clear oil. $^1$H NMR: 8.41 (dd,J=4.9, 1.5 Hz, 1H), 8.24 (d,J=2.0 Hz, 1H), 7.67 (dt,J=7.8, 2.0 Hz, 1H), 7.40=7.15 (m,10H), 5.78 (s,1H), 4.86 (s,2H), 3.77 (q,J=9.3 Hz, 2H), 3.21 (br s,1H). MS calcd. 436.1; MS (M+1) 437.1. The HCl salt was prepared by adding 1.0 M HCl in ether solution to the free base in ether suspension, stirring for 10 min then collecting the ppt by filtration.

Optionally, the HCl salt can be prepared by adding 1.0 M HCl in ether solution to the free base in ether suspension, stirring for 10 min then collecting the ppt by filtration.

By a method similar to the method of Example 475 the following compounds were prepared:

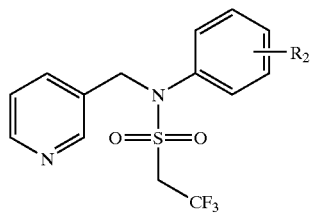

| No. | R2 | Data |
|---|---|---|
| 476 | 4-(α-hydroxybenzyl) | ¹H NMR: 8.38(dd,J=4.9, 2.0Hz, 1H), 8.21(d, J=1.5Hz, 1H), 7.61(dt, J=7.8, 1.5Hz, 1H), 7.33–7.09(m, 10H), 5.72(d, J=2.5Hz, 1H), 4.79(s, 2H), 3.71(q, J=9.3Hz, 2H), 2.71(d, J=3.4Hz, 1H) |
| 477 | 4-(α-hydroxy-2-methylsulfanyl benzyl) | ¹H NMR: 8.39(dd, J=4.9, 2.0Hz, 1H), 8.24(d, J=1.5Hz, 1H), 7.65(dt, J=7.8, 1.5Hz, 1H), 7.43–7.38(m, 3H), 7.27–7.13(m, 6H), 6.20(d, J=1.5Hz, 1H),4.85(s, 2H), 3.78(q, J=9.3Hz, 2H), 3.60(br s, 1H),2.38(s, 3H). MS calcd. 482.1; MS (M+1) 483.1 |
| 478 | 3-(α-hydroxy-2-methylsulfanyl benzyl) | ¹H NMR: 8.40(dd, J=4.9, 2.0Hz, 1H), 8.22(d, J=2.0Hz, 1H), 7.62(dt, J=7.8, 1.5Hz, 1H), 7.39–7.33(m, 2H), 7.32–7.15(m, 6H), 7.06(d, J=7.8Hz, 1H),6.14(d, J=3.4Hz, 1H), 4.85(AofAB, d, J=14.8Hz, 1H), 4.80(BofAB, d, J=14.8Hz, 1H), 3.84–3.70(m, 2H), 3.53(d, J=4.3Hz, 1H), 2.39(s, 3H). MS calcd. 482.1; MS (M+1) 483.1 |
| 479 | 4-(α-hydroxy-2-methoxybenzyl) | ¹H NMR: 8.45(dd, J=4.9, 1.5Hz, 1H), 8.29(d, J=2.0Hz, 1H), 7.67(dd, J=8.3Hz, 1H), 7.38(d, J=8.3Hz, 2H), 7.29–7.20(m, 3H), 7.16(d, J=8.6Hz, 2H), 6.94(dt, J=1.0, 7.8Hz, 1H), 6.88(d, J=8.3Hz, 1H), 6.01(d, J=4.9Hz, 1H), 4.87(s, 2H), 3.78(q, J=9.3Hz, 2H), 3.77(s, 3H) |
| 480 | 3-(α-hydroxy-2-methoxybenzyl) | ¹H NMR: 8.42(dd, J=4.9, 1.5Hz, 1H), 8.24(d, J=2.0Hz, 1H), 7.63(dt, J=7.8, 2.0Hz, 1H), 7.37(d, J=7.3Hz, 1H), 7.34–7.24(m, 3H), 7.22–7.17(m, 2H), 7.09(br d, J=9.0Hz, 1H), 6.96(dt, J=1.0, 7.3Hz, 1H), 6.88(d, J=8.3Hz, 1H), 6.03(s, 1H), 4.87(s, 2H), 3.80(br s, 1H), 3.79(q, J=9.3Hz, 2H), 3.77(s, 3H). |
| 481 | 4-(α-hydroxy-3,4-difluorobenzyl) | ¹H NMR: 8.41(dd, J=4.9, 2.0Hz, 1H), 8.23(d, J=1.5Hz, 1H), 7.69(dt, J=7.8, 2.0Hz, 1H), 7.34(d, J=7.3Hz, 2H), 7.24(dd, J=4.9, 4.0Hz, 1H), 7.21–7.07(m, 4H), 7.03(m, 1H), 5.73(s, 1H), 4.87(s, 2H), 3.79(q, J=9.3Hz, 2H), 3.34(br s, 1H). MS calcd. 472.1; MS (M+1) 473.1 |
| 482 | 3-(α-hydroxy-3,4-difluorobenzyl) | ¹H NMR: 8.29(d, J=3.9Hz, 1H), 8.12(d, J=1.5Hz, 1H), 7.57(dt, J=7.8, 2.0Hz, 1H), 7.34–7.24(m, 2H), 7.18–7.11(m, 3H), 7.09–6.96(m, 2H), 6.89(m, 1H), 5.63(s, 1H), 4.82(s, 2H), 4.67(br s, 1H), 3.77(q, J=9.3Hz, 2H). MS calcd. 472.1; MS (M+1) 473.1 |
| 483 | 4-(α-hydroxy-2-phenylbenzyl) | ¹H NMR: 8.46(d, 1H, J=3.4Hz), 8.26(s, 1H), 7.76–7.60(m, 1H), 7.56–7.45(m, 1H), 7.42–7.30(m, 5H), 7.44–7.15(m, 4H), 7.15–7.00(m, 5H), 5.89(d, 1H, J=3.4Hz), 4.85(s, 2H), 3.76(q, 2H, J=9.8Hz |
| 484 | 3-(α-hydroxy-2-phenylbenzyl) | ¹H NMR: 8.45(m, 1H), 8.22(d, 1H), 7.62–7.57(m, 1H), 7.43–7.30(m, 6H), 7.28–7.14(m, 5H), 7.10–6.98(m, 3H), 5.90(s, 1H), 4.80(q, 2H), 3.82–3.62(q, 2H) |
| 485 | 4-(1-hydroxy-1-(5-methylpyrid-2-yl)methyl) | ¹H NMR: 8.50(d, 1H), 8.37(s, 1H), 8.31(s, 1H), 7.63(d, 1H), 7.15(m, 6H), 7.00(d, 1H), 5.68(d, 1H), 4.84(s, 2H), 3.78(q, 2H), 2.32(s, 3H). |
| 486 | 3-(1-hydroxy-1-(5-methylpyrid-2-yl)methyl) | ¹H NMR: 8.49(m, 1H), 8.35(d, 1H, J=1.5Hz), 7.70–7.65(d, 2H, 7.8Hz), 7.57–7.52(m, 1H), 7.46–7.16(m, 7H), 6.26(d, 1H), 4.87(s, 1H), 3.88(q, 2H) |
| 487 | 4-(α-hydroxy-2-trifluoromethylbenzyl) | ¹H NMR: 8.47(q, 1H, J=2.0, 2.93), 8.24(s, 1H, J=2.0Hz), 7.70–7.52(m, 3H), 7.46–7.08(m, 8H), 6.24(d, 1H), 4.83(s, 2H), 3.75(q, 2H) |
| 488 | 3-(α-hydroxy-2-fluorobenzyl) | ¹H NMR: 8.43(d, 1H), 8.24(s, 1H), 7.68(m, 1H), 7.42–6.88(m, 9H), 5.78(s, 1H), 4.87(s, 2H), 3.86(q, 2H) |
| 489 | 4-(α-hydroxy-2-fluorobenzyl) | ¹H NMR: 8.46(d, 1H, J=3.4), 8.30(s, 1H), 7.65(m, 1H), 7.47–7.38(m, 3H), 7.30–6.82(m, 6H), 6.12(d, 1H), 4.87(s, 2H), 3.75(q, 2H, J=8.8Hz) |
| 490 | 4-(α-hydroxy-3-fluorobenzyl) | ¹H NMR: 8.43(s, 1H), 8.24(s, 1H), 7.68(m, 1H), 7.42–6.88(m, 9H), 5.78(s, 1H), 4.87(s, 2H), 3.86(q, 2H). |

EXAMPLE 491

N-(3-(Benzyl)phenyl)-N-(2,2,2-trifluoroethanesulfonyl)pyrid-3-ylmethylamine

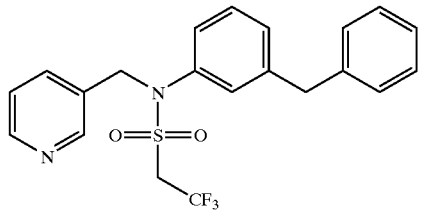

To a solution of N-3-(α-hydroxybenzyl)phenyl)-N-(2,2,2-trifluoroethanesulfonyl)pyrid-3-ylmethylamine (0.050 g, 0.115 mmol) in 2 mL DCM and 0.5 mL triethylsilane was added trifluoroacetic acid (0.3 mL). The reaction was stirred at ambient temperature overnight and poured into saturated NaHCO$_3$ solution and extracted with EtOAc. The combined extracts were dried over MgSO$_4$, filtered and concentrated. The residue was chromatographed on silica gel with 4:1 to 2:1 DCM/EtOAc to give 0.025 g of a clear oil (52% yield). $^1$H NMR: 8.51 (dd,J=4.9, 1.5 Hz, 1H), 8.22 (d,J=2.0 Hz, 1H), 7.69 (dt,J=7.8, 2.0 Hz, 1H), 7.32–7.20 (m,4H), 7.18–7.11 (m,6H), 4.86 (s,2H), 3.94 (s,2H), 3.79 (q,J=9.3 Hz, 2H). MS calcd. 420.1; MS (M+1) 421.1. Optionally, the HCl salt can be prepared by adding 1.0 M HCl in ether solution to the free base in ether suspension, stirring for 10 min then collecting the ppt by filtration.

By a method similar to the method of Example 491 the following compounds were prepared:

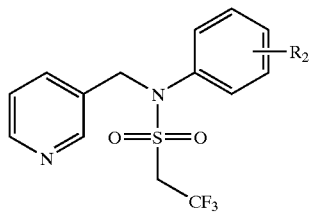

| No. | R$_2$ | Data |
|---|---|---|
| 492 | 4-(2-methylsulfanylbenzyl) | $^1$H NMR: 8.50(vbr s, 2H), 7.71(br d, J=7.8Hz, 1H), 7.29(br s, 1H), 7.23(m, 2H), 7.17(br d, J=8.3Hz, 2H), 7.11(m, 2H), 7.05(br d, 8.3Hz, 2H), 3.87(s, 2H), 4.04(s, 2H), 3.79(q, J=9.3Hz, 2H), 2.41(s, 3H). MS calcd. 466.1; MS (M+1) 467.0. |
| 493 | 3-(2-methylsulfanylbenzyl) | $^1$H NMR: 8.50(br s, 1H), 8.31(br s, 1H), 7.63(d, J=7.8Hz, 1H), 7.28–7.15(m, 5H), 7.11(dt, J=1.5, 6.8Hz, 1H), 7.02(m, 3H), 4.73(s, 2H), 4.03(s, 2H), 3.78(q, J=9.3Hz, 2H), 2.42(s, 3H). MS calcd. 466.1; MS (M+1) 467.0 |
| 494 | 4-(2-methoxybenzyl) | $^1$H NMR: 8.50(br d, J=3.9Hz, 1H), 8.33(br d, J=7.8Hz, 1H), 7.68(br d, J=7.8Hz, 1H), 7.28–7.16(m, 4H), 7.12–7.20(m, 3H), 6.92–6.85(m, 2H), 4.86(s, 2H), 3.93(s, 2H), 3.79(q, J=9.3Hz, 2H), 3.78(s, 3H) |
| 495 | 3-(2-methoxybenzyl) | $^1$H NMR: 8.48(d, J=3.4Hz, 1H), 8.30(d, J=1.5Hz, 1H), 7.61(dt, J=7.8, 2.0Hz, 1H), 7.24–7.15(m, 4H), 7.06(br s, 1H), 7.03–6.95(m, 2H), 6.91–6.84(m, 2H), 4.84(s, 2H), 3.91(s, 2H), 3.77(s, 3H), 3.75(q, J=9.3Hz, 2H) |
| 496 | 4-(3,4-difluorobenzyl) | $^1$H NMR: 8.51(dd, J=4.9, 1.5Hz, 1H), 8.31(d, J=2.0Hz, 1H), 7.69(dt, J=7.8, 2.0Hz, 1H), 7.25(dd, J=7.8, 4.9Hz, 1H), 7.17–7.04(m, 5H), 6.93(m, 1H), 6.86(m, 1H), 4.87(s, 2H), 3.89(s, 2H), 3.80(q, J=9.3Hz, 2H) |
| 497 | 3-(3,4-difluorobenzyl) | $^1$H NMR: 8.50(dd, J=4.9, 1.5Hz, 1H), 8.29(d, J=1.5Hz, 1H), 7.62(dt, J=7.8, 2.0Hz, 1H), 7.31(t, J=7.8Hz, 1H), 7.21(dd, J=7.8, 4.9Hz, 1H), 7.15–7.02(m, 3H), 6.91(s, 1H), 6.82–6.71(m, 2H), 4.85(s, 2H), 3.85(s, 2H), 3.79(q, J=9.3Hz, 2H). MS calcd. 456.1; MS (M+1) 457.1 |
| 498 | 4-(2-phenylbenzyl) | $^1$H NMR: 8.52(br s, 1H), 8.31(br s, 1H), 7.66(d, 1H, J=7.8Hz), 7.30(m, 4H), 7.27–7.17(m, 4H), 7.13(m, 2H), 7.01(d, 2H, J=8.4Hz), 6.88(d, 2H, J=8.4Hz), 4.84(s, 2H), 3.92(s, 2H), 3.76(q, 2H, J=9.3Hz). MS calcd 496.1; MS (M+1) 497.1 |
| 499 | 3-(2-phenylbenzyl) | $^1$H NMR: 8.42(br s, 1H), 7.19(br s, 1H), 7.51(d, 1H, J=7.8Hz), 7.28–7.09(m, 7H), 7.06(m, 3H), 6.99(m, 1H), 6.88(d, 1H, J=8.3Hz), 6.82(d, 1H, J=7.8Hz), 6.67(s, 1H), 4.70(s, 2H), 3.83(s, 2H), 3.62(q, 2H, J=9.3Hz). MS calcd 496.1; MS (M+1) 497.1 |

EXAMPLE 500

N-(3-Methoxycarbonylphenyl)-N-(ethanesulfonyl)pyrid-3-ylmethylamine

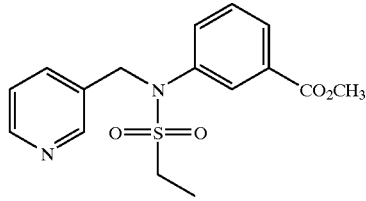

Into a 0° C. solution of N-(3-methoxycarbonylphenyl)pyrid-3-ylmethylamine (204 g, 0.842 mole, 1 eq) in dichloroethane (3610 mL) and pyridine (1775 mL) was added ethanesulfonyl chloride (114 mL, 1.2 mole, 1.43 eq). The reaction was allowed to warm to room temperature overnight. The dark red reaction was stirred with potassium carbonate (204 g) for 30 minutes and then filtered and concentrated to dryness. The residue was purified by Biotage, eluting with 3:1 to 2:1 DCM/EtOAc mixture to give the title compound as a white solid (137.0 g, 49% yield).

EXAMPLE 501

N-(3-(Hydroxymethyl)phenyl)-N-(ethanesulfonyl)pyrid-3-ylmethylamine

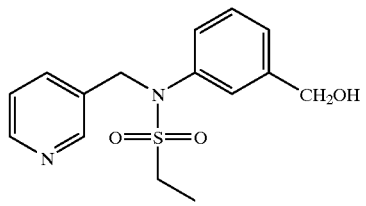

Into a −78° C. solution of N-(3-methoxycarbonylphenyl)-N-(ethanesulfonyl)pyrid-3-ylmethylamine (75 g, 0.224 mole, 1 eq) in THF was added slowly DIBAl-H (561 mL, 1M in toluene, 2.5 eq). The mixture was stirred for 1 hour and then was warmed to 0° C. with an ice water bath and stirred for 2 h. The reaction was carefully quenched with methanol (18.50 mL, 0.396 mole, 1.8 eq). It was then diluted with ether (4650 mL) and Saturated Rochelle's salt (2775 mL) and stirred vigorously overnight. The layers were separated and the aqueous extracted with EtOAc (2000 mL). The combined organics were washed with brine, dried with $MgSO_4$, filtered and concentrated. The residue was chromatographed, eluting with 1:1 DCM/EtOAc to give the title compound as a white solid (51.4 g, 43% Yield).

EXAMPLE 502

N-(3-Formylphenyl)-N-(ethanesulfonyl)pyrid-3-ylmethylamine

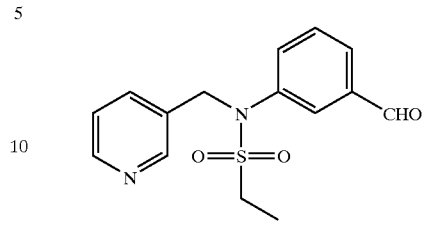

Into a −78° C. solution of DMSO (20.8 mL, 0.269 mole, 3.1 eq) in DCM (460 mL) was added oxalyl chloride (16 mL, 0.109 mole, 1.25 eq) dropwise and stirred for 15 minutes. N-(3-(Hydroxymethyl)phenyl)-N-(ethanesulfonyl)pyrid-3-ylmethylamine (26.4 g, 0.86 mole, 1 eq) was added dropwise via addition funnel as a solution in DCM (146 mL). The reaction mixture was stirred for 30 min. then TEA (102 mL, 1 mole, 11.7 eq) was added via addition funnel. The reaction mixture was allowed to warmed to 0° C. with an ice bath and stirred for 1 hour with a $N_2$ sweep through a bleach/caustic scrubber. The reaction mixture was poured into saturated $NaHCO_3$ and diluted with diethyl ether (2000 mL). The layers were separated and the aqueous layer backextracted with diethyl ether (1000 mL). The combined organics were washed with brine (1000 mL), dried with $MgSO_4$, filtered and concentrated. The residue was purified by flash chromatography, eluting with 1:1 DCM/EtOAc to give the title compound as a white solid (15.0 g, 57.2).

EXAMPLE 503

N-(4-(Hydoxymethyl)phenyl)-N-(ethanesulfonyl)pyrid-3-ylmethylamine

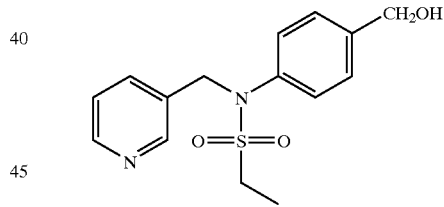

To a −78° C. solution of N-(4-methoxycarbonylphenyl)pyrid-3-ylmethylamine (105 g, 0.433 moles, leg) in THF (17 volumes) was added slowly DIBAl-H (1M in toluene, 1084 mL, 1.084 moles, 2.5 eq,) and held cold for 1 hour. The reaction was then allowed to warm to 0° C. for 2 h. The reaction was carefully quenched with methanol (1.8 eq). It was then diluted with ether (62 volumes) and Saturated Rochelle's salt (37 volumes) and stirred vigorously overnight. The layers were separated and the aqueous extracted with EtOAc. The combined organics were washed with brine, dried with $MgSO_4$, filtered, and concentrated to give N-(4-hydroxymethylphenyl)pyrid-3-ylmethylamine (88.2 g, 95% Yield).

To a 0° C. solution of give N-(4-hydroxymethylphenyl)pyrid-3-ylmethylamine (75 g, 0.35 moles, leg) and imidazole (26.21 g, 0.384 moles, 1.1 eq) in DCM was added slowly t-butyldimethylsilyl chloride (85.09 g, 564.5 moles, 1.6 eq) and held cold for ¼ hour. The reaction was then allowed to warm to 0° C. overnight. The reaction was partitioned with water and DCM. The organic layer was stripped to give N-(4-t-butyldimeythsilyloxymethylphenyl)pyrid-3-ylmethylamine a yellow solid (115 g, 100% yield)

To a 0° C. solution of N-(4-t-butyldimeythsilyloxymethylphenyl)pyrid-3-ylmethylamine (115.25 g, 0.351 moles, 1 eq) in dichloromethane (DCM, 17.7 volumes) and pyridine (8.7 volumes) was added ethanesulfonyl chloride (50.26 g, 0.391 moles, 1.1 eq). The reaction was allowed to warm to room temperature overnight. The dark red reaction was stirred with $K_2CO_3$ (1 wt eq) for 30 minutes and then filtered and concentrated to dryness. The residue was purified by Biotage with 3:1 to 2:1 DCM/EtOAc to give N-(4-t-butyldimeythsilyloxymethylphenyl)-N-(ethylsulfonyl)pyrid-3-ylmethylamine a yellow solid (91.24 g, 62% yield).

To a 0° C. solution of N-(4-t-butyldimeythsilyloxymethylphenyl)-N-(ethylsulfonyl)pyrid-3-ylmethylamine (90.61 g, 0.215 moles, 1 eq) in DCM (10 volumes) was added tetrabutylammonium fluoride (1.0 M in THF, 252.4 mL, 1.17 eq) dropwise and stirred for 15 minutes. The bath was removed and the reaction allowed to stir overnight. Washed with sat. $Na_2CO_3$ solution, water, and then brine. Dried the organics with $Na_2SO_4$. Stripped to yellow oil. Combined lots and prepped clean with 50/50 EtOAc/DCM on Biotage 75. Triturated solid product to give the title compound (30.0 g, 46% yield).

EXAMPLE 504

N-(4-Formylphenyl)-N-(ethanesulfonyl)pyrid-3-ylmethylamine

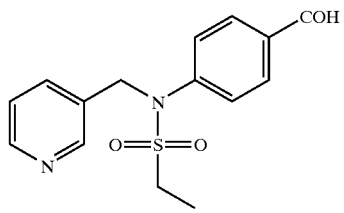

To a solution of DMSO (0.190 mL, 2.68 mmol) in 4 mL DCM at −78° C. was added oxalyl chloride (0.146 mL, 1.67 mmol) dropwise. After 15 min a solution of N-(4-(hydoxymethyl)phenyl)-N-(ethanesulfonyl)pyrid-3-ylmethylamine (0.241 g, 0.669 mmol) was added via cannula. The reaction was stirred for 30 min and triethylamine (0.932 mL, 6.69 mmol) was added and warmed to 0° C. over 1 h. The mixture was poured into saturated $NaHCO_3$ solution and diluted with ether. The organic layer was washed with $H_2O$ and brine, dried over $MgSO_4$, filtered, and concentrated. The residue was chromatographed on silica gel with 5:1 DCM/EtOAc to give 173 mg of a clear oil (72%). $^1H$ NMR: 9.97 (s,1H), 8.50 (dd,J=4.9, 1.5 Hz, 1H), 8.35 (d,J=2.0 Hz, 1H), 7.87 (m,2H), 7.66 (dt,J=7.8, 2.0 Hz, 1H), 7.44 (m,2H), 7.24 (ddd,J=7.8, 4.9, 1.0 Hz, 1H), 4.97 (s,2H), 3.84 (q,J=9.3 Hz, 2H).

EXAMPLE 505

N-(3-(Phenoxymethyl)phenyl)-N-(ethanesulfonyl)pyrid-3-ylmethylamine

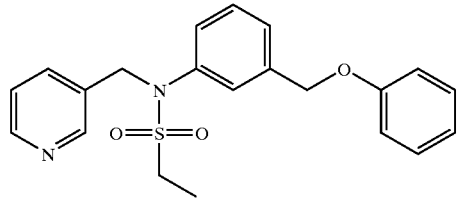

To a solution of triphenylphosphine (0.141 g, 0.539 mmol) in 3.5 mL THF was added diethylazodicarboxylate (0.165 g, 0.539 mmol). After 5 min phenol (0.061 g, 0.646 mmol) was added as a solution in 2 mL THF. After 5 min N-(3-(hydroxymethyl)phenyl)-N-(ethanesulfonyl)pyrid-3-ylmethylamine (0.165 g, 0.539 mmol) was added as a solution in 2 mL THF and the reaction was stirred for 3 days. The mixture was diluted with EtOAc, washed with 1 N NaOH and brine, dried over $MgSO_4$, filtered and concentrated. The residue was chromatographed on silica gel with 4:1 to 2:1 DCM/EtOAc to give the title compounds as a clear oil. $^1H$ NMR: 8.48 (d,J=1.5 Hz, 1H), 8.36 (s,1H), 7.64 (d,J=7.8 Hz, 1H), 7.36–7.23 (m,5H), 7.19 (m,2H), 6.95 (t,J=7.8 Hz, 1H), 6.91 (d,J=7.8 Hz, 1H), 5.01 (s,2H), 4.84 (s,2H), 3.03 (q,J=7.6 Hz, 2H), 1.39 (t,J=7.6 Hz, 3H). MS calcd. 382.1; MS (M+1) 383.1.

EXAMPLE 506

N-(4-(Phenoxymethyl)phenyl)-N-(ethanesulfonyl)pyrid-3-ylmethylamine

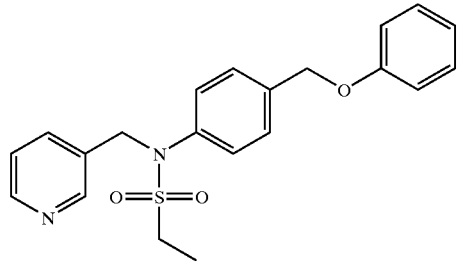

The title compound was prepared using a method similar to the method of Example 505 using N-(4-hydroxymethylphenyl)-N-(ethylsulfonyl)pyrid-3-ylmethylamine. $^1H$ NMR: 8.41 (d,1H,J=3.4 Hz), 8.29 (d,1H, J=1.5 Hz), 7.63 (d,1H,J=7.8 Hz), 7.00–7.40 (m,7H), 6.86 (m,3H), 4.92 (s,2H), 4.81,(s,2H), 3.00 (q,2H,J=7.3 Hz), 1.34 (t,3H,J=7.3 Hz). MS calcd 382.1; MS (M+1) 383.1.

By a method similar to the method of Example 475 the following compounds were prepared:

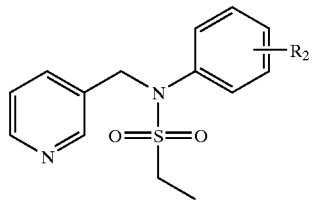

| No. | R2 | Data |
|---|---|---|
| 507 | 3-(α-hydroxybenzyl) | $^1$H NMR: 8.43(dd, J=4.9, 1.5Hz, 1H), 8.29(d, J=2.0Hz, 1H), 7.63(dt, J=8.3, 1.5Hz, 1H), 7.36–7.21(m, 8H), 7.19–7.12(m, 2H), 5.77(s, 1H), 4.84(s, 2H), 3.06(q, J=7.3Hz, 2H), 2.68(br s, 1H), 1.39(t, J=7.3Hz, 3H) |
| 508 | 4-(α-hydroxybenzyl) | $^1$H NMR: 8.48(d, 1H, J=3.9Hz), 8.35(br s, 1H), 7.73(d, 1H, J=7.8Hz), 7.34(m, 5H), 7.30–7.23(m, 3H), 7.21(d, 2H, J=8.3Hz), 5.80(s, 2H), 4.88(s, 2H), 3.07(q, 2H, J=7.3Hz), 1.41(t, 3H, J=7.3Hz). MS calcd 382.1; MS (M+1) 383.1 |
| 509 | 3-(α-hydroxy-2-fluorobenzyl) | $^1$H NMR: 8.46(d, 1H, J=3.4Hz), 8.32(s, 1H), 7.62(m, 1H), 7.42–6.92(m, 9H), 6.00(s, 1H), 4.85(s, 2H), 3.06(m, 2H), 1.38(m, 3H). MS calcd 400.1; MS (M+1) 401.1 |
| 510 | 3-(α-hydroxy-3-fluorobenzyl) | $^1$H NMR: 8.46(d, 1H), 8.34(s, 1H), 7.62(d, 1H), 7.40–7.15(m, 6H), 7.04–6.88(m, 3H), 5.75(s, 1H), 4.85(s, 2H), 3.07(q, 2H, J=7.3Hz), 1.40(t, 3H, 7.3Hz). MS calcd 400.1; MS (M+1) 401.1 |

EXAMPLE 511

N-(3-(α-Hydroxy-4-ethoxycarbonylbenzyl)phenyl)-N-(ethanesulfonyl)pyrid-3-ylmethylamine

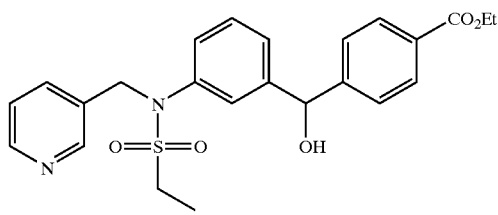

A solution of ethoxycarbonylphenylzinc iodide in THF (Rieke Metals, Inc.) (0.5 M, 2.8 ml) was evaporated to dryness under nitrogen. To the residue was added chromiun (III) chloride (0.210 g, 1.33 mmole), N-(3-formylphenyl)-N-(2,2,2-trifuoroethylsulfonyl)pyrid-3-ylmethylamine (0.210 g, 0.7 mmole), and tetramethylurea (0.5+1.5 ml), followed by chlorotrimethylsilane (0.7 ml, 0.55 mmole) dropwise. The mixture was stirred overnight at room temperature. A few pieces of ice, 1 ml of saturated NaHCO$_3$ and 1 ml of ethylene diamine were added to the reaction mixture, which was filtered. The organic layer was washed with brine, after extraction with ethyl acetate. Evaporation afforded the crude product, that was chromatographed on a silica-gel column eluted with ethyl acetate and chloroform to give the title compound. $^1$H NMR: 8.44 (d,1H, J=4.1 Hz), 8.29 (s,1H), 7.99 (d,2H,J=8 Hz), 7.62 (d,1H), 7.34–7.14 (m,7H), 5.80 (s,1H), 4.85 (s,2H), 4.36 (q,2H, J=7.1 Hz), 3.05 (q,2H,J=7.4 Hz), 1.41 (m,6H). MS calcd. 454.2; MS (M+1) 455.2.

EXAMPLE 512

N-(3-(α-Hydroxy-3-ethoxycarbonylbenzyl)phenyl)-N-(ethanesulfonyl)pyrid-3-ylmethylamine

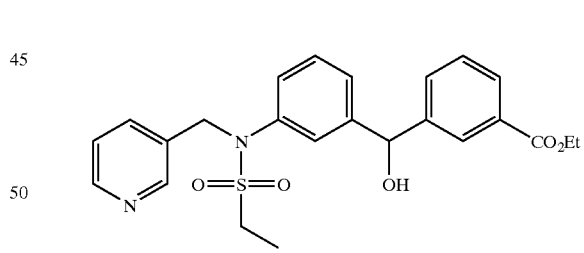

The title compound was prepared using a method similar to the method of Example 511 using 3-ethoxycarbonylphenylzinc chloride (Rieke Metals Inc.) as starting materials. $^1$H NMR: 8.43–8.29 (m,2H), 7.63 (d,1H), 7.40–7.00 (m,9H), 5.80 (s,1H), 4.85 (s,2H), 4.36 (q,2H), 3.08 (m,4H), 1.38 (m, 0.6H). MS calcd 454.2; MS (M+1) 455.2.

By a method similar to the method of Example 491 the following compounds were prepared:

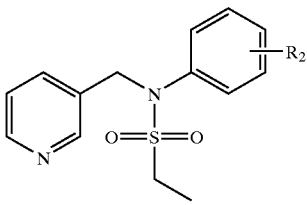

| No. | R2 | Data |
|---|---|---|
| 513 | 3-(4-ethoxy-carbonyl benzyl) | ¹H NMR: 8.48(d, 1H, J=4.3Hz), 8.33(s, 1H), 7.95(d, H, J=8.2Hz), 7.62(d, 1H, J=7.8Hz), 7.27–6.94(m, 7H), 4.85(s, 2H), 4.36(q, 2H, J=7.3Hz), 3.95(s, 2H), 3.10(q, 2H, J=7.0Hz), 2.04(1H), 1.38(m, 6H). MS calcd 438.2; MS (M+1) 439.1 |
| 514 | 3-(2-fluoro-benzyl) | ¹H NMR: 8.47(m, 1H), 8.36(d, 1H, J=2.0Hz), 7.64(m, 1H), 7.26–6.96(m, 9H), 4.85(s, 2H), 3.93(s, 2H), 3.08(q, 2H). MS calcd 384.1; MS (M+1) 385.2 |

EXAMPLE 515

N-(3-(α-Fluorobenzyl)phenyl)-N-(ethanesulfonyl)pyrid-3-ylmethylamine

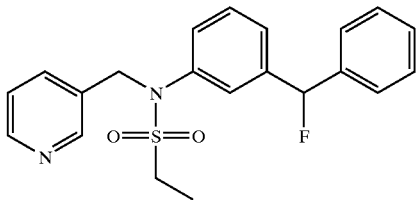

To a solution of N-(3-(α-hydroxybenzyl)phenyl)-N-(ethylsulfonyl)pyrid-3-ylmethylamine (0.106 g, 2.77 mmol) in DCM was added DAST (0.040 mL, 3.05 mmol). The reaction was stirred overnight and poured into saturated NaHCO₃ solution and extracted with EtOAc, dried over MgSO₄, filtered, and concentrated. The residue was chromatographed on silica gel with 2:1 DCM/EtOAc to give the title compound as a clear oil. ¹H NMR: 8.47 (dd,J=4.9, 1.5 Hz, 1H), 8.33 (d,J=2.0 Hz, 1H), 7.63 (dt,J=7.8, 2.0 Hz, 1H), 7.38–7.28 (m,4H), 7.24–7.16 (m,6H), 4.89 (AofAB,d,J=14.8 Hz, 1H), 4.83 (BofABd,J=14.8 Hz, 1H), 3.07 (q,J=7.3 Hz, 2H), 1.40 (t,J=7.3 Hz, 3H). MS calcd. 384.1; MS (M+1) 385.1.

EXAMPLE 516

N-(4-(α-Fluorobenzyl)phenyl)-N-(ethanesulfonyl)pyrid-3-ylmethylamine

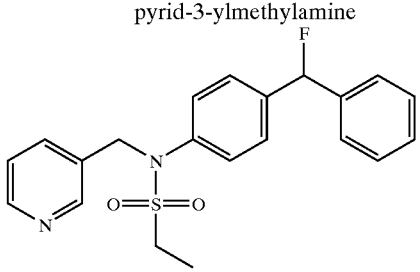

By the method of Example 515 using N-(4-(α-hydroxybenzyl)phenyl)-N-(ethylsulfonyl)pyrid-3-ylmethylamine gave the title compound. ¹H NMR: 8.49 (d,1H,J=3.9 Hz), 8.37 (br s,1H), 7.72 (d,1H,J=7.8 Hz), 7.37 (m,3H), 7.31–7.23 (m,7H), 6.41 (d,1H,J=49.9 Hz), 4.90 (s,2H), 3.08 (q,2H,J=7.3 Hz), 1.43 (t,3H,J=7.3 Hz). MS calcd 384.1; MS (M+1) 385.2.

EXAMPLE 517

N-(3-Benzoylphenyl)-N-(ethanesulfonyl)pyrid-3-ylmethylamine

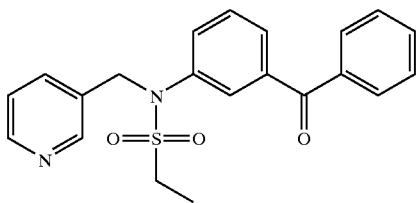

To a solution of N-(3-(α-hydroxybenzyl)phenyl)-N-(ethylsulfonyl)pyrid-3-ylmethylamine (0.717 g, 1.87 mmol) in 10 mL DCM was added activated MnO₂ (0.489 g, 5.62 mmol). The reaction was gently heated and sonicated for 5 min then stirred overnight. Another portion of MnO₂ (0.489 g, 5.62 mmol) was added and it was sonicated and stirred overnight again. The mixture was filtered through Celite and concentrated to give a pure white solid. ¹H NMR: 8.52 (dd,J=4.9, 1.5 Hz, 1H), 8.40 (d,J=2.0 Hz, 1H), 7.74–7.66 (m,5H), 7.61 (m,1H), 7.51–7.42 (m,4H), 7.25 (dd,J=7.8, 4.9 Hz, 1H), 4.93 (s,2H), 3.14 (q,J=7.3 Hz, 2H), 1.45 (t,J=7.3 Hz, 3H). MS calcd. 380.1; MS (M+1) 381.1.

EXAMPLE 518

N-(4-Benzoylphenyl)-N-(ethanesulfonyl)pyrid-3-ylmethylamine

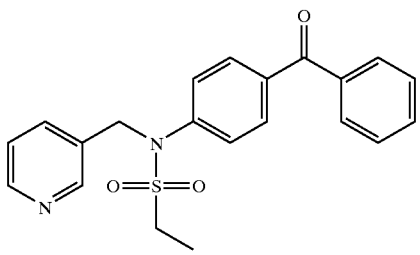

By the method of Example 517 using N-(4-(α-hydroxybenzyl)phenyl)-N-(ethylsulfonyl)pyrid-3-ylmethylamine the tittle compound was obtained. ¹H NMR: 8.51 (d,1H,J=3.9 Hz), 8.44 (br s,1H), 7.79–7.71 (m,4H), 7.59 (m,1H), 7.48 (m, 2H), 7.41 (d,2H,J=8.3 Hz), 7.26 (m,2H), 4.99 (s,2H), 3.15 (q,2H,J=7.3 Hz), 1.46 (t,3H,J=7.3 Hz). MS calcd 380.1; MS (M+1) 381.1.

EXAMPLE 519

N-(3-(1-Phenylvinyl)phenyl)-N-(ethanesulfonyl)pyrid-3-ylmethylamine

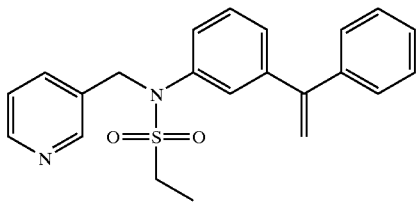

To a suspension of methyltriphenylphosphonium bromide (0.269 g, 0.752) in 3 mL THF at 0° C. was added KHMDS (0.5 M in toluene, 1.5 mL, 0.752 mmol). The mixture was warmed to ambient temperature for 1 h and N-(3-benzoylphenyl)-N-(ethylsulfonyl)pyrid-3-ylmethylamine (0.143 g, 0.376 mmol) as a solution in 3 mL THF was added via cannula. After 3 h the mixture was poured into saturated NaHCO$_3$ solution and Extracted with EtOAc, dried over MgSO$_4$, filtered and concentrated. The residue was chromatographed with 10:1 to 5:1 DCM/EtOAc to give the title compound as a clear oil. $^1$H NMR: 8.50 (dd,J=4.9, 1.5 Hz, 1H), 8.35 (d,J=2.0 Hz, 1H), 7.70 (dt,J=7.8, 2.0 Hz, 1H), 7.37–7.19 (m,9H), 7.14 (m,1H), 5.48 (d,J=1.0 Hz, 1H), 5.39 (d,J=1.0 Hz, 1H), 4.85 (s,2H), 3.09 (q,J=7.3 Hz, 2H), 1.41 (t,J=7.3 Hz, 3H). MS calcd. 378.1; MS (M+1) 379.1.

EXAMPLE 520

N-(4-(1-Phenylvinyl)phenyl)-N-(ethanesulfonyl)pyrid-3-ylmethylamine

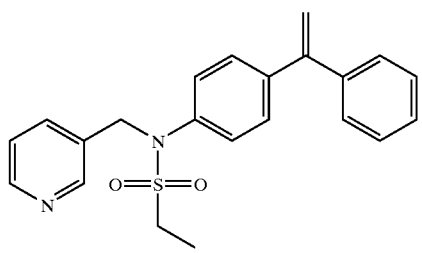

By the method of Example 519 using N-(4-benzoylphenyl)-N-(ethylsulfonyl)pyrid-3-ylmethylamine the tittle compound was obtained. $^1$H NMR: 8.51 (d,1H,J=3.9 Hz), 8.44 (br s,1H), 7.79–7.71 (m,4H), 7.59 (m,1H), 7.48 (m, 2H), 7.41 (d,2H,J=8.3 Hz), 7.26 (m,2H), 4.99 (s,2H), 3.15 (q,2H,J=7.3 Hz), 1.46 (t,3H,J=7.3 Hz). MS calcd 380.1; MS (M+1) 381.1.

EXAMPLE 521

N-(3-(α-Methylbenzyl)phenyl)-N-(ethanesulfonyl)pyrid-3-ylmethylamine

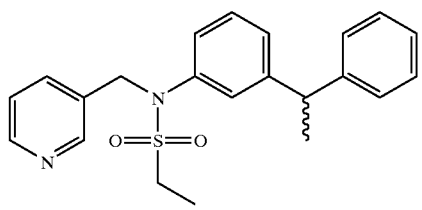

The title compound was prepared using a method similar to the method of Example 491 using N-[3-(1-phenylvinyl)phenyl]-N-(ethylsulfonyl)pyrid-3-ylmethylamine. $^1$H NMR: 8.47 (dd,J=4.9, 1.5 Hz, 1H), 8.32 (d,J=2.0 Hz, 1H), 7.61 (dt,J=7.8, 2.0 Hz, 1H), 7.30–7.05 (m,9H), 6.99 (m,1H), 4.82 (s,2H), 4.08 (q,J=7.3 Hz, 1H), 3.04 (q,J=7.3 Hz, 2H), 1.56 (d,J=7.3 Hz, 3H), 1.38 (t,J=7.3 Hz, 3H). MS calcd. 380.2; MS (M+1) 381.2.

EXAMPLE 522

N-(4-(α-Methylbenzyl)phenyl)-N-(ethanesulfonyl)pyrid-3-ylmethylamine

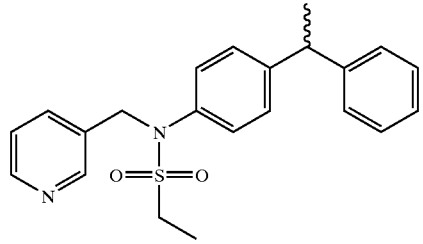

The title compound was prepared using a method similar to the method of Example 491 using N-[3-(1-phenylvinyl)phenyl]-N-(ethylsulfonyl)pyrid-3-ylmethylamine. $^1$H NMR: 8.49 (dd,1H,J=4.4, 1.0 Hz), 8.35 (d,1H,J=1.5 Hz), 7.72 (d,1H,J=7.8 Hz), 7.31–7.11 (m,10H), 4.86 (s,2H), 4.10 (q,1H,J=7.3 Hz), 3.07 (q,2H,J=7.3 Hz), 1.59 (d,3H,J=7.3 Hz), 1.41 (q,3H,J=7.3 Hz). MS calcd 380.2; MS (M+1) 381.3.

Preparation 11

N-(3-Iodo-4-methylphenyl)pyrid-3-ylmethylamine

The title compound was prepared using a method similar to the method of Preparation 8 with 3-iodo-4-methylaniline as starting material. $^1$H NMR: 8.61 (d,J=1.5 Hz, 1H), 8.53 (dd,J=4.9, 2.0 Hz, 1H), 7.67 (dt,J=7.8, 1.5 Hz, 1H), 7.27 (ddd,J=7.8, 4.9, 1.0 Hz, 1H), 7.15 (d,J=2.5 Hz, 1H), 7.00 (d,J=8.3 Hz, 1H), 6.52 (dd,J=7.8, 2.5 Hz, 1H), 4.30 (d,J=5.4 Hz, 2H), 3.97 (br s,1H), 2.31 (s,3H).

EXAMPLE 523

N-(3-Iodo-4-methylphenyl)-N-(ethanesulfonyl)pyrid-3-ylmethylamine

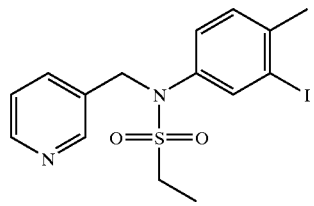

The title compound was prepared using a method similar to the method of Example 467 using N-(3-iodo-4-methylphenyl)pyrid-3-ylmethylamine. $^1$H NMR: 8.50 (d,J= 3.4 Hz, 1H), 8.36 (d,J=1.6 Hz, 1H), 7.69 (m,2H), 7.26 (t,J=5.9 Hz, 1H), 7.14 (d,J=7.8 Hz, 1H), 7.08 (dd,J=7.8, 2.0 Hz, 1H), 4.84 (s,2H), 3.08 (q,J=7.3 Hz, 2H), 1.42 (t,J=7.3 Hz, 1H).

EXAMPLE 524

N-(3-Formyl-4-methylphenyl)-N-(ethanesulfonyl)pyrid-3-ylmethylamine

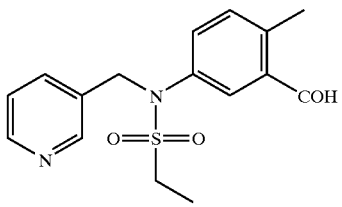

A mixture of N-(3-iodo-4-methylphenyl)-N-(ethylsulfonyl)pyrid-3-ylmethylamine (0.415 g, 0.997 mmol), sodium formate (0.102 g, 1.50 mmol), and dichlorobis(triphenylphosphine)palladium (0.014 g, 0.020 mmol) were combined in 1.0 mL DMF and purged with anhydrous CO gas. The mixture was heated to 100° C. for 1.5 h. The reaction was poured into saturated $NaHCO_3$ solution and extracted with EtOAc. The combined fractions were washed with $H_2O$ and brine, dried over $MgSO_4$, filtered and concentrated. The mixture was chromatographed on silica gel with 1:1 EtOAc/DCM to give the title compound as a clear oil. $^1$H NMR: 10.11 (s,1H), 8.38 (br s,1H), 8.26 (br s,1H). 7.60 (m,2H), 7.13 (m,1H), 7.00 (s,2H), 4.80 (s,2H), 3.00 (q,J=7.3 Hz, 2H), 2.52 (s,3H), 2.35 (t,J=7.3 Hz, 3H).

EXAMPLE 525

N-(3-(α-Hydroxybenzyl)-4-methylphenyl)-N-ethanesulfonyl)pyrid-3-ylmethylamine

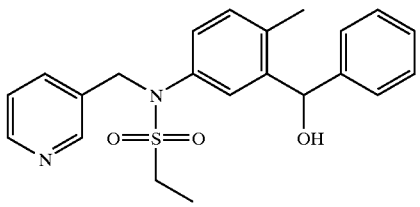

The title compound was prepared using a method similar to the method of Example 475 using N-(3-formyl-4-methylphenyl)-N-(ethylsulfonyl)pyrid-3-ylmethylamine. $^1$H NMR: 8.46 (br s,1H), 8.30 (br s,1H), 7.69 (br d,J=7.8 Hz, 1H), 7.45 (s,1H), 7.36–7.19 (m,4H), 7.13 (d,J=6.3 Hz, 2H), 7.06 (m,2H), 5.87 (s,1H), 4.91 (AofAB,d,J=14.7 Hz, 1H), 4.82 (BofAB,d,J=14.7 Hz, 1H), 3.08 (q,J=7.3 Hz, 2H), 2.54 (br s,1H), 2.13 (s,3H), 1.41 (t,J=7.3 Hz, 3H). MS calcd. 396.2; MS (M+1) 397.2.

EXAMPLE 526

N-(3-Benzyl-4-methylphenyl)-N-(ethanesulfonyl)pyrid-3-ylmethylamine

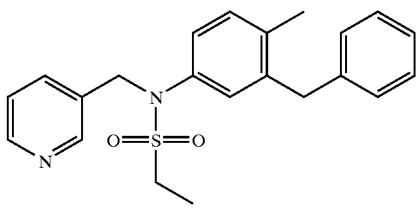

The title compound was prepared using a method similar to the method of Example 491 using N-(3-(α-hydroxybenzyl)-4-methylphenyl)-N-ethanesulfonyl)pyrid-3-ylmethylamine. $^1$H NMR: 8.49 (d,J=3.9,1H), 8.32 (br s,1H), 7.67 (br d,J=7.8 Hz, 1H), 7.28–7.17 (m,4H), 7.09 (d,J=7.8 Hz, 1H), 7.02 (dd,J=7.8, 2.0 Hz, 1H), 6.97 (d,J=7.4 Hz, 2H), 6.88 (d,J=2.3 Hz, 1H), 4.81 (s,2H), 3.88 (s,2H), 3.06 (q,J=7.3 Hz, 2H), 2.18 (s,3H), 1.39 (t,J=7.3 Hz, 3H). MS calcd. 380.2; MS (M+1) 381.2.

EXAMPLE 527

N-(3-(4-t-Butylphenoxy)-4-methylphenyl)-N-(ethanesulfonyl)pyrid-3-ylmethylamine

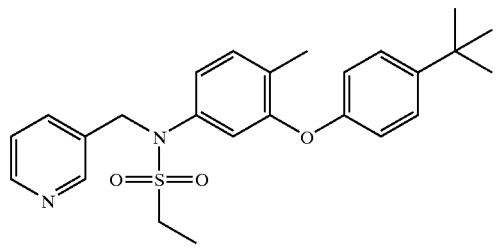

The title compound was prepared following Example 342 using N-(3-iodo-4-methylphenyl)-N-(ethanesulfonyl)pyrid-3-ylmethylamine and 4-tert-butylphenol and purifying via radial chromatography eluting with 50:50 to 53:47 THF/hexanes gave the title compound. $^1$H NMR (400 MHz) 1.32 (9H, s), 1.39 (3H, t, J=7.8 Hz), 2.19 (3H, s), 3.07 (2H, q, J=7.8 Hz), 4.79 (2H, s), 6.70 (3H, m), 6.92 (1H, dd, J=2.0, 7.8 Hz), 7.16 (1H, d, J=7.8 Hz), 7.20–7.31 (3H, m), 7.67 (1H, d, J=8.3 Hz), 8.31 (1H, bs), 8.50 (1H, bs). HRMS calculated 439.2055 [M+H]+ Found 439.2073.

EXAMPLE 528

N-(3-(2-Methoxyphenoxy)benzyl)-N-(2,2,2-trifluoroethanesulfonyl)pyrid-3-ylmethylamine

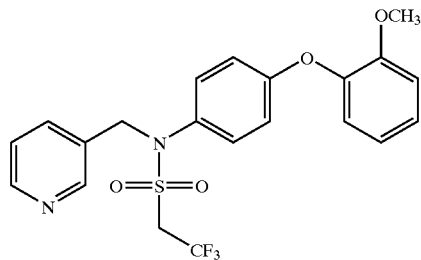

The title compound was prepared following Example 1 using 3-(2-benzyloxyphenoxy)benzyl amine gave the title compound which was isolated as its HCl salt. $^1$H NMR: 8.53 (s,1H), 8.40 (s,1H), 7.62 (d,1H,J=8 Hz), 7.14–7.24 (m,4H), 6.85–7.00 (m,4H), 6.77 (s,1H), 4.39 (s,2H), 4.30 (s, 2H), 3.80 (s,3H), 3.56–3.58 (m,3H). MS calcd. 466.48; MS (M+1) 467.9.

EXAMPLE 529

N-(3-(2-Methoxyphenoxy)benzyl)-N-(ethanesulfonyl)pyrid-3-ylmethylamine

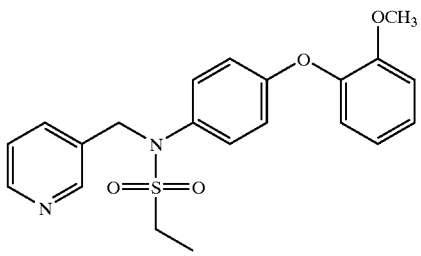

The title compound was prepared following Example 1 using 3-(2-benzyloxyphenoxy)benzyl amine gave the title compound which was isolated as its HCl salt. ¹H NMR: 8.51(d,1H,J=4 Hz), 8.39 (s,1H), 7.65(d,1H,J=8 Hz), 7.13–7.24 (m,4H), 6.84–7.02 (m,4H), 6.78 (s,1H), 4.34 (s,2H), 4.25 (s,2H), 3.81 (s,3H), 2.92–2.96 (m,2H), 1.28 (t,3H,J=8 Hz). MS calcd. 412.5; MS (M+1) 413.6.

EXAMPLE 530

N-(3-(2-Phenylvinyl)phenyl)-N-(ethanesulfonyl)pyrid-3-ylmethylamine

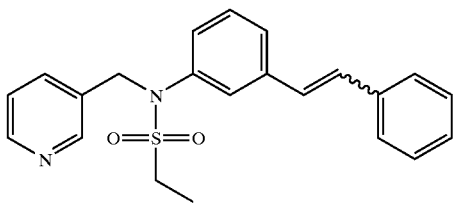

Benzyltriphenylphosphonium bromide (0.765 g, 1.77 mmol) was dispersed into THF (12 ml) and cooled at 0° C. To the cooled suspension was added dropwise a solution of potassium bis(trimethylsilyl)amide (0.5 M, 3.5 ml, 1.75 mmol). After stirring at 0° C. for 1 h, a solution of). N-(3-formyl-phenyl)-N-(ethylsulfonyl)pyrid-3-ylmethylamine (0.304 g, 1.0 mmol) in THF was added. The reaction mixture was stirred at ambient temperature for 2 h. Evaporation and chromatography on silica-gel eluting with toluene-EtOAc to give the title compound. ¹H NMR: 8.48 (d,1H,J=3.4 Hz), 8.30 (d,1H,J=2.0 Hz), 7.65 (d,1H,J=7.8 Hz), 7.30–6.74 (m,8H), 6.60 (q,2H,J=12.2, 37.1 Hz), 4.68 (s,2H), 2.87 (q,2H,J=7.3 Hz), 1.28 (t,3H,J=7.4 Hz). MS calcd 378.1; MS (M+1) 379.1.

EXAMPLE 531

N-(3-(2-Phenylethyl)phenyl)-N-(ethanesulfonyl)pyrid-3-ylmethylamine

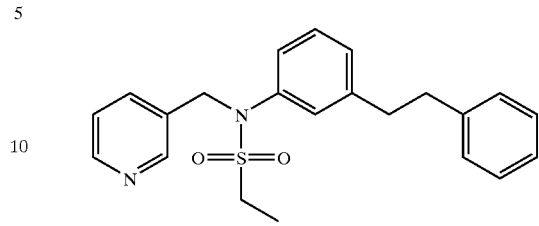

N-(2-phenylvinylphenyl)-N-(ethylsulfonyl)pyrid-3-ylmethylamine (0.50 g, 0.13 mmol) was dissolved in ethanol (5 ml), followed by addition of 5% platinum-on-carbon (0.38 g). After flushing with hydrogen, the mixture was stirred under hydrogen-ballon at ambient temperature overnight and filtered. Upon evaporation, it underwent chromatography on silica-gel with eluent of toluene and EtOAc and gave 0.32 g (64% yield). ¹H NMR: 8.48 (d,1H,J=3.4), 8.34 (s,1H), 7.68 (s,1H), 7.30–6.86(m,10H), 4.81 (s,2H), 3.04–2.82 (m,6H), 1.38 (t,3H, J=7.3 Hz). MS calcd 380.2; MS (M+1) 381.1.

EXAMPLE 532

N-(3 (Prop-1-en-1-yl)phenyl)-N-(ethanesulfonyl)pyrid-3-ylmethylamine

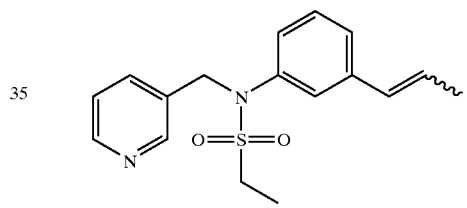

The title compound was prepared using a method similar to the method of Example 530 using N-(3-formylphenyl)-N-(ethylsulfonyl)pyrid-3-ylmethylamine. ¹H NMR: 8.39 (d,1H,J=1.5 Hz), 8.30 (s,1H), 7.62 (d,1H,J=8.3 Hz), 7.22–6.80 (m,5H), 6.25 (d,1H,J=10.3), 5.70 (m,1H), 4.80 (s,1H), 3.01 (q,2H,7.4 Hz), 1.72 (d,3H,J=6.4 Hz), 1.34 (t,3H,J=7.3 Hz). MS calcd 316.1; MS (M+1) 317.1.

EXAMPLE 533

N-(3-(2-N,N-Diethylamidovinyl)phenyl)-N-(ethanesulfonyl)pyrid-3-ylmethylamine

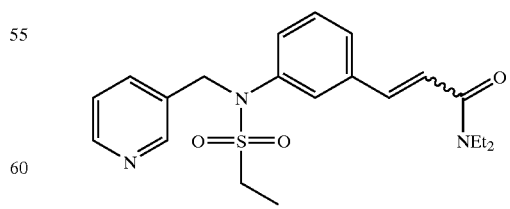

The title compound was prepared using a method similar to the method of Example 530 using N-(3-formylphenyl)-N-(ethylsulfonyl)pyrid-3-ylmethylamine. ¹H NMR: 8.41 (d,1H,J=3.4 Hz), 8.32 (s,1H), 7.70–7.03 (m,9H), 6.61 (d,1H, 15.1 Hz), 4.83 (s,1H), 3.39 (m,2H), 3.05 (m,2H), 1.36 (t,3H,J=7.3 Hz), 1.26–1.04 (m,6H). MS calcd 401.2;MS (M+1) 402.2.

EXAMPLE 534

N-(3-(2-Ethoxycarbonylvinyl)phenyl)-N-(ethanesulfonyl)pyrid-3-ylmethylamine

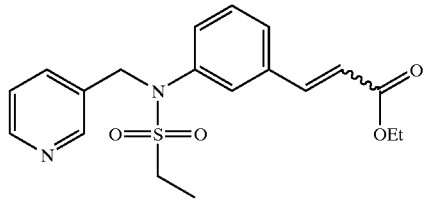

The title compound was prepared using a method similar to the method of Example 530 using N-(3-formylphenyl)-N-(ethylsulfonyl)pyrid-3-ylmethylamine. ¹H NMR: 8.50 (d,1H,J=1.5 Hz), 8.37 (s,1H), 7.80–7.50 (m,2H), 7.30–7.10 (m,4H), 4.90 (s,2H), 4.25 (q,2H,J=7.3 Hz), 3.10 (q, 2H, 7.3 Hz), 1.50–1.28 (m,6H). MS calcd 374.1; MS (M+1) 375.1.

EXAMPLE 535

N-(3-Propylphenyl)-N-(ethanesulfonyl)pyrid-3-ylmethylamine

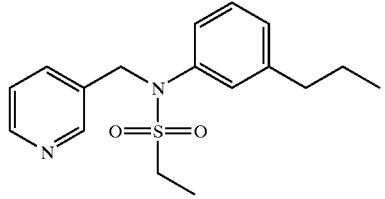

The title compound was prepared using a method similar to the method of Example 431. ¹H NMR: 8.48 (d,1H,J=3.4 Hz), 8.35 (d,1H,J=1.5 Hz), 7.70 (d,1H, 7.8 Hz), 7.21 (m,2H), 7.05 (m,3H), 4.87 (s,2H), 3.10 (q, 2H,J=7.8 Hz), 2.50 (t,2H,J=7.3 Hz), 1.75–1.20 (m,6H), 0.85 (t,3H,J=7.3 Hz). MS calcd 318.1; MS (M+1) 319.1.

EXAMPLE 536

N-(3-Trifluoromethoxyphenyl)-N-(2,2,2-trifluoroethanesulfonyl)pyrid-3-ylmethylamine

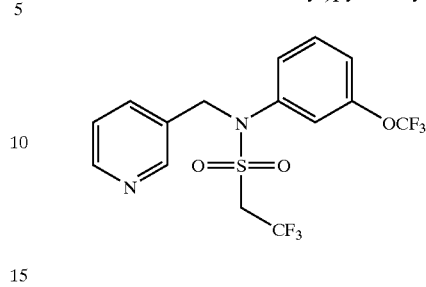

3-(Ttrifluoromethoxy)aniline (0.602 g, 3.4 mmol) and pyridine-3-caroxaldehyde (0.400 g, 3.7 mmol) were dissolved in methanol (10 ml). The solution was refluxed for 3 h and then cooled in an ice-bath. To the solution was added sodium borohydride (0.212 g, 5.5 mmol) in portions. The reaction mixture was stirred at ambient temperature overnight. After addition of small pieces of ice, the solvent was evaporated to near dryness. The residue was dissoved in cold water and extracted with ethyl acetate. The organic phase was washed with brine and dried over MgSO₄. Filtration and evaporation afforded N-(3-trifluoromethoxyphenyl)pyrid-3-ylmethylamine. ¹H NMR: 8.43–8.44 (m,2H), 7.60(d,1H), 7.00–7.30 (m,3H), 6.20–6.40 (m,2H), 4.27 (d,5.4 Hz). MS calcd 268.1; MS (M+1) 269.0.

N-(3-trifluoromethoxyphenyl)pyrid-3-ylmethylamine (0.270 g, 1 mmol) and pyridine were dissolved in dichloroethane (2 ml). The solution was cooled in an ice-bath. To the solution was added 2,2,2-trifluoroethylsulfonyl chloride (0.274 g, 1.5 mmol). The mixture was stirred at room temperature overnight. Upon removing solvent, the residue was dissolved in water and extracted with EtOAc. The organic phase was washed with brine concentrated. The residue was chromatographed to afford the title compound. ¹H NMR: 8.42 (d,1H,J=6.4 Hz), 8.20 (d,1H,J=2.0 Hz), 7.57 (d,1H,J=9.8 Hz), 7.40–6.85 (m,5H), 4.81 (s,2H), 3.72 (q,2H, J=7.8 Hz). MS calcd 414.1; MS (M+1) 415.1.

By a method similar to the method of Example 536 the following compounds were prepared:

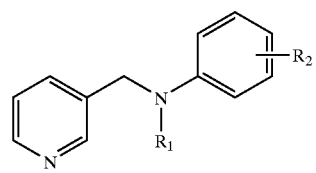

| No. | R1 | R2 | Data |
|---|---|---|---|
| 537 | SO₂CH₂CH₃ | 3-trifluoromethoxy | ¹H NMR: 8.42(s, 1H), 8.29(s, 1H), 7.60(d, 1H), 7.00–7.30(m, 5H), 4.81(s, 2H), 3.01(q, 2H, J=7.3Hz), 1.35(t, 3H, J=7.3). MS calcd 360.1; MS (M+1) 361.2. |
| 538 | SO₂CH₂CF₃ | 4-trifluoromethyl | ¹H NMR: 8.43(d, 1H, J=3.9Hz), 8.26(s, 1H), 7.56(m, 3H), 7.00–7.30(m, 3H), 4.85(s, 2H), 3.72(q, 2H, J=8.3Hz). MS calcd 398.05; MS (M+1) 399.1 |
| 539 | SO₂CH₂CF₃ | 4-trifluoromethoxy | ¹H NMR: 8.44(d, 1H, J=3.9Hz), 8.25(d, 1.5Hz), 7.59(d, 1H, J=7.8Hz), 5.00–7.30(m, 5H), 4.80(s, 2H), 3.72(q, 2H, J=8.8Hz). MS calcd 414.1; MS (M+1) 415.1 |

-continued

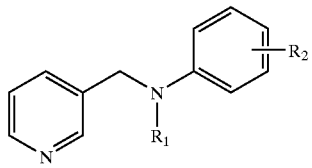

| No. | R1 | R2 | Data |
|---|---|---|---|
| 540 | SO₂CH₂CH₃ | 4-trifluoromethoxy | ¹H NMR: 8.42(d, 1H, J=3.4Hz), 8.29(d, 1H, J=2.0Hz), 7.61(d, 1H, J=7.8Hz), 7.00–7.25(m, 5H), 4.79(s, 2H), 3.01(q, 2H, J=7.3Hz), 1.35(t, 3H, J=7.3Hz). MS calcd 360.1; MS (M+1) 361.2 |
| 541 | SO₂CH₂CF₃ | 3-methoxy | ¹H NMR: 8.41(d, 1H, J=3.4Hz), 8.26(s, 1H), 7.59(d, 1H, J=7.8Hz), 7.17(m, 2H), 6.60–6.86(m, 3H), 4.79(s, 2H), 3.50–3.82(m, 5H). MS calcd 360.1; MS (M+1) 361.1 |
| 542 | SO₂CH₂CF₃ | 4-(prop-2-yl) | ¹H NMR: 8.42(d, 1H, J=3.9Hz), 8.23(1H), 7.62(d, 1H, J=7.8Hz), 6.96–7.26(m, 5H), 4.78(s, 2H), 3.71(q, 2H, J=9.3Hz), 2.79(quint, 1H, J=7.3Hz), 1.13(d, 6H, J=7.8Hz). MS calcd 372.1; MS (M+1) 373.2. |
| 543 | SO₂CH₂CF₃ | 2-triflurormethoxy | ¹H NMR: 8.44(m, 1H), 8.18(d, 1H, J=2.0Hz), 7.62(d, 1H, J=7.8Hz), 6.80–7.40(m, 5H), 3.80(q, 2H, J=9.3Hz). MS calcd 414.1; MS (M+1) 415.1 |
| 544 | SO₂CH₂CF₃ | 3-(prop-2-yloxy) | ¹H NMR: 8.41(d, 1H, J=3.4Hz), 8.26(d, 1H, J=1.5Hz), 7.59(d, 1H, J=7.8Hz), 7.10–7.22(m, 2H), 6.56–6.80(m, 3H), 4.79(s, 2H), 4.34(m, 1H, J=5.9Hz), 3.73(q, 2H, J=9.2Hz), 1.17(d, 6H, J=5.9Hz). MS calcd 388.1; MS (M+1) 389.2 |

EXAMPLE 545

N-(3-Benzyl-4-chlorophenyl)-N-(2,2,2-trifluoroethanesulfonyl)pyrid-3-ylmethylamine

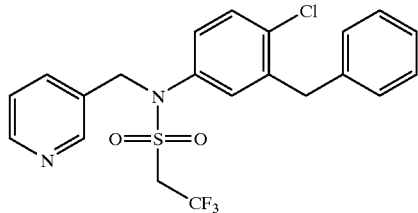

2-Chloro-5-nitrobenzophenone (1.3 g, 5.0 mmol), tin(II) chloride (4.5 g, 20 mmol), and ethanol (20 ml) were mixed and heated at 70° C. for 1 h. After cooling to room temperature, to the reaction mixture were added ice, EtOAc and aqueous NaHCO₃ and it was stirred for 30 min. The organic layer was washed with brine and dried over MgSO₄. Filtration and evaporation afforded 5-amino-2-Chlorobenzophenone. ¹H NMR, 7.85(m,2H), 7.30–7.66 (m,3H7.20 (d,1H,J=8.8 Hz), 6.60–6.80 (m,2H). MS calcd 231.1; MS (M+1) 232.0.

5-Amino-2-chlorobenzophenone (1.2 g, 5.2 mmol) and pyridine-3-carboxaldehyde (0.642 g, 6 mmol) were dissolved in methanol. The solution was refluxed for 2 h and then cooled in ice-bath. To the cold solution was added sodium borohydride (0.741 g, 19.5 mmol) in portions. The reaction mixture was stirred at ambient temperature overnight. After addition of small pieces of ice, most of the solvent was evaporated. The residue was dissolved in water and extracted with EtOAc. The combined organic layer was washed with brine and dried over MgSO₄. Upon filtering and evaporation, solid precipitated, when chloroform was added to the oil. After cooling for a while, filtration and drying gave N-(3-(α-hydroxybenzyl)-4-chlorophenyl)pyrid-3-methylamine. ¹H NMR, 8.40–8.70 (m,2H), 7.65 (d,1H), 7.00–7.50 (m,7H), 6.83 (d,1H,J=2.5 Hz), 6.43 (d, 1H), 6.14 (s,1H). MS calcd 324.1; MS (M+1) 325.1.

N-(3-(α-hydroxybenzyl)-4-chlorophenyl)pyrid-3-methylamine (0.105 g, 0.32 mmol) was dispersed into methylene chloride (5 ml) and triethylsilane (1 ml). The mixture was cooled in an ice-bath. To the cooled suspension was added trifluoroacetic acid (0.6 ml) and then stirred overnight. The reaction mixture was cooled at 0° C., to which was added ice, aqueous NaHCO₃ and chloroform. The organic phase was washed with brine and evaporated to dryness. Chromatography afforded N-(3-benzyl-4-chlorophenyl)pyrid-3-ylmethylamine. ¹H NMR: 8.53 (d,2H, J=14 Hz), 7.19 (d,1H,J=8 Hz), 7.00–7.40 (m,8H), 6.20–6.40 (m,2H), 4.27 (s,2H), 3.99 (s,2H). MS calcd 308.1; MS (M+1) 309.1.

N-(3-benzyl-4-chlorophenyl)pyrid-3-ylmethylamine (0.04 g, 0.13 mmol) and pyridine (1 ml) was dissolved in DCM. The reaction was cooled in an ice-bath to which was added dropwise 2,2,2-trifluoroethylsulfonyl chloride (0.59 g, 0.32 mmol). The mixture was stirred at room temperature overnight. After evaporation of solvent, the residue was dissolved in EtOAc and washed with cold NaHCO₃ and brine, and evaporated to dryness. Chromatography gave the title compound. ¹H NMR: 8.51 (d,1H,J=3.9 Hz), 8.27 (s,1H), 7.59 (d,1H,J=7.8 Hz), 7.34 (t,1H,J=8.3 Hz), 7.28 (d,2H,J=7.8 Hz), 7.21 (m,2H), 8.03 (m,3H), 6.89 (d,1H,J= 2.4 Hz), 4.78 (s,2H), 4.01 (s,2H), 3.73 (q,2H,J=9.3 Hz). MS calcd 454.1; MS (M+1) 455.0.

Preparation 12

N-(4-(3-Hydroxyphenyl)pyrid-3-ylmethylamine

3-Pyridinecarboxaldehyde (0.550 g, 5 mmol) and 3-aminophenol (0.540 g, 5 mmol) were dissolved into methanol (15 ml). To the solution was added a mixture of sodium cyanoborohydride (0.378 g, 6 mmol) and zinc chloride (0.408 g, 3.0 mmol) in methanol at room temperature. The reaction mixture was stirred for 2.5 h. Most of the methanol was evaporated under reduced pressure. Ice water was added to the residue. It was filtered and the layers were separated. The aqueous layer was extracted with EtOAc. The combined organic layers were washed with brine, dried over $MgSO_4$, filtered, and concentrated to give the title compound. $^1H$ NMR: 8.53 (s,1H), 8.45 (d,1H,J=3.9 Hz), 7.72 (d,1H,J=7.8 Hz), 7.24–7.30 (m,2H), 6.95–7.01 (m1H), 4.27 (s,2H). MS calcd. 200.1; MS (M+1) 201.1.

EXAMPLE 546

N-(4-(3-Cyclobutyloxyphenyl)-N-(2,2,2-trifluoroethanesulfonyl)pyrid-3-ylmethylamine

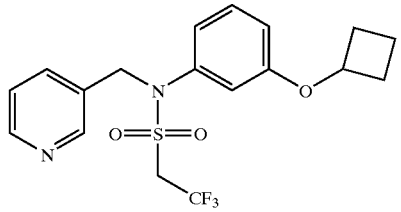

Sodium hydride (60% in mineral oil, 0.072 g, 1.8 mmol) was suspended in DMF at 0° C. To the dispersion was added dropwise N-(3-hydroxyphenyl)pyrid-3-ylmethylamine (0.250 g, 1.24 mmol) as a solution in DMF. The reaction mixture was stirred at room temperature for 30 min. Then bromocyclobutane (0.25 g, 1.84 mmol) was added as a solution in DMF. The reaction was concentrated and the residue was diluted with water, extracted with EtOAc, washed with brine, dried over $MgSO_4$, filtered and concentrated. The residue was purified by silica-gel chromatography to give N-(4-(3-Cyclobutyloxyphenyl)pyrid-3-ylmethylamine. $^1H$ NMR:, 8.61 (d,1H,J=2.3 Hz), 8.51 (q,1H,J=1.6, 3.13), 7.68 (m,1H), 7.25 (m,1H), 7.04 (t,1H,1.7 Hz), 6.18–6.24 (m,2H), 6.09 (t,1H,J=2.3 Hz), 4.6 (quint,1H, J=6.7 Hz), 2.33–2.42 (m,2H,), 2.06–2.18 (m,2H), 1.76–1.88 (m,1H), 1.57–1.70 (m,1H). MS calcd. 254.1; MS (M+1) 255.1.

To a solution of give N-(4-(3-Cyclobutyloxyphenyl) pyrid-3-ylmethylamine (0.180 g, 0.71 mmol) in DCM (5 ml) and pyridine (1 ml) was dropped a solution of 2,2,2-trifluoroethylsulfonyl chloride (0.156 g, 0.85 mmol) in DCM (1 ml) at 0° C. The reaction mixture was stirred overnight ambient temperature. After evaporation of solvent, the residue was diluted with ice water and extracted with EtOAc. The organic layer was washed with brine, evaporated and chromatographed on silica gel eluting with chloroform/ethyl acetate to give the title compound. $^1H$ NMR: 8.50 (d,1H,J=4.7 Hz), 8.34 (s,1H), 7.65–7.69 (m,1H), 7.21–7.26 (m,2H), 6.74–6.80 (m,2H), 6.63 (t,1H,J=2.0 Hz), 4.53 (q,1H,J=7.0 Hz), 3.80 (q,2H,J=8.0 Hz), 2.82–2.90 (m,2H), 2.03–2.15 (m,2H), 1.77–1.89 (m,1H), 1.60–1.73 (m,2H). MS calcd. 400.1; MS (M+1) 401.2.

By a method similar to the method of Example 546 the following compounds were prepared:

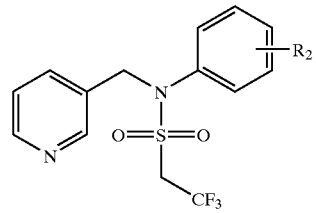

| No. | R2 | Data |
|---|---|---|
| 547 | 3-isobutyloxy | $^1H$ NMR: 8.51(m, 1H), 8.35(d, 1H, J=2.0Hz), 7.68(m, 1H), 7.25(m, 2H), 6.66–6.90(m, 3H), 4.88(s, 2H), 3.80(q, 2H, J=9.0Hz), 3.61(d, 2H, J=5.7Hz), 2.01(m, 1HJ=6.6Hz), 1.00(d, 6H, J=6.5Hz). MS calcd; MS (M+1) |
| 548 | 3-sec-butoxyl | $^1H$ NMR: 8.48(d, 1H, J=3.5Hz), 8.35(s, 1H), 7.67(m, 1H), 7.20–7.28(m, 2H), 6.60–6.90(m, 3H), 4.87(s, 2H), 4.17(m, 1H, J=6.2Hz), 3.82(q, 2H, J=9.0Hz), 1.45–1.75(m, 2H,), 1.20(d, 3H, J=5.9Hz), 0.92(t, 3H, J=7.4Hz). MS calcd 402.1; MS (M+1) 403.2 |
| 549 | 3-cyclopentyloxy | $^1H$ NMR: 8.52(d, 1H, J=4.3Hz), 8.35(s, 1H), 7.68(m, 1H), 7.26(m, 2H), 6.60–6.90(m, 3H), 4.87(s, 2H), 4.62(m, 2H), 3.82(q, 2H, J=9.0Hz), 1.40–2.00(m, 8H). MS calcd 414.1; MS (M+1) 415.2 |
| 550 | 3-cyclohexyloxy | $^1H$ NMR: 8.20–8.40(m, 2H), 7.69(m, 1H), 7.25(m, 2H), 6.60–6.94(m, 3H), 4.87(s, 2H), 4.11(m, 1H), 3.83(q, 2H, J=8.8Hz), 1.10–2.00(m, 10H). MS calcd 428.1; MS (M+1) 429.1 |
| 551 | 3-(1-ethoxycarbonyl-1,1-dimethyl methoxy) | $^1H$ NMR: 8.49(m, 1H), 8.33(d, 1H, J=1.9Hz), 7.66(m, 1H), 7.24(m, 2H), 6.60–6.90(m, 3H), 4.85(s, 2H), 4.17(q, 2H, J=7.5Hz), 3.80(q, 2H, J=9.4Hz), 1.52(s, 6H), 1.20(t, 3H, J=7.0Hz). MS calcd 460.1; MS (M+1) 461.1. |

-continued

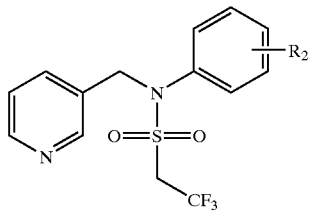

| No. | R2 | Data |
|---|---|---|
| 552 | 3-(1-ethoxycarbonyl-1-methylmethoxy) | ¹H NMR: 8.51(m, 1H), 8.35(d, 1H, J=1.9Hz), 7.66(m, 1H), 7.24(m, 2H), 6.82(m, 3H), 4.87(s, 2H), 4.64(q, 1H, J=6.6Hz), 4.18(q, 2H, J=7.0Hz), 3.80(q, 2H, J=9.0Hz), 1.60(s, 6H), 1.23(t, 3H, J=8.9Hz). MS calcd 446.1; MS (M+1) 447.0. |
| 553 | 3-(1-(ethoxycarbonyl)-cyclobut-1-yloxy) | ¹H NMR: 8.50(m, 1H), 8.32(d, 1H, J=2.0Hz), 7.66(m, 1H), 7.25(m, 2H), 6.50–6.90(m, 3H), 4.85(s, 2H), 3.88(q, 2H, J=7.3Hz), 3.78(q, 2H, J=9.0Hz), 2.68(m, 2H), 2.36(m, 2H), 2.00(m, 2H), 1.13(t, 3H, J=7.0Hz). MS calcd 472.1; MS (M+1) 473.1. |
| 554 | 3-pent-3-yloxy | ¹H NMR: 8.51(m, 1H), 8.35(d, 1H, J=2.0Hz), 7.67(m, 1H), 7.24(m, 2H), 6.60–6.90(m, 3H), 4.87(s, 2H), 3.98(m, 1H, J=5.5Hz), 3.82(q, 2H, J=9.3Hz), 1.59(m, 4H), 0.89(t, 6H, J=7.4Hz). MS calcd 416.1; MS (M+1) 417.1 |
| 555 | 3-pent-2-yloxy | ¹H NMR: 8.50(m, 1H), 8.35(d, 1H, J=2.0Hz), 7.67(m, 1H), 7.23(m, 2H), 6.60–6.90(m, 3H), 4.87(s, 2H), 4.24(m, 1H, J=5.9Hz), 3.82(q, 2H, J=9.0Hz), 1.27–1.80(m, 4H), 1.21(d, 3H, J=5.9Hz), 0.90(t, 3H, J=7.1Hz). MS calcd 416.1; MS (M+1) 417.2 |
| 556 | 3-(2,2,2-trifluoroethoxy)- | ¹H NMR: 8.52(m, 1H), 8.35(d, 1H, J=1.6Hz), 7.67(m, 1H), 7.26(m, 2H), 6.70–6.98(m, 3H), 4.89(s, 2H), 4.26(q, 2H, J=7.8Hz), 3.81(q, 2H, J=8.4Hz). MS calcd 428.1; MS (M+1) 429.1 |
| 557 | 3-(2-methyl-butyloxy) | ¹H NMR: 8.51(s, 1H), 8.35(d, 1H, J=2.4Hz), 7.67(m, 1H), 7.24(m, 2H), 6.60–6.90(m, 3H), 4.88(s, 2H), 3.80(q, 2H, J=9.0Hz), 3.62(m, 2H), 1.78(m, 1H), 1.52(m, 1H), 1.23(m, 1H), 0.95(m, 6H). MS calcd 416.1; MS (M+1) 417.2 |
| 558 | 3-(ethoxycarbonyl methoxy) | ¹H NMR: 8.50(d, 1H, J=4.9Hz), 8.35(d, 1H, J=2.0Hz), 7.65(m, 1H), 7.26(m, 2H), 6.60–6.90(m, 3H), 4.87(s, 2H), 4.53(s, 2H), 4.24(q, 2H, J=7.3Hz), 3.80(q, 2H, J=8.8Hz), 1.27(t, 3H, J=7.3Hz). MS calcd 432.1; MS (M+1) 433.0 |

EXAMPLE 559

N-(3-(2-Fluoro-4-cyanophenoxy)phenyl)-N-(ethanesulfonyl)pyrid-3-ylmethylamine

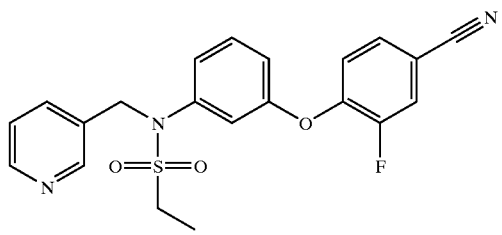

Prepare by the method of Example 342 using 3,4-diflouro-4-cyanobenzene and N-(3-hydroxyphenyl)-N-(ethanesulfonyl)pyrid-3-ylmethylamine, purifying via radial chromatography eluting with 50:50 to 60:40 THF/hexanes, to give the title compound. Anal Calcd for $C_{21}H_{18}FN_3O_3S$: C, 61.30; H, 4.41; N, 10.21. Found: C, 61.32; H, 4.50; N, 10.07. MS found 412.0 [M+H]⁺.

EXAMPLE 560

N-(4-(2-Fluoro-4-amidophenoxy)phenyl)-N-(2,2,2-trifluoroethanesulfonyl)pyrid-3-ylmethylamine

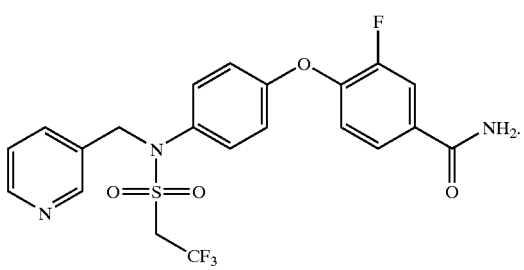

A solution of N-(4-hydroxyphenyl)-3-pyridylmethylamine (1.0 equiv.) in DMF (0.1–0.3M) was treated with sodium hydride (1.0–1.5 equiv.)(60% dispersion in mineral oil). The reaction mixture was allowed to stir at room temperature for 30 minutes. The solution was then treated with 3,4-difluorobenzonitrile (1.6 equiv.) and allowed to stir. When complete (about 3 hours) the reaction mixture was partitioned between ethyl acetate/0.1M $K_2CO_3$, the organic layer separated, and the aqueous layer extracted 3 times with ethyl acetate. The organic layers were combined, washed with brine, and dried over $MgSO_4$. The organic phase was concentrated in vacuo and purified by recrystallization from ethyl acetate/hexanes to give N-(4-(2-fluoro-4-cyanophenoxy)phenyl)-3-pyridylmethyl-amine $^1$H NMR(400 MHz, DMSO-$d_6$): 4.29(2H, d, J=5.9 Hz), 6.40 (1H, t, J=5.5 Hz), 6.63–6.65(2H, m), 6.83(1H, t, J=8.6 Hz), 6.90–6.92(2H, m), 7.33–7.36(1H, m), 7.55–7.57(1H, m), 7.74–7.76(1H, m), 7.93–7.97(1H, m), 8.43–8.44(1H, m), 8.58(1H, s). MS Found 320.1 [M+H]$^+$.

A solution (0.1M) of N-(4-(2-fluoro-4-cyanophenoxy) phenyl)-3-pyridylmethylamine (1.0 equiv.) in 85% v/v $H_2SO_4$ was allowed to stir at room temperature for 18 to 24 hours. The reaction mixture was poured over ice and neutralized with an appropriate amount of concentrated NaOH. The mixture was extracted 3 times with ethyl acetate, washed with brine, dried over $MgSO_4$, and concentrated in vacuo to give N-(4-(2-fluoro-4-amidophenoxy)phenyl)-3-pyridylmethylamine as a crystalline solid. $^1$H NMR (400 MHz, DMSO-$d_6$): 4.28(2H, d, J=5.9 Hz), 6.31(1H, t, J=6.1 Hz), 6.61–6.64(2H, m), 6.81(1H, t, J=8.6 Hz), 6.84–6.87 (2H, m), 7.33–7.36(1H, m), 7.38(1H, s), 7.60–7.63(1H, m), 7.73–7.80(2H, m), 7.93(1H, s), 8.43–8.44(1H, m), 8.58(1H, d, J=2.0 Hz). MS Found 338.1 [M+H]$^+$.

A solution of N-(4-(2-fluoro-4-amidophenoxy)phenyl)-3-pyridylmethylamine (1.0 equiv.) in DCM/pyridine(1/1 v/v) (0.2M) was cooled to 0° C. and treated with 2,2,2-trifluoroethanesulfonyl chloride (1.2 equiv.). The mixture was allowed to stir while the temperature was maintained at 0–2° C. The reaction was complete in approximately 5 minutes. The reaction mixture was partitioned between ethyl acetate/0.1 M $K_2CO_3$, the organic layer separated, and the aqueous layer extracted 2–4 times with ethyl acetate. The organic layers were combined, washed with brine, and dried over $MgSO_4$. The organic phase was concentrated in vacuo and purified via preparative HPLC eluting with methanol (2%)/ethyl acetate. The title compound was afforded by recrystallization from ethyl acetate/hexanes. Anal Calcd for $C_{21}H_{17}F_4N_3O_4S$: C, 52.17; H, 3.54; N, 8.69. Found: C, 51.78; H, 3.47; N, 8.45. MS found 484.1 [M+H]$^+$.

The HCl salt was obtained by combining N-(4-(2-fluoro-4-amidophenoxy)phenyl)-N-(2,2,2-trifluoroethanesulfonyl) pyrid-3-ylmethylamine (1 equiv.) in acetonitrile (0.4M) and adding 1.1 equiv. of HCl (0.27M), the solution was cooled to −78° C., and lyophilized over a 72 hour period to afford the HCl salt. Anal Calcd for $C_{21}H_{17}F_4N_3O_4S \cdot HCl \cdot 0.8H_2O$: C, 47.21; H, 3.70; N, 7.86; Cl, 6.64. Found: C, 46.97; H, 3.56; N, 7.74; Cl, 7.03. $^1$H NMR(400 MHz, DMSO-$d_6$): 4.83(2H, q, J=9.8 Hz), 5.05(2H, s), 7.00–7.02(2H, m), 7.20(1H, t, J=8.6 Hz), 7.38–7.40(2H, m), 7.51(1H, s), 7.73–7.75(1H, m), 7.80–7.84(1H, m), 7.85–7.88(1H, m), 8.06(1H, s), 8.24(1H, d, J=8.1 Hz), 8.67(1H, s), 8.71(1H, d, J=4.8 Hz). MS found 484.1 [M+H]$^+$.

EXAMPLE 561

N-(3-(2-Fluoro-4-cyanophenoxy)phenyl)-N-(2,2,2-trifluoroethanesulfonyl)pyrid-3-ylmethylamine

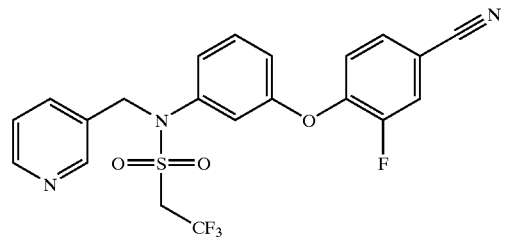

Prepare by the method of Example 342 using N-(3-hydroxyphenyl)-3-pyridylmethylamine and 3,4-difluror-4-cyanobenzene gave N-(3-(2-fluoro-4-cyanophenoxy) phenyl) pyrid-3-ylmethylamine which was purified by recrystallization from ethyl acetate/hexanes. $^1$H NMR(400 MHz): 4.25(1H, s), 4.36(2H, d, J=5.5 Hz), 6.30(1H, t, J=2.0 Hz), 6.38(1H, m), 6.48(1H, m), 6.96(1H, t, J=8.2 Hz), 7.17(1H, t, J=8.20 Hz), 7.28(1H, m), 7.33(1H, d, J=8.6 Hz), 7.44(1H, m), 7.67(1H, d, J=7.8 Hz), 8.55(1H, s), 8.61(1H, s). MS Found 320.2 [M+H]$^+$.

Sulfonation by the method of Example 526 in 1.8:1 dichloroethane/pyridine (0.25M) and raising the temperature after addition of to 45° C. for 1 hour and 15 minutes after addition of the 2,2,2-trifluroroethanesulfonyl chloride. Next, 50 mg of anhydrous $K_2CO_3$ was added to the reaction mixture and it was allowed to stir for 45 minutes. The mixture was next filtered through Celite® (521) and concentrated in vacuo. The crude material was chromatographed via normal phase radial chromatography eluting with 1:1 to 0:1 hexanes/THF. The material was chromatographed a second time via normal phase radial chromatography eluting with 30:70 acetone/hexanes to give the title compound. Anal Calcd for $C_{21}H_{15}F_4N_3O_3S$: C, 54.19; H, 3.25; N, 9.03. Found: C, 54.28; H, 3.30; N, 8.97. MS found 466.1 [M+H]$^+$.

EXAMPLE 562

N-(3-(2,4-Difluoro-4-cyanophenoxy)phenyl)-N-(2,2,2-trifluoroethanesulfonyl)pyrid-3-ylmethylamine

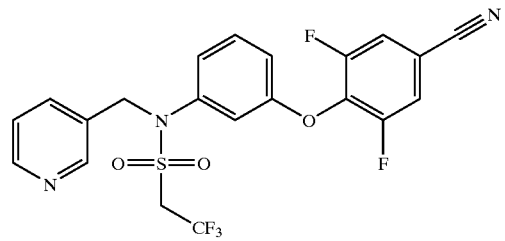

Prepare by the method of Example 351 using N-(3-hydroxyphenyl)-3-pyridylmethylamine and 3,4,5-difluror-4-cyanobenzene gave N-(3-(2,4-difluoro-4-cyanophenoxy) phenyl) pyrid-3-ylmethylamine which was purified by recrystallization from ethyl acetate/hexanes. $^1$H NMR(400 MHz, DMSO): 4.24(2H, d, J=5.9 Hz), 6.11(1H, m), 6.15 (1H, t, J=2.2 Hz), 6.35(1H, m), 6.50(1H, t, J=5.9 Hz), 7.00(1H, t, J=8.1 Hz), 7.32(1H, m), 7.67(1H, m), 8.00(2H, m), 8.43(1H, d, J=3.4 Hz), 8.51(1H, s). MS Found 338.2 [M+H]$^+$.

The title compound was prepared following the procedure Example 526 using N-(3-(2,5-difluoro-4-cyanophenoxy)phenyl)-3-pyridylmethylamine and 2,2,2-trifluoroethanesulfonyl chloride in 2:1 dichloroethane/pyridine (0.23M) and the temperature was raised to 40° C. for 4 hours after addition of 2,2,2-trifluoroethanesulfonyl chloride. Next, 50 mg of anhydrous K$_2$CO$_3$ was added to the reaction mixture and it was allowed to stir for 40 minutes. The mixture was next filtered through Celite® (521) and concentrated in vacuo. The crude material was chromatographed via normal phase radial chromatography eluting with 20:80 ethyl acetate/dichloromethane gave the title compound. Anal Calcd for C$_{21}$H$_{14}$F$_5$N$_3$O$_3$S: C, 52.18; H, 2.92; N, 8.69. Found: C, 52.12; H, 2.84; N, 8.61. MS found 484.0 [M+H]$^+$.

EXAMPLE 563

N-(4-(2-Fluoro-4-cyanophenoxy)phenyl)-N-(ethanesulfonyl)pyrid-3-ylmethylamine

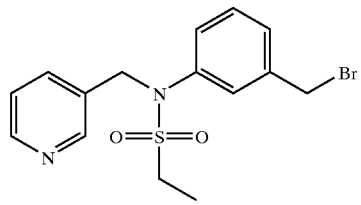

Prepare by the method of Example 351 using N-(4-hydroxyphenyl-N-(ethanesulfonyl)-3- and 3,4-difluorobenzonitrile and purifying via radial chromatography eluting with 50:50 to 60:40 THF/hexanes. Anal Calcd for C$_{21}$H$_{18}$FN$_3$O$_3$S: C, 61.30; H, 4.41; N, 10.21. Found: C, 61.32; H, 4.50; N, 10.07.

EXAMPLE 564

N-(4-(2-Fluoro-4-amidophenoxy)phenyl)-N-(ethanesulfonyl)pyrid-3-ylmethylamine

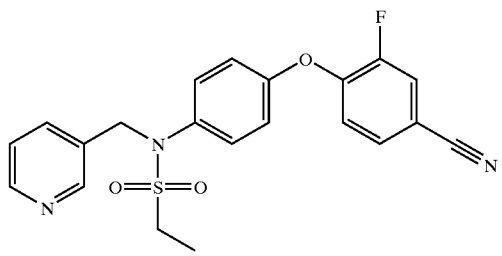

Prepare by the method of Example 560 using N-(4-(2-fluoro-4-cyanophenoxy)phenyl)-N-(ethanesulfonyl)pyrid-3-ylmethylamine and 85% aqueous H$_2$SO$_4$ (0.1M). The resultant solution was stirred for 3 days. (The reaction does not take 3 days and can be monitored by TLC). The pH of the reaction was adjusted to 10 with 5 N NaOH followed by saturated aqueous NaHCO3 and extracted twice with ethyl acetate. The combined extracts were washed with brine, dried over sodium sulfate, filtered, and concentrated in vacuo. The crude product was purified via reverse-phase chromatography affording the HCl salt. Anal Calcd for C$_{21}$H$_{20}$FN$_3$O$_4$S.0.9HCl: C, 54.56; H, 4.56; N, 9.09. Found: C, 54.72; H, 4.55; N, 8.95. MS found 430.4 [M+H]+

EXAMPLE 565

N-(3-(Bromomethyl)phenyl)-N-(ethanesulfonyl)pyrid-3-ylmethylamine

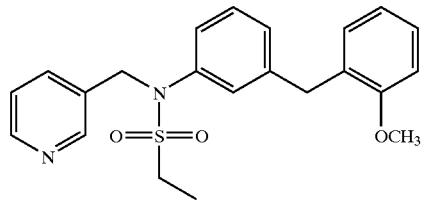

Resin-supported triphenylphosphine (1.6 g, 3 mmol per gram resin) was dispersed on dichloromethane. At 0° C., bromine (0.850 g, 5.3 mmol) solution was added dropwise to the resin. And the mixture was stirred for 15 min, followed by dropping a solution of N-(3-hydroxymethylphenyl)-N-(ethylsulfonyl)pyrid-3-ylmethylamine (0.930 g, 3 mmol). After 1 h, the resin was filtered and washed with CHCl$_3$. Evaporation afforded the title compound. $^1$H NMR:, 8.81 (s,1H), 8.68 (d,1H, J=5.4 Hz), 8.47 (d,1H,J=8.3 Hz), 7.91 (m,1H), 7.26–7.39 (m,1H), 5.16 (s,2H), 4.40 (s,2H), 3.12 (q,2H,J=7.3 Hz), 1.40 (t,3H, J=7.3 Hz). MS calcd. 370.0; MS (M+1) 371.1.

EXAMPLE 566

N-(3-(2-Methoxybenzyl)phenyl)-N-(ethanesulfonyl)pyrid-3-ylmethylamine

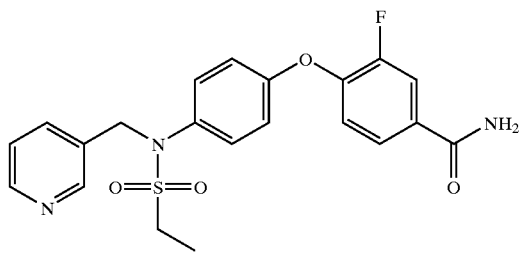

The flask was charged with N-(3-bromomethylphenyl)-N-(ethylsulfonyl)pyrid-3-ylmethylamine (0.180 g, 0.500 mmol), 2-methoxyphenylboronic acid (0.113 g, 0.75 mmol), 4.5 ml of DME, 1.5 ml of 2 M Na$_2$CO$_3$, and terakis(triphenylphosphine) palladium(0) (0.018 g, 0.016 mmol). After N$_2$-flushing, the mixture was heated at 50° C. overnight. The reaction mixture was concentrated, diluted with water, and extracted with EtOAc. The organic layer was washed with brine and concentrated. The residue was chromatographed on a silica-gel column with 1:1 to 1:3 toluene/EtOAc to afford the title compound. $^1$H NMR:, 8.37 (d,1H, J=3.9 Hz), 8.24 (s,1H), 7.55 (d,1H,J=7.8 Hz), 6.74–7.17 (m,9H), 4.76 (s,2H), 3.80 (s,2H), 3.69 (s,2H), 2.94 (q,2H, J=7.3 Hz), 1.32 (t,3H,J=7.3 Hz). MS calcd. 396.2; MS (M+1) 397.2.

By a method similar to the method of Example 566 the following compounds were prepared:

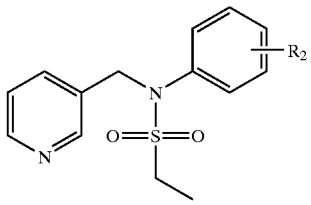

| No. | R₂ | Data |
|---|---|---|
| 567 | 3-(2-trifluoromethyl benzyl) | ¹H NMR: 8.47(d, 1H, J=4.9Hz), 8.31(br s, 1H), 7.65(m, 2H), 7.44(m, 1H), 7.33(m, 1H), 7.25(d, 1H, J=7.8Hz), 7.21(dd, 1H, J=7.8, 4.9Hz), 7.11(br dd, 2H, J=7.8Hz), 7.06(br d, 1H, J=7.3Hz), 7.01(br d, 1H, J=7.8Hz), 6.95(br s, 1H), 4.12(s, 2H), 3.06(q, 2H, J=7.3Hz), 1.40(t, 3H, J=7.3Hz). MS calcd 434.1; MS (M+1) 435.2 |
| 568 | 3-(4-cyanobenzyl) | ¹H NMR: 8.48(d, 1H, J=3.9Hz), 8.31(s, 1H), 7.66(d, 1H, J=7.8Hz), 7.55(d, 2H, J=7.8Hz), 7.27(m, 2H), 7.20(m, 1H), 7.13(m, 2H), 7.04(d, 1H, J=7.3Hz), 6.97(s, 1H), 4.85(s, 2H), 3.95(s, 2H), 3.08(q, 2H, J=7.3Hz), 1.41(t, 3H, J=7.3Hz). MS calcd 391.1; MS (M+1) 392.3 |
| 569 | 3-(2-chlorobenzyl) | ¹H NMR: 8.48(br s1H), 8.33(br s, 1H), 7.66(br d, 1H, J=7.8Hz), 7.36(m, 1H), 7.28–7.17(m, 4H), 7.09(br d, 2H, J=7.8Hz), 7.02(m, 2H), 4.04(d, 2H), 3.07(q, 2H, J=7.3Hz), 1.40(m, 3H, J=7.3Hz). MS calcd 400.1; MS (M+1) 401.0 |
| 570 | 3-(4-fluorobenzyl) | ¹H NMR: 8.56(d, 1H, J=4.4Hz), 8.42(s, 1H), 7.95(t, 1H, J=7.4Hz), 7.72(d, 1H, J=7.6Hz), 7.27(m, 1H), 7.21(t, 1H, J=7.6Hz), 7.05(m, 3H), 6.94(m, 3H), 4.86(s, 2H), 3.84(s, 2H), 3.06(q, 2H, J=7.3Hz), 1.40(t, 3H, J=7.3Hz). MS calcd 384.1; MS (M+1) 385.2 |
| 571 | 3-(thien-2-ylmethyl) | ¹H NMR: 8.47(d, 1H, J=4.9Hz), 8.34(d, 1H, J=1.5Hz), 7.66(d, 1H, J=8.3Hz), 7.25(t, 1H, J=7.3Hz), 7.20(dd, 1H, J=7.8, 4.9Hz), 7.17–6.17(m, 4H), 6.91(dd, 1H, J=4.9, 3.4Hz), 6.69(d, 1H, J=2.5Hz), 4.86(s, 2H), 4.10(s, 2H), 3.08(q, 2H, J=7.3Hz), 1.43(t, 3H, J=7.3Hz). MS calcd 372.1; MS (M+1) 373.1 |
| 572 | 3-(thien-3-ylmethyl) | ¹H NMR: 8.48(d, 1H, J=3.9Hz), 8.33(s, 1H), 7.67(d, 1H, J=7.8Hz), 7.26–7.20(m, 3H), 7.10(d, 2H, J=7.3Hz), 7.02(s, 1H), 6.78(m, 2H), 3.91(s, 2H), 3.08(q, 2H, J=7.3Hz), 1.41(t, 3H, J=7.3Hz). MS calcd 372.1; MS (M+1) 373.1 |
| 573 | 3-(2-bromobenzyl) | ¹H NMR: 8.38(d, 1H, J=3.4Hz), 8.24(d, 1H, J=1.5Hz), 7.56(d, 1H, J=8.3Hz), 7.46(d, 1H, J=7.3Hz), 7.12(m, 3H), 7.01(m, 3H), 6.93(m, 2H), 4.75(s, 2H), 3.95(s, 2H), 2.98(q, 2H, J=7.3Hz), 1.30(t, 3H, J=7.3Hz). MS calcd 446.1; MS (M+1) 447.1 |
| 574 | 3-(5-methyl-thiophen-2-yl)methyl | ¹H NMR: 8.47(dd, 1H, J=4.9, 1.6Hz), 8.35(d, 1H, J=1.6Hz), 7.66(dt, 1H, J=7.8, 2.0Hz), 7.26–7.18(m, 2H), 7.15–7.07(m, 3H), 6.54(m, 1H), 6.46(d, 1H, J=3.1Hz). 4.84(s, 2H), 4.00(s, 2H), 3.07(q, 2H, J=7.3Hz), 2.41(s, 3H), 1.41(t, 3H, J=7.3Hz). MS calcd 386.1; MS (M+1) 387.1 |
| 575 | 3-(2,4-difluorobenzyl) | ¹H NMR: 8.8.49(dd, 1H, J=4.7, 1.1Hz), 8.34(d, 1H, J=1.5Hz), 7.67(d, 1H, J=7.8Hz), 7.22(m, 2H), 7.08(m, 2H), 7.01(s, 1H), 6.94(m, 1H), 6.78(m, 2H), 4.84(s, 2H), 3.85(s, 2H), 3.08(q, 2H, J=7.3Hz), 1.41(t, 3H, J=7.3Hz). MS calcd 402.1; MS (M+1) 403.1 |
| 576 | 3-(2,4-dichlorobenzyl) | |

Preparation 13

N-(4-(4-Cyanophenyl)phenyl)-N-ethylsulfonylamine

4-Amino-4'-cyanobiphenyl (1.03 g, 5.3 mmol) (TCI) was dissolved in a mixture of 8 ml dichloromethane/2 ml pyridine was treated with ethanesulfonyl chloride (0.61 g, 5.3 mmol) and stirred for 18 h at room temperature. The solution was diluted with dichloromethane and washed twice with 1N HCl. The organic phase was separated, dried over sodium sulfate, filtered, and concentrated in vacuo to afford the title compound. ¹H NMR: 7.75 (d,2H,J=8 Hz), 7.67 (d,2H,J=8 Hz), 7.60 (d,2H,J=8 Hz), 7.37 (d,2H,J=8 Hz), 6.90 (s,1H), 3.22 (q,2H,J=8 Hz), 1.45 (t,3H,J=8 Hz).

Preparation 14

N-(2-Methoxy-5-phenyl)phenyl)-N-ethanesulfonylamine

The title compound was prepared using a method similar to the method of Preparation 13 using 5-phenyl-O-anisidine. MS calcd. 291.3; MS (M+−1) 290.2.

Preparation 15

N-(1-(4-Bromophenyl)ethyl)pyrid-3-ylmethylamine

A solution of 4-bromo-α-methylbenzylamine (1.5 g, 7.7 mmol), 3-pyridinecarboxaldehyde (0.8 g, 7.5 mmol), and sodium triacetoxyborohydride (2.25 g, 10.5 mmol) in 60 ml of 1,2-dichloroethane was stirred at room temperature for 18 h. The solution was diluted with dichloromethane and washed twice with a saturated sodium bicarbonate solution, once with water, and once with brine. The organic layer was separated, dried over sodium sulfate, filtered, and concentrated in vacuo to afford the title compound. $^1$H NMR: 8.70 (m,2H), 7.85 (m,1H), 7.67 (d,2H,J=8 Hz), 7.45 (d,2H,J=8 Hz), 7.43 (m,1H), 3.95 (q,1H,J=8 Hz), 3.83 (q,ABX,2H), 1.57 (d,3H,J=8 Hz). MS calcd. 291.2; MS (M+1) 292.1.

Preparation 16

N-(1-(4-Bromophenyl)ethyl)-N-ethylsulfonylamine

4-Bromo-α-methylbenzylamine (8.15 g, 40.73 mmol) and (4.15 g, 41.00 mmol) triethylamine dissolved in 150 ml dichloromethane was treated slowly with ethanesulfonyl chloride (5.27 g, 41.00 mmol) and stirred for 15 minutes. The reaction mixture was extracted with 50 ml 1N HCl/15 ml brine. The organic layer was separated, dried sodium sulfate, filtered, and concentrated in vacuo to afford the title compound. $^1$H NMR: 7.52 (d,2H,J=12 Hz), 7.25 (d,2H,J=12 Hz), 4.77 (m,1H), 4.63 (m,1H), 2.77 (m,2H), 1.56 (d,3H,J=8 Hz), 1.27 (t,3H,J=8 Hz). MS calcd. 292.2; MS (M+–1) 291.1.

EXAMPLE 577

N-(1-(4-Bromophenyl)ethyl)-N-(ethanesulfonyl) pyrid-3-ylmethylamine

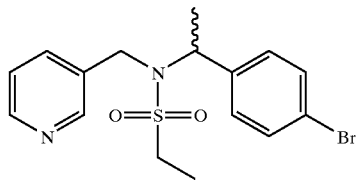

N-(1-(4-Bromophenyl)ethyl)-N-ethylsulfonylamine (1.25 g, 4.28 mmol), and (0.75 g, 4.6 mmol) of 3-picolyl chloride hydrochloride, and (5.1 g, 37 mmol) of potassium carbonate were dissolved in 40 ml DMF. Additional 3-picolyl chloride hydrochloride (0.75 g, 4.6 mmol) was added after 30 minutes and the mixture stirred 20 h at room temperature. The mixture was diluted with 120 ml ethyl acetate and 60 ml of water and transferred to a separatory funnel. The organic layer was separated and washed twice with water. The organic layer was again separated and dried over sodium sulfate, filtered, and concentrated in vacuo to afford a dark oil. The oil was purified by radial chromatography on a 6 micron silica plate eluting with 1 to 4% methanol/dichloromethane to afford after concentration of fractions the title compound. MS calcd. 383.2; MS (M+1) 384.1.

Preparation 17

N-(Ethylsulfonyl)pyrid-3-ylmethylamine

3-Aminomethylpyridine (2.15 g, 19.88 mmol) was dissolved in 40 ml dichloromethane. Ethanesulfonyl chloride (2.56 g, 19.9 mmol) was added to the mixture and stirred for 18 h. To the resultant precipitate was added 40 ml diethyl ether and decanted from the solid. The solid was partitioned between a mixture of 100 ml dichloromethane/20 ml isopropyl alcohol and 20 ml of a saturated sodium bicarbonate solution. The organic layer was separated and the aqueous phase extracted twice with the 80/20 mixture of dichloromethane/isopropyl alcohol. The organic layers were combined, dried over sodium sulfate, filtered, and concentrated in vacuo to afford the title compound. $^1$H NMR: 8.67 (s,1H), 8.60 (d,1H,J=4 Hz), 7.90 (m,1H), 7.42 (m,1H), 5.77 (t,1H,J=6 Hz), 4.38 (d,2H,J=6 Hz), 3.07 (t,2H,J=8 Hz), 1.38 (t,3H,J=8 Hz). MS calcd. 200.2; MS (M+1) 201.1.

Preparation 18

4-Cyanophenylboronic acid

A solution of 4-bromobenzonitrile (91 g, 0.50 mole) in THF (1.1 L) was dried in the presence of activated 3 Å molecular sieves at room temp. This solution was filtered and cooled to –100° C. A 1.6 M solution of n-butyllithium in hexanes (355 mL. 0.567 mol) was added to the cold solution over 15 min while maintaining the internal temperature between –105 and –93° C. To the resulting orange reaction mixture was added trimethylborate (81 g, 0.78 mol) over 3 min, briefly increasing the reaction temperature to –72° C. The reaction mixture was recooled to –100° C. over 5 minutes and then was allowed to warm slowly to room temperature over 2.3 h. The reaction mixture was acidified with 4N HCl to pH 2.2, and was diluted with $CH_2Cl_2$ (200 mL). The aqueous layer was separated and the organic layer was washed with brine (2×200 mL), dried over anhydrous $MgSO_4$, filtered, and the solvent removed under reduced pressure to a pale yellow solid. This solid was additionally purified by dissolution in 1N NaOH and extraction into $CH_2Cl_2$/THF (1:1, 2×200 mL). The aqueous phase was acidified with 4N HCl to pH 2.2 and was extracted into $CH_2Cl_2$/THF (1:1, 500 mL). The combined organic extracts were concentrated to a crude solid (64.6 g) that was triturated with diethyl ether (160 mL) and dried under vacuum to afford the intermediate title compound (44.0 g, 59.9%) as a white powder. $^1$H NMR ($d_6$-acetone, 300 MHz): δ 8.03 (d, 2H, J=8.1), 7.75 (d, 2H, J=8.4), 7.54 (s, 2H).

Preparation 19

N-(3-(4-Cyanophenyl)phenyl)pyrid-3-ylmethylamine

A solution of N-(3-bromophenyl)pyridin-3-ylmethylamine (364 mg, 1.38 mmol), 4-cyanophenylboronic acid (305 mg, 2.08 mmol), sodium carbonate (2.15 ml of a 2M aqueous solution, 4.3 mmol), and tetrakis(triphenylphosphine)palladium(0) (70 mg, 0.061 mmol), under a nitrogen atmosphere was refluxed in dioxane (15 ml) for 6 h, then cooled to room temperature. The mixture was diluted with dichloromethane (70 ml) and water (15 ml). The organics were separated, dried over sodium sulfate, filtered, and concentrated to a brown solid. The solid was purified by radial chromatography eluting with 2 to 4% methanol/dichloromethane to afforded the title compound. MS calcd. 285.3; MS (M+1) 286.3.

Preparation 20

N-(3-(4-(N'-Methanesulfonyl-N'-t-butoxycarbonylaminoethyl)phenyl)pyrid-3-ylmethylamine To a 10° C. solution of phenethylamine (12.1 g, 0.100 mol) and triethylamine (11.1 g, 0.110 mol) in $CH_2Cl_2$ (50 mL) was added methanesulfonyl chloride (12.6 g, 0.110 mol) dropwise over 10 min. The solution was stirred at room temperature for 1.5 h and was then washed with 1 N HCl (5×20 mL). The organic phase was directly concentrated to provide the intermediate title compound, N-(methylsulfonyl)(2-phenylethyl)amine, (21.2 g, 93.3%) as an oil. $^1$H NMR (300 MHz) 7.32 (m, 2H), 7.23 (m, 3H), 4.30 (br s, 1H), 3.40 (t, 2H, J=3.9), 2.88 (t, 2H, J=4.2), 2.81 (s, 3H).

To a stirring room temperature solution of N-(methylsulfonyl)-N-(2-phenylethyl)amine (205 g, 1.03 moles), water (200 mL), 95% sulfuric acid (111 g, 1.08 moles) in acetic acid (1 L), was added iodine (111 g, 0.438 mol) and periodic acid (45.6 g, 0.206 mol). The reaction mixture was warmed to 70–75° C. for 3 h. The heat was removed and the dark violet reaction mixture was allowed to proceed overnight at room temperature. Potassium hydroxide pellets (85%, 143 g, 2.16 moles) were added to neutralized the sulfuric acid and then enough saturated aqueous sodium sulfite was added to decolorize the mixture to afford a white suspension. The suspension was cooled to 15° C. and filtered. The filter cake was triturated thoroughly with water and was then dissolved in $CH_2Cl_2$ (1 L) and extracted with additional water (2×200 mL). The organic phase was concentrated under reduced pressure to provide N-(2-(4-iodophenyl)ethyl)-N-(methylsulfonyl)amine, (201 g, 60.2%) as a white powder. $^1$H NMR (300 MHz) 7.64 (d, 2H, J=4.8), 6.97 (d, 2H, J=5.1), 4.37 (br t, 1H, J=4), 3.36 (app. q, 2H, J=3.9), 2.85 (s, 3H), 2.82 (t, 2H, J=3.9).

A room temperature solution of N-(2-(4-iodophenyl)ethyl)-N-(methylsulfonyl)amine (201 g, 0.618 mol), 4-dimethylaminopyridine (3.8 g, 0.031 mol) and di-t-butyl dicarbonate (162 g, 0.744 mol) in DCM (1 L) was allowed to stir overnight. The reaction mixture was washed with water (2×400 mL) and the organic phase was concentrated to about 600 mL and hexanes (400 mL) was added. This combined solution was washed again with water (400 mL) and was concentrated to a solid that was suspended in hexanes (600 mL) and filtered. The collected solids were dried under reduced pressure to afford the intermediate title compound, N-(t-butoxycarbonyl)-N-(2-(4-iodophenyl)ethyl)-N-(methylsulfonyl)amine (241.5 g, 91.5%) as a white solid. $^1$H NMR (300 MHz) 7.63 (d, 2H, J=7.8), 6.98 (d, 2H, J=7.8), 3.88 (t, 2H, J=6.9), 3.10 (s, 3H), 2.88 (t, 2H, J=6.9), 1.51 (s, 9H).

To a degassed solution of N-(t-butoxycarbonyl)-N-(2-(4-iodophenyl)ethyl)-N-(methylsulfonyl)amine (128 g, 0.300 mol), triethylamine (91.1 g, 0.900 mol), and 1,1'-bis(diphenylphosphino)ferrocenedichloropalladium (II)-$CH_2Cl_2$ complex (2.9 g, 0.0035 mol) in acetonitrile (600 mL) was added pinacolborane (50 g, 0.391 mol) dropwise. The mixture was stirred at 70–74° C. for 8 h and then was cooled to room temperature. The reaction mixture was concentrated to a fluid oil that was partitioned between MTBE (500 mL) and water (500 mL). The organic phase was separated and washed with water (2×200 mL) and concentrated to a residue that was partially dissolved with heptane (1 L). The heptane soluble fraction was filtered through Celite® 521 and concentrated to an oil (95 g). The residue was dissolved in acetone (600 mL) and heptane (600 mL) and filtered through Celite® 521. The combined filtrates were concentrated to 95 g of a mixture of a 3:1 molar ratio ($^1$H NMR, 81.0% by weight) of intermediate title compound, N-(t-butoxycarbonyl)-N-(methylsulfonyl)-N-(2-(4-(4,4,5,5-tetramethyl(1,3,2-dioxaborolan-2-yl))phenyl)ethyl)amine and its protio derivative. $^1$H NMR (300 MHz) 7.75 (d, 2H, J=7.8), 7.23 (d, 2H, J=8.1), 3.87 (t, 2H, J=8.1), 2.99 (s, 3H), 2.90 (t, 2H, J=7.5), 1.53 (s, 9H), 1.33 (s, 6H), 1.27 (s, 6H).

To a room temperature solution of N-(t-butoxycarbonyl)-N-(methylsulfonyl)-N-(2-(4-(4,4,5,5-tetramethyl(1,3,2-dioxaborolan-2-yl))phenyl)ethyl)amine (81.0% potent, 95 g, 0.18 mol) in acetone (2 L) was added 1N ammonium acetate (1L) and sodium periodate (145 g, 0.678 mol) with stirring. The reaction was allowed to proceed overnight. The reaction mixture was concentrated to remove the acetone, and the aqueous phase was decanted away from the oily product. The aqueous phase was extracted with DCM (100 mL) and MTBE (2×100 mL). The combined oily product and organic phases were adjusted to pH 12.5 with the addition of 1 N NaOH. The phases were separated, and the organic phase was extracted with 1 N NaOH (100 mL) and water (2×100 mL). HPLC analysis (60% $CH_3CN$/40% $H_2O$, 2 mL/min, Zorbax C-18, 205 nm) of the organic phase indicated that the product had been removed from this phase. The aqueous phases (containing product) were finally combined and washed with $CH_2Cl_2$ (100 mL) and MTBE (2×100 mL). The aqueous phase was added to $CH_2Cl_2$ (450 mL) and 1 N $H_2SO_4$ was added until the aqueous phase was at pH 3.05. The phases were separated and the aqueous phase was extracted with $CH_2Cl_2$ (100 mL). The combined organic extracts (containing product) were concentrated to an oil (58.5 g) that crystallized overnight. The resulting solid mass was triturated with 10% MTBE in heptane (100 mL) to afford, after filtration and drying under reduced pressure, N-(t-butoxycarbonyl)-N-(methylsulfonyl)-N-(2-(4-boronic acid)phenyl) ethyl) amine (47.7 g, 77.2%) as a white powder. $^1$H NMR ($d_6$-DMSO, 300 MHz) δ 7.83 (d, 2H, J=4.8), 7.24 (d, 2H, J=5.1), 7.12 (s, 2H), 3.90 (t, 2H, J=3.9), 3.12 (s, 3H), 2.95 (t, 2H, J=4.5), 1.52 (s, 9H).

A solution of N-(3-bromophenyl)pyridin-3-ylmethylamine (180 mg, 0.68 mmol), N-(t-butoxycarbonyl)-N-(methylsulfonyl)-N-(2-(4-boronic acid)phenyl)ethyl)amine (350 mg, 0.1.0 mmol), and dioxane (12 ml) stirring under nitrogen was treated with 2M sodium carbonate(1.36 ml, 2.7 mmol) and tetrakis(triphenylphosphine) palladium (0)(35 mg, 0.030 mmol). This was heated to reflux for four hours, after which the reaction was concentrated in vacuo. The concentrated reaction mixture was then purified on a Chromatotron using a 4000 micron plate and 3% methanol/dichloromethane as the solvent system. The product containing fractions were collected and concentrated in vacuo to yield an oil, which was dissolved into ether/hexanes and concentrated in vacuo to give the title compound as an off-white foam. $^1$H NMR: 8.60–8.70 (s, 1H), 8.50–8.60 (s, 1H), 7.75–7.80 (d, 1H, J=12 Hz), 7.60–7.70 (m, 1H), 7.45–7.55 (m, 2H), 7.20–7.35 (m, 3H), 7.00–7.10 (m, 1H), 6.75–6.80 (d, 2H, 10 Hz), 4.40–4.45 (s, 1H), 3.85–4.00 (m, 2H), 3.40–3.50 (q, 2H, 16 Hz), 2.90–3.00 (m, 3H), 1.50–1.60 (s, 9H), 1.20–1.30 (m, 2H). MS calcd. 481.6; MS (M+1) 482.1.

Preparation 21

N-Methyl-4-(4,4,5,5-tetramethyl-[1,3,2]dioxaborolan-2-yl)-benzamide

4-Carboxyphenylboronic acid (10.0 g, 60.3 mmol) was suspended in 100 mL of toluene and pinnacol added (7.1 g, 60.3 mmol). The reaction was heated to reflux with a Dean-Stark trap attached. The reaction became homogenous upon heating. After 2 h reflux the reaction was allowed to stand overnight and white needles were collected by filtration, rinsed with toluene, and vacuum dried to 4-(4,4,5,5-tetramethyl-[1,3,2]dioxaborolan-2-yl)-benzoic acid 12.2 g (81%). MS (FD MS): M=248. Analysis calculated for $C_{13}H_{17}BO_4$: C, 62.94; H, 6.91 Found: C, 62.71; H, 6.91.

4-(4,4,5,5-Tetramethyl-[1,3,2]dioxaborolan-2-yl)-benzoic acid (6.0 g, 24.2 mmol) was suspended in 20 mL of thionyl chloride, 3 drops of DMF added and the reaction heated to reflux under nitrogen. The solid dissolved upon warming. After refluxing 2 h the reaction was concentrated in vacuo and dried to a white solid under vacuum. The acid chloride was dissolved in 30 mL of THF and cooled to 0° C. 40% aqueous methylamine (10.4 mL) was added dropwise. After the addition was complete the ice bath was removed and stirring continued for 30 min. The reaction was concentrated in vacuo (3×1:1 EtOAc:toluene) then extracted with ether/water. The organic layer was dried over sodium sulfate, filtered and concentrated to 5.2 g (83%) of the title compound as a white solid. MS (FD MS): M=261. Analysis calculated for $C_{14}H_{20}BNO_3$: C, 64.40; H, 7.72; N, 5.36. Found: C, 64.09; H, 7.70; N, 5.28.

EXAMPLE 578

N-(4-(4-Cyanophenyl)phenyl)-N-(ethanesulfonyl)pyrid-3-ylmethylamine

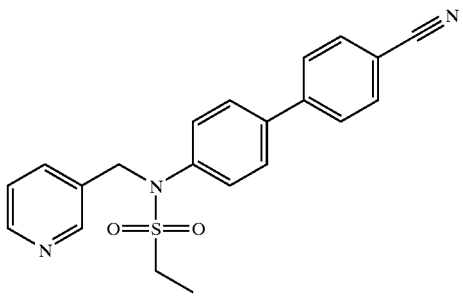

A solution of N-(4-(4-cyanophenyl)phenyl)-N-ethylsulfonylamine (200 mg, 0.7 mmol), 3-picolyl chloride hydrochloride (123 mg, 0.75 mmol), and cesium carbonate (2.3 g, 7.0 mmol) was dissolved in 10 ml DMF and stirred for 18 h at room temperature. The mixture was diluted with 80 ml ethyl acetate, 20 ml water. The organic phase was separated and washed twice with 25 ml of water. The organic phase was then dried over sodium sulfate, filtered, and concentrated in vacuo to an oily residue. The residue was flushed through a 20 g mega bond elut silica column with 0 to 5% methanol/ethyl acetate. The desired fractions were concentrated in vacuo to afford the title compound. $^1$H NMR: 8.55 (bs,1H), 8.41 (bs,1H), 7.78 (d,1H,J=8 Hz), 7.72 (d,2H,J=12 Hz), 7.6 (d,2H,J=12 Hz), 7.52 (d,2H,J=12 Hz), 7.35 (d,2H,J=12 Hz), 7.29 (m,1H), 4.95 (s,1H), 3.15 (q,2H, J=8 Hz), 1.45 (t,3H,J=8 Hz). MS calcd. 377.5; MS (M+1) 378.2.

EXAMPLE 579

N-((2-Methoxy-5-phenyl)phenyl)-N-(ethanesulfonyl)pyrid-3-ylmethylamine

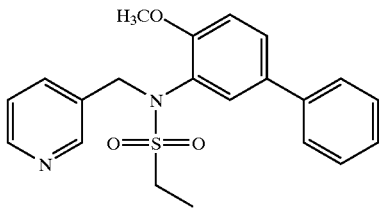

The title compound was prepared using a method similar to the method of Example 545 using N-(2-methoxy-5-phenyl)phenyl)-N-ethanesulfonylamine. $^1$H NMR: 8.5 (d,1H,J=4 Hz), 8.41 (s,1H), 7.88 (m,1H), 7.51 (dd,1H,J=4, 8 Hz), 7.28–7.45 (m,7H), 7.0 (d,1H,J=8 Hz), 4.9 (s,2H), 3.98 (s,1H), 3.16 (q,2H,J=8 Hz), 1.45 (t,3H,J=8 Hz). MS calcd. 382.5; MS (M+1) 383.1.

EXAMPLE 580

N-(1-(4-Bromophenyl)ethyl)-N-(2,2,2-trifluroethanesulfonyl)pyrid-3-ylmethylamine

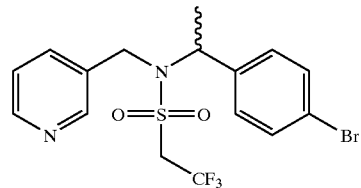

A solution of N-(1-(4-bromophenyl)ethyl)pyrid-3-ylmethylamine (630 mg, 2.16 mmol) and 4-(dimethylamino)pyridine (263 mg, 2.16 mmol) in 18 ml of dichloromethane was treated with 2,2,2-trifluoroethylsulfonyl chloride (420 mg, 2.3 mmol) with stirring for 15 minutes at room temperature. The solution was concentrated to approximately 2 ml and directly purified by radial chromatography on a 1 micron silica plate, eluting with 3% methanol/dichloromethane. The fractions were concentrated to afford the title compound. $^1$H NMR: 8.52 (bs,1H), 8.42 (bs,1H), (d,1H,J=8 Hz), 7.45 (d,2H,J=8 Hz), 7.22 (d,2H,J=8 Hz), 5.25 (q,1H,J=8 Hz), 4.38 (q,2H,ABX), 3.6 (q,2H,J=12 Hz), 1.68 (d,3H,J=8 Hz). MS calcd. 437.3; MS (M+1),(M+2), 438.0,439.0.

EXAMPLE 581

N-(3-(4-Cyanophenyl)phenyl)-N-(2,2,2-trifluoroethylsulfonyl)pyrid-3-ylmethylamine

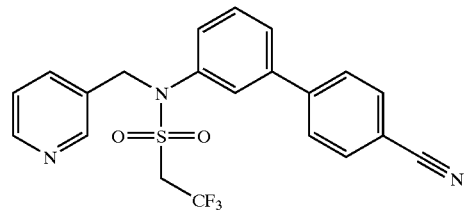

A solution of N-(3-(4-cyanophenyl)phenyl)pyrid-3-ylmethylamine (255 mg, 0.894 mmol) in 8 ml dichloromethane/2 ml pyridine was treated with 2,2,2-trifluoroethylsulfonyl chloride in 3 portions of 171 mg (0.94 mmol) over 1 h at 45° C. The solution was cooled and diluted with 60 ml diethyl ether and washed successively with water and saturated sodium bicarbonate solution. The organics were separated, dried over sodium sulfate, filtered, and concentrated to an oil. The oil was purified by radial chromatography on a 2 micron silica plate eluting with 2 to 4% methanol/dichloromethane to afford the title compound. $^1$H NMR: 8.65 (bs,1H), 8.42 (bs,1H), 7.85 (m,1H), 7.75 (d,2H,J=8 Hz), 7.58 (d,2H,J=8 Hz), 7.30–7.55 (m,5H), 5.02 (s,2H), 3.78 (q,2H,J=8 Hz). MS calcd. 431.44; MS (M+1) 432.1.

EXAMPLE 582

N-((3-Iodophenyl)methyl)-N-(ethylsulfonyl)pyrid-3-ylamine

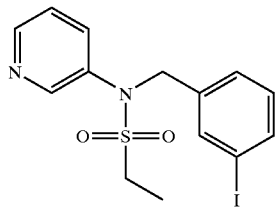

A solution of 3-aminopyridine (2.15 g, 22.84 mmol) and ethanesulfonyl chloride (2.18 ml, 22.84 mmol) in dichloromethane (150 ml) was stirred for 20 h at room temperature. The mixture was washed with 30 ml saturated sodium bicarbonate solution and extracted with 15% isopropanol/dichloromethane. The organics were combined, dried over sodium sulfate, filtered, and concentrated in vacuo to give N-(ethanesulfonyl)-3-aminopyridine (2.15 g, as a crude solid. The solid was dissolved in N,N-dimethylformamide (50 ml) and treated with potassium carbonate (6.37 g, 22.8 mmol) and 3-iodobenzyl bromide (6.80 g, 22.8 mmol) with stirring at room temperature for 3 h. The mixture was diluted with ethyl acetate (150 ml) and washed four times with water (100 ml). The organics were separated, dried over sodium sulfate, filtered, and concentrated in vacuo to afford a crude residue. The residue was purified on a 200 g pad of silica eluting with 3% methanol/dichloromethane to afford the title compound. MS calcd. 402.3; MS (M+1) 403.1.

EXAMPLE 583

N-((3-Iodophenyl)methyl)-N-(ethylsulfonyl)pyrid-3-ylmethylamine

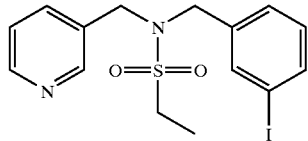

A solution of N-(ethylsulfonyl)pyrid-3-ylmethylamine (1.1 g, 5.5 mmol), cesium carbonate (1.79 g, 5.5 mmol), and 3-iodobenzyl bromide (1.64 g, 5.5 mmol) was stirred in N,N-dimethylformamide (25 ml) for 5 h at room temperature. The mixture was diluted with ethyl acetate (100 ml) and washed four times with water (50 ml). The organics were separated, dried over sodium sulfate, filtered, and concentrated in vacuo to a crude residue. The residue was purified by radial chromatography on a 4 micron silica plate eluting with 3% methanol/dichloromethane to afford the title compound. 1H NMR: 8.6 (d,1H,J=4 Hz), 8.41 (s,1H), 7.75 (m,1H), 7.65 (m,1H), 7.60 (s,1H), 7.25–7.40 (m,2H), 7.08 (m,1H), 4.43 (s,2H), 4.33 (s,2H), 3.08 (q,2H,J=8 Hz), 1.43 (t,3H,J=8 Hz). MS calcd. 416.3; MS (M+1) 417.1.

EXAMPLE 584

N-(1-(4-(2,4-Difluorophenyl)phenyl)ethyl)-N-(ethanesulfonyl)pyrid-3-ylmethylamine

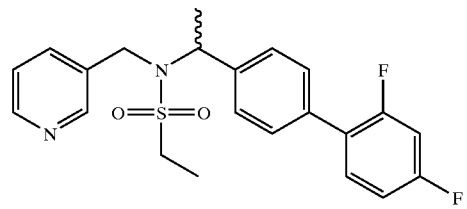

A solution of N-(1-(4-bromophenyl)ethyl)-N-(ethanesulfonyl)pyrid-3-ylmethylamine (200 mg, 0.52 mmol), 2,4-difluorophenylboronic acid (124 mg, 0.78 mmol), sodium carbonate (0.78 ml of a 2M aqueous solution, 1.56 mmol), and tetrakis(triphenylphosphine)palladium(0) (26 mg, 0.023 mmol), under a nitrogen atmosphere was refluxed in dioxane (8 ml) for 6 h, then cooled to room temperature. The mixture was concentrated to a tan residue and resuspended in 2 ml dichloromethane. The suspension was subjected to purification by radial chromatography on a 2 micron silica plate eluting with 2 to 4% methanol/dichloromethane to afford the title compound. $^1$H NMR: 8.45 (bs,1H), 8.37 (bs,1H), 7.62 (d,1H,J=8 Hz), 7.45 (m,5H), 7.15 (m,1H), 6.95 (m,2H), 5.30 (q,1H,J=8 Hz), 4.35 (s,2H), 2.92 (q,2H,J=8 Hz), 1.67 (d,3H,J=8 Hz), 1.37 (t,3H, J=8 Hz). MS calcd. 416.5; MS (M+1) 417.1.

By a method similar to the method of Example 584 the following compounds were prepared:

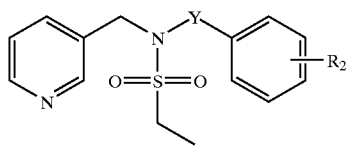

| No. | Y | R$_2$ | Data |
|---|---|---|---|
| 585 | CH(CH$_3$) | 4-(4-cyanophenyl) | $^1$H NMR: 8.42(bs, 1H), 8.35(bs, 1H), 7.45–7.80(m, 9H), 7.21(m, 1H), 5.33(q, 1H, J=8Hz), 4.37(s, 2H), 2.95(q, 2H, J=8Hz), 1.70(d, 3H, J=8Hz), 1.40(t, 3H, J=8Hz). MS calcd. 405.5; MS (M+1) 406.2 |
| 586 | CH$_2$ | 3-(2,4-difluorophenyl) | $^1$H NMR: 8.57(bs, 1H), 8.45(bs, 1H), 7.58(d, 1H, J=8Hz), 7.15–7.35(m, 6H), 6.75–6.85(m, 2H), 4.87(s, 2H), 3.07(q, 2H, J=8Hz), 1.36(t, 3H, J=8Hz). MS calcd. 388.4; MS (M+1) 389.2 |

-continued

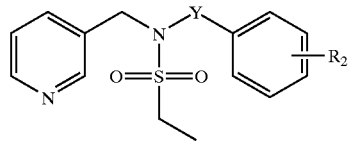

| No. | Y | R₂ | Data |
|---|---|---|---|
| 587 | CH₂ | 3-(4-cyanophenyl) | ¹H NMR: 8.53(bs, 1H), 8.42(bs, 1H), 7.78(m, 1H), 7.75(d, 2H, J=8Hz), 7.63(d, 2H, J=8Hz), 7.3–7.55(m, 5H), 4.49(s, 3H), 4.47(s, 3H), 3.12(q, 2H, J=8Hz), 1.45(t, 3H, J=8Hz). MS calcd. 391.5; MS (M+1) 392.2 |
| 588 | CH₂ | 3-(3-methanesulfonyl aminophenyl) | ¹H NMR: 8.65(bs, 1H), 8.58(bs, 1H), 7.9(d, 1H, J=8Hz), 7.70(m, 1H), 7.30–7.5(m, 9H), 4.54(s, 2H), 4.48(s, 2H), 3.13(q, 2H, J=8Hz), 3.09(s, 3H), 1.45(t, 3H, J=8Hz). MS calcd. 459.6; MS (M+1) 460.2 |
| 589 | CH₂ | 3-(4-N-methylamidophenyl) | ¹H NMR: 8.48(bs, 2H), 7.88(d, 2H, J=8Hz), 7.78(m, 1H), 7.60(d, 2H, J=8Hz), 7.54(m, 1H), 7.25–7.45(m, 4H), 6.35(m, 1H), 4.48(s, 2H), 3.10(q, 2H, J=8Hz), 3.07(d, 3H, J=4Hz), 1.45(t, 3H, J=8Hz). MS calcd. 423.5; MS (M+1) 423.2 |

By a method similar to the method of Example 584 the wing compounds were prepared:

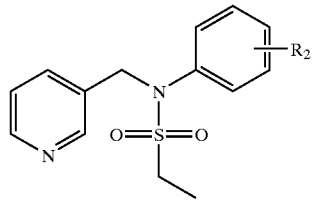

| No. | R₂ | Data |
|---|---|---|
| 590 | 3-(4-cyanophenyl) | ¹H NMR: 8.45(bs, 2H), 7.90(d, 1H, J=8Hz), 7.58(d, 2H, J=8Hz), 7.42(d, 2H, J=8Hz), 7.28–7.4(m, 5H), 4.90(s, 2H), 2.95(q, 2H, J=8Hz), 1.32(t, 3H, J=8Hz). MS calcd. 377.5; MS (M+1) 378.2 |
| 591 | 3-(2,4-difluorophenyl) | ¹H NMR: 8.65(bs, 1H), 8.47(bs, 1H), 7.95(m, 1H), 7.25–7.45(m, 6H), 6.85–7.0(m, 2H), 5.0(s, 2H), 3.15(q, 2H, J=8Hz), 1.47(t, 3H, J=8Hz). MS calcd. 388.4; MS (M+1) 389.1 |
| 592 | 3-(3-methanesulfonyl aminophenyl) | ¹H NMR: 8.63(s, 1H), 8.58(bs, 1H), 7.9(m, 1H), 7.56(s, 1H), 7.25–7.5(m, 9H), 5.05(s, 2H), 3.3(q, 2H, J=8Hz), 3.08(s, 3H), 1.45(t, 3H, J=8Hz). MS calcd. 445.6; MS (M+1) 446.2 |
| 593 | 3-((3,5-bis-triflurormethyl)phenyl) | ¹H NMR: 8.60(bs, 1H), 8.45(bs, 1H), 7.90(m, 3H), 7.35–7.55(m, 5H), 5.05(s, 2H), 3.20(q, 2H, J=8Hz), 1.52(t, 3H, J=8Hz). MS calcd. 488.5; MS (M+1) 489.1 |
| 594 | 3-phenyl | ¹H NMR: 8.49(bs, 1H), 8.41(bs, 1H), 7.90(m, 1H), 7.80(m, 1H), 7.15–7.45(m, 9H), 4.90(s, 2H), 3.07(q, 2H, J=8Hz), 1.38(t, 3H, J=8Hz). MS calcd. 352.5; MS (M+1) 353.2 |
| 595 | 3-((4-(2-trifluroacetylamino)ethyl)phenyl) | ¹H NMR: 8.65(bs, 1H), 8.57(bs, 1H), 7.92(m, 1H), 7.40–7.55(m, 4H), 7.20–7.30(m, 5H), 6.35(m, 1H), 5.15(s, 2H), 3.7(m, 2H), 3.20(q, 2H, J=8Hz), 2.95(m, 2H), 1.50(t, 3H, J=8Hz). MS calcd. 491.5; MS (M+1) 492.1 |
| 596 | 3-(4-acetylaminophenyl) | ¹H NMR: 8.55(bs, 1H), 8.50(bs, 1H), 7.95(m, 1H), 7.60(m, 3H), 7.35–7.55(m, 6H), 7.22(m, 1H), 5.03(s, 2H), 3.17(q, 2H, J=8Hz), 2.25(s, 3H), 1.45(t, 3H, J=8Hz). MS calcd. 409.5; MS (M+1) 410.1 |
| 597 | 3-(4-methanesulfonylphenyl) | ¹H NMR: 8.57(bs, 1H), 8.43(bs, 1H), 8.03(d, 2H, J=16Hz), 7.85(m, 1H), 7.70(d, 2H, J=16Hz), 7.45–7.55(m, 3H), 7.35(m, 2H), 5.0(s, 2H), 3.18(q, 2H, J=8Hz), 3.12(s, 3H), 1.50(t, 3H, J=8Hz). MS calcd. 430.6; MS (M+1) 431.1 |

-continued

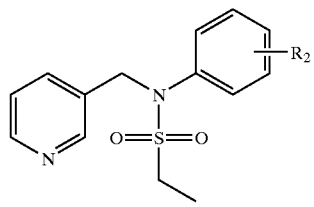

| No. | R₂ | Data |
|---|---|---|
| 598 | 3-(4-trifluoromethoxyphenyl) | ¹H NMR: 8.57(bs, 1H), 8.45(bs, 1H), 7.85(m, 1H), 7.40–7.55(m, 5H), 7.35(m, 1H), 7.25–7.30(m, 3H), 5.0(s, 2H), 3.15(q, 2H, J=8Hz), 1.50(t, 3H, J=8Hz). MS calcd. 436.5; MS (M+1) 437.0 |
| 599 | 3-(pryid-4-yl) | ¹H NMR: 8.68(bs, 2H), 8.55(bs, 1H), 8.45(bs, 1H), 7.82(m, 1H), 7.40–7.60(m, 6H), 7.32(m, 1H), 5.0(s, 2H), 3.17(q, 2H, J=8Hz), 1.50(t, 3H, J=8Hz). MS calcd. 353.4; MS (M+1) 354.2 |
| 600 | 3-(3-trifluoromethylphenyl) | ¹H NMR: 8.55(bs, 1H), 8.47(bs, 1H), 7.92(m, 1H), 7.45–7.70(m, 7H), 7.40(m, 1H), 7.32(m, 1H), 5.03(s, 2H), 3.17(q, 2H, J=8Hz), 1.50(t, 3H, J=8Hz). MS calcd. 420.5; MS (M+1) 421.1 |
| 601 | 3-(4-carboxyphenyl) | ¹H NMR: 8.70(bs, 1H), 8.62(bs, 1H), 8.15(m, 3H), 7.20–7.70(m, 7H), 5.12(s, 2H), 3.20(q, 2H, J=8Hz), 1.52(t, 3H, J=8Hz). MS calcd. 396.5; MS (M+1) 397.1 |
| 602 | 3-(4-(N'-methanesulfonyl-N'-t-butoxycarbonylaminoethyl)phenyl) | MS calcd. 573.7; MS (M+1) 574.2 |
| 603 | 3-(2-methylphenyl) | ¹H NMR (Methanol d₄): 8.40–8.60(br s, 2H), 8.00–8.10(m, 1H), 7.50–7.65(br s, 1H), 7.35–7.50(br s, 2H), 7.15–7.30(m, 5H), 7.05–7.15(br s, 1H), 5.00–5.15(s, 2H), 3.20–3.35(m, 2H), 2.05–2.20(s, 3H), 1.40–1.50(m, 3H). MS calcd. 480.51; MS (M+1) 367.2 (isolated as the trifluoroacetic acid salt) |
| 604 | 3-(2-methoxyphenyl) | ¹H NMR (Methanol d₄): 8.40–8.50(br s, 2H), 7.90–8.00(d, 1H, J=10Hz), 7.50–7.55(s, 1H), 7.40–7.50(m, 1H), 7.25–7.40(m, 4H), 7.20–7.25(d, 1H, J=16Hz), 6.95–7.10(m, 2H), 5.00–5.05(s, 2H), 3.70–3.80(s, 3H), 3.20–3.30(m, 2H), 1.40–1.50(m, 3H). MS calcd. 496.5; MS (M+1) 383.2 (isolated as the trifluoroacetic acid salt) |
| 605 | 3-(2-trifluoromethylphenyl) | ¹H NMR (Methanol d₄): 8.50–8.60(br s, 2H), 8.05–8.15(d, 1H, J=8Hz), 7.70–7.80(d, 1H, J=16Hz), 7.50–7.70(m, 3H), 7.40–7.50(m, 2H), 7.30–7.35(m, 2H), 7.20–7.30(m, 1H), 5.05–5.15(s, 2H), 3.20–3.35(m, 2H), 1.35–1.45(m, 3H). MS calcd. 534.5; MS (M+1) 421.2 (isolated as the trifluoroacetic acid salt) |
| 606 | 3-(2-chlorophenyl) | ¹H NMR: 8.45–8.55(s, 1H), 8.35–8.45(s, 1H), 7.70–7.80(d, 1H, J=10Hz), 7.40–7.50(m, 1H), 7.35–7.40(m, 2H), 7.25–7.35(m, 3H), 7.20–7.35(m, 3H), 4.90–4.95(s, 2H), 3.10–3.20(m, 2H), 1.40–1.50(t, 3H, J=8Hz). MS calcd. 386.9; MS (M+1) 387.2 |
| 607 | 3-(2-fluorophenyl) | ¹H NMR (Methanol d₄): 8.40–8.50(br s, 2H), 7.85–7.95(d, 1H, J=10Hz), 7.50–7.55(s, 1H), 7.30–7.50(m, 6H), 7.15–7.30(m, 2H), 5.00–5.10(s, 2H), 3.20–3.35(m, 2H), 1.40–1.50(t, 3H, J=8Hz). MS calcd. 484.5; MS (M+1) 371.1 (isolated as the trifluoroacetic acid salt) |
| 608 | 3-(3,5-difluorophenyl) | ¹H NMR (Methanol d₄): 8.55–8.40(br s, 2H), 7.90–8.00(d, 1H, J=10Hz), 7.50–7.60(m, 2H), 7.40–7.50(m, 3H), 7.15–7.25(d, 2H, J=16Hz), 6.90–7.00(m, 1H), 5.00–5.10(s, 2H), 3.20–3.35(m, 2H), 1.40–1.50(m, 3H). MS calcd. 502.4; MS (M+1) 389.2 (isolated as the trifluoroacetic acid salt) |
| 609 | 3-(3-acetylaminophenyl) | ¹H NMR: 8.45–8.50(d, 1H, J=8Hz), 8.40–8.45(s, 1H), 7.70–7.75(d, 1H, J=16Hz), 7.50–7.60(m, 2H), 7.45–7.50(d, 1H, J=16Hz), 7.40–7.45(s, 1H), 7.35–7.40(m, 2H), 7.20–7.30(m, 3H), 4.90–4.95(s, 2H), 3.45–3.50(q, 1H, 12Hz), 3.10–3.20(q, 2H, J=16Hz), 2.20–2.25(s, 3H), 1.40–1.50(t, 3H, J=8Hz). MS calcd. 446.0; MS (M+1) 410.2 (isolated as the hydrochloric acid salt) |

EXAMPLE 610

N-((4-Methyl-3-(4-cyanophenyl)phenyl)-N-(ethanesulfonyl)pyrid-3-ylmethylamine

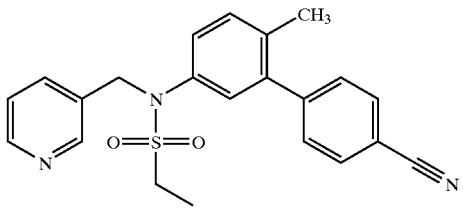

A solution of N-(3-iodo-4-methylphenyl)-N-(ethylsulfonyl)pyrid-3-ylmethylamine (103 mg, 0.247 mmol) and 4-cyanophenylboronic acid (55 mg, 0.371 mmol) in 4 ml of 1,4-dioxane stirring under nitrogen was treated with 2M sodium carbonate (0.37 mL, 0.741 mmol) and tetrakis(triphenylphosphine)palladium(0) (12.6 mg, 0.011 mmol). This was refluxed for three hours and then allowed to stir at room temperature for 16 hours. The reaction had not completed after this time so the reaction was treated with an additional 5.7 mg (0.005 mmol) of tetrakis(triphenylphosphine)palladium(0) and refluxed for two hours. The reaction was then cooled to room temperature and concentrated in vacuo. This was then dissolved in a minimal amount of dichloromethane and purified on a Chromatotron (200 omicron plate) with 3% methanol/dichloromethane to give a residue which was recrystallized using ether/hexanes to give the title compound. $^1$H NMR: 8.45–8.55 (d, 1H, J=4 Hz), 8.35–8.40 (s, 1H), 7.75–7.80 (d, 1H, J=12 Hz), 7.65–7.70 (d, 1H, J=12 Hz), 7.20–7.35 (m, 5H), 7.15–7.20 (m, 1H), 7.00–7.05 (s, 1H), 4.85–4.95 (s, 2H), 3.05–3.15 (q, 2H, J=10z), 2.15–2.20 (s, 3H), 1.40–1.50 (t, 3H, J=8 Hz); MS calcd. 391.5; MS (M+1)=392.1.

EXAMPLE 611

N-(3-(4-(2-Methanesulfonylaminoethyl)phenyl)phenyl)-N-(2,2,2-trifluoroethanesulfonyl)pyrid-3-ylmethylamine

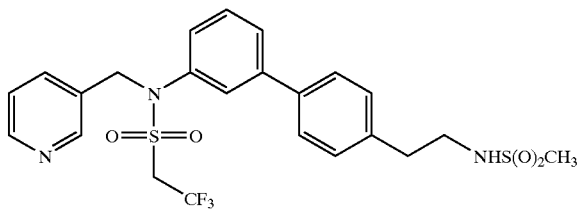

A solution of N-(3-(4-(N'-methanesulfonyl-N'-t-butoxycarbonylaminoethyl)phenyl)pyrid-3-ylmethylamine and 2,2,2-trifluoroethanesulfonyl chloride (134 mg, 0.735 mmol) in 3:1 dichloromethane/pyridine (4 mL) was stirred for 16 hours after which the reaction had not completed yet. Another 67 mg (0.368 mmol) of 2,2,2-trifluoroethanesulfonyl chloride was added and the reaction was heated to 45° C. for 30 minutes. The reaction was then allowed to cool to room temperature. Ether was used to extract the organic material, which was washed four times with deionized water. The organic layer was then dried with sodium carbonate, filtered, and concentrated in vacuo. The concentrated mixture was then dissolved in a minimal amount of dichloromethane and purified on a Chromatotron (6000 micron plate) using 3% methanol/dichloromethane. The proper fractions were collected and concentrated in vacuo and treated with 3 mL of 2:1 trifluoroacetic acid:dichloromethane and stirred for 1 hour to take off the Boc protecting group. Acetonitrile was then added and the reaction was concentrated in vacuo in order to remove any water. This step was repeated two additional times, which left an oil. The oil was treated with 0.64 mL (0.64 mmol) of 1M hydrochloric acid, 5 mL of ether, and 5 mL hexanes, which caused the title compound to precipitate out of solution. The solid was filtered and collected. This yielded the title compound as the HCl salt. $^1$H NMR (Methanol d$_4$): 8.35–8.45 (br s, 2H), 7.80–7.90 (d, 1H, J=12 Hz), 7.55–7.60 (d, 1H, J=16 Hz), 7.40–7.55 (m, 4H), 7.30–7.40 (m, 4H), 5.00–5.05 (s, 2H), 4.30–4.40 (q, 4H, J=16 Hz), 3.25–3.35 (s, 4H), 2.80–2.9 (m, 4H). MS calcd. 564.0; MS (M+1)=528.3.

EXAMPLE 612

N-((3-(4-Amidophenyl)phenyl)-N-(ethanesulfonyl)pyrid-3-ylmethylamine

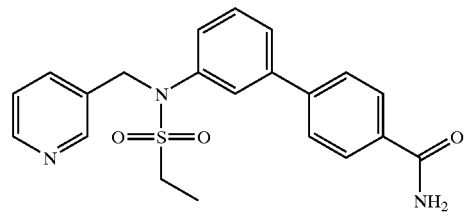

N-((3-(4-Cyanophenyl)phenyl)-N-(ethanesulfonyl)pyrid-3-ylmethylamine (147 mg, 0.36 mmol) was treated with concentrated sulfuric acid (2.5 ml) for 22 h at room temperature. The reaction was neutralized with 50 weight % aqueous sodium hydroxide to pH 7.0. This milky solution was extracted three times with 15% isopropanol/dichloromethane and the organics were combined and concentrated in vacuo to a tan solid. The solid was purified by radial chromatography on a 1 micron silica plate eluting with 3 to 10% methanol/dichloromethane to afford the title compound (49 mg, 35%). $^1$H NMR:8.56 (s,1H), 8.5 (s,1H), 7.95 (m,1H), 7.90 (d,2H,J=8 Hz), 7.72 (d,2H,J=8 Hz), 7.3–7.58 (m,5H), 6.20 (bs,1H), 5.75 (bs,1H), 5.05 (s,2H), 3.17 (q,2H,J=8 Hz), 1.5 (t,3H,J=8 Hz). MS calcd. 395.5; MS (M+1) 396.1.

EXAMPLE 613

N-(3-(4-(2-Methanesulfonylaminoethyl)phenyl)phenyl)-N-(ethanesulfonyl)pyrid-3-ylmethylamine

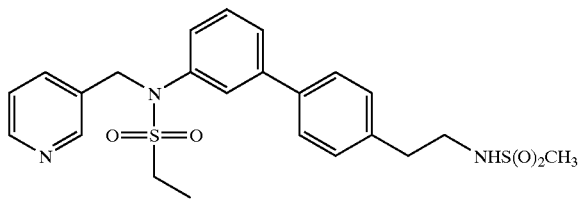

A solution of N-(3-(4-(N'-methanesulfonyl-N'-t-butoxycarbonylaminoethyl)phenyl)phenyl)-N-(ethanesulfonyl)pyrid-3-ylmethylamine (78 mg, 0.136 mmol) in 2 ml dichloromethane/3 ml trifluoroacetic acid was stirred for 40 minutes at room temperature. The mixture was diluted with acetonitrile and concentrated to an oil. The oil was dissolved in 0.5 ml dichloromethane and treated with ethereal HCl to afford the title compound as the HCl slat. $^1$H NMR (d$_4$ methanol): 8.80 (bs,1H), 8.73 (bs,1H), 8.60 (m,1H), 8.0 (m,1H), 7.66 (m,1H), 7.57 (m,1H), 7.52 (d,2H, J=8 Hz), 7.43 (m,2H), 7.35 (d,2H,J=8 Hz), 5.23 (s,2H), 3.32 (m,4H), 2.87 (t,2H,J=8 Hz), 2.82 (s,3H), 1.40 (t,3H,J=8 Hz). MS calcd. 510.1; MS (M+1−HCl) 474.1.

EXAMPLE 614

N-((3-(2-Methyl-4-cyanophenyl)phenyl)-N-(ethanesulfonyl)pyrid-3-ylmethylamine

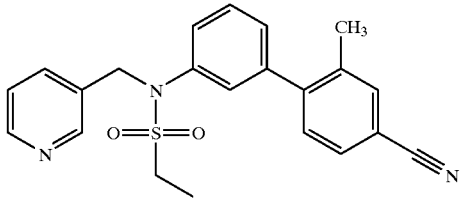

In a one pot reaction, a solution of 4-bromo-3-methylbenzonitrile (166 mg, 0.845 mmol), bis(pinacolato) diboron (236 mg, 0.93 mmol), potassium acetate (249 mg, 2.5 mmol), and DMSO (7 mL) was stirred under nitrogen until all the materials present were dissolved. Then 55 mg (0.068 mmol) palladium(II) chloride (dppf) complex with dichloromethane (1:1) was introduced to the solution, which was then heated to 80° C. for three hours. During this time the solution turned a dark brown color.

The reaction was allowed to cool to room temperature after the three hours had passed N-(3-bromophenyl)-N-(ethanesulfonyl)pyrid-3-ylmethylamine (300 mg, 0.845 mmol), 2M sodium carbonate (1.25 mL, 2.5 mmol) and another equivalent of palladium(II) chloride (dppf) complex with dichloromethane (1:1) (55 mg, 0.068 mmol) were added to the reaction. The reaction was then stirred under nitrogen while being heated to 120° C. for 16 hours.

After 16 hours, the reaction was allowed to cool again. Dichloromethane was used for the extraction and the crude was washed with water and brine. After the washing, the organic layer was dried with sodium sulfate, filtered, and concentrated in vacuo. This was then purified using a Chromatotron (4000 micron plate) and 2% methanol/dichloromethane. The fractions containing the product were collected and concentrated in vacuo and recrystallized from ether/hexanes to give the title compound. $^1$H NMR: 8.45–8.55 (d, 1H, J=8 Hz), 8.30–8.40 (s, 1H), 7.70–7.80 (d, 1H, J=16 Hz), 7.45–7.55 (m, 1H), 7.40–7.50 (t, 2H, J=16 Hz), 7.25–7.35 (m, 3H), 7.15–7.20 (m, 1H), 7.10–7.15 (s, 1H), 4.90–5.00 (s, 2H), 3.05–3.10 (q, 2H, J=10 Hz), 2.05–2.10 (s, 3H), 1.4–1.5 (t, 3H, J=16 Hz). MS calcd. 391.5; MS (M+1) 392.2.

Preparation 22

N-(4-(2,4-Difluorophenoxy)phenyl)-N-ethylsulfonylamine

Ethanesulfonyl chloride (9.4 mL, 99 mmol) was added dropwise over 5 min to a dark gray solution of 4-(2,4-difluorophenoxy)aniline (20.0 g, 90 mmol) and 4-dimethylaminopyridine (16.6 g, 136 mmol) in methylene chloride (180 mL) at room temperature under nitrogen, after which the mixture was stirred at room temperature for 26 h. The mixture was washed with saturated aqueous sodium bicarbonate solution (200 mL), brine (100 mL), dried over MgSO$_4$, filtered and the solvent was removed under reduced pressure to afford the crude product as an amber oil. This residue was triturated with diethyl ether (300 mL) and filtered to provide an amber solid. This material was further purified by flash column chromatography on silica gel, eluting with ethyl acetate/chloroform (1:9), to provide the title compound as an off-white powder: $^1$H NMR (300 MHz, DMSO-d$_6$) 9.69 (s, 1H), 7.52–7.44 (m, 1H), 7.28–7.09 (m, 2H), 7.20 (d, J=8.8 Hz, 2H), 6.95 (d, J=8.8 Hz, 2H), 3.03 (q, J=7.6 Hz, 2H), 2.50 (t, J=1.6 Hz, 3H).

Preparation 23

N-(4-(2,4-Difluorophenoxy)phenyl)-N-(2,2,2-trifluoroethanesulfonyl)amine 2,2,2-Trifluoroethanesulfonyl chloride (10.0 g, 54.8 mmol) was added dropwise to a solution of 4-(2,4-difluorophenoxy)aniline (11.0 g, 50.0 mmol) and 4-dimethylaminopyridine (9.1 g, 74.6 mmol) in methylene chloride (100 mL) at 0° C. under nitrogen. The mixture was slowly warmed to room temperature, stirring for a total of 72 h. The mixture was washed with saturated aqueous sodium bicarbonate solution (200 mL), dried over MgSO$_4$, filtered and the solvent was removed under reduced pressure to afford the crude product as an orange oil. This residue was purified by flash column chromatography on silica gel, eluting with ethyl acetate/chloroform (1:4), to provide the title compound as a yellow solid: mp 105–108° C.; TLC R$_f$ (1:9 ethyl acetate/chloroform)=0.75; $^1$H NMR (300 MHz, CDCl$_3$) 7.23 (d, J=8.9 Hz, 2H), 7.14–6.87 (m, 3H), 6.93 (d, J=8.9 Hz, 2H), 3.76 (q, J=8.8 Hz, 2H) ppm; APCI MS m/z 366 [C$_{14}$H$_{10}$F$_5$NO$_3$S—H]$^-$.

Preparation 24

(2-Fluoropyridin-3-yl)methanol

Thionyl chloride (0.43 mL, 5.87 mmol) was added to a slurry of 2-fluoronicotinic acid (9, 0.69 g, 4.89 mmol) and N,N-dimethylformamide (0.1 mL, catalytic amount) in benzene (60 mL) at room temperature under nitrogen, after which the mixture was heated at reflux for 3 h. The solvent was removed under reduced pressure to provide an amber oil that was dissolved in 1,4-dioxane (40 mL) under nitrogen. The solution was treated with sodium borohydride (0.38 g, 10.0 mmol) and the mixture was stirred at room temperature for 24 h. The suspension was diluted with saturated NaHCO$_3$ solution (200 mL) and extracted with diethyl ether (3×200 mL). The combined organic extracts were dried over Na$_2$SO$_4$, filtered and the solvents were removed under reduced pressure to provide the title compound: $^1$H NMR (300 MHz) 8.13 (d, J=3.7 Hz, 1H), 7.93–7.88 (m, 1H), 7.24–7.19 (m, 1H), 4.78 (s, 2H), 2.14 (bs, 1H) ppm.

Preparation 25

(2-Methylpyridin-3-yl)methanol

To a slurry of lithium aluminum hydride (500 mg, 13.2 mmol) in anhydrous tetrahydrofuran (45 mL) at 0° C. under nitrogen was added dropwise a solution of methyl 2-methylnicotinate (17, 1.0 g, 6.6 mmol) in anhydrous tetrahydrofuran (5 mL). After 1 h the suspension was diluted with water (1 mL) and 6 N NaOH solution (5 mL). The precipitate was removed by vacuum filtration and the filtrate was dried over Na$_2$SO$_4$, filtered, and the solvent was removed under reduced pressure to provide the title compound as a light yellow oil: $^1$H NMR (300 MHz) 8.37 (d, J=4.9 Hz, 1H), 7.72 (d, J=7.6 Hz, 1H), 7.14 (dd, J=7.6 Hz, 4.9 Hz, 1H), 4.72 (s, 2H), 2.95–2.74 (bs, 1H), 2.53 (s, 3H) ppm.

Preparation 26

(6-Methylpyridin-3-yl)methanol

To a slurry of lithium aluminum hydride (500 mg, 13.2 mmol) in anhydrous tetrahydrofuran (45 mL) at 0° C. under nitrogen was added dropwise a solution of methyl 4-methylnicotinate (15, 1.0 g, 6.6 mmol) in anhydrous tetrahydrofuran (5 mL). After 1.5 h the suspension was diluted with water (1 mL) and 6 N NaOH solution (5 mL). The precipitate was removed by vacuum filtration and the filtrate was dried over $Na_2SO_4$, filtered, and the solvent was removed under reduced pressure to provide the title compound as a light yellow oil: $^1$H NMR (300 MHz) 8.34 (s, 1H), 7.60 (d, J=7.9 Hz, 1H), 7.12 (d, J=7.9 Hz, 1H), 4.65 (s, 2H), 4.18–4.10 (bs, 1H), 2.51 (s, 3H) ppm.

Preparation 27

(6-Fluoropyridin-3-yl)methanol

Thionyl chloride (0.29 mL, 4.08 mmol) was added to a slurry of 6-fluoronicotinic acid (13, 0.48 g, 3.40 mmol) and N,N-dimethylformamide (0.1 mL, catalytic amount) in benzene (40 mL) at room temperature under nitrogen, after which the mixture was heated at reflux for 3 h. The solvent was removed under reduced pressure to provide an amber oil that was dissolved in 1,4-dioxane (25 mL) under nitrogen. The solution was treated with sodium borohydride (0.26 g, 6.80 mmol) and the mixture was stirred at room temperature for 24 h. The suspension was diluted with sat. $NaHCO_3$ solution (200 mL) and extracted with diethyl ether (3×200 mL). The combined organic extracts were dried over $Na_2SO_4$, filtered and the solvents were removed under reduced pressure to provide the title compound as a colorless oil: $^1$H NMR (300 MHz) 8.20 (s, 1H), 7.87–7.81 (dt, J=8.0, 2.3 Hz, 1H), 6.97–6.93 (dd, J=8.4, 2.8 Hz, 1H), 4.73 (s, 2H), 2.04 (bs, 1H) ppm.

EXAMPLE 615

N-(4-(2,4-Difluorophenoxy)phenyl)-N-(ethanesulfonyl)-2-fluoropyrid-3-ylmethylamine

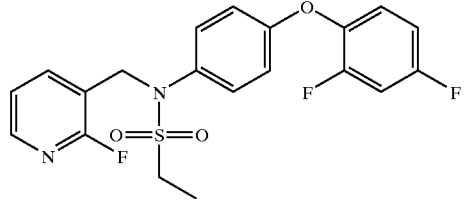

Di-tert-butyl azodicarboxylate (0.36 g, 1.57 mmol) was added to a suspension of (2-fluoropyridin-3-yl)methanol (10, 0.20 g, 1.57 mmol), N-(4-(2,4-difluorophenoxy)phenyl)-N-ethylsulfonylamine (0.49 g, 1.56 mmol) and polystyrene resin-bound triphenylphosphine (0.52 g, 1.57 mmol, ~3 mmol/g) in anhydrous tetrahydrofuran (5 mL) at 0° C. under nitrogen. The resulting yellow suspension was warmed to room temperature and stirred for 19 h, after which additional polystyrene resin bound triphenylphosphine (0.52 g, 1.57 mmol, ~3 mmol/g) and di-tert-butyl azodicarboxylate (0.36 g, 1.57 mmol) were added. This solution was stirred for 24 h after which the suspension was diluted with anhydrous tetrahydrofuran (100 mL) and the solids were removed by vacuum filtration. The filtrate solvent was removed under reduced pressure to provide the crude product as a yellow oil. This oil was purified by medium pressure liquid chromatography on silica gel, eluting with hexanes/ethyl acetate (7:3), to provide a colorless oil. This oil was triturated with hexanes/ethyl acetate (4–5 mL) to give the title compound as a white powder (0.28 g, 53%): mp 110–112° C.; TLC $R_f$ (3:2 hexanes/ethyl acetate)= 0.44; $^1$H NMR (300 MHz) 8.11 (m, 1H), 7.90 (m, 1H), 7.24–7.15 (m, 3H), 7.11–7.03 (m, 1H), 6.98–6.86 (m, 2H), 6.84 (d, J=6.8 Hz, 2H), 4.91 (s, 2H), 3.15–3.07 (q, J=7.4 Hz, 2H), 1.43 (t, J=7.4 Hz, 1H) ppm; $^{13}$C NMR (75 MHz) 163.3, 161.3, 160.1, 157.8, 156.5, 153.1, 147.5 (d, J=14.9 Hz), 141.7, 139.1, 133.6, 130.5, 123.8 (d, J=9.7 Hz), 122.1, 119.1 (d, J=29.2 Hz), 117.5, 112.0 (d, J=22.9 Hz), 106.0 (t, J=24.3 Hz), 49.1, 46.0, 8.44 ppm; APCI MS m/z 423 $[C_{20}H_{17}F_3N_2O_3S+H]^+$. Anal. Calcd. for $C_{20}H_{17}F_3N_2O_3S$: C, 56.87; H, 4.06; N, 6.63. Found: C, 56.90; H, 4.10; N, 6.45.

By a method similar to the method of Example 615 the following compounds were prepared:

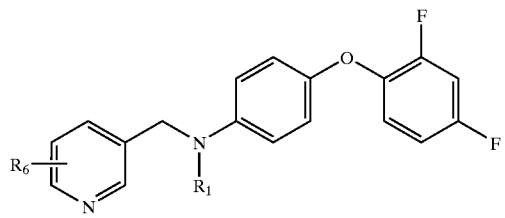

| No. | $R_1$ | $R_6$ | Data |
|---|---|---|---|
| 616 | $SO_2CH_2CF_3$ | 2-fluoro | mp 114–115° C.; TLC $R_f$ (7:3 hexanes/ethyl acetate)=0.45; $^1$H NMR (300MHz) 8.13(m, 1H), 7.90(m, 1H), 7.22–7.11(m, 3H), 7.10–7.05(m, 1H), 6.99–6.90(m, 2H), 6.87(d, J=8.9Hz, 2H), 4.92(s, 2H), 3.86–3.77(q, J=9.1Hz, 2H) ppm; $^{13}$C NMR (75MHz) 163.3, 161.4, 160.1, 158.5, 158.1, 156.5, 153.2, 147.9(d, J=14.9Hz), 141.7, 138.9, 131.9, 130.8, 123.9(d, J=9.7Hz), 122.2, 118.3(d, J=29.3Hz), 117.7, 112.2(d, J=22.9Hz), 106.0(t, J=21.9Hz), 52.6(q, J=31.9Hz), 49.8ppm; APCI MS m/z 477$[C_{20}H_{14}F_6N_2O_3S+H]^+$. Anal. Calcd. for $C_{20}H_{14}F_6N_2O_3S$: C, 50.42; H, 2.96; N, 5.88. Found: C, 50.05; H, 2.79; N, 5.72 |

-continued

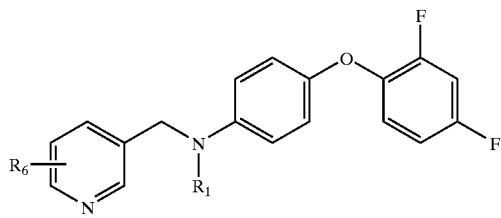

| No. | $R_1$ | $R_6$ | Data |
|---|---|---|---|
| 617 | SO$_2$CH$_2$CH$_3$ | 6-fluoro | mp 103–105° C.; TLC R$_f$ (1:1 hexanes/ethyl acetate)=0.38; $^1$H NMR (300MHz) 7.92(d, J=2.2Hz, 1H), 7.86–7.80(dt, J=8.0, 2.4Hz, 1H), 7.13(d, J=9.0Hz, 2H), 7.10–7.04(m, 1H), 6.98–6.87(m, 2H), 6.84(d, J=8.9Hz, 2H), 4.81(s, 2H), 3.12–3.05(q, J=7.4Hz, 2H), 1.43(t, J=7.4Hz, 1H) ppm; $^{13}$C NMR (75MHz) 165.3, 162.1, 161.3(d, J=10.2Hz), 158.0, 156.5(d, J=12.5Hz), 153.2(d, J=12.2Hz), 147.9(d, J=15.0Hz), 142.2, 139.1(d, J=12.1Hz), 133.3, 130.9, 130.3, 124.0(d, J=9.8Hz), 117.5, 112.0(d, J=22.9Hz), 110.1(d, J=37.5Hz), 106.0(t, J=22.0Hz), 52.6, 46.1, 8.50ppm; APCI MS m/z 423 [C$_{20}$H$_{17}$F$_3$N$_2$O$_3$S+H]$^+$. Anal. Calcd. for C$_{20}$H$_{17}$F$_3$N$_2$O$_3$S: C, 56.87; H, 4.06; N, 6.63. Found: C, 56.78; H, 3.97; N, 6.53 |
| 618 | SO$_2$CH$_2$CF$_3$ | 6-fluoro | mp 107–109° C.; TLC R$_f$ (3:2 hexanes/ethyl acetate)=0.54; $^1$H NMR (300MHz) 7.90(d, J=2.3Hz, 1H), 7.84–7.78(dt, J=2.4, 8.0Hz, 1H), 7.11(d, J=9.0Hz, 2H), 7.15–7.06(m, 2H), 7.00–6.90(m, 2H), 6.87(d, J=8.9Hz, 2H), 4.83(s, 2H), 3.83–3.76(q, J=9.1Hz, 2H)ppm; $^{13}$C NMR (75MHz) 165.5, 162.3, 161.4(d, J=10.3Hz), 158.6, 156.6(d, J=12.4Hz), 153.2(d, J=12.2Hz), 148.1(d, J=15.1Hz), 142.1(d, J=8.2Hz), 138.8, 131.5, 131.0 129.5, 124.1(d, J=9.7Hz), 120.2, 117.7, 112.3(d, J=23.0Hz), 110.3(d, J=37.6Hz), 106.0(t, J=21.9Hz), 53.4, 52.7(q, J=31.7Hz)ppm; APCI MS m/z 477[C$_{20}$H$_{14}$F$_6$N$_2$O$_3$S+H]$^+$. Anal. Calcd. for C$_{20}$H$_{14}$F$_6$N$_2$O$_3$S: C, 50.42; H, 2.96; N, 5.88. Found: C, 50.40; H, 2.87; N, 5.77 |
| 619 | SO$_2$CH$_2$CH$_3$ | 6-methyl | mp 108–111° C.; TLC R$_f$ (9:1 methylene chloride/methanol)=0.52; $^1$H NMR (300MHz) 8.20(d, J=2.0Hz, 1H), 7.59(dd, J=2.3Hz, 8.0Hz, 1H), 7.13(d, J=9.0Hz, 1H), 7.15–7.06(m, 3H), 6.86–6.83(m, 3H), 6.84(d, J=8.9Hz, 1H), 4.79(s, 2H), 3.11–3.04(q, J=7.4Hz, 2H), 2.51(s, 3H), 1.72(s, H), 1.43(t, J=7.4Hz, 1H)ppm; $^{13}$C NMR (75MHz) 161.2(d, J=10.2Hz), 158.6, 158.0(d, J=10.2Hz), 157.8, 156.5(d, J=12.2Hz), 153.2(d, J=12.2Hz), 149.5, 139.2(d, J=11.9Hz), 137.2, 133.6, 131.0, 129.3, 123.9(d, J=9.7Hz), 123.6, 117.5, 112.0(d, J=22.9Hz), 106.0(t, J=22.0Hz), 53.3, 46.1, 24.5, 8.5ppm; APCI MS m/z 419[C$_{21}$H$_{20}$F$_2$N$_2$O$_3$S+H]$^+$. Anal. Calcd. for C$_{21}$H$_{20}$F$_2$N$_2$O$_3$S: C, 60.27; H, 4.82; N, 6.69. Found: C, 59.94; H, 4.76; N, 6.58 |
| 620 | SO$_2$CH$_2$CF$_3$ | 6-methyl | mp 94–96° C.; TLC R$_f$ (4:6 hexanes/ethyl acetate)=0.58; $^1$H NMR (300MHz) 8.16(d, J=2.1Hz, 1H), 7.59(dd, J=2.3Hz, 7.9Hz, 2H), 7.13(d, J=9.0Hz, 1H), 7.09–7.06(m, 2H), 6.99–6.86(m, 3H), 6.86(d, J=8.9Hz, 1H), 4.81(s, 2H), 3.85–3.76(q, J=9.1Hz, 2H), 2.52(s, 3H), 1.61(s, 2H)ppm; $^{13}$C NMR (75MHz) 161.4(d, J=10.2Hz), 159.0, 158.4, 158.1(d, J=10.2Hz), 157.8, 156.6(d, J=12.2Hz), 153.2(d, J=12.2Hz), 149.5, 139.0(d, J=12.0Hz), 137.1, 131.9, 131.1, 128.4, 124.0(d, J=9.8Hz), 123.7, 120.3, 117.6, 112.1(d, J=22.9Hz), 106.0(t, J=22.0Hz), 54.1, 53.4–52.1(q, J=31.7Hz), 24.6ppm; APCI MS m/z 473[C$_{21}$H$_{17}$F$_5$N$_2$O$_3$S+H]$^+$. Anal. Calcd. for C$_{21}$H$_{17}$F$_5$N$_2$O$_3$S: C, 53.39; H, 3.63; N, 5.93. Found: C, 53.34; H, 3.44; N, 5.82 |

-continued

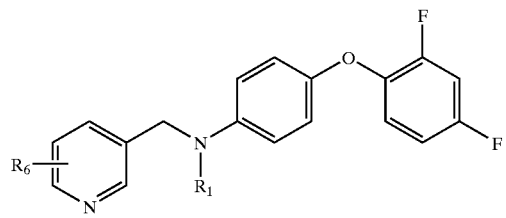

| No. | $R_1$ | $R_6$ | Data |
|---|---|---|---|
| 621 | $SO_2CH_2CH_3$ | 2-methyl | TLC $R_f$ (9:1 methylene chloride/methanol)=0.47; $^1$H NMR (300MHz) 8.37(d, J=4.9Hz, 1H), 7.55(d, J=7.7Hz, 1H), 7.17(d, J=9.2Hz, 2H), 7.10–7.02(m, 3H), 6.98–6.88(m, 3H), 6.83(d, J=8.9Hz, 2H), 4.88(s, 2H), 3.14–3.07(q, J=7.4Hz, 2H), 2.46(s, 3H), 1.45(t, J=7.3Hz, 1H)ppm; $^{13}$C NMR (75MHz) 161.4, 157.9, 157.3, 156.8, 154.1, 148.5, 139.4, 137.5, 134.2, 131.0, 130.0, 124.3, 122.2, 117.5, 112.3(d, J=22.9Hz), 106.3(t, J=22.0Hz), 52.5, 45.6, 28.8, 23.7, 8.7ppm; APCI MS m/z 419$[C_{21}H_{20}F_2N_2O_3S+H]^+$. Anal. Calcd. for $C_{21}H_{20}F_2N_2O_3S \cdot 0.10H_2O$: C, 60.02; H, 4.84; N, 6.67. Found: C, 59.86; H, 4.91; N, 6.74 |
| 622 | $SO_2CH_2CF_3$ | 2-methyl | TLC $R_f$ (7:3 ethyl acetate/hexanes=0.46; $^1$H NMR (300MHz) 8.38(d, J=4.8Hz, 1H), 7.54(d, J=7.7Hz, 1H), 7.15(d, J=9.0Hz, 1H), 7.12–7.04(m, 3H), 6.99–6.88(m, 3H), 6.85(d, J=9.0Hz, 1H), 4.90(s, 2H), 3.85–3.76(q, J=9.1Hz, 2H), 2.41(s, 3H)ppm; $^{13}$C NMR (75MHz) 161.4(d, J=10.3Hz), 158.5, 158.0(d, J=9.9Hz), 157.4, 156.6(d, J=10.2Hz), 153.2(d, J=10.2Hz), 149.2, 138.9(d, J=10.3Hz), 137.8, 132.0, 130.9, 129.3, 123.9(t, J=3.9Hz), 121.8, 120.3, 117.6, 112.1(d, J=22.9Hz), 106.0(t, J=22.0Hz), 53.5, 53.1–52.0(q, J=31.8Hz), 22.3ppm; APCI MS m/z 473$[C_{21}H_{17}F_5N_2O_3S+H]^+$. Anal. Calcd. for $C_{21}H_{17}F_5N_2O_3S$: C, 53.39; H, 3.63; N, 5.93. Found: C, 53.73; H, 3.76; N, 6.07 |

Preparation 28

N-(Ethylsulfonyl)-N-(3-(N'-(2-chlorophenyl)-N'-methylsulfonamide)aniline

To a solution of 2-chloro-N-methylaniline (4.96 mmol, 1.1 eq., 702 mg) and pyridine (5.86 mmol, 464 mg) in 20 mL of methylene chloride was added 3-nitrobenzenesulfonyl chloride (4.51 mmol, 1.0 g) in one portion. The reaction mixture was stirred 16 hr and diluted with methylene chloride and water. The aqueous layer was separated and extracted once with methylene chloride. The combined organic layers were extracted once with a saturated solution of aqueous sodium carbonate, once with water, and then dried over sodium sulfate. The crude product was purified using flash chromatography (10–60% ethyl acetate/hexane) to give N-(2-chlorophenyl)-N-methyl-(3-nitrophenyl)sulfonamide which solidifies on standing. $^1$H NMR (300 MHz) 3.29 (s, 3H), 7.25–7.45 (m, 4H), 7.71 (t, J=7.82 Hz, 1H), 8.06 (d, J=7.82 Hz, 1H), 8.40–8.50 (m, 1H), 8.60–8.65 (m, 1H). MS (ESI): m/e 327.13, 329.13 (M+1).

A solution of N-(2-chlorophenyl)-N-methyl-(3-nitrophenyl)sulfonamide (2.6 mmol, 848 mg) and tin (II) chloride dihydrate (10.4 mmol, 2.35 g) were heated for 4 hr at reflux in 15 mL of methanol. The reaction mixture was cooled to room temperature and diluted with 20 mL of ethyl acetate and 10 mL of a saturated solution of aqueous sodium carbonate. Heavy gas evolution was observed upon addition of aqueous sodium carbonate to the reaction mixture. The reaction mixture was stirred 1 hr and then filtered through a plug of Celite®. The layers were separated and the organic layer was extracted once with a saturated solution of aqueous sodium carbonate, once with brine, and then dried with sodium sulfate. The crude product was purified using flash chromatography (0–5% ethyl acetate/methylene chloride) to give N-(2-chlorophenyl)-N-methyl-(3-aminophenyl)sulfonamide as an off white foam. $^1$H NMR (300 MHz) 3.13 (s, 3H), 3.80 (br s, 2H), 6.80–6.87 (m, 1H), 7.02–7.25 (m, 6H), 7.30–7.38 (m, 1H). MS (ESI): m/e 297.2, 299.2 (M+1).

To a solution of N-(2-Chlorophenyl)-N-methyl-(3-aminophenyl)sulfonamide (3.38 mmol, 1.0 g), DMAP (0.83 mmol, 120 mg) and pyridine (16.9 mol, 1.33 mL) in 20 mL methylene chloride was added ethanesulfonyl chloride (12.2 mmol, 3.6 eq., 1.56 g) in two portions. The reaction mixture was stirred 10 hr and diluted with then methylene chloride and water. The layers were separated and the aqueous layer was extracted once with methylene chloride. The combined organic layers were extracted once with a saturated solution of aqueous sodium carbonate and then dried with sodium sulfate. The crude product was purified using flash chromatography (0–30% ethyl acetate/methylene chloride) to give the title compound. $^1$H. NMR (300 MHz) 1.36 (t, J=5.87 Hz, 3H), 3.10–3.16 (m, 2H), 3.23 (s, 3H), 7.04 (s, 1H), 7.22–7.60 (m, 8H). MS (ESI): m/e 389.01, 390.88 (M+1).

EXAMPLE 623

N-(3-(N'-Methyl-N'-(2-chlorophenylsulfonamido)phenyl))-N-(ethanesulfonyl)pyrid-3-ylmethylamine

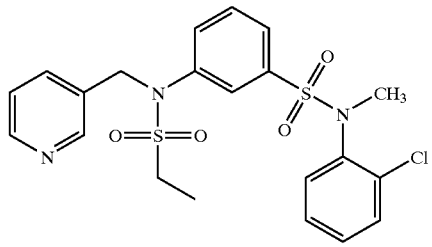

To a solution of (0.48 mmol, 186.6 mg) dissolved in 5 mL of anhydrous DMF was added a 1.0 M solution of lithium bis(trimethylsilyl)amide in hexane (1.2 mmol, 2.5 eq., 1.2 mL). The solution was stirred 5 min. and 3-picolyl chloride hydrochloride (0.50 mmol, 82 mg) was added in one portion. After overnight stirring, the reaction mixture was concentrated to dryness under vacuum. The residue was dissolved in methanol and loaded onto a 2 g SCX ion exchange cartridge (Varian Sample Preparation, 0.75 meq/g loading). After washing with additional methanol the crude product was eluted from the column using 10 mL of a 2.0 M solution of ammonia in methanol. The crude produce was purified using mass guided revere phase semi-preparative chromatography (ESI detection; ACN with 0.1% TFA/water with 0.1% TFA; Flow rate 25 mL/min.; 10% organic for 1 min. then a gradient over 12 min. to 95% organic then 95% organic for 1 min.) to give the TFA salt of the product as an oil after solvent evaporation. The purified sample was desalted using a 1 g SCX ion exchange column as previously described (methanol washing solvent and 2.0 M ammonia in methanol the eluting solvent) to give the title compound. $^1$H NMR (300 MHz) 1.40 (t, J=7.43 Hz, 3H), 3.04 (q, J=7.43 Hz, 2H), 3.18 (s, 3H), 4.89 (s, 2H), 7.20–7.30 (m, 3H), 7.32–7.37 (m, 1H), 7.44–7.52 (m, 3H), 7.65–7.75 (m, 3H), 8.39 (br s, 1H), 8.51 (br s, 1H). MS (ESI): m/e 480.2, 482.2 (M+1).

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

In practice, the compounds of formula I are usually administered in the form of pharmaceutical compositions, that is, in admixture with pharmaceutically acceptable carriers or diluents, the proportion and nature of which are determined by the chemical properties of the selected compound of formula I, the chosen route of administration, and standard pharmaceutical practice.

Thus, the present invention provides pharmaceutical compositions comprising a compound of the formula I and a pharmaceutically acceptable diluent.

The compounds of formula I can be administered by a variety of routes. In effecting treatment of a patient afflicted with disorders described above, a compound of formula I can be administered in any form or mode which makes the compound bioavailable in an effective amount, including oral and parenteral routes. For example, compounds of formula I can be administered orally, by inhalation, subcutaneously, intramuscularly, intravenously, transdermally, intranasally, rectally, occularly, topically, sublingually, buccally, and the like. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions of the present invention are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and nontoxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I or its pharmaceutical salt from about 0.1 to about 10% w/v (weight per unit volume).

In order to more fully illustrate the operation of this invention, typical pharmaceutical compositions are described below. The examples are illustrative only, and are not intended to limit the scope of the invention in any way.

Formulation 1

A typical tablet, appropriate for use in this method, may be prepared using conventional techniques and may contain:

|  | Amount per Tablet | Concentration by Weight (%) |
| --- | --- | --- |
| Compound of formula I | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg Ph. Eur. | 0.3 |
| TOTAL | 105.45 mg | 100 |

Formulation 2

Hard gelatin capsules may be prepared using the following ingredients:

|  | Amount per Tablet | Concentration by Weight (%) |
| --- | --- | --- |
| Compound of formula I | 0.1 mg | 0.05 |
| starch dried | 200 mg | 95.2 |
| magnesium stearate | 10 mg | 4.8 |
| TOTAL | 210.1 mg | 100 |

The above ingredients are mixed and filled into hard gelatin capsules in 210.1 mg quantities.

Formulation 3

Suspensions each containing 1 mg of medicament per 5 mL dose are as follows:

|  | Amount per 5 mL of suspension |
| --- | --- |
| Compound of formula I | 1 mg |
| sodium carboxymethyl cellulose | 50 mg |
| syrup | 1.25 mL |
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The compounds of formula I are potentiators of metabotropic glutamate (mGlu) receptor function, in particular they are potentiators of $mGlu_2$ and/or $mGlu_3$ receptors. That is, the compounds of formula I do not appear to bind at the glutamate recognition site on the mGlu receptor, but in the presence of glutamate or a glutamate agonist, the compounds of formula I increase mGlu receptor response. The present potentiators are expected to have their effect at mGlu receptors by virtue of their ability to increase the response of such receptors to glutamate or glutamate agonists, enhancing the function of the receptors. The behavior of the potentiators of formula I at $mGlu_2$ receptors is shown in Example A which is suitable to identify potentiators useful for carrying out the present invention.

EXAMPLE A

[$^3$H]-2S-2-Amino-2-(1S,2S-2-carboxycyclopropan-1-yl)-3-(xanth-9-yl) propionic acid Receptor Binding

[$^3$H]-2S-2-Amino-2-(1S,2S-2-carboxycyclopropan-1-yl)-3-(xanth-9-yl) propionic acid (17.5 Ci/mmol) was tritiated by Chemsyn Laboratories. Membranes from $mGlu_2$ receptor expressing RGT cells were prepared by harvesting adherent cells from confluent T-150 flasks with a cell scraper. Cells and media were then placed in 50 ml conical tubes and centrifuged at 4° C. at 1000 g for 5 minutes. The supernatant was removed and the pellet was frozen at −10° C. until use. Washed cell membranes were prepared by adding 20 ml of 10 mM potassium phosphate buffer pH 7.6 @ 5° C.+100 mM potassium bromide and homogenizing with an Ultra-Turrax tissuemizer for 15 seconds at 90% output. The homogenate was centrifuged at 48,000×g for 10 minutes at 5° C. This last step was repeated two times, and the final pellet was resuspended in 10 ml of the same buffer and reserved on ice until initiating the binding assay.

[$^3$H]-2S-2-Amino-2-(1S,2S-2-carboxycyclopropan-1-yl)-3-(xanth-9-yl) propionic acid can by assayed by the method described by Johnson et al. *Neuropharmacology* 38: 1519–1529 (1999). Accordingly, [$^3$H]-2S-2-amino-2-(1S,2S-2-carboxycyclopropan-1-yl)-3-(xanth-9-yl) propionic acid binding was assayed in a reaction mixture containing 10 mM potassium phosphate (pH 7.6), 100 mM potassium bromide and generally 1 nM [$^3$H]-2S-2-amino-2-(1S,2S-2-carboxycyclopropan-1-yl)-3-(xanth-9-yl) propionic acid, (final volume 500 μl). The incubation was initiated by the addition of the membrane suspension, (about 15 μg membrane protein), and allowed to continue on ice for 30 min. Incubation was terminated by rapid filtration with a Brandel cell harvester through glass fiber Whatman GF/B filters pre-wet with the same potassium phosphate buffer assay buffer (at 4° C.). The filters were washed five times with 1 ml of buffer. Filter sections were transferred to minivials and 5 ml of Fisher Scientific ScintiSafe liquid scintillation cocktail was added to each vial. Vials were allowed to set for several hours prior to counting on a Beckman LS6000 liquid scintillation counter.

Displacement of 1 nM [$^3$H]-2S-2-amino-2-(1S,2S-2-carboxycyclopropan-1-yl)-3-(xanth-9-yl) propionic acid binding was assayed in homogenates derived from a mGlu$_2$ receptor expressing cell line. At concentrations up to 100 μM, the potentiator of formula I did not significantly displace [$^3$H]-2S-2-amino-2-(1S,2S-2-carboxycyclopropan-1-yl)-3-(xanth-9-yl) propionic acid binding. Displacement of 1 nM [3H]-2S-2-Amino-2-(1S,2S-2-carboxycyclopropan-1-yl)-3-(xanth-9-yl)propionic acid is presented in the table below.

| Treatment | K$_I$ (μM) | (95% Confidence Interval) |
|---|---|---|
| Glutamate | 7.8 | (1.1–15.7) |
| Compound of Example 16 | >100 | |

Potentiation of Glutamate-Induced Increase in Intracellular Calcium with a mGluR$_2$ Expressing Cell Line.

Cell lines expressing human mGlu$_2$ receptors were derived as previously described (Desai, Burnett, Mayne, Schoepp, *Mol. Pharmacol.* 48, 648–657, 1995) and cultured in DMEM with 5% dialyzed fetal bovine serum, 1 mM glutamine, 1 mM sodium pyruvate, 50 μg/ml Geneticin G418, and 0.2 mg/ml hygromycin B. Confluent cultures were passaged weekly. These cells are referred to as RGT cells for Rat Glutamate Transporter, and have been co-transfected with the glutamate/aspartate transporter GLAST. The RGT cell line expressing the mGluR$_2$ receptors was stably transfected with the promiscuous G-protein, Galpha15 to change the signaling pathway to the mGlu$_2$ receptor to one that could be easily measured through release of intracellular calcium. Thus, intracellular calcium levels were monitored before and after the addition of drugs on a Fluorometric Imaging Plate Reader (i.e. FLIPR, Molecular Devices). The following buffer was used throughout as an assay buffer: 10 mM KCl, 138 mM NaCl, 5 mM Ca Cl$_2$, 1 mM MgCl$_2$, 4 mM NaH$_2$PO$_4$, 10 mM Glucose, 10 mM HEPES, pH 7.4. Cells that had been plated 48 h prior at a density of 30–40,000 cells per well in a 96-well plate were loaded with a calcium-sensitive dye for 90 min at 25° C. Fluo-3 (2 mM in DMSO, Molecular Probes) were mixed with an equal volume of 10% pluronic acid in DMSO, and diluted to 8 μM into the buffer described above containing 10% fetal bovine serum to make the loading buffer. Following loading of the cells, the loading buffer was removed and replaced with assay buffer prior to drug addition and monitoring on the FLIPR. Results are analyzed by taking the difference of the peak height minus the background fluorescence and expressing the results as a percent of the maximal glutamate response (30 μM glutamate, typically about 30–50,000 Relative Fluorescent Units).

Data from such an experiment using a representative compound of the present invention is presented in the table below.

| Treatment | % Maximal Glutamate Response (as defined by 30 μM Glutamate) mean ± SD |
|---|---|
| 20 μM Compound of Example 1 | 2.3 ± 0.8% |
| 0.5 μM L-glutamate | 1.9 ± 1.0% |
| 20 μM Compound of Example 1 + 0.5 μM L-glutamate | 85.5 ± 5.8%* |

*p < 0.05, ANOVA followed by contrast analysis

As seen from the results above the compounds of formula I potentiate the response of the mGlu$_2$ receptor to glutamate. This response can be blocked by pretreatment of the cells with the mGlu$_{2/3}$ antagonists 2S-2-amino-2-(1S,2S-2-carboxycyclopropan-1-yl)-3-(xanth-9-yl) propionic acid. Taken together with the inability of these compounds to displace [$^3$H]-2S-2-amino-2-(1S,2S-2-carboxycyclopropan-1-yl)-3-(xanth-9-yl) propionic acid-labeled receptors, these results show that the compounds of formula I act at a site other than the glutamate recognition site to potentiate the effects of glutamate at mGlu receptors.

Using the procedure of Example A, the effect of representative compounds of the present invention on the response of different mGluR$_2$ glutamate-site agonists (such as glutamate, 2R,4R-4-aminopyrrolidine-2,4-dicarboxylic acid (APDC), and 2S,2'R,3'R)-2-(2',3'-dicarboxycyclopropyl) glycine (DCG IV), (Schoepp, D. D., Jane, D. E., Monn, J. A., *Neuropharmacology* 38: 1431–1476, (1999)) is presented in the tables below.

| | Buffer | 3 μM Compound of Example 22 |
|---|---|---|
| | % Maximal Response (mean ± SD, n = 2) | |
| Buffer | 0.0 ± 3.2% | 4.7 ± 0.4% |
| 30 μM APDC | 100.7 ± 1.6% | 120.3 ± 10.0% |
| 10 μM APDC | 107.2 ± 3.6% | 119.1 ± 4.0% |
| 3 μM APDC | 80.3 ± 9.3% | 114.0 ± 0.8%* |
| 1 μM APDC | 16.8 ± 1.5% | 92.0 ± 3.4%* |
| 300 nM APDC | 1.7 ± 0.4% | 28.4 ± 1.7%* |
| 100 nM APDC | −0.8 ± 0.5% | 0.2 ± 0.6% |
| 30 nM APDC | 1.3 ± 0.1% | 0.5 ± 1.5% |
| 1 nM APDC | 0.3 ± 1.2% | 0.1 ± 0.7% |
| Buffer | 0.0 ± 0.7% | 3.7 ± 1.4% |
| 30 μM DCG IV | 68.5 ± 0.14% | 138.2 ± 7.1% |
| 10 μM DCG IV | 79.3 ± 10.8% | 147.9 ± 1.5% |
| 3 μM DCG IV | 68.3 ± 5.1% | 153.0 ± 2.8% |
| 1 μM DCG IV | 67.9 ± 15.0% | 141.1 ± 5.9% |
| 300 nM DCG IV | 34.3 ± 6.3% | 132.9 ± 5.5% |
| 100 nM DCG IV | 4.2 ± 0.8% | 83.3 ± 10.5% |

-continued

| | | |
|---|---|---|
| 30 nM DCG IV | 4.5 ± 4.3% | 11.1 ± 6.1% |
| 1 nM DCG IV | 4.3 ± 3.5% | −0.1 ± 0.6% |

| | Buffer | 1 μM Compound of Example 16 |
|---|---|---|
| | % Maximal Response (mean ± SD, n=2) | |
| Buffer | 0.0 ± 0.3% | 1.6 ± 1.0% |
| 24 μM Glutamate | 100.0 ± 5.8% | 95.4 ± 2.4% |
| 8 μM Glutamate | 96.7 ± 3.2% | 98.4 ± 6.4% |
| 2.4 μM Glutamate | 83.5 ± 4.6% | 92.5 ± 4.4% |
| 800 nM Glutamate | 16.9 ± 8.2% | 62.9 ± 0.1% |
| 240 nM Glutamate | −0.1 ± 0.4% | 17.4 ± 2.8% |
| 80 nM Glutamate | 0.1 ± 0.1% | 0.3 ± 1.1% |
| 24 nM Glutamate | 0.2 ± 0.2% | 0.1 ± 0.8% |
| 8 nM Glutamate | −0.7 ± 0.3% | 2.8 ± 1.9% |

| | Buffer + | 1 μM Compound of Example 1 | 1 μM Compound of Example 9 |
|---|---|---|---|
| | % Maximal Response (mean ± SD, n = 2) | | |
| | 0.0 ± 2.6% | 0.1 ± 0.1% | 4.2 ± 2.7% |
| 30 μM Glutamate | 107.2 ± 11.7% | 116.7 ± 4.3% | 108.0 ± 12.3% |
| 10 μM Glutamate | 108.2 ± 4.8% | 107.6 ± 10.7% | 102.9 ± 6.2% |
| 3 μM Glutamate | 84.2 ± 4.3% | 112.1 ± 10.3% | 101.6 ± 8.1% |
| 1 μM Glutamate | 22.6% (N=1) | 79.2 ± 14.6% | 93.1 ± 2.5% |
| 300 nM Glutamate | −1.1 ± 0.6% | 42.5 ± 4.3% | 60.0 ± 10.6% |
| 100 nM Glutamate | −1.0 ± 1.2% | 1.5 ± 1.2% | 20.5 ± 4.3% |
| 30 nM Glutamate | −1.6 ± 0.4% | 2.2 ± 1.3% | 4.7 ± 0.4% |
| 10 nM Glutamate | −1.1 ± 0.6% | −0.3 ± 0.2% | 2.4 ± 0.3% |

*$p < 0.05$, t-test vs. agonists alone

The results in the tables above demonstrate the ability of compounds of the present invention to potentiate the effects of $mGlu_2$ receptor agonists such as glutamate, APDC, and DCG IV. It is recognized that the compounds of the present invention would be expected to increase the effectiveness of glutamate and glutamate agonists of the $mGlu_2$ receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

In one embodiment of the present invention provides methods of treating neurological and psychiatric disorders associated with glutamate dysfunction, comprising: administering to a patient in need thereof an effective amount of a potentiator of metabotropic glutamate receptors.

Specifically, the present invention provides a method of treating neurological and psychiatric disorders associated with glutamate dysfunction, comprising: administering to a patient in need thereof an effective amount of a potentiator of $mGlu_2$ and/or $mGlu_3$ receptors, that is, the present invention provides methods using an effective amount of a potentiator of $mGlu_2$ receptors, an effective amount of a potentiator of $mGlu_3$ receptor, or an effective amount of a potentiator of $mGlu_2$ and $mGlu_3$ receptors.

In a preferred embodiment the present invention provides a method for treating migraine, comprising: administering to a patient in need thereof an effective amount of a metabotropic glutamate potentiator, in particular a potentiator of $mGlu_2$ and/or $mGlu_3$ receptors.

In another preferred embodiment the present invention provides a method for treating anxiety, comprising: administering to a patient in need thereof an effective amount of a metabotropic glutamate potentiator, in particular a potentiator of $mGlu_2$ and/or $mGlu_3$ receptors.

Particularly preferred anxiety disorders are generalized anxiety disorder, panic disorder, and obsessive compulsive disorder.

In another preferred embodiment the present invention provides a method for treating schizophrenia, comprising: administering to a patient in need thereof an effective amount of a metabotropic glutamate potentiator, in particular a potentiator of $mGlu_2$ and/or $mGlu_3$ receptors.

In yet another preferred embodiment the present invention provides a method for treating epilepsy, comprising: administering to a patient in need thereof an effective amount of a metabotropic glutamate potentiator, in particular a potentiator of $mGlu_2$ and/or $mGlu_3$ receptors.

Because the compounds of formula I enhance the normal physiological function of the mGlu receptors, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity (including tremors) seizures, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

At present, the fourth edition of the Diagnostic and Statistical Manual of Mental Disorders (DSM-IV™) (1994, American Psychiatric Association, Washington, D.C.), provides a diagnostic tool for identifying many of the disorders described herein. The skilled artisan will recognize that there are alternative nomenclatures, nosologies, and classification systems for neurological and psychiatric disorders described herein and that these systems evolve with medical scientific progress.

Because the compounds of formula I potentiate mGlu receptor response, in particular $mGlu_2$ and/or $mGlu_3$ receptor response, to glutamate and glutamate agonists. Such agonists are easily recognized and some are available in the art. Schoepp, D. D., Jane, D. E., Monn, J. A., *Neuropharmacology* 38: 1431–1476, (1999).

Thus, a more particular embodiment, it is understood that the present invention extends to a method of potentiating the action of a glutamate receptor agonist at the Group II mGlu receptors, comprising administering to a patient in need thereof an effective amount of a $mGluR_{2/3}$ potentiator, in particular a compound of formula I, in combination with a potentiated amount of an mGlu receptor agonist. Such a combination may be advantageous in that it may augment the activity and selectivity of mGlu agonist.

As used herein, the term "patient" refers to a warm blooded animal such as a mammal which is afflicted with one or more neurological and psychiatric disorders associated with glutamate dysfunction. It is understood that guinea pigs, dogs, cats, rats, mice, horses, cattle, sheep, and humans are examples of animals within the scope of the meaning of the term. It is also understood that this invention relates specifically to the potentiation of mammalian metabotropic glutamate receptors.

It is also recognized that one skilled in the art may affect the neurological and psychiatric disorders by treating a patient presently afflicted with the disorders or by prophylactically treating a patient afflicted with the disorders with an effective amount of the compound of formula I. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

As used herein, the term "effective amount" of a compound of formula I refers to an amount, that is, the dosage which is effective in treating the neurological and psychiatric disorders described herein.

An effective amount can be readily determined by the attending diagnostician, as one skilled in the art, by the use of conventional techniques and by observing results obtained under analogous circumstances. In determining an effective amount, the dose of a compound of formula I, a number of factors are considered by the attending diagnostician, including, but not limited to: the compound of formula I to be administered; the co-administration of an mGlu agonist, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.1 milligram per kilogram of body weight per day (mg/kg/day) to about 100 mg/kg/day. Preferred amounts are able to be determined by one skilled in the art.

As used herein, the term "potentiated amount" refers to an amount of an mGlu agonist, that is, the dosage of agonist which is effective in treating the neurological and psychiatric disorders described herein when administered in combination with an effective amount of a compound of formula I. A potentiated amount is expected to be less than the amount that is required to provided the same effect when the mGlu agonist is administered without an effective amount of a compound of formula I.

A potentiated amount can be readily determined by the attending diagnostician, as one skilled in the art, by the use of conventional techniques and by observing results obtained under analogous circumstances. In determining a potentiated amount, the dose of an mGlu agonist to be administered in combination with a compound of formula I, a number of factors are considered by the attending diagnostician, including, but not limited to: the mGlu agonist selected to be administered, including its potency and selectivity; the compound of formula I to be co-administered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGlu agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

Of the neurological and psychiatric disorders associated with glutamate dysfunction which are treated according to the present invention, the treatment of migraine, anxiety, schizophrenia, and epilepsy are particularly preferred. Particularly preferred anxiety disorders are generalized anxiety disorder, panic disorder, and obsessive compulsive disorder.

Thus, in a preferred embodiment the present invention provides a method for treating migraine, comprising: administering to a patient in need thereof an effective amount of a compound of formula I or a pharmaceutical composition thereof.

In one of the available sources of diagnostic tools, *Dorland's Medical Dictionary* ($23^{rd}$ Ed., 1982, W.B. Saunders Company, Philidelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment the present invention provides a method for treating anxiety, comprising: administering to a patient in need thereof an effective amount of a compound of formula I or a pharmaceutical composition thereof.

At present, the fourth edition of the Diagnostic and Statistical Manual of Mental Disorders (DSM-IV™) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

A number of preclinical laboratory animal models for migraine and anxiety have been described. One commonly used model of migraine is the dural extravasation model that has been described by Phebus et al., Life Sci., 61(21), 2117–2126 (1997) which can be used to evaluate the present compounds.

EXAMPLE B

Animal Model of Dural Protein Extravasation

Harlan Sprague-Dawley rats (250–350 g) were anesthetized with sodium pentobarbital intraperitoneally (65 mg/kg) and placed in a stereotaxic frame (David Kopf Instruments) with the incisor bar set at −3.5 mm. Following a midline sagital scalp incision, two pairs of bilateral holes were drilled through the skull (6 mm posteriorly, 2.0 and 4.0 mm laterally, all coordinates referenced to bregma). Pairs of stainless steel stimulating electrodes, insulated except at the tips (Rhodes Medical Systems, Inc.), were lowered through the holes in both hemispheres to a depth of 9 mm.

The femoral vein was exposed and a dose of the test compound was injected intravenously (i.v.) at a dosing volume of 1 ml/kg or, in the alternative, test compound was administered orally (p.o.) via gavage at a volume of 2 ml/kg. Approximately 8 minutes post i.v. injection, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 40 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 mm steps) on each dural sample. The mean and standard deviation of the measurements were determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side, over the amount of extravasation in the unstimulated side, was calculated. Control animals dosed only with saline, yielded a ratio of approximately 1.9. In contrast, a compound which effectively prevented the extravasation in the dura from the stimulated side would yield a ratio of approximately 1.0.

Data from such an experiment using a representative compound of the present invention is presented in the table below.

Inhibition of Dural Protein Extravasation

| Compound | Dose | Route of Admin | Extrav. Ratio ± s.e.m. | n |
|---|---|---|---|---|
| vehicle | 1 mL/kg | i.v. | 1.89 ± 0.08 | 9 |
| Example 16 | 10 pg/kg | i.v. | 1.87 ± 0.07 | 4 |
| Example 16 | 100 pg/kg | i.v. | 1.37 ± 0.07 | 3 |
| Example 16 | 1 ng/kg | i.v. | 1.04 ± 0.05 | 3 |
| Example 16 | 100 ng/kg | i.v. | 0.99 ± 0.004 | 3 |

The fear potentiated startle response model has been extensively used as a model of anxiety and can be used to evaluate the present compounds. Davis, *Psychopharmacol.*, 62, 1 (1979); Davis, *Behav. Neurosci.*, 100, 814 (1986); Davis, *Tr. Pharmacol. Sci.*, 13, 35 (1992).

EXAMPLE C

Fear Potentiated Startle Paradigm

Male Sprague-Dawley rats weighing 325–400 g were purchased from Harlan Sprague-Dawley, Inc. (Cumberland, Ind.) and given a one week acclimation period before testing. Rats were individually housed with food and water ad libitum in an animal room on a 12-hour light/dark cycle with lights on between 6:00 A.M. and 6:00 P.M. The compound of Example 16 was prepared in a suspension of 5% ethanol, 0.5% CMC, 0.5% Tween 80 and 99% water. 2S-2-amino-2-(1S,2S-2-carboxycyclopropan-1-yl)-3-(xanth-9-yl) propionic acid was prepared in sterile water. Control rats were given the respective vehicle.

The fear potentiated startle paradigm is conducted over three consecutive days. All three days begin with a 5-minute adaptation period before the trial starts. On day one (baseline startle) after the adaptation period, the animal receives 30 trials of 120 dB auditory noise. The mean startle amplitude ($V_{max}$) is used to assign animals to groups with similar means before conditioning begins. Day two consists of conditioning the animals. Each animal receives 0.5 mA of shock for 500 msec preceded by a 5 second presentation of light which remains on for the duration of the shock. Ten presentations of the light and shock are administered. Day three is the testing trial where drug administration occurs prior to testing. Twenty-four hours after conditioning, startle testing sessions are conducted. Ten trials of acoustic startle (120 dB), non-light paired, are presented at the beginning of the session. This is followed by 20 random trials of the noise alone and 20 random trials of noise preceded by light. Excluding the first 10 trials, the startle response amplitudes for each trial type are averaged for each animal. Data is presented as the difference between light+noise and noise-alone. Differences in startle response amplitudes were analyzed by JMP statistical software using a One-way Anova (analysis of variance, t-test). Group differences were considered to be significant at $p<0.05$.

Data from such an experiment using a representative compound of the present invention is presented in the table below. In the experiment shown below the compound of Example 16 was given i.p. 30 minutes prior to testing.

| Dose Response Experiment | |
|---|---|
| Compound of Example 16 (mg/kg) | Difference in Startle Amplitude ($V_{max}$) + S.E. |
| Exp. 1 Control | 188 + 47 |
| 0.03 | 108 + 41 |
| 0.3 | 154 + 38 |
| 3.0 | 21 + 24* |
| Exp. 2 Control | 455 + 106 |
| 1.0 | 120 + 87* |
| 3.0 | 148 + 86* |
| 10.0 | 105 + 91* |

*$P < 0.05$

In another preferred embodiment the present invention provides a method for treating epilepsy, comprising: administering to a patient in need thereof an effective amount of a compound of formula I or a pharmaceutical composition thereof.

At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

Various electroshock-induces models has been extensively used as a model of seizure disorders.

EXAMPLE D

Electroshock-induced Seizures

Application of electrical stimulation by corneal electrodes to mice can induce tonic hindlimb-extensor seizures. Blockade of tonic extensor seizures induced by electroshock is considered predictive for drugs which block seizure propagation and may be effective in preventing various seizures in humans, including epileptic seizures.

Vehicle or a dose of a test drug are administered to groups of 5 to 10 mice each. Thirty minutes later, electroshock (10 mA, 0.2 sec duration) is administered by transcorneal electrodes. The number of mice exhibiting tonic extensor seizures in each group is recorded. The data are reported as the percentage of mice which are protected from seizures.

Data from such an experiment using a representative compound of the present invention is presented in the table below.

| Compound of Example 590 (mg/kg, ip) | Percent Protection |
|---|---|
| vehicle | 0% |
| 30 | 60% |
| 100 | 100% |

What is claimed is:

1. A method of treating neurological and psychiatric disorders associated with glutamate dysfunction, comprising: administering to a patient in need thereof an effective amount of a compound of the formula

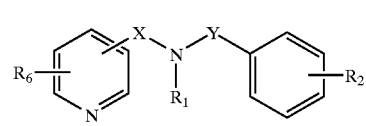

formula I wherein $R_1$ is —$SO_2R_5$ wherein $R_5$ is selected from the group consisting of alkyl, cycloalkyl, and fluorinated alkyl;

$R_2$ is from 1 to 3 substituents independently selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

or two $R_2$ substituents are taken together, on adjacent positions, to form a fused cycloalkyl or a methylenedioxy ring, and one $R_2$ substituent is selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

$R_6$ is from 1 to 2 substituents independently selected from the group consisting of hydrogen, alkyl, alkoxy, trifluoromethyl, halogen, phenoxy, and substituted phenoxy; provided that when $R_6$ is phenoxy or substituted phenoxy, the phenoxy or substituted phenoxy group is not attached to the pyridyl moiety in an adjacent position to X;

X is selected from the group consisting of

—$CH_2$—, —$CHR_7$—, and —$CH_2CH_{12}$— wherein $R_7$ is lower alkyl;

Y is a bond;

provided at least one $R_2$ is phenoxy or substituted phenoxy and the phenoxy or substituted phenoxy group is attached at the 3-position or 4-position;

and the pharmaceutically acceptable salts thereof and the pyridyl N-oxides thereof.

2. A pharmaceutical composition comprising a compound of formula 1 as claimed in claim 4 and a pharmaceutically acceptable diluent.

3. A method of treating anxiety, comprising: administering to a patient in need thereof an effective amount of a compound of formula I as claimed in claim 1.

4. A method of treating migraine, comprising: administering to a patient in need thereof an effective amount of a compound of formula I as claimed in claim 1.

5. A method of treating schizophrenia, comprising: administering to a patient in need thereof an effective amount of a compound of formula I as claimed in claim 1.

6. A method of treating epilepsy, comprising: administering to a patient in need thereof an effective amount of a compound of formula I as claimed in claim 1.

7. A method of treating neurological and psychiatric disorders associated with glutamate dysfunction, comprising: administering to a patient in need thereof an effective amount of an mGluR potentiator of a compound of formula I as claimed in claim 1.

8. A method according to claim 7 wherein the mGluR potentiator is a mGluR$_2$ potentiator.

9. A method according to claim 7 wherein the mGluR potentiator is a mGluR$_3$ potentiator.

10. A compound of the formula

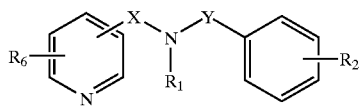

formula I wherein

R$_1$ is

—SO$_2$R$_5$ wherein R$_5$ is selected from the group consisting of alkyl, cycloalkyl, and fluorinated alkyl;

R$_2$ is from 1 to 3 substituents independently selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

provided at least one of the R$_2$ substituents is substituted phenoxy and the substituted phenoxy group is attached at the 3-position or 4-position;

or two R$_2$ substituents are taken together, on adjacent positions, to form a fused cycloalkyl or a methylenedioxy ring, and one R$_2$ substituent is selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

R$_6$ is from 1 to 2 substituents independently selected from the group consisting of hydrogen, alkyl, alkoxy, trifluoromethyl, halogen, phenoxy, and substituted phenoxy; provided that when R$_6$ is phenoxy or substituted phenoxy, the phenoxy or substituted phenoxy group is not attached to the pyridyl moiety in the adjacent position to X;

X is selected from the group consisting of —CH$_2$—, —CHR$_7$—, and —CH$_2$CH$_2$— wherein R$_7$ is lower alkyl;

Y is a bond;

and the pharmaceutically acceptable salts thereof and the pyridyl N-oxides thereof.

11. A compound according to claim 10 wherein the pyridyl moiety is attached to X at the 3-position.

12. A compound according to claim 10 wherein the pyridyl moiety is attached to X at the 4-position.

13. A compound according to claim 11 or 12 wherein R$_2$ is from 1 to 3 substituents independently selected from the group consisting of hydrogen, hydroxy, trisubstituted silyloxy, alkyl, substituted alkyl, alkenyl, substituted alkenyl, alkoxy, substituted alkoxy, cycloalkoxy, substituted cycloalkoxy, cycloalkyl, substituted cycloalkyl, halogen, cyano, nitro, phenyl, substituted phenyl, pyridyloxy, thiophenoxy, substituted thiophenoxy, phenylsulfinyl, substituted phenylsulfinyl, phenylsulfonyl, substituted phenylsulfonyl, benzoyl, substituted benzoyl, phenoxy, and substituted phenoxy;

provided at least one of the R$_2$ substituents is substituted phenoxy.

14. A compound according to claim 13 wherein R$_2$ is selected from group consisting of substituted alkyl, substituted phenyl, thiophenoxy, substituted thiophenoxy, and substituted phenoxy.

15. A compound according to claim 14 wherein R$_2$ is substituted phenoxy.

16. A compound according to claim 10, 11 or 12 wherein at least one of the R$_2$ substituents is attached in the 3-position.

17. A compound according to claim 10, 11 or 12 wherein at least one of the R$_2$ substituents is attached in the 4-position.

18. A compound according to claim 10 wherein at least one R$_2$ is substituted phenoxy and one of the substituents is selected from the group consisting of alkyl, substituted alkyl, alkoxy, substituted alkoxy, halogen, cyano, amido, and substituted amido.

19. A compound according to claim 10, 11, 12 or 18 wherein X is a —CH$_2$—.

20. A compound according to claim 13 wherein at least one of the R$_2$ substituents is attached in the 3-position.

21. A compound according to claim 13 wherein at least one of the R$_2$ substituents is attached in the 4-position.

22. A compound of formula I as claimed in claim 10 selected from the group consisting of N-(3-(2-Methoxyphenoxy)phenyl)-N-(2,2,2-trifluoroethylsulfonyl)pyrid-3-ylmethylamine, N-(3-(2-Benzyloxyphenoxy)phenyl)-N-(2,2,2-trifluoroethylsulfonyl)pyrid-3-ylmethylamine, N-(4-(2-Methoxyphenoxy)-3-chlorophenyl)-N-(2,2,2-trifluoroethylsulfonyl)pyrid-3-ylmethylamine, N-(4-(2,6-Dimethoxyphenoxy)-3-chlorophenyl)-N-(2,2,2-trifluoroethylsulfonyl)pyrid-3-ylmethylamine, N-(4-(2-Benzyloxyphenoxy)phenyl)-N-(2,2,2-trifluoroethylsulfonyl)pyrid-3-ylmethylamine, N-(4-(2-Methoxyphenoxy)phenyl)-N-(ethylsulfonyl)pyrid-3-ylmethylamine, N-(4-(2-Methoxyphenoxy)phenyl)-N-(cyclopropylsulfonyl)pyrid-3-ylmethylamine, N-(4-(2-Methoxyphenoxy)-3-chlorophenyl)-N-ethylsulfonyl)pyrid-3-ylmethylamine, N-(4-(2-Methoxyphenoxy)-3- chlorophenyl)-N-cyclopropylsulfonyl)pyrid-3-ylmethylamine, N-(4-(2-Methoxyphenoxy)phenyl)-N-(2,2,2-trifluoroethylsulfonyl)pyrid-3-ylmethylamine, N-(4-(2-Ethoxyphenoxy)phenyl)-N-(2,2,2-tri fluoroethylsulfonyl)pyrid-3-ylmethylamine, N-(4-(2-Ethoxyphenoxy)phenyl)-N-(ethylsulfonyl)pyrid-3-ylmethylamine, N-(4-(2-Ethoxyphenoxy)phenyl)-N-(cyclopropylsulfonyl)pyrid-3-ylmethylamine, N-(3-(2-Methoxyphenoxy)phenyl)-N-(cyclopropylsulfonyl)pyrid-3-ylmethylamine, N-(3-(2-Methoxyphenoxy)phenyl)-N-(ethylsulfonyl)pyrid-3-ylmethylamine, N-(4-(2-Hydroxyphenoxy)phenyl)-N-(2,2,2-trifluoroethylsulfonyl)pyrid-3-ylmethylamine, N-(3-(2-Hydroxyphenoxy)phenyl)-N-(2,2,2-trifluoroethylsulfonyl)pyrid-3-ylmethylamine, N-(4-(4-Benzyloxyphenoxy)phenyl)-N-(methylsulfonyl)pyrid-3-ylmethylamine, N-(4-(4-Cyclohexylphenoxy)phenyl)-N-(methylsulfonyl)pyrid-3-yl methylamine, N-(4-(4-Benzylphenoxy)phenyl)-N-(methylsulfonyl)pyrid-3-ylmethylamine, N-(4-(4-Thiophenoxyphenoxy)phenyl)-N-(methylsulfonyl)pyrid-3-ylmethylamine, N-(4-(4-Benzyloxyphenoxy)phenyl)-N-(ethylsulfonyl)pyrid-3-ylmethylamine, N-(4-(4-Cyclohexylphenoxy)phenyl)-N-(ethylsulfonyl)pyrid-3-ylmethylamine, N-(4-(4-Benzylphenoxy)phenyl)-N-(ethylsulfonyl)pyrid-3-ylmethylamine, N-(4-(4-Thiophenoxyphenoxy)phenyl)-N-(ethylsulfonyl)pyrid-3-ylmethylamine, N-(4-(4-Benzyloxyphenoxy)phenyl)-N-(2,2,2-trifluoroethylsulfonyl)pyrid-3-ylmethylamine, N-(4-(4-Cyclohexylphenoxy)phenyl)-N-(2,2,2-trifluoroethylsulfonyl)pyrid-3-ylmethylamine, N-(4-(4-Benzylphenoxy)phenyl)-N-(2,2,2-trifluoroethylsulfonyl)pyrid-3-ylmethylamine, N-(4-(4-Thiophenoxyphenoxy)phenyl)-N-(2,2,2-trifluoroethylsulfonyl)pyrid-3-ylmethylamine, N-(4-(4-Benzyloxyphenoxy)phenyl)-N-(trifluoromethylsulfonyl)pyrid-3-ylmethylamine, N-(4-(4-Cyclohexylphenoxy)phenyl)-N-(trifluoromethylsulfonyl)pyrid-3-ylmethylamine, N-(4-(4-Benzylphenoxy)phenyl)-N-(trifluoromethylsulfonyl)pyrid-3-ylmethylamine, N-(4-(4-Thiophenoxyphenoxy)phenyl)-N-(trifluoromethylsulfonyl)pyrid-3-ylmethylamine, N-(4-(4-Benzyloxyphenoxy)phenyl)-N-(propylsulfonyl)pyrid-3-ylmethylamine, N-(4-(4-Cyclohexylphenoxy)phenyl)-N-(propylsulfonyl)pyrid-3-ylmethylamine, N-(4-(4-Benzylphenoxy)phenyl)-N-(propylsulfonyl)pyrid-3-ylmethylamine, N-(4-(4-Thiophenoxyphenoxy)phenyl)-N-(propylsulfonyl)pyrid-3-ylmethylamine, N-(4-(4-Benzyloxyphenoxy)phenyl)-N-(ethylsulfonyl)pyrid-2-ylmethylamine, N-(4-(4-Cyclohexylphenoxy)phenyl)-N-(ethylsulfonyl)pyrid-2-ylmethylamine, N-(4-(4-Benzylphenoxy)phenyl)-N-(ethylsulfonyl)pyrid-2-ylmethylamine, N-(4-(4-Thiophenoxyphenoxy)phenyl)-N-(ethylsulfonyl)pyrid-2-ylmethylamine, N-(4-(4-Benzyloxyphenoxy)phenyl)-N-(2,2,2-trifluoroethylsulfonyl)pyrid-2-ylmethylamine, N-(4-(4-Cyclohexylphenoxy)phenyl)-N-(2,2,2-trifluoroethylsulfonyl)pyrid-2-ylmethylamine, N-(4-(4-Benzylphenoxy)phenyl)-N-(2,2,2-trifluoroethylsulfonyl)pyrid-2-yl methylamine, N-(4-(4-Thiophenoxyphenoxy)phenyl)-N-(2,2,2-trifluoroethylsulfonyl)pyrid-2-ylmethylamine, N-(4-(3,4-Methylenedioxyphenoxy)phenyl)-N-(methylsulfonyl)pyrid-3-ylmethylamine, N-(4-(5,6,7,8-Tetrahydronaphth-2-yloxy)phenyl)-N-(methylsulfonyl)pyrid-3-ylmethylamine, N-(4-(4-Pyrid-2-yloxyphenoxy)phenyl)-N-(methylsulfonyl)pyrid-3-ylmethylamine, N-(4-(3,4-Methylenedioxyphenoxy)phenyl)-N-(ethylsulfonyl)pyrid-3-ylmethylamine, N-(4-(5,6,7,8-Tetrahydronaphth-2-yloxy)phenyl)-N-(ethylsulfonyl)pyrid-3-ylmethylamine, N-(4-(4-Pyrid-2-yloxyphenoxy)phenyl)-N-(ethylsulfonyl)pyrid-3-ylmethylamine, 4-(4-(3,4-Methylenedioxyphenoxy)phenyl)-N-(2,2,2-trifluoroethylsulfonyl)pyrid-3-ylmethylamine, N-(4-(5,6,7,8-Tetrahydronaphth-2-yloxy)phenyl)-N-(2,2,2-trifluoroethylsulfonyl)pyrid-3-ylmethylamine, N-(4-(4-Pyrid-2-yloxyphenoxy)phenyl)-N-(2,2,2-trifluoroethylsulfonyl)pyrid-3-ylmethylamine, N-(4-(3,4-Methylenedioxyphenoxy)phenyl)-N-(trifluoromethylsulfonyl)pyrid-3-ylmethylamine, N-(4-(5,6,7,8-Tetrahydronaphth-2-yloxy)phenyl)-N-(trifluoromethylsulfonyl)pyrid-3-ylmethylamine, N-(4-(4-Pyrid-2-yloxyphenoxy)phenyl)-N-(trifluoromethylsulfonyl)pyrid-3-ylmethylamine, N-(4-(3,4-Methylenedioxyphenoxy)phenyl)-N-(propylsulfonyl)pyrid-3-ylmethylamine, N-(4-(5,6,7,8-Tetrahydronaphth-2-yloxy)phenyl)-N-(propylsulfonyl)pyrid-3-ylmethylamine, N-(4-(4-Pyrid-2-yloxyphenoxy)phenyl)-N-(propylsulfonyl)pyrid-3-ylmethylamine, N-(4-(3,4-Methylenedioxyphenoxy)phenyl)-N-(ethylsulfonyl)pyrid-2-ylmethylamine, N-(4-(5,6,7,8-Tetrahydronaphth-2-yloxy)phenyl)-N-(ethylsulfonyl)pyrid-2-ylmethylamine, N-(4-(4-Pyrid-2-yloxyphenoxy)phenyl)-N-(ethylsulfonyl)pyrid-2-ylmethylamine, N-(4-(3,4-Methylenedioxyphenoxy)phenyl)-N-(2,2,2-trifluoroethylsulfonyl)pyrid-2-ylmethylamine, N-(4-(5,6,7,8-Tetrahydronaphth-2-yloxy)phenyl)-N-(2,2,2-trifluoroethylsulfonyl)pyrid-2-ylmethylamine, N-(4-(4-Pyrid-2-yloxyphenoxy)phenyl)-N-(2,2,2-trifluoroethylsulfonyl)pyrid-2-ylmethylamine, N-(4-(4-Chlorophenoxy)phenyl)-N-(methylsulfonyl)pyrid-3-ylmethylamine, N-(4-(3-Trifluoromethylphenoxy)phenyl)-N-(methylsulfonyl)pyrid-3-ylmethylamine, N-(4-(2-Methoxyphenoxy)phenyl)-N-(methylsulfonyl)pyrid-3-ylmethylamine, N-(4-(4-Cyanophenoxy)phenyl)-N-(methylsulfonyl)pyrid-3-ylmethylamine, N-(4-(2,4-Difluorophenoxy)phenyl)-N-(methylsulfonyl)pyrid-3-ylmethylamine, N-(4-(4-Chlorophenoxy)phenyl)-N-(ethylsulfonyl)pyrid-2-ylmethylamine, N-(4-(3-Trifluoromethylphenoxy)phenyl)-N-(ethylsulfonyl)pyrid-2-ylmethylamine, N-(4-(2-Methoxyphenoxy)phenyl)-N-(ethylsulfonyl)pyrid-2-ylmethylamine, N-(4-(4-Cyanophenoxy)phenyl)-N-(ethylsulfonyl)pyrid-2-ylmethylamine, N-(4-(2,4-Difluorophenoxy)phenyl)-N-(ethylsulfonyl)pyrid-2-ylmethylamine, N-(4-(4-Chlorophenoxy)phenyl)-N-(2,2,2-trifluoroethylsulfonyl)pyrid-2-ylmethylamine, N-(4-(3-Trifluoromethylphenoxy)phenyl)-N-(2,2,2-trifluoroethylsulfonyl)pyrid-2-ylmethylamine, N-(4-(2-Methoxyphenoxy)phenyl)-N-(2,2,2-trifluoroethylsulfonyl)pyrid-2-ylmethylamine, N-(4-(4-Cyanophenoxy)phenyl)-N-(2,2,2-trifluoroethylsulfonyl)pyrid-2-ylmethylamine, N-(4-(2,4-Difluorophenoxy)phenyl)-N-(2,2,2-trifluoroethylsulfonyl)pyrid-2-ylmethylamine, N-(4-(4-Chlorophenoxy)phenyl)-N-(ethylsulfonyl)pyrid-3-ylmethylamine, N-(4-(3-Trifluoromethylphenoxy)phenyl)-N-(ethylsulfonyl)pyrid-3-ylmethylamine, N-(4-(2-Methoxyphenoxy)phenyl)-N-(ethylsulfonyl)pyrid-3-ylmethylamine, N-(4-(4-Cyanophenoxy)phenyl)-N-(ethylsulfonyl)pyrid-3-ylmethylamine, N-(4-(2,4-Difluorophenoxy)phenyl)-N-(ethylsulfonyl)pyrid-3-ylmethylamine, N-(4-(4-Chlorophenoxy)phenyl)-N-(2,2,2-trifluoroethylsulfonyl)pyrid-3-ylmethylamine, N-(4-(3-Trifluoromethylphenoxy)phenyl)-N-(2,2,2-trifluoroethylsulfonyl)pyrid-3-ylmethylamine, N-(4-(2-Methoxyphenoxy)phenyl)-N-(2,2,2-trifluoroethylsulfonyl)pyrid-3-ylmethylamine, N-(4-(4-Cyanophenoxy)phenyl)-N-(2,2,2-trifluoroethylsulfonyl)pyrid-3-ylmethylamine, N-(4-(2,4-Difluorophenoxy)phenyl)-N-(2,2,2-trifluoroethylsulfonyl)pyrid-3- ylmethylamine, N-(4-(4-Chlorophenoxy)phenyl)-N-(trifluoromethylsulfonyl)pyrid-3-ylmethylamine, N-(4-(3-Trifluoromethylphenoxy)phenyl)-N-(trifluoromethylsulfonyl)pyrid-3-ylmethylamine, N-(4-(2-Methoxyphenoxy)phenyl)-N-(trifluoromethylsulfonyl)pyrid-3-ylmethylamine, N-(4-(4-Cyanophenoxy)phenyl)-N-(trifluoromethylsulfonyl)pyrid-3-ylmethylamine, N-(4-(2,4-Difluorophenoxy)phenyl)-N-(trifluoromethylsulfonyl)pyrid-3-ylmethylamine, N-(4-(4-Chlorophenoxy)phenyl)-N-(propylsulfonyl)pyrid-3-ylmethylamine, N-(4-(3-Trifluoromethylphenoxy)phenyl)-N-(propylsulfonyl)pyrid-3-ylmethylamine, N-(4-(2-Methoxyphenoxy)phenyl)-N-(propylsulfonyl)pyrid-3-ylmethylamine, N-(4-(4-Cyanophenoxy)phenyl)-N-(propylsulfonyl)pyrid-3-ylmethylamine, N-(4-(2,4-Difluorophenoxy)phenyl)-N-(propylsulfonyl)pyrid-3-ylmethylamine, N-(2-Chloro-5-methyl-4-(phenoxy)phenyl)-N-(methylsulfonyl)pyrid-3-ylmethylamine, N-(3-Chloro-4-(phenoxy)phenyl)-N-(methylsulfonyl)pyrid-3-ylmethylamine, N-(2-Methyl-4-(phenoxy)phenyl)-N-(methylsulfonyl)pyrid-3-ylmethylamine, N-(3-Trifluoromethyl-4-(phenoxy)phenyl)-N-(methylsulfonyl)pyrid-3-ylmethylamine, N-(4-(4-Nitrophenoxy)phenyl)-N-(methylsulfonyl)pyrid-3-ylmethylamine, N-(2-Chloro-5-methyl-4-(phenoxy)phenyl)-N-(ethylsulfonyl)pyrid-3-ylmethylamine, N-(3-Chloro-4-(phenoxy)phenyl)-N-(ethylsulfonyl)pyrid-3-ylmethylamine, N-(2-Methyl-4-(phenoxy)phenyl)-N-(ethylsulfonyl)pyrid-3-ylmethylamine, N-(3-Trifluoromethyl-4-(phenoxy)phenyl)-N-(ethylsulfonyl)pyrid-3-ylmethylamine, N-(4-(4-Nitrophenoxy)phenyl)-N-(ethylsulfonyl)pyrid-3-ylmethylamine, N-(2-Chloro-5-methyl-4-(phenoxy)phenyl)-N-(2,2,2-trifluoroethylsulfonyl)pyrid-3-ylmethylamine, N-(3-Chloro-4-(phenoxy)phenyl)-N-(2,2,2-trifluoroethylsulfonyl)pyrid-3-ylmethylamine, N-(2-Methyl-4-(phenoxy)phenyl)-N-(2,2,2-trifluoroethylsulfonyl)pyrid-3-ylmethylamine, N-(3-Trifluoromethyl-4-(phenoxy)phenyl)-N-(2,2,2-trifluoroethylsulfonyl)pyrid-3-ylmethylamine, N-(4-(4-Nitrophenoxy)phenyl)-N-(2,2,2-trifluoroethylsulfonyl)pyrid-3-ylmethylamine, N-(2-Chloro-5-methyl-4-(phenoxy)phenyl)-N-(trifluoromethylsulfonyl)pyrid-3-ylmethylamine, N-(3-Chloro-4-(phenoxy)phenyl)-N-(trifluoromethylsulfonyl)pyrid-3-ylmethylamine, N-(2-Methyl-4-(phenoxy)phenyl)-N-(trifluoromethylsulfonyl)pyrid-3-ylmethylamine, N-(3-Trifluoromethyl-4-(phenoxy)phenyl)-N-(trifluoromethylsulfonyl)pyrid-3-ylmethylamine, N-(4-(4-Nitrophenoxy)phenyl)-N-(trifluoromethylsulfonyl)pyrid-3-ylmethylamine, N-(2-Chloro-5-methyl-4-(phenoxy)phenyl)-N-(propylsulfonyl)pyrid-3-ylmethylamine, N-(3-Chloro-4-(phenoxy)phenyl)-N-(propylsulfonyl)pyrid-3-ylmethylamine, N-(2-Methyl-4-(phenoxy)phenyl)-N-(propylsulfonyl)pyrid-3-ylmethylamine, N-(3-Trifluoromethyl-4-(phenoxy)phenyl)-N-(propylsulfonyl)pyrid-3-ylmethylamine, N-(4-(4-Nitrophenoxy)phenyl)-N-(propylsulfonyl)pyrid-3-ylmethylamine, N-(2-Chloro-5-methyl-4-(phenoxy)phenyl)-N-(ethylsulfonyl)pyrid-2-ylmethylamine, N-(3-Chloro-4-(phenoxy)phenyl)-N-(ethylsulfonyl)pyrid-2-ylmethylamine, N-(2-Methyl-4-(phenoxy)phenyl)-N-(ethylsulfonyl)pyrid-2-ylmethylamine, N-(3-Trifluoromethyl-4-(phenoxy)phenyl)-N-(ethylsulfonyl)pyrid-2-ylmethylamine, N-(4-(4-Nitrophenoxy)phenyl)-N-(ethylsulfonyl)pyrid-2-ylmethylamine, N-(2-Chloro-5-methyl-4-(phenoxy)phenyl)-N-(2,2,2-trifluoroethylsulfonyl)pyrid-2-ylmethylamine, N-(3-Chloro-4-(phenoxy)phenyl)-N-(2,2,2-trifluoroethylsulfonyl)pyrid-2-ylmethylamine, N-(2-Methyl-4-(phenoxy)phenyl)-N-(2,2,2-trifluoroethylsulfonyl)pyrid-2-ylmethylamine, N-(3-Trifluoromethyl-4-(phenoxy)phenyl)-N-(2,2,2-trifluoroethylsulfonyl)pyrid-2-ylmethylamine, N-(4-(4-Nitrophenoxy)phenyl)-N-(2,2,2-trifluoroethylsulfonyl)pyrid-2-ylmethylamine, N-(4-(2-Methoxyphenoxy)phenyl)-N-(2,2,2-trifluoroethylsulfonyl)-6-methoxypyrid-3-ylmethylamine, N-(4-(2-Methoxyphenoxy)phenyl)-N-(ethylsulfonyl)-6-methoxypyrid-3-ylmethylamine, N-(4-(2-Methoxyphenoxy)phenyl)-N-(2,2,2-trifluoroethylsulfonyl)-6-methylpyrid-3-ylmethylamine, N-(4-(2-Methoxyphenoxy)phenyl)-N-(ethylsulfonyl)-6-methylpyrid-3-ylmethylamine, N-(4-(2-Methoxyphenoxy)phenyl)-N-(2,2,2-trifluoroethylsulfonyl)-6-(4-chlorophenoxy)pyrid-3-ylmethylamine, N-(4-(2-Methoxyphenoxy)phenyl)-N-(ethylsulfonyl)-6-(4-chlorophenoxy)pyrid-3-ylmethylamine, N-(4-(2-Methoxyphenoxy)phenyl)-N-(2,2,2-trifluoroethylsulfonyl)-2-chloropyrid-3-ylmethylamine, N-(4-(2-Methoxyphenoxy)phenyl)-N-(ethylsulfonyl)-2-chloropyrid-3-ylmethylamine, N-(4-(2-Methoxyphenoxy)phenyl)-N-(2,2,2-trifluoroethylsulfonyl)-2-phenoxypyrid-3-ylmethylamine, N-(4-(2-Methoxyphenoxy)phenyl)-N-(ethylsulfonyl)-2-phenoxypyrid-3-ylmethylamine, N-(4-(2-Methoxyphenoxy)phenyl)-N-(2,2,2-trifluoroethylsulfonyl)-6-chloropyrid-3-ylmethylamine, N-(4-(2-Methoxyphenoxy)phenyl)-N-(ethylsulfonyl)-6-chloropyrid-3-ylmethylamine, N-(4-(2-Methoxyphenoxy)phenyl)-N-(2,2,2-trifluoroethylsulfonyl)-2-chloro-6-methylpyrid-3-ylmethylamine, N-(4-(2-Methoxyphenoxy)phenyl)-N-(ethylsulfonyl)-2-chloro-6-methylpyrid-3-ylmethylamine, N-(4-(2-Methoxyphenoxy)phenyl)-N-(2,2,2-trifluoroethylsulfonyl)pyrid-4-ylmethylamine, N-(4-(2-Methoxyphenoxy)phenyl)-N-(ethylsulfonyl)pyrid-4-ylmethylamine, N-(4-(2,6-Dimethoxyphenoxy)phenyl)-N-(cyclopropylsulfonyl)pyrid-3-ylmethylamine, N-(4-(2,6-Dimethoxyphenoxy)phenyl)-N-(ethylsulfonyl)pyrid-3-ylmethylamine, N-(4-(2,6-Dimethoxyphenoxy)phenyl)-N-(2,2,2-trifluoroethylsulfonyl)pyrid-3-ylmethylamine, N-(4-(2,6-Dimethoxyphenoxy)phenyl)-N-(ethylsulfonyl)pyrid-2-ylmethylamine, N-(4-(2,6-Dimethoxyphenoxy)phenyl)-N-(2,2,2-trifluoroethylsulfonyl)pyrid-2-ylmethylamine, N-(4-(2,6-Dimethoxyphenoxy)phenyl)-N-(ethylsulfonyl)pyrid-4-ylmethylamine, N-(4-(2,6-Dimethoxyphenoxy)phenyl)-N-(2,2,2-trifluoroethylsulfonyl)pyrid-4-ylmethylamine, N-(4-(2,6-Dichlorophenoxy)phenyl)-N-(cyclopropylsulfonyl)pyrid-3-ylmethylamine, N-(4-(2,6-Dichlorophenoxy)phenyl)-N-(ethylsulfonyl)pyrid-3-ylmethylamine, N-(4-(2,6-Dichlorophenoxy)phenyl)-N-(2,2,2-trifluoroethylsulfonyl)pyrid-3-ylmethylamine, N-(4-(2,6-Dichlorophenoxy)phenyl)-N-(ethylsulfonyl)pyrid-2-ylmethylamine, N-(4-(2,6-Dichlorophenoxy)phenyl)-N-(2,2,2-trifluoroethylsulfonyl)pyrid-2-ylmethylamine, N-(4-(2,6-Dichlorophenoxy)phenyl)-N-(ethylsulfonyl)pyrid-4-ylmethylamine, N-(4-(2,6-Dichlorophenoxy)phenyl)-N-(2,2,2-trifluoroethylsulfonyl)pyrid-4-ylmethylamine, N-(4-(2-Isopropoxyphenoxy)phenyl)-N-(cyclopropylsulfonyl)pyrid-3-ylmethylamine, N-(4-(2-Isopropoxyphenoxy)phenyl)-N-(ethylsulfonyl)pyrid-3-ylmethylamine, N-(4-(2-Isopropoxyphenoxy)phenyl)-N-(2,2,2-trifluoroethylsulfonyl)pyrid-3-ylmethylamine, N-(4-(2-Isopropoxyphenoxy)phenyl)-N-(ethylsulfonyl)pyrid-2-ylmethylamine, N-(4-(2-Isopropoxyphenoxy)phenyl)-N-(2,2,2-trifluoroethylsulfonyl)pyrid-2-ylmethylamine, N-(4-(2-Isopropoxyphenoxy)phenyl)-N-(ethylsulfonyl)pyrid-4-ylmethylamine, N-(4-(2-Isopropoxyphenoxy)phenyl)-N-(2,2,2-trifluoroethylsulfonyl)pyrid-4-ylmethylamine, N-(4-(2-Fluoro-6-methoxyphenoxy)phenyl)-N-

(cyclopropylsulfonyl)pyrid-3-ylmethylamine, N-(4-(2-Fluoro-6-methoxyphenoxy)phenyl)-N-(2,2,2-trifluoroethylsulfonyl)pyrid-3-ylmethylamine, N-(4-(2-Fluoro-6-methoxyphenoxy)phenyl)-N-(ethylsulfonyl)pyrid-3-ylmethylamine, N-(4-(2-Fluoro-6-methoxyphenoxy)phenyl)-N-(ethylsulfonyl)pyrid-2-ylmethylamine, N-(4-(2-Fluoro-6-methoxyphenoxy)phenyl)-N-(2,2,2-trifluoroethylsulfonyl)pyrid-2-ylmethylamine, N-(4-(2-Fluoro-6-methoxyphenoxy)phenyl)-N-(ethylsulfonyl)pyrid-4-ylmethylamine, N-(4-(2-Fluoro-6-methoxyphenoxy)phenyl)-N-(2,2,2-trifluoroethylsulfonyl)pyrid-4-ylmethylamine, N-(4-(2-Trifluoromethylphenoxy)phenyl)-N-(cyclopropylsulfonyl)pyrid-3-ylmethylamine, N-(4-(2-Trifluoromethylphenoxy)phenyl)-N-(2,2,2-trifluoroethylsulfonyl)pyrid-3-ylmethylamine, N-(4-(2-Trifluoromethylphenoxy)phenyl)-N-(ethylsulfonyl)pyrid-3-ylmethylamine, N-(4-(2-Trifluoromethylphenoxy)phenyl)-N-(ethylsulfonyl)pyrid-2-ylmethylamine, N-(4-(2-Trifluoromethylphenoxy)phenyl)-N-(2,2,2-trifluoroethylsulfonyl)pyrid-2-ylmethylamine, N-(4-(2-Trifluoromethylphenoxy)phenyl)-N-(ethylsulfonyl)pyrid-4-ylmethylamine, N-(4-(2-Trifluoromethylphenoxy)phenyl)-N-(2,2,2-trifluoroethylsulfonyl)pyrid-4-ylmethylamine, N-(4-(2-Isopropyl-5-methylphenoxy)phenyl)-N-(cyclopropylsulfonyl)pyrid-3-ylmethylamine, N-(4-(2-Isopropyl-5-methylphenoxy)phenyl)-N-(2,2,2-trifluoroethylsulfonyl)pyrid-3-ylmethylamine, N-(4-(2-Isopropyl-5-methylphenoxy)phenyl)-N-(ethylsulfonyl)pyrid-3-ylmethylamine, N-(4-(2-Isopropyl-5-methylphenoxy)phenyl)-N-(ethylsulfonyl)pyrid-2-ylmethylamine, N-(4-(2-Isopropyl-5-methylphenoxy)phenyl)-N-(2,2,2-trifluoroethylsulfonyl)pyrid-2-ylmethylamine, N-(4-(2-Isopropyl-5-methylphenoxy)phenyl)-N-(ethylsulfonyl)pyrid-4-ylmethylamine, N-(4-(2-Isopropyl-5-methylphenoxy)phenyl)-N-(2,2,2-trifluoroethylsulfonyl)pyrid-4-ylmethylamine, N-(4-(2-Cyclopentylphenoxy)phenyl)-N-(cyclopropylsulfonyl)pyrid-3-ylmethylamine, N-(4-(2-Cyclopentylphenoxy)phenyl)-N-(2,2,2-trifluoroethylsulfonyl)pyrid-3-ylmethylamine, N-(4-(2-Cyclopentylphenoxy)phenyl)-N-(ethylsulfonyl)pyrid-3-ylmethylamine, N-(4-(2-Cyclopentylphenoxy)phenyl)-N-(ethylsulfonyl)pyrid-2-ylmethylamine, N-(4-(2-Cyclopentylphenoxy)phenyl)-N-(2,2,2-trifluoroethylsulfonyl)pyrid-2-ylmethylamine, N-(4-(2-Cyclopentylphenoxy)phenyl)-N-(ethylsulfonyl)pyrid-4-ylmethylamine, N-(4-(2-Cyclopentylphenoxy)phenyl)-N-(2,2,2-trifluoroethylsulfonyl)pyrid-4-ylmethylamine, N-(4-(2-Methoxyphenoxy)phenyl)-N-(2,2,2-trifluoroethylsulfonyl)-2-(2,2,2-trifluoroethoxy)pyrid-3-ylmethylamine, N-(4-(2-Isopropoxyphenoxy)phenyl)-N-(2,2,2-trifluoroethylsulfonyl)-2-(2,2,2-trifluoroethoxy)pyrid-3-ylmethylamine, N-(4-(2-Fluoro-6-methoxyphenoxy)phenyl)-N-(2,2,2-trifluoroethylsulfonyl)-2-(2,2,2-trifluoroethoxy)pyrid-3-ylmethylamine, N-(4-(4-Hydroxyphenoxy)phenyl)-N-(2,2,2-trifluoroethanesulfonyl)pyrid-3-ylmethylamine, N-(3-(2-Methoxyphenylsulfinyl)phenyl)-N-(ethanesulfonyl)pyrid-3-ylmethylamine, N-(4-(2,4-Difluorophenoxy)phenyl)-N-(2,2,2-trifluoroethanesulfonyl)pyrid-3-ylmethylamine, N-(4-(2-Methoxyphenoxy)phenyl)-N-(2,2,2-trifluoroethanesulfonyl)pyrid-3-ylmethylamine, N-(4-(3-Benzyloxyphenyl)-N-(2,2,2-trifluoroethanesulfonyl)pyrid-3-ylmethylamine, N-(4-(3-Hydroxyphenoxy)phenyl)-N-(2,2,2-trifluoroethanesulfonyl)pyrid-3-ylmethylamine, N-(4-(2-Cyanophenoxy)phenyl)-N-(2,2,2-trifluoroethanesulfonyl)pyrid-3-ylmethylamine, N-(4-(2-Cyanophenoxy)phenyl)-N-(ethanesulfonyl)pyrid-3-ylmethylamine, N-(3-(2-Methoxyphenoxy)phenyl)-N-(ethylsulfonyl)pyrid-3-ylmethylamine, N-(3-(2-phenylphenoxy)phenyl)-N-(ethylsulfonyl)pyrid-3-ylmethylamine, N-(4-(2-Fluorophenoxy)phenyl)-N-(ethanesulfonyl)pyrid-3-ylmethylamine, N-(4-(3-Fluorophenoxy)phenyl)-N-(ethanesulfonyl)pyrid-3-ylmethylamine, N-(4-(4-Fluorophenoxy)phenyl)-N-(ethanesulfonyl)pyrid-3-ylmethylamine, N-(4-(2,4-Difluorophenoxy)phenyl)-N-(ethanesulfonyl)pyrid-3-ylmethylamine, N-(4-(2-trifluoromethoxyphenoxy)phenyl)-N-(ethanesulfonyl)pyrid-3-ylmethylamine, N-(4-(4-fluoro-2-methyphenoxyl)phenyl)-N-(ethanesulfonyl)pyrid-3-ylmethylamine, N-(4-(4-trifluoromethoxyphenoxy)phenyl)-N-(ethanesulfonyl)pyrid-3-ylmethylamine, N-(4-(2,4-dimethylphenoxy)phenyl)-N-(ethanesulfonyl)pyrid-3-ylmethylamine, N-(4-(4-methylphenoxy)phenyl)-N-(ethanesulfonyl)pyrid-3-ylmethylamine, N-(4-(4-isopropylphenoxy)phenyl)-N-(ethanesulfonyl)pyrid-3-ylmethylamine, N-(4-(4-t-butylphenoxy)phenyl)-N-(ethanesulfonyl)pyrid-3-ylmethylamine, N-(4-(2-methylphenoxy)phenyl)-N-(ethanesulfonyl)pyrid-3-ylmethylamine, N-(4-(2-Amidophenoxy)phenyl)-N-(ethanesulfonyl)pyrid-3-ylmethylamine, N-(4-(3-Methylsulfinylphenoxy)phenyl)-N-(ethanesulfonyl)pyrid-3-ylmethylamine, N-(4-(4-t-butyl-2-fluorophenoxy)phenyl)-N-(ethanesulfonyl)pyrid-3-ylmethylamine, N-(4-(4-fluoro-2-n-propylphenoxy)phenyl)-N-(ethanesulfonyl)pyrid-3-ylmethylamine, N-(4-(4-Carbonylmethoxyphenoxy)phenyl)-N-(ethanesulfonyl)pyrid-3-ylmethylamine, N-(4-(4-amidomethylphenoxy)phenyl)-N-(ethanesulfonyl)pyrid-3-ylmethylamine, N-(4-(3-t-butylphenoxy)phenyl)-N-(ethanesulfonyl)pyrid-3-ylmethylamine, N-(4-(2-methoxyphenoxy)phenyl)-N-(ethanesulfonyl)pyrid-3-ylmethylamine, N-(4-(3-methylphenoxy)phenyl)-N-(ethanesulfonyl)pyrid-3-ylmethylamine, N-(4-(2-chlorophenoxy)phenyl)-N-(ethanesulfonyl)pyrid-3-ylmethylamine, N-(4-(4-Amidophenoxy)phenyl)-N-(ethanesulfonyl)pyrid-3-ylmethylamine, N-(4-(2-methylphenoxy)phenyl)-N-(ethanesulfonyl)pyrid-3-ylmethylamine, N-(4-(4-Methylsulfonylphenoxy)phenyl)-N-(ethanesulfonyl)pyrid-3-ylmethylamine, N-(4-(2-(prop-2-yl)phenoxy)phenyl)-N-(ethanesulfonyl)pyrid-3-ylmethylamine, N-(4-(2-ethylphenoxy)phenyl)-N-(ethanesulfonyl)pyrid-3-ylmethylamine, N-(4-(4-Sulfonylamidophenoxy)phenyl)-N-(ethanesulfonyl)pyrid-3-ylmethylamine, N-(4-(2,4-Difluorophenoxy)phenyl)-N-(ethanesulfonyl)-1-pyrid-3-ylethylamine, N-((3-Benzyloxyphenoxy)phenyl)-N-(ethanesulfonyl)pyrid-3-ylmethylamine, N-(3-(2-fluorophenoxy)phenyl)-N-(ethylsulfonyl)pyrid-3-ylmethylamine, N-(3-(3-fluorophenoxy)phenyl)-N-(ethylsulfonyl)pyrid-3-ylmethylamine, N-(3-(4-fluorophenoxy)phenyl)-N-(ethylsulfonyl)pyrid-3-ylmethylamine, N-(3-(2,4-difluorophenoxy)phenyl)-N-(ethylsulfonyl)pyrid-3-ylmethylamine, N-(3-(2-ethoxyphenoxy)phenyl)-N-(ethylsulfonyl)pyrid-3-ylmethylamine, N-(3-(2-phenylphenoxy)phenyl)-N-(ethylsulfonyl)pyrid-3-ylmethylamine, N-(3-(4-trifluoromethoxyphenoxy)phenyl)-N-(ethylsulfonyl)pyrid-3-ylmethylamine, N-(3-(4-methylphenoxy)phenyl)-N-(ethylsulfonyl)pyrid-3-ylmethylamine, N-(3-(2-methyl-4-fluorophenoxy)phenyl)-N-(ethylsulfonyl)pyrid-3-ylmethylamine, N-(3-(2-trifiuoromethoxyphenoxy)phenyl)-N-(ethylsulfonyl)pyrid-3-ylmethylamine, N-(3-(4-Amidomethylphenoxy)phenyl)-N-(ethylsulfonyl)pyrid-3-ylmethylamine, N-(3-(4-Amidophenoxy)phenyl)-N-(ethylsulfonyl)pyrid-3-ylmethylamine, N-(3-(4-Methylsulfonylphenoxy)phenyl)-

N-(ethylsulfonyl)pyrid-3-ylmethylamine, N-(3-(4-Methylsulfinylphenoxy)phenyl)-N-(ethylsulfonyl)pyrid-3-ylmethylamine, N-(3-(4-t-butylphenoxy)phenyl)-N-(ethylsulfonyl)pyrid-3-ylmethylamine, N-(3-(3-methylphenoxy)phenyl)-N-(ethylsulfonyl)pyrid-3-ylmethylamine, N-(3-(2-n-propyl -4-fluorophenoxy)phenyl)-N-(ethylsulfonyl)pyrid-3-ylmethylamine, N-(3-(2-chlorophenoxy)phenyl)-N-(ethylsulfonyl)pyrid-3-ylmethylamine, N-(3-(2-methylphenoxy)phenyl)-N-(ethylsulfonyl)pyrid-3-ylmethylamine, N-(3-(4-carbonylmethoxyphenoxy)phenyl)-N-(ethylsulfonyl)pyrid-3-ylmethylamine, N-(3-(3-t-butylphenoxy)phenyl)-N-(ethylsulfonyl)pyrid-3-ylmethylamine, N-(3-(4-fluoro-2-(3-hydroxy-3-methylbutyl)phenoxy)phenyl)-N-(ethylsulfonyl)pyrid-3-ylmethylamine, N-(3-(2-fluoro-4-t-butylphenoxy)phenyl)-N-(ethylsulfonyl)pyrid-3-ylmethylamine, N-(3-(4-Cabonylmethoxymethylphenoxy)phenyl)-N-(ethylsulfonyl)pyrid-3-ylmethylamine, N-(3-(3-Amidophenoxy)phenyl)-N-(ethylsulfonyl)pyrid-3-ylmethylamine, N-(3-(2,4-diflurophenoxy)phenyl)-N-(ethylsulfonyl)pyrid-3-ylmethylamine, N-(3-(2,4,6-triflurophenoxy)phenyl)-N-(ethylsulfonyl)pyrid-3-ylmethylamine, N-(3-(2-(prop-2-yl)phenoxy)phenyl)-N-(ethylsulfonyl)pyrid-3-ylmethylamine, N-(3-(2-ethylphenoxy)phenyl)-N-(ethylsulfonyl)pyrid-3-ylmethylamine, N-(3-(4-Sulfonylamidophenoxy)phenyl)-N-(ethylsulfonyl)pyrid-3-ylmethylamine, N-(3-(phenoxy)phenyl)-N-(ethylsulfonyl)pyrid-3-ylmethylamine, N-(3-(2-Fluorophenoxy)phenyl)-N-(2,2,2-trifluorethanesulfonyl)pyrid-3-ylmethylamine, N-(3-(2-Methylphenoxy)phenyl)-N-(2,2,2-trifluorethanesulfonyl)pyrid-3-ylmethylamine, N-(3-(4-Carboxymethylphenoxy)phenyl)-N-(ethanesulfonyl)pyrid-3-ylmethylamine, N-(4-(2-Fluoro-4-methylphenoxy)phenyl)-N-(ethanesulfonyl)pyrid-3-ylmethylamine, N-(3-(2-methoxy-phenoxy))phenyl)-N-(2,2,2-trifluoroethanesulfonyl)pyrid-3-ylmethylamine, N-(4-(2-benzyloxy-phenoxy))phenyl)-N-(2,2,2-trifluoroethanesulfonyl)pyrid-3-ylmethylamine, N-(3-(4-fluoro-2-methoxy-phenoxy))phenyl)-N-(ethanesulfonyl)pyrid-3-ylmethylamine, N-(3-(4-fluoro-2-methoxy-phenoxy))phenyl)-N-(2,2,2-trifluoroethanesulfonyl)pyrid-3-ylmethylamine, N-(3-(2-bromo-phenoxy))phenyl)-N-(ethanesulfonyl)pyrid-3-ylmethylamine, N-(3-(2,3-dimethoxy-phenoxy))phenyl)-N-(ethanesulfonyl)pyrid-3-ylmethylamine, N-(3-(2-chloro-phenoxy))phenyl)-N-(ethanesulfonyl)pyrid-3-ylmethylamine, N-(3-(2-chloro-6-methyl-phenoxy))phenyl)-N-(ethanesulfonyl)pyrid-3-ylmethylamine, N-(3-(2-isopropoxy-phenoxy))phenyl)-N-(ethanesulfonyl)pyrid-3-ylmethylamine, N-(3-fluoro-5-(2-methoxy-phenoxy))phenyl)-N-(2,2,2-trifluoroethanesulfonyl)pyrid-3-ylmethylamine, N-(3-fluoro-5-(2-methoxy-phenoxy))phenyl)-N-(ethanesulfonyl)pyrid-3-ylmethylamine, N-(3-(2-methoxy-phenoxy))phenyl)-N-(3,3,3-trifluoropropanesulfonyl)pyrid-3-ylmethylamine, N-(3-(2-bromo-phenoxy))phenyl)-N-(2,2,2-trifluoroethanesulfonyl)pyrid-3-ylmethylamine, N-(3-(2,3-dimethoxy-phenoxy))phenyl)-N-(2,2,2-trifluoroethanesulfonyl)pyrid-3-ylmethylamine, N-(3-(2-chloro-phenoxy))phenyl)-N-(ethanesulfonyl)pyrid-3-ylmethylamine, N-(3-(2-chloro-phenoxy))phenyl)-N-(2,2,2-trifluoroethanesulfonyl)pyrid-3-ylmethylamine, N-(3-(2-chloro-6-methyl-phenoxy))phenyl)-N-(2,2,2-trifluoroethanesulfonyl)pyrid-3-ylmethylamine, N-(3-(2-isoporopoxy-phenoxy))phenyl)-N-(2,2,2-trifluoroethanesulfonyl)pyrid-3-ylmethylamine, N-(3-(4-t-butylphenoxy)-4-methylphenyl)-N-(ethanesulfonyl)pyrid-3-ylmethylamine, N-(3-(2-Fluoro-4-cyanophenoxy)phenyl)-N-(ethanesulfonyl)pyrid-3-ylmethylamine, N-(4-(2-Fluoro-4-amidophenoxy)phenyl)-N-(2,2,2-trifluoroethanesulfonyl)pyrid-3-ylmethylamine, N-(3-(2-Fluoro-4-cyanophenoxy)phenyl)-N-(2,2,2-trifluoroethanesulfonyl)pyrid-3-ylmethylamine, N-(3-(2,4-Difluoro-4-cyanophenoxy)phenyl)-N-(2,2,2-trifluoroerhanesulfonyl)pyrid-3-ylmethylamine, N-(4-(2-Fluoro-4-cyanophenoxy)phenyl)-N-(ethanesulfonyl)pyrid-3-ylmethylamine, N-(4-(2-Fluoro-4-amidophenoxy)phenyl)-N-(ethanesulfonyl)pyrid-3-ylmethylamine, N-(4-(2,4-Difluorophenoxy)phenyl)-N-(ethanesulfonyl)-2-fluoropyrid-3-ylmethylamine, N-(4-(2,4-Difluorophenoxy)phenyl)-N-(2,2,2-trifluoroethanesulfonyl)-2-fluoropyrid-3-ylmethylamine, N-(4-(2,4-Difluorophenoxy)phenyl)-N-(ethanesulfonyl)-6-fluoropyrid-3-ylmethylamine, N-(4-(2,4-Difluorophenoxy)phenyl)-N-(2,2,2-trifluoroethanesulfonyl)-6-fluoropyrid-3-ylmethylamine, N-(4-(2,4-Difluorophenoxy)phenyl)-N-(ethanesulfonyl)-2-methylpyrid-3-ylmethylamine, N-(4-(2,4-Difluorophenoxy)phenyl)-N-(2,2,2-trifluoroethanesulfonyl)-2-methylpyrid-3-ylmethylamine, N-(4-(2,4-Difluorophenoxy)phenyl)-N-(ethanesulfonyl)-6-methylpyrid-3-ylmethylamine, and N-(4-(2,4-Difluorophenoxy)phenyl)-N-(2,2,2-trifluoroethanesulfonyl)-6-methylpyrid-3-ylmethylamine.

23. A compound according to claim 14 wherein at least one of the $R_2$ substituents is attached in the 3-position.

24. A compound according to claim 15 wherein at least one of the $R_2$ substituents is attached in the 3-position.

25. A compound according to claim 14 wherein at least one of the $R_2$ substituents is attached in the 4-position.

26. A compound according to claim 15 wherein at least one of the $R_2$ substituents is attached to the 4-position.

27. A compound according to claim 14 wherein X is a —$CH_2$—.

28. A compound according to claim 15 wherein X is a —$CH_2$—.

29. A compound according to claim 14 wherein X is a —$CH_2$— and Y is a bond.

30. A compound according to claim 15 wherein X is a —$CH_2$— and Y is a bond.

\* \* \* \* \*

UNITED STATES PATENT AND TRADEMARK OFFICE
CERTIFICATE OF CORRECTION

PATENT NO. : 6,800,651 B2
DATED : October 5, 2004
INVENTOR(S) : Coleman et al.

It is certified that error appears in the above-identified patent and that said Letters Patent is hereby corrected as shown below:

Column 152,
Line 59, reads "...and –$CH_2CH_{12}$- wherein..." should read -- ...and –$CH_2CH_2$–... --

Column 155,
Line 4, reads "...–N-(2,2,2-tri fluoroethylsulfonyl)" should read -- ...–N–(2,2,2-trifluoroethylsulfonyl) --

Column 159,
Line 28, reads "...N-(cthylsulfonyl)" should read -- ...N-(ethylsulfonyl) --

Column 161,
Line 6, reads "...N-(3-(2-n-propyl –4-fluorophenoxy))" should read -- ...N-(3-(2-n-propyl-4-fluorophenoxy) --

Column 162,
Line 19, reads "trifluoroerhanesulfonyl)pyrid-3-..." should read
-- trifluoroethanesulfonyl)pyrid-3-... --

Signed and Sealed this

Tenth Day of May, 2005

JON W. DUDAS
*Director of the United States Patent and Trademark Office*